US010053478B2

(12) United States Patent
Reiley et al.

(10) Patent No.: US 10,053,478 B2
(45) Date of Patent: Aug. 21, 2018

(54) COX-2-TARGETING, PLATINUM-CONTAINING CONJUGATES AND THEIR USE IN THE TREATMENT OF TUMORS AND CANCERS

(71) Applicant: Reiley Pharmaceuticals, Inc., San Jose, CA (US)

(72) Inventors: Mark A. Reiley, Washington, DC (US); B. Michael Silber, San Francisco, CA (US); Xiaoqi Chen, Palo Alto, CA (US)

(73) Assignee: REILEY PHARMACEUTICALS, INC., San Jose, CA (US)

( * ) Notice: Subject to any disclaimer, the term of this patent is extended or adjusted under 35 U.S.C. 154(b) by 110 days.

(21) Appl. No.: 14/975,504

(22) Filed: Dec. 18, 2015

(65) Prior Publication Data

US 2016/0200752 A1     Jul. 14, 2016

Related U.S. Application Data

(60) Provisional application No. 62/107,626, filed on Jan. 26, 2015, provisional application No. 62/101,849, filed on Jan. 9, 2015.

(51) Int. Cl.
  *C07F 15/00* (2006.01)
  *A61K 47/48* (2006.01)

(52) U.S. Cl.
  CPC ........ *C07F 15/0013* (2013.01); *A61K 47/481* (2013.01)

(58) Field of Classification Search
  CPC ........................... C07F 15/0013; A61K 47/481
  See application file for complete search history.

(56) References Cited

U.S. PATENT DOCUMENTS

| | | | |
|---|---|---|---|
| 5,245,018 A | 9/1993 | Kondo et al. | |
| 5,279,811 A | 1/1994 | Bergstein et al. | |
| 6,045,773 A | 4/2000 | Isakson et al. | |
| 6,306,890 B1 | 10/2001 | Kalgutkar et al. | |
| 6,491,893 B1 | 12/2002 | Babich | |
| 6,692,724 B1 | 2/2004 | Yang et al. | |
| 7,736,624 B2 | 6/2010 | Marnett et al. | |
| 8,143,302 B2 | 3/2012 | Marnett et al. | |
| 8,865,130 B2 | 10/2014 | Marnett et al. | |
| 9,050,378 B2 | 6/2015 | Yang et al. | |
| 9,161,735 B2 | 10/2015 | Bradford et al. | |
| 2004/0097735 A1 | 5/2004 | Mahmood et al. | |
| 2005/0079133 A1 | 4/2005 | Yang et al. | |
| 2005/0129619 A1 | 6/2005 | Yang et al. | |
| 2005/0136001 A1 | 6/2005 | McBride et al. | |
| 2007/0148092 A1 | 6/2007 | Biswal et al. | |
| 2007/0231266 A1 | 10/2007 | Low et al. | |
| 2007/0292352 A1 | 12/2007 | Marnett et al. | |
| 2008/0241256 A1 | 10/2008 | Kuhn | |
| 2009/0180951 A1 | 7/2009 | Zimmerman et al. | |
| 2009/0252678 A1 | 10/2009 | Marnett et al. | |
| 2010/0111858 A1 | 5/2010 | Howard et al. | |
| 2010/0254910 A1 | 10/2010 | Marnett et al. | |
| 2011/0286923 A1 | 11/2011 | Satchi-Fainaro et al. | |
| 2012/0128588 A1 | 5/2012 | Takashima et al. | |
| 2012/0276005 A1 | 11/2012 | Yang et al. | |
| 2013/0039853 A1 | 2/2013 | Yang et al. | |
| 2013/0052138 A1 | 2/2013 | Marnett et al. | |

FOREIGN PATENT DOCUMENTS

| | | |
|---|---|---|
| CA | 2789869 A1 | 10/2010 |
| EP | 2463263 B1 | 4/2014 |
| WO | 1995/09564 A1 | 4/1995 |
| WO | 2000/41514 A2 | 7/2000 |
| WO | 2001/40239 A2 | 6/2001 |
| WO | 2001/83436 A2 | 11/2001 |
| WO | 2003/086476 A1 | 10/2003 |
| WO | 2003/092742 A1 | 11/2003 |
| WO | 2003/101948 A2 | 12/2003 |
| WO | 2005/002293 A2 | 1/2005 |
| WO | 2006/050058 A2 | 5/2006 |
| WO | 2007/035906 A2 | 3/2007 |
| WO | 2008/045604 A2 | 4/2008 |
| WO | 2011/008985 A2 | 1/2011 |
| WO | 2011/016376 A1 | 2/2011 |
| WO | 2016/111834 A1 | 7/2016 |

OTHER PUBLICATIONS

Neumann et al. "Conjugates of Cisplatin and Cyclooxygenase Inhibitors as Potent Antitumor Agents Overcoming Cisplatin Resistance" ChemMedChem, 2014, vol. 9, pp. 1150-1153.*

Abiraj et al., "Tetraamine-Derived Bifunctional Chelators for Technetium-99m Labelling: Synthesis, Bioconjugation and Evaluation as Targeted SPECT Imaging Probes for GRP-Receptor-Positive Tumours", Chemistry: A European Journal, 2010, vol. 16, 2010, pp. 2115-2124.

Alberto et al., "First Application of fac-[$^{99m}$Tc(OH$_2$)$_3$(CO)$_3$]+ in Bioorganometallic Chemistry: Design, Structure, and in Vitro Affinity of a 5-HT$_{1A}$ Receptor Ligand Labeled with $^{99m}$Tc", J. Am. Chem. Soc. vol. 121, No. 25, 1999, pp. 6076-6077.

Amo et al., "Two-Colour Screening in Combinatorial Chemistry: Prospecting for Enantioselectivity in a Library of Steroid-Based Receptors", Tetrahedron, vol. 65, Journal Homepage: www.elsevier.com/locate/tet, 2009, pp. 6370-6381.

Baran et al., "Direct Coupling of Pyrroles with Carbonyl Compounds: Short Enantioselective Synthesis of (S)-Ketorolac", Supporting information for this article is available on the WWW Under http://www.angewandte.org or from the author, Angew. Chem. Int. Ed., vol. 44, 2005, pp. 609-612.

(Continued)

*Primary Examiner* — Joseph R Kosack

(74) *Attorney, Agent, or Firm* — Morrison & Foerster LLP

(57) ABSTRACT

The present disclosure provides platinum-containing conjugates that selectively target and kill tumor/cancer cells. The conjugates contain a moiety that selectively targets COX-2, which is overexpressed by a broad range of tumor/cancer cells.

5 Claims, 16 Drawing Sheets

(56) References Cited

OTHER PUBLICATIONS

Battle et al., "Platinum(IV) Analogues of AMD473 (cis-[PtCl$_2$(NH$_3$)(2-picoline)]): Preparative, Structural, and Electrochemical Studies", Inorganic Chemistry, vol. 45, No. 16, 2006, pp. 6317-6322.
Bernard et al., "Aqueous Synthesis of Derivatized Cyclopentadienyl Complexes of Technetium and Rhenium Directed toward Radiopharmaceutical Application", Inorganic Chemistry, vol. 42, No. 4, 2003, pp. 1014-1022.
Bernard et al., "Targeting Cyclooxygenase-2 in Hematological Malignancies: Rationale and Promise", Current Pharmaceutical Design, vol. 14, No. 21, 2008, pp. 2051-2060.
Blobaum et al., "The 2'-Trifluoromethyl Analogue of Indomethacin is a Potent and Selective COX 2 Inhibitor", ACS Medicinal Chemistry Letter, vol. 4, 2013, pp. 486-490.
Boros et al., "Design, Synthesis, and Imaging of Small Amphiphilic Rhenium and $^{99m}$Technetium Tricarbonyl Complexes", Bioconjugate Chem., vol. 20, No. 5, 2009, pp. 1002-1009.
Cheff et al., "A Drug of Such Damned Nature. Challenges and Opportunities in Translational Platinum Drug Research", Journal of Medicinal Chemistry, vol. 60, 2017, pp. 4517-4532.
Chen et al., "Synthesis and Biological Evaluation of $^{99m}$Tc, Re-Monoamine-Monoamide Conjugated to 2-(4-Aminophenyl) Benzothiazole as Potential Probes for β-Amyloid Plaques in the Brain", Bioorganic & Medicinal Chemistry Letters, vol. 18, 2008, pp. 1442-1445.
Chen et al., "Synthesis and Biological Evaluation of a Novel $^{99m}$Tc Cyclopentadienyl Tricarbonyl Complex ([(Cp-R)$^{99m}$Tc(CO)$_3$]) for Sigma-2 Receptor Tumor Imaging", Bioorganic & Medicinal Chemistry Letters, vol. 22, 2012, pp. 6352-6357.
Cheng et al., "Technetium-99m Labeled Pyridyl Benzofuran Derivatives as Single Photon Emission Computed Tomography Imaging Probes for β-Amyloid Plaques in Alzheimer's Brains", Journal of Medicinal Chemistry, vol. 55, 2012, pp. 2279-2286.
Costa et al., "The Synthesis of Biologically Relevant Conjugates of Re(CO)$_3$ Using Pyridine-2-Carboxyaldehyde", J Organomet Chem, Jun. 15, 2013, vol. 734, 2013, 18 pages.
Eisenhut et al., "Melanoma Uptake of $^{99m}$Tc Complexes Containing the N-(2-Diethylaminoethyl)benzamide Structural Element", Journal of Medicinal Chemistry, vol. 45, No. 26, 2002, pp. 5802-5805.
Friebe et al., "[$^{99m}$Tc]Oxotechnetium(V) Complexes of Amine-Amide-Dithiol Chelates with Dialkylaminoalkyl Substituents as Potential Diagnostic Probes for Malignant Melanoma", Journal of Medicinal Chemistry, vol. 44, No. 19, 2001, pp. 3132-3140.
Fritzberg et al., "Synthesis and Biological Evaluation of Technetium-99m MAG$_3$ as a Hippuran Replacement", J Nucl Med., vol. 27, 1986, pp. 111-116.
Guay et al., "Carrageenan-Induced Paw Edema in Rat Elicits a Predominant Prostaglandin E$_2$ (PGE$_2$) Response in the Central Nervous System Associated with the Induction of Microsomal PGE$_2$ Synthase-1*", The Journal of Biological Chemistry ,vol. 279, No. 23, Jun. 4, 2004, pp. 24866-24872.
Hansen et al., "Rhenium( V) Oxo Complexes Relevant to Technetium Renal Imaging Agents Derived from Mercaptoacetylglycylglycylaminobenzoic Acid Isomers. Structural and Molecular Mechanics Studies", Inorg. Chem., vol. 31, No. 13, 1992, pp. 2801-2808.
Harman et al., "Structural Basis of Enantioselective Inhibition of Cyclooxygenase-1 by S-α Substituted Indomethacin Ethanolamides", The Journal of Biological Chemistry vol. 282, No. 38, Sep. 21, 2007, pp. 28096-28105.
Hirano et al., "General Method for the $^{11}$C-Labeling of 2-Arylpropionic Acids and Their Esters: Construction of a PET Tracer Library for a Study of Biological Events Involved in COXs Expression", Chem. Eur. J., vol. 16, 2010, pp. 4250-4258.
International Preliminary Report on Patentability and Written Opinion received for PCT Patent Application No. PCT/US2015/066886, dated Jul. 11, 2017, 7 pages.

International Search Report and Written Opinion received for PCT Patent Application No. PCT/US2015/036915, dated Sep. 15, 2015, 7 pages.
International Preliminary Report on Patentability received for PCT Patent Application No. PCT/US2015/036915, dated Jan. 5, 2017, 6 pages.
International Search Report and Written Opinion received for PCT Patent Application No. PCT/US2015/066886, dated Apr. 25, 2016, 13 pages.
Invitation to Pay Additional Fee received for PCT Patent Application No. PCT/US2015/066886, dated Feb. 4, 2016, 3 pages.
Itoh "$^{99m}$Tc-MAG3: Review of Pharmacokinetics, Clinical Application to Renal Diseases and Quantification of Renal Function", Annals of Nuclear Medicine vol. 15, No. 3, 2001, pp. 179-190.
Kalgutkar et al., "Biochemically Based Design of Cyclooxygenase-2 (COX-2) Inhibitors: Facile Conversion of Nonsteroidal Antiinflammatory Drugs to Potent and Highly Selective COX-2 Inhibitors", PNAS, vol. 97, No. 2, Jan. 18, 2000, pp. 925-930.
Kalgutkar et al., "Ester and Amide Derivatives of the Nonsteroidal Antiinflammatory Drug, Indomethacin, as Selective Cyclooxygenase-2 Inhibitors", Journal of Medicinal Chemistry, vol. 43, No. 15, 2000, pp. 2860-2870.
Kalgutkar et al., "Indolyl Esters and Amides Related to Indomethacin are Selective COX-2 inhibitors", Bioorganic & Medicinal Chemistry, vol. 13, 2005, pp. 6810-6822.
Kocher, David C. , "TechneScan MAG3™ Kit for the Preparation of Technetium Tc 99m Mertiatide Rx Only.", "Radioactive Decay Tables," DOE/TIC-11026, vol. 108, 1981, 2 pages.
Kozak et al., "Enantiospecific, Selective Cyclooxygenase-2 Inhibitors", Bioorganic & Medicinal Chemistry Letters, vol. 12, 2002, pp. 1315-1318.
Ktaifani et al., "Synthesis of 2-Methyl-2-Propoxypropyl Isocyanide and its Cu(I) Tetraflouroborate Complex", Chemical Papers, vol. 62, No. 3, 2008, pp. 329-333.
Kurumbail et al., "Structural Basis for Selective Inhibition of Cyclooxygenase-2 by Anti-Inflammatory Agents", Nature, vol. 384, Dec. 1996, pp. 644-648.
Laube et al., "Radiolabeled COX-2 Inhibitors for Non-Invasive Visualization of COX-2 Expression and Activity—A Critical Update", Molecules, vol. 18, 2013, pp. 6311-6355.
Li et al., "Novel Cyclopentadienyl Tricarbonyl Complexes of $^{99m}$Tc Mimicking Chalcone as Potential Single-Photon Emission Computed Tomography Imaging Probes for β-Amyloid Plaques in Brain", J. Med. Chem., vol. 56, 2013, pp. 471-482.
Meltzer et al., "A Technetium-99m SPECT Imaging Agent Which Targets the Dopamine Transporter in Primate Brain", Journal of Medicinal Chemistry, vol. 40, No. 12, 1997, pp. 1835-1844.
Moth et al., "Stereoselective Binding of Indomethacin Ethanolamide Derivatives to Cyclooxygenase-1", Journal of Medicinal Chemistry, vol. 48, No. 10, 2005, pp. 3613-3620.
Muchowski et al., "Synthesis and Antiinflammatory and Analgesic Activity of 5-Aroyl-1,2-dihydro-3H-pyrrolo[1,2-a ] pyrrole-1-carboxylic Acids and Related Compounds", J. Med. Chem., vol. 28, 1985, pp. 1037-1049.
Muller et al., "Organometallic 99mTc-technetium(I)- and Re-rhenium(I)- Folate Derivatives for Potential use in Nuclear Medicine", Journal of Organometallic Chemistry vol. 689, 2004, pp. 4712-4721.
Nantel et al., "Distribution and Regulation of Cyclooxygenase-2 in Carrageenan-Induced inflammation", British Journal of Pharmacology vol. 128, 1999, pp. 853-859.
Neil et al., "Preparation and Structural Characterization of Monoamine-Monoamide Bis( thiol) Oxo Complexes of Technetium(V) and Rhenium( V)", Inorganic Chemistry, vol. 33, No. 2, 1994, pp. 319-323.
Neumann et al., "Conjugation of Cisplatin Analogues and Cyclooxygenase Inhibitors to Overcome Cisplatin Resistance", ChemMedChem, vol. 10, 2015, pp. 183-192.
Non Final Office Action received for U.S. Appl. No. 14/746,349, dated Jan. 27, 2017, 16 pages.
Ogawa et al., "Development of a Rhenium-186-Labeled MAG3-Conjugated Bisphosphonate for the Palliation of Metastatic Bone

(56) References Cited

OTHER PUBLICATIONS

Pain Based on the Concept of Bifunctional Radiopharmaceuticals", Bioconjugate Chem. vol. 16, 2005, pp. 751-757.
Ono et al., "$^{99m}$Tc/Re Complexes Based on Flavone and Aurone as SPECT Probes for Imaging Cerebral β-Amyloid Plaques", Bioorganic & Medicinal Chemistry Letters, vol. 20, 2010, pp. 5743-5748.
Ono et al., "Synthesis and Evaluation of Novel Chalcone Derivatives with $^{99m}$Tc/Re Complexes as Potential Probes for Detection of β-Amyloid Plaques", ACS Chem. Neurosci, vol. 1, 2010, pp. 598-607.
Oya et al., "Small and Neutral Tc$^V$O BAT, Bisaminoethanethiol (N$_2$S$_2$) Complexes for Developing New Brain Imaging Agents", Nuclear Medicine & Biology, vol. 25, 1998, pp. 135-140.
Pacelli et al., "Imaging COX-2 Expression in Cancer Using PET/SPECT Radioligands: Current Status and Future Directions", J. Label Compd. Radiopharm, vol. 57, 2014, pp. 317-322.
Penning et al., "Synthesis and Biological Evaluation of the 1,5-Diarylpyrazole Class of Cyclooxygenase-2 Inhibitors: Identification of 4-[5-(4-Methylphenyl)-3-(Trifluoromethyl)-1H-pyrazol-1-yl]Benzenesulfonamide (SC-58635, Celecoxib)", Journal of Medicinal Chemistry, vol. 40, No. 9,1997, pp. 1347-1365.
Seibert et al., "Pharmacological and Biochemical Demonstration of the Role of Cyclooxygenase 2 in Inflammation and Pain", Proc. Natl. Acad. Sci. USA vol. 91, 1994, pp. 12013-12017.
Shalini et al., "Mechanism of Anti-Inflammatory Effect of Tricin, A Flavonoid Isolated from Njavara Rice Bran in LPS Induced hPBMCs and Carrageenan induced Rats", Molecular Immunology vol. 66, 2015, pp. 229-239.
Shen et al., "Non-Steroid Anti-Inflammatory Agents", Journal of the American Chemical Society, vol. 85, Feb. 20, 1963, pp. 488-489.
Siddik, Zahid H., "Cisplatin: Mode of Cytotoxic Action and Molecular Basis of Resistance", Oncogene, vol. 22, 2003, pp. 7265-7279.
Tietz et al., "Radiotracers for Molecular Imaging of Cyclooxygenase-2 (COX-2) Enzyme", Current Medicinal Chemistry, vol. 20, 2013, pp. 4350-4369.
Tiseo et al., "Cisplatin or Carboplatin in the Treatment of Non-Small Cell Lung Cancer: A Comprehensive Review", Oncol Rev, vol. 1, 2007, pp. 162-169.
Uddin et al., "Design, Synthesis, and Structure—Activity Relationship Studies of Fluorescent Inhibitors of Cycloxygenase-2 as Targeted Optical Imaging Agents", Bioconjugate Chem. vol. 24, 2013, pp. 712-723.
Uddin et al., "Fluorinated COX-2 Inhibitors as Agents in PET Imaging of Inflammation and Cancer", Cancer Prevention Research, vol. 4, No. 10, Oct. 2011, pp. 1536-1545.
Uddin et al., "Podophyllotoxin Analogues Active Versus Trypanosoma Brucei", Bioorganic & Medicinal Chemistry Letters, vol. 20, 2010, pp. 1787-1791.
Uddin et al., "Selective Visualization of Cyclooxygenase-2 in Inflammation and Cancer by Targeted Fluorescent Imaging Agents", Cancer Research, vol. 70, No. 9, May 1, 2010, pp. 3618-3627.
Uddin et al., "Trifluoromethyl Fluorocoxib A Detects Cyclooxygenase 2 Expression in Inflammatory Tissues and Human Tumor Xenografts", ACS Medical Chemistry Letters, vol. 5, 2014, pp. 446-450.
Uehara et al., "Technetium-99m-Labeled Long Chain Fatty Acid Analogues Metabolized by β-Oxidation in the Heart", Journal of Medicinal Chemistry, vol. 50, 2007, pp. 543-549.
V et al., "Mechanisms of Effects of Platinum (II) and (IV) Complexes. Comparison of Cisplatin and Oxaliplatin with Satraplatin and La-12, New Pt (IV)-Based Drugs A Minireview", Scripta Medica, vol. 81, No. 2, Jun. 2008, pp. 105-116.
Vries et al., "Synthesis and In Vivo Evaluation of $^{18}$F-Desbromo-DuP-697 as a PET Tracer for Cyclooxygenase-2 Expression", The Journal of Nuclear Medicine, vol. 44, No. 10, Oct. 2003, pp. 1700-1706.
Wang et al., "Methods for MAG3 Conjugation and $^{99m}$Tc Radiolabeling of Biomolecules", Nature Protocols, vol. 1, No. 3, 2006, pp. 1477-1480.
Wang et al., "Novel Cyclopentadienyl Tricarbonyl $^{99m}$Tc Complexes Containing 1-Piperonylpiperazine Moiety: Potential Imaging Probes for Sigma-1 Receptors", Journal of Medicinal Chemistry, vol. 57, 2014, pp. 7113-7125.
Westerberg et al., "Synthesis of Novel Bifunctional Chelators and Their Use in Preparing Monoclonal Antibody Conjugates for Tumor Targeting", J. Med. Chem. ,vol. 32, No. 1, 1989, pp. 236-243.
Wilson et al., "Synthetic Methods for the Preparation of Platinum Anticancer Complexes", Chemical Reviews, vol. 114, 2014, pp. 4470-4495.
Wyk et al., "Synthesis and $^{99m}$Tc Labelling of MMI (MIBI) and its Ethyl Analogue EMI", Appl. Radial. Isot. vol. 42, No. 7, 1991, pp. 687-689.
Yamamoto et al., "$^{11}$C-Labeled Analogs of Indomethacin Esters and Amides for Brain Cyclooxygenase-2 Imaging: Radiosynthesis, in Vitro Evaluation and in Vivo Characteristics in Mice", Chem. Pharm. Bull., vol. 59, No. 8, Aug. 2011, pp. 938-946.

\* cited by examiner

COX-2-TARGETING, PLATINUM-CONTAINING CONJUGATES AND THEIR USE IN THE TREATMENT OF TUMORS AND CANCERS

CROSS-REFERENCE TO RELATED APPLICATIONS

This application claims priority to U.S. Provisional App. No. 62/101,849, filed on Jan. 9, 2015, and U.S. Provisional App. No. 62/107,626, filed on Jan. 26, 2015, the entire disclosure of each of which is incorporated herein by reference.

BACKGROUND OF THE DISCLOSURE

Cancer is one of the principal causes of death in the world. Many potent drugs have been developed to treat cancer, but their utility has been limited because they kill normal cells as well as cancer cells.

SUMMARY OF THE DISCLOSURE

The present disclosure provides conjugates that selectively target and kill tumor/cancer cells. The expression of cyclooxygenase II (COX-2) is upregulated in many benign and malignant tumor/cancer cells. In some embodiments, the conjugates comprise a COX-2-targeting moiety and a platinum-containing antitumor agent. The term "antitumor agents" includes antitumor agents and anticancer agents. In some embodiments, the COX-2-targeting moiety comprises a non-steroidal anti-inflammatory drug (NSAID). In certain embodiments, the COX-2-targeting moiety comprises a COX-2-selective inhibitor. In further embodiments, the platinum-containing antitumor agent is of Formula I:

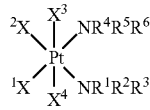

(I)

wherein $X^1$, $X^2$, $X^3$, $X^4$, $NR^1R^2R^3$ and $NR^4R^5R^6$ are as defined below. In additional embodiments, the conjugates further comprise a linker between the COX-2-targeting moiety and the platinum-containing antitumor agent. In some embodiments, the linker increases the selectivity of the conjugates for COX-2.

The disclosure further provides pharmaceutical compositions comprising the conjugates and methods of treating tumors/cancers with the conjugates in human and veterinary medicine.

BRIEF DESCRIPTION OF THE DRAWINGS

A better understanding of features and advantages of the present disclosure will be obtained by reference to the following detailed description, which sets forth illustrative embodiments of the disclosure, and the accompanying drawings.

DETAILED DESCRIPTION OF THE DISCLOSURE

Figure 1:
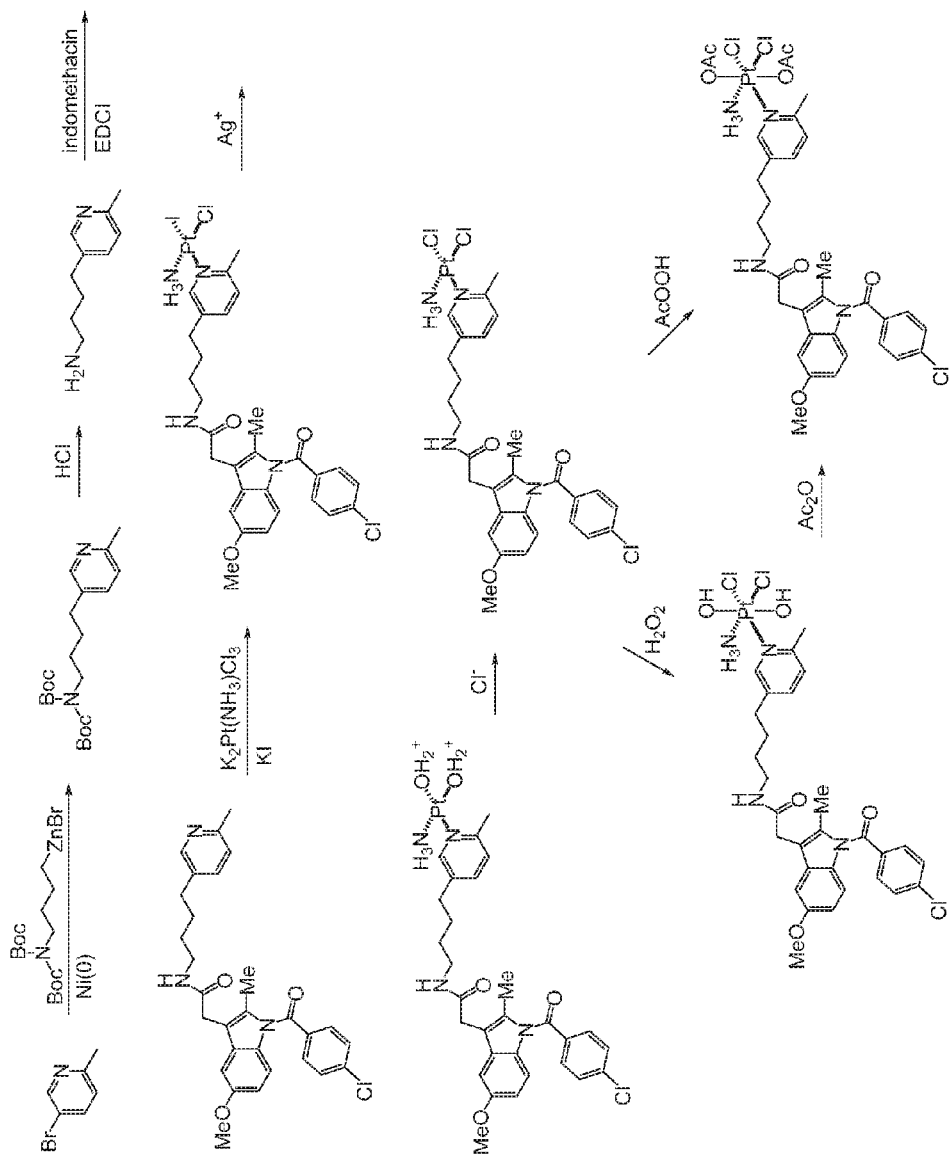
FIGS. 1-16 describe exemplary synthesis of representative conjugates comprising a COX-2-targeting moiety, a linker and a platinum-[e.g., platinum(II)- or platinum(IV)-] containing antitumor agent.

While various embodiments of the present disclosure are described herein, it will be obvious to those skilled in the art that such embodiments are provided by way of example only. Numerous modifications and changes to, and variations and substitutions of, the embodiments described herein will be apparent to those skilled in the art without departing from the disclosure. It is understood that various alternatives to the embodiments described herein may be employed in practicing the disclosure. It is also understood that every embodiment of the disclosure may optionally be combined with any one or more of the other embodiments described herein which are consistent with that embodiment.

Where elements are presented in list format (e.g., in a Markush group), it is understood that each possible subgroup of the elements is also disclosed, and any one or more elements can be removed from the list or group.

It is also understood that, unless clearly indicated to the contrary, in any method described or claimed herein that includes more than one act, the order of the acts of the method is not necessarily limited to the order in which the acts of the method are recited, but the disclosure encompasses embodiments in which the order is so limited.

It is further understood that, in general, where an embodiment in the description or the claims is referred to as comprising one or more features, the disclosure also encompasses embodiments that consist of, or consist essentially of, such feature(s).

It is also understood that any embodiment of the disclosure, e.g., any embodiment found within the prior art, can be explicitly excluded from the claims, regardless of whether or not the specific exclusion is recited in the specification.

Headings are included herein for reference and to aid in locating certain sections. Headings are not intended to limit the scope of the embodiments and concepts described in the sections under those headings, and those embodiments and concepts may have applicability in other sections throughout the entire disclosure.

All patent literature and all non-patent literature cited herein are incorporated herein by reference in their entirety to the same extent as if each patent literature or non-patent literature were specifically and individually indicated to be incorporated herein by reference in its entirety.

I. Definitions

As used in the specification and the appended claims, the indefinite articles "a" and "an" and the definite article "the" can include plural referents as well as singular referents unless specifically stated otherwise.

The term "exemplary" as used herein means "serving as an example, instance, or illustration". Any embodiment characterized herein as "exemplary" is not necessarily to be construed as preferred or advantageous over other embodiments.

The term "about" or "approximately" means an acceptable error for a particular value as determined by one of ordinary skill in the art, which depends in part on how the value is measured or determined. In certain embodiments, the term "about" or "approximately" means within one standard deviation. In some embodiments, when no particular margin of error (e.g., a standard deviation to a mean value given in a chart or table of data) is recited, the term "about" or "approximately" means that range which would encompass the recited value and the range which would be included by rounding up or down to the recited value as well, taking into account significant figures. In certain embodiments, the term "about" or "approximately" means within 20%, 15%, 10% or 5% of the specified value. Whenever the term "about" or "approximately" precedes the first numerical value in a series of two or more numerical values or in a series of two or more ranges of numerical values, the term "about" or "approximately" applies to each one of the numerical values in that series of numerical values or in that series of ranges of numerical values.

Whenever the term "at least" or "greater than" precedes the first numerical value in a series of two or more numerical values, the term "at least" or "greater than" applies to each one of the numerical values in that series of numerical values.

Whenever the term "no more than" or "less than" precedes the first numerical value in a series of two or more numerical values, the term "no more than" or "less than" applies to each one of the numerical values in that series of numerical values.

The term "pharmaceutically acceptable" refers to a substance (e.g., an active ingredient or an excipient) that is suitable for use in contact with the tissues and organs of a subject without excessive irritation, allergic response, immunogenicity and toxicity, is commensurate with a reasonable benefit/risk ratio, and is effective for its intended use. A "pharmaceutically acceptable" carrier or excipient of a pharmaceutical composition is also compatible with the other ingredients of the composition.

The term "therapeutically effective amount" refers to an amount of a compound that, when administered to a subject, is sufficient to prevent development of, or to alleviate to some extent, or to abrogate, the disease or disorder being treated. The term "therapeutically effective amount" also refers to an amount of a compound that is sufficient to elicit a biological or medical response of a cell, tissue, organ, system, animal or human which is sought by a researcher, veterinarian, medical doctor or clinician.

The terms "treat", "treating", and "treatment" include alleviating or abrogating a disease or disorder, and alleviating or eradicating one or more causes of the disease or disorder. Reference to "treatment" of a disease or disorder is intended to include prevention of the disease or disorder. The terms "prevent", "preventing", and "prevention" include delaying or precluding the onset of a disease or disorder, precluding a subject from acquiring a disease or disorder, and reducing a subject's risk of acquiring a disease or disorder. In some embodiments, treatment refers to ameliorating a disease or disorder, or improving the condition of a patient having a disease or disorder.

The term "subject" refers to an animal, including but not limited to a mammal, such as a primate (e.g., a human, a chimpanzee and a monkey), a rodent (e.g., a rat, a mouse, a gerbil and a hamster), a lagomorph (e.g., a rabbit), a swine (e.g., a pig), an equine (e.g., a horse), a canine (e.g., a dog) and a feline (e.g., a cat). The terms "subject" and "patient" are used interchangeably herein in reference, e.g., to a mammalian subject, such as a human subject.

A "residue" of a non-steroidal anti-inflammatory drug (NSAID) is a portion of the NSAID that retains its ability to bind to cyclooxygenase. In certain embodiments, a residue of an NSAID refers to the portion of the compound remaining after removal of a hydrogen atom or a hydroxyl, methyl or methoxy group from the NSAID. The residue of the NSAID can be directly associated with a platinum-containing antitumor agent, or can be indirectly associated with such an antitumor agent (e.g., via a linker).

The terms "halogen", "halide" and "halo" refer to fluoride, chloride, bromide, and iodide.

The terms "sulfhydryl" and "mercapto" refer to —SH.

The term "alkyl" refers to a linear or branched, saturated monovalent hydrocarbon radical, wherein the alkyl group may optionally be substituted with one or more substituents as described herein. In certain embodiments, an alkyl group is a linear saturated monovalent hydrocarbon radical that has 1 to 20 ($C_{1-20}$) or more, 1 to 10 ($C_{1-10}$) or more, or 1 to 6 ($C_{1-6}$) or more, carbon atoms, or is a branched saturated monovalent hydrocarbon radical that has 3 to 20 ($C_{3-20}$) or more, 3 to 10 ($C_{3-10}$) or more, or 3 to 6 ($C_{3-6}$) or more, carbon atoms. As an example, the term "$C_{1-6}$ alkyl" refers to a linear saturated monovalent hydrocarbon radical of 1 to 6 carbon atoms or a branched saturated monovalent hydrocarbon radical of 3 to 6 carbon atoms. Linear $C_{1-6}$ and branched $C_{3-6}$ alkyl groups may also be referred to as "lower alkyl". Non-limiting examples of alkyl groups include methyl, ethyl, propyl (including all isomeric forms, such as n-propyl and isopropyl), butyl (including all isomeric forms, such as n-butyl, isobutyl, sec-butyl and tert-butyl), pentyl (including all isomeric forms, such as n-pentyl), and hexyl (including all isomeric forms, such as n-hexyl).

The terms "alkylene" and "-alkyl-" refer to a divalent alkyl group, which may optionally be substituted with one or more substituents as described herein.

The term "alkenyl" refers to a linear or branched, unsaturated monovalent hydrocarbon radical that contains one or more carbon-carbon double bonds, wherein the alkenyl group may optionally be substituted with one or more substituents as described herein. In certain embodiments, an alkenyl group contains one, two, three or more carbon-carbon double bonds. In certain embodiments, an alkenyl group is a linear unsaturated monovalent hydrocarbon radical that has 2 to 20 ($C_{2-20}$) or more, 2 to 10 ($C_{2-10}$) or more, or 2 to 6 ($C_{2-6}$) or more, carbon atoms, or is a branched unsaturated monovalent hydrocarbon radical that has 3 to 20 ($C_{3-20}$) or more, 3 to 10 ($C_{3-10}$) or more, or 3 to 6 ($C_{3-6}$) or more, carbon atoms.

The term "alkynyl" refers to a linear or branched, unsaturated monovalent hydrocarbon radical that contains one or more carbon-carbon triple bonds, wherein the alkynyl group may optionally be substituted with one or more substituents as described herein. In certain embodiments, an alkynyl group contains one, two, three or more carbon-carbon triple bonds. In certain embodiments, an alkynyl group is a linear unsaturated monovalent hydrocarbon radical that has 2 to 20 ($C_{2-20}$) or more, 2 to 10 ($C_{2-10}$) or more, or 2 to 6 ($C_{2-6}$) or more, carbon atoms, or is a branched unsaturated monovalent hydrocarbon radical that has 4 to 20 ($C_{4-20}$) or more, 4 to 10 ($C_{4-10}$) or more, or 4 to 6 ($C_{4-6}$) or more, carbon atoms.

The term "alkoxy" refers to an —O-alkyl group, which may optionally be substituted with one or more substituents as described herein.

The term "haloalkyl" refers to an alkyl group that is substituted with one or more halide atoms. In certain embodiments, a haloalkyl group is substituted with one, two, three, four, five, six or more halide atoms. A haloalkyl group may optionally be substituted with one or more additional substituents as described herein.

The term "hydroxyalkyl" refers to an alkyl group that is substituted with one or more hydroxyl (—OH) groups. In certain embodiments, a hydroxyalkyl group is substituted with one, two, three, four, five or more —OH groups. A hydroxyalkyl group may optionally be substituted with one or more additional substituents as described herein.

The term "aminoalkyl" refers to an alkyl group that is substituted with one or more —$NH_2$ groups. In certain embodiments, an aminoalkyl group is substituted with one, two, three, four, five or more —NH$_2$ groups. An aminoalkyl group may optionally be substituted with one or more additional substituents as described herein.

The term "-alkylcycloalkyl" refers to an alkyl group that is substituted with one or more cycloalkyl groups. In certain embodiments, an -alkylcycloalkyl group is substituted with one, two, three or more cycloalkyl groups. An -alkylcycloalkyl group may optionally be substituted with one or more additional substituents as described herein.

The term "-alkylheterocyclyl" refers to an alkyl group that is substituted with one or more heterocyclyl groups. In certain embodiments, an -alkylheterocyclyl group is substituted with one, two, three or more heterocyclyl groups. An -alkylheterocyclyl group may optionally be substituted with one or more additional substituents as described herein.

The term "-alkylaryl" refers to an alkyl group that is substituted with one or more aryl groups. In certain embodiments, an -alkylaryl group is substituted with one, two, three or more aryl groups. An -alkylaryl group may optionally be substituted with one or more additional substituents as described herein.

The term "-alkylheteroaryl" refers to an alkyl group that is substituted with one or more heteroaryl groups. In certain embodiments, an -alkylheteroaryl group is substituted with one, two, three or more heteroaryl groups. An -alkylheteroaryl group may optionally be substituted with one or more additional substituents as described herein.

The term "cycloalkyl" refers to a cyclic saturated, bridged or non-bridged monovalent hydrocarbon radical, which may optionally be substituted with one or more substituents as described herein. In certain embodiments, a cycloalkyl group has from 3 to 10 ($C_{3-10}$) or more, or from 3 to 8 ($C_{3-8}$) or more, or from 3 to 6 ($C_{3-6}$) or more, carbon atoms. Non-limiting examples of cycloalkyl groups include cyclopropyl, cyclobutyl, cyclopentyl, cyclohexyl, cycloheptyl, cyclooctyl, norbornyl, decalinyl and adamantyl.

The terms "heterocyclyl" and "heterocyclic" refer to a monocyclic non-aromatic group or a multicyclic group that contains at least one non-aromatic ring, wherein at least one non-aromatic ring contains one or more heteroatoms independently selected from O, S and N. The non-aromatic ring containing one or more heteroatoms may be attached or fused to one or more saturated, partially unsaturated, or aromatic rings. In certain embodiments, a heterocyclyl or heterocyclic group has from 3 to 15 or more, or 3 to 12 or more, or 3 to 10 or more, or 3 to 8 or more, or 3 to 6 or more, ring atoms. In some embodiments, a heterocyclyl or heterocyclic group is a monocyclic, bicyclic or tricyclic ring system, which may include a fused or bridged ring system, and in which nitrogen or sulfur atoms may optionally be oxidized, nitrogen atoms may optionally be quaternized, and one or more rings may be partially or fully saturated, or aromatic. A heterocyclyl or heterocyclic group may be attached to the main structure at any heteroatom or carbon atom which results in the creation of a stable compound. Examples of heterocyclyl or heterocyclic groups include without limitation azepinyl, azetidinyl, aziridinyl, benzodioxanyl, benzodioxolyl, benzofuranonyl, benzopyranonyl, benzopyranyl, benzotetrahydrofuranyl, benzotetrahydrothienyl, benzothiopyranyl, β-carbolinyl, chromanyl, decahydroisoquinolinyl, dihydrobenzisothiazinyl, dihydrobenzisoxazinyl, dihydrofuryl, dihydropyranyl, dihydropyrazinyl, dihydropyridinyl, dihydropyrazolyl, dihydropyrimidinyl, dihydropyrrolyl, dioxolanyl, dithianyl, furanonyl, imidazolidinyl, imidazolinyl, indolinyl, indolizinyl, isobenzotetrahydrofuranyl, isobenzotetrahydrothienyl, isochromanyl, isoindolinyl, isothiazolidinyl, isoxazolidinyl, morpholinyl, octahydroindolyl, octahydroisoindolyl, oxazolidinonyl, oxazolidinyl, oxiranyl, piperazinyl, piperidinyl, 4-piperidonyl, pyrrolidinyl, pyrrolinyl, quinuclidinyl, tetrahydrofuryl, tetrahydrofuranyl (oxolanyl), tetrahydroisoquinolinyl, tetrahydropyranyl, tetrahydrothienyl (tetrahydrothiophenyl, thiolanyl), thiamorpholinyl (thiomorpholinyl), thiazolidinyl and 1,3,5-trithianyl. A heterocyclyl or heterocyclic group may optionally be substituted with one or more substituents as described herein.

The term "aryl" refers to a monocyclic aromatic hydrocarbon group or a multicyclic group that contains at least one aromatic hydrocarbon ring. In certain embodiments, an aryl group has from 6 to 15 or more, or 6 to 12 or more, or 6 to 10 or more, ring atoms. Non-limiting examples of aryl groups include phenyl, naphthyl, fluorenyl, azulenyl, anthryl, phenanthryl, biphenyl and terphenyl. The aromatic hydrocarbon ring of an aryl group may be attached or fused to one or more saturated, partially unsaturated, or aromatic rings—e.g., dihydronaphthyl, indenyl, indanyl and tetrahydronaphthyl (tetralinyl). An aryl group may optionally be substituted with one or more substituents as described herein.

The term "heteroaryl" refers to a monocyclic aromatic group or a multicyclic group that contains at least one aromatic ring, wherein at least one aromatic ring contains one or more heteroatoms independently selected from O, S and N. The heteroaromatic ring may be attached or fused to one or more saturated, partially unsaturated, or aromatic rings that may contain only carbon atoms or that may contain one or more heteroatoms. A heteroaryl group may be attached to the main structure at any heteroatom or carbon atom which results in the creation of a stable compound. In certain embodiments, a heteroaryl group has from 5 to 15 or more, or 5 to 12 or more, or 5 to 10 or more, ring atoms. Examples of monocyclic heteroaryl groups include without limitation pyrrolyl, pyrazolyl, pyrazolinyl, imidazolyl, oxazolyl, isoxazolyl, thiazolyl, thiadiazolyl, isothiazolyl, furanyl, thienyl (thiophenyl), oxadiazolyl, triazolyl, tetrazolyl, pyridyl, pyrazinyl, pyrimidinyl, pyridazinyl and triazinyl. Non-limiting examples of bicyclic heteroaryl groups include indolyl, benzothiazolyl, benzothiadiazolyl, benzoxazolyl, benzisoxazolyl, benzothienyl (benzothiophenyl), quinolinyl, tetrahydroisoquinolinyl, isoquinolinyl, benzimidazolyl, benzotriazolyl, indolizinyl, benzofuranyl, isobenzofuranyl, chromonyl, coumarinyl, cinnolinyl, quinazolinyl, quinoxalinyl, indazolyl, naphthyridinyl, phthalazinyl, quinazolinyl, purinyl, pyrrolopyridinyl, furopyridinyl, thienopyridinyl, dihydroisoindolyl and tetrahydroquinolinyl. Examples of tricyclic heteroaryl groups include without limitation carbazolyl, benzindolyl, dibenzofuranyl, phenanthrollinyl, acridinyl, phenanthridinyl and xanthenyl. A heteroaryl group may optionally be substituted with one or more substituents as described herein.

The term "hydrocarbyl" refers to a monovalent hydrocarbon radical, whether aliphatic, partially or fully unsaturated, acyclic, cyclic or aromatic, or any combination of the preceding. In certain embodiments, a hydrocarbyl group has 1 to 40 or more, 1 to 30 or more, 1 to 20 or more, or 1 to 10 or more, carbon atoms. The term "hydrocarbylene" refers to a divalent hydrocarbyl group. A hydrocarbyl or hydrocarbylene group may optionally be substituted with one or more substituents as described herein.

The term "heterohydrocarbyl" refers to a hydrocarbyl group in which one or more of the carbon atoms are independently replaced by a heteroatom selected from oxygen, sulfur, nitrogen and phosphorus. In certain embodiments, a heterohydrocarbyl group has 1 to 40 or more, 1 to 30 or more, 1 to 20 or more, or 1 to 10 or more, carbon atoms, and 1 to 10 or more, or 1 to 5 or more, heteroatoms. The term "heterohydrocarbylene" refers to a divalent hydrocarbyl group. Examples of heterohydrocarbyl and heterohydrocarbylene groups include without limitation ethylene glycol and polyethylene glycol moieties, such as (—CH$_2$CH$_2$O—)$_n$H (a monovalent heterohydrocarbyl group) and (—CH$_2$CH$_2$O—)$_n$ (a divalent heterohydrocarbylene group) where n is an integer from 1 to 12 or more, and propylene glycol and polypropylene glycol moieties, such as (—CH$_2$CH$_2$CH$_2$O—)$_n$H and (—CH$_2$CH(CH$_3$)O—)$_n$H (monovalent heterohydrocarbyl groups) and (—CH$_2$CH$_2$CH$_2$O—)$_n$ and (—CH$_2$CH(CH$_3$)O—)$_n$ (divalent heterohydrocarbylene groups) where n is an integer from 1 to 12 or more. A heterohydrocarbyl or heterohydrocarbylene group may optionally be substituted with one or more substituents as described herein.

Each group described herein (including without limitation alkyl, alkenyl, alkynyl, cycloalkyl, heterocyclyl, aryl, heteroaryl, hydrocarbyl and heterohydrocarbyl), whether as a primary group or as a substituent group, may optionally be substituted with one or more substituents, in certain embodiments with one to six or more substituents, independently selected from the group consisting of halide, cyano, nitro, hydroxyl, sulfhydryl, amino, —OR$^8$, —SR$^8$, —NR$^9$R$^{10}$, alkyl, alkenyl, alkynyl, haloalkyl, hydroxyalkyl, aminoalkyl, -alkylcycloalkyl, -alkylheterocyclyl, -alkylaryl, -alkylheteroaryl, cycloalkyl, heterocyclyl, aryl, heteroaryl, —C(=O)R$^8$, —C(=NR$^{11}$)R$^8$, —S(=O)R$^8$, —S(=O)$_2$R$^8$, —S(=O)$_2$OR$^{12}$, —C(=O)OR$^{12}$, —OC(=O)R$^8$, —C(=O)NR$^9$R$^{10}$, —NR$^8$C(=O)R$^8$, —S(=O)$_2$NR$^9$R$^{10}$, —NR$^8$S(=O)$_2$R$^8$, —OC(=O)OR$^8$, —OC(=O)NR$^9$R$^{10}$, —NR$^8$C(=O)OR$^8$, —NR$^8$C(=O)NR$^9$R$^{10}$, —NR$^8$C(=NR$^{11}$)NR$^9$R$^{10}$, —P(=O)(R$^8$)$_2$, —P(=O)(OR$^{12}$)R$^8$, —P(=O)(OR$^{12}$)$_2$, —OP(=O)(R$^8$)$_2$, —OP(=O)(OR$^{12}$)R$^8$, and —OP(=O)(OR$^{12}$)$_2$, wherein:

each occurrence of R$^8$ independently is hydrogen, alkyl, haloalkyl, hydroxyalkyl, aminoalkyl, -alkylcycloalkyl, -alkylheterocyclyl, -alkylaryl, -alkylheteroaryl, cycloalkyl, heterocyclyl, aryl or heteroaryl;

each occurrence of R$^9$ and R$^{10}$ independently is hydrogen, alkyl, haloalkyl, hydroxyalkyl, aminoalkyl, -alkylcycloalkyl, -alkylheterocyclyl, -alkylaryl, -alkylheteroaryl, cycloalkyl, heterocyclyl, aryl or heteroaryl, or R$^9$ and R$^{10}$, together with the nitrogen atom to which they are attached, form a heterocyclic or heteroaryl ring;

each occurrence of R$^{11}$ independently is hydrogen, —OR$^8$, alkyl, haloalkyl, hydroxyalkyl, aminoalkyl, -alkylcycloalkyl, -alkylheterocyclyl, -alkylaryl, -alkylheteroaryl, cycloalkyl, heterocyclyl, aryl or heteroaryl; and each occurrence of R$^{12}$ independently is hydrogen, Z, alkyl, haloalkyl, hydroxyalkyl, aminoalkyl, -alkylcycloalkyl, -alkylheterocyclyl, -alkylaryl, -alkylheteroaryl, cycloalkyl, heterocyclyl, aryl or heteroaryl, wherein each occurrence of Z independently is H$^+$, Li$^+$, Na$^+$, K$^+$, Cs$^+$, Mg$^{+2}$, Ca$^{+2}$, or —$^+$N(R$^8$)$_2$R$^9$R$^{10}$.

II. Targeted Antitumor Conjugates

The present disclosure provides conjugates that selectively target and deliver a lethal payload to tumor/cancer cells, a wide variety of which overexpress COX-2. In some embodiments, the conjugates comprise a COX-2-targeting moiety and a platinum-containing antitumor agent. In additional embodiments, the conjugates further comprise a linker connecting the COX-2-targeting moiety to the platinum-containing antitumor agent. The term "antitumor agents" encompasses antitumor agents and anticancer agents.

In some embodiments, the COX-2-targeting moiety comprises a non-steroidal anti-inflammatory drug (NSAID), or an analog, derivative, residue or salt thereof. In certain embodiments, the NSAID is selected from the group consisting of acetic acid derivatives, anthranilic acid derivatives (fenamates), enolic acid derivatives (oxicams), propionic acid derivatives, salicylates, COX-2-selective inhibitors, other kinds of NSAIDs, and analogs, derivatives, residues and salts thereof. Non-limiting examples of: (1) acetic acid derivatives include aceclofenac, diclofenac, etodolac, indomethacin, ketorolac, nabumetone, sulindac, sulindac sulfide, sulindac sulfone and tolmetin; (2) anthranilic acid derivatives (fenamates) include flufenamic acid, meclofenamic acid, mefenamic acid and tolfenamic acid; (3) enolic acid derivatives (oxicams) include droxicam, isoxicam, lornoxicam, meloxicam, piroxicam and tenoxicam; (4) propionic acid derivatives include fenoprofen, flurbiprofen, ibuprofen, dexibuprofen, ketoprofen, dexketoprofen, loxoprofen, naproxen and oxaprozin; (5) salicylates include diflunisal, salicylic acid, acetylsalicylic acid (aspirin), choline magnesium trisalicylate, and salsalate; (6) COX-2-selective inhibitors include apricoxib, celecoxib, etoricoxib, firocoxib, fluorocoxibs (e.g., fluorocoxibs A-C), lumiracoxib, mavacoxib, parecoxib, rofecoxib, tilmacoxib (JTE-522), valdecoxib, 4-O-methylhonokiol, DuP-697, CG100649, NS-398, SC-58125, benzothieno[3,2-d]pyrimidin-4-one sulfonamide thio-derivatives, and COX-2 inhibitors derived from *Tribulus terrestris*; and (7) other kinds of NSAIDs include anilinopyridinecarboxylic acids (e.g., clonixin), sulfonanilides (e.g., nimesulide), and dual inhibitors of lipooxygenase (e.g., 5-LOX) and cyclooxygenase (e.g., COX-2) (e.g., chebulagic acid, licofelone, 2-(3,4,5-trimethoxyphenyl)-4-(N-methylindol-3-yl)thiophene, and di-tert-butylphenol-based compounds [e.g., DTPBHZ, DTPINH, DTPNHZ and DTPSAL]); and analogs, derivatives, residues and salts thereof. In further embodiments, the COX-2-targeting moiety comprises: (1) an indole-based compound/NSAID disclosed generically or specifically in U.S. Pat. No. 6,306,890; (2) a furan-, pyrrole- or thiophene-based compound/NSAID disclosed generically or specifically in U.S. Pat. No. 6,492,413; or (3) an ester or secondary amide derivative of an NSAID as disclosed in U.S. Pat. No. 6,762,182; or an analog, derivative, residue or salt thereof.

In certain embodiments, the COX-2-targeting moiety comprises a COX-2-selective inhibitor, or an analog, derivative, residue or salt thereof. The COX-2-selective inhibitor can promote selective accumulation of the conjugate in COX-2-overexpressing tumor/cancer cells. In further embodiments, the COX-2-targeting moiety comprises an indole-based NSAID, or an analog, derivative, residue or salt thereof. In yet further embodiments, the COX-2-targeting moiety comprises a propionic acid derivative, or an analog, derivative, residue or salt thereof.

In some embodiments, the COX-2-targeting moiety comprises indomethacin, ketorolac, naproxen, ibuprofen, fenoprofen, flurbiprofen, ketoprofen, loxoprofen, oxaprozin, apricoxib, celecoxib, etoricoxib, lumiracoxib, rofecoxib or valdecoxib, or an analog, derivative, residue or salt thereof. In certain embodiments, the COX-2-targeting moiety is selected from the group consisting of:

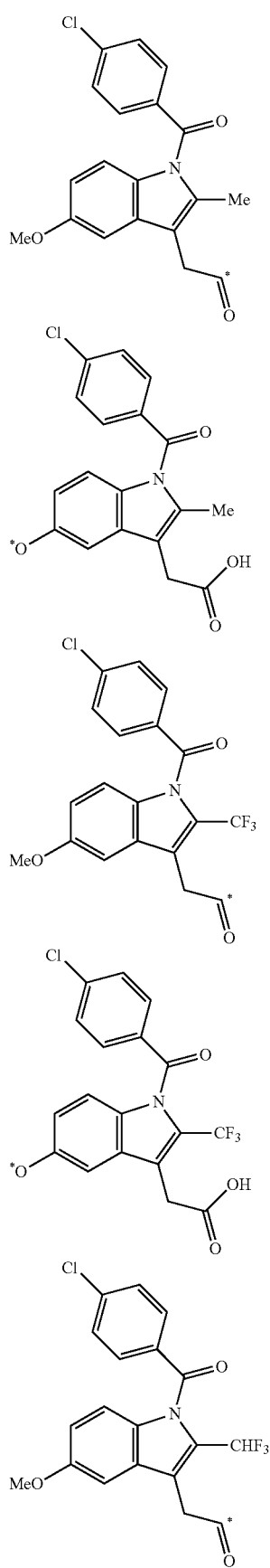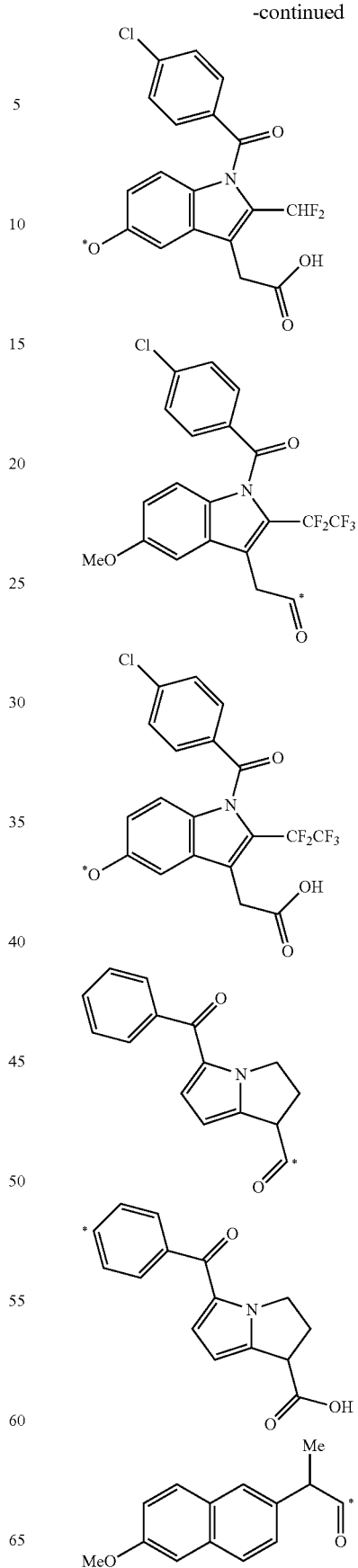

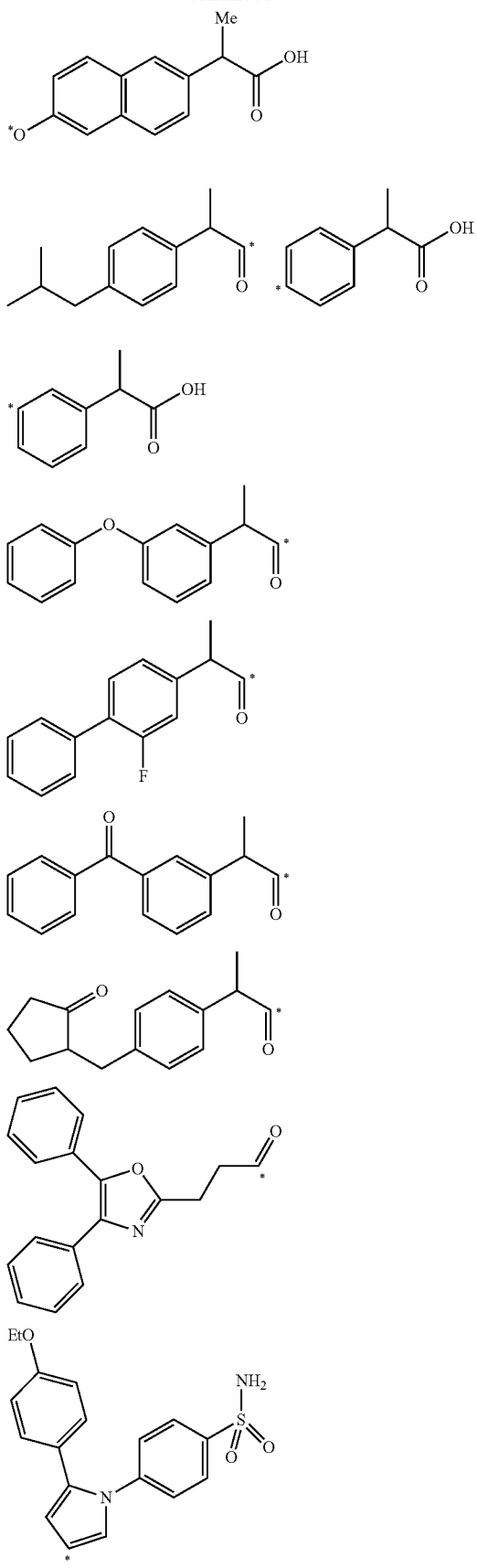
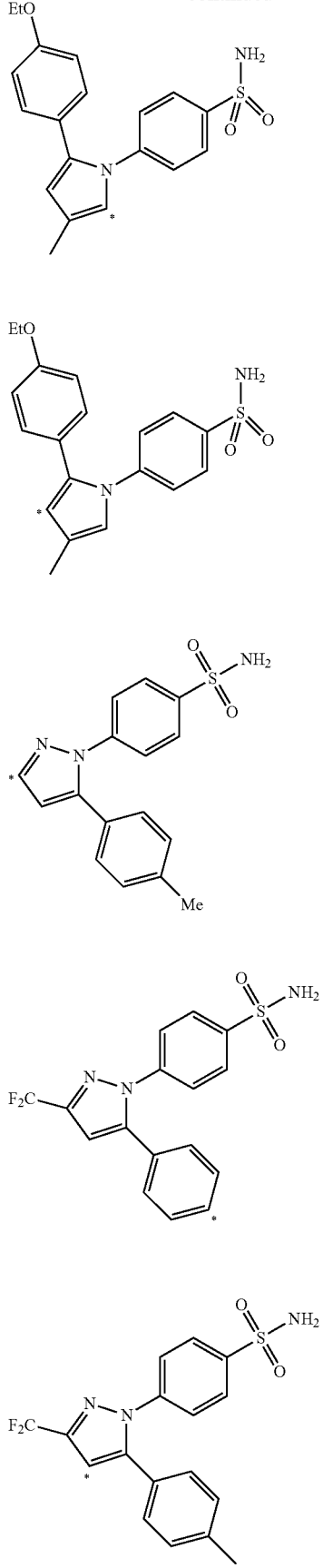

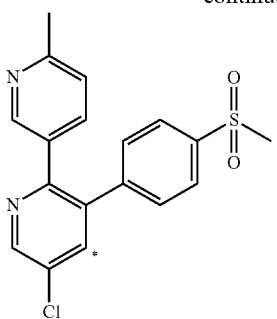
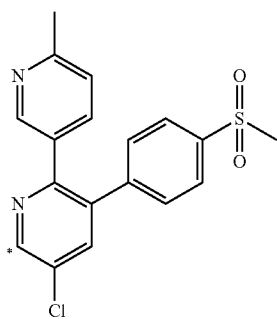
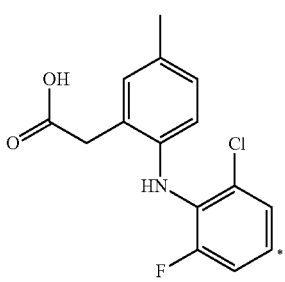
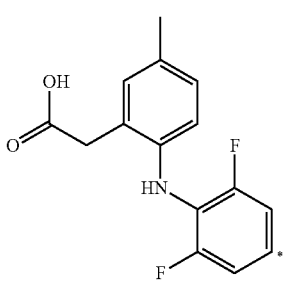
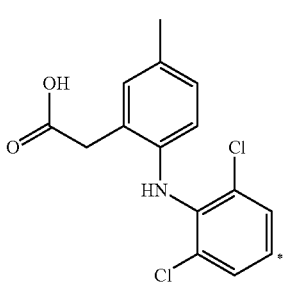

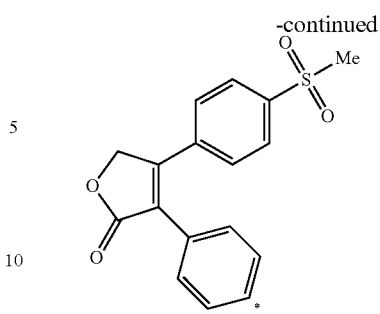
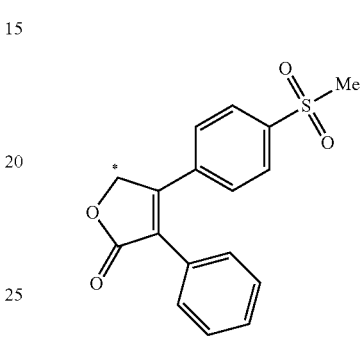
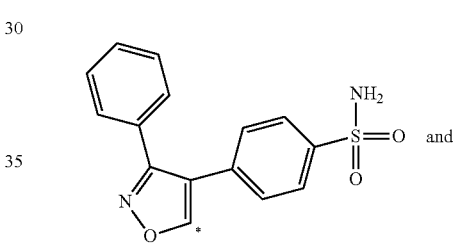
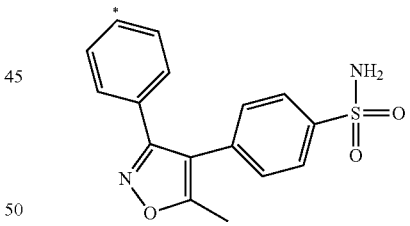

and pharmaceutically acceptable salts thereof, wherein the methyl group of any methyl-containing COX-2-targeting moiety can optionally be replaced with —CF₃, and an atom marked with an asterisk (*) is a site where the COX-2-targeting moiety is connected to the remainder of the conjugate.

In some embodiments, the COX-2-targeting moiety comprises indomethacin, or an analog, derivative, residue or salt thereof. In further embodiments, the indomethacin compound is an ester or an amide (e.g., a secondary amide) of indomethacin, which can have enhanced selectivity for COX-2. The ester or amide portion of the indomethacin compound may or may not be part of a linker. In certain embodiments, the indomethacin compound is

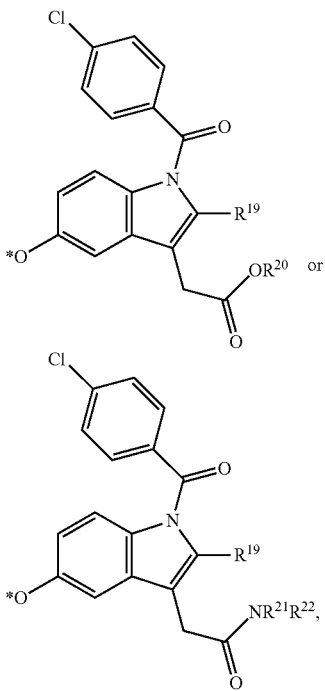

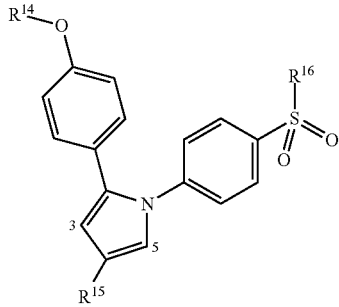

wherein:

$R^{19}$ is $C_1$-$C_3$ alkyl or $C_1$-$C_3$ haloalkyl (e.g., —CH$_3$, —CH$_2$F, —CHF$_2$, —CF$_3$, —CH$_2$CH$_3$, —CH$_2$CF$_3$ or —CF$_2$CF$_3$);

$R^{20}$ is alkyl, cycloalkyl or heterocycyl, or $R^{20}$ and the oxygen atom to which it is attached form a heterocycyl group, each of which can optionally be substituted;

$R^{21}$ and $R^{22}$ independently are —H, alkyl, cycloalkyl or heterocycyl, or $R^{21}$, $R^{22}$ and the nitrogen atom to which they are attached form a heterocyclyl group, each of which can optionally be substituted; and the oxygen atom marked with an asterisk (*) is a site where the indomethacin compound is connected to the remainder of the conjugate.

In other embodiments, the COX-2-targeting moiety comprises apricoxib, or an analog, derivative, residue or salt thereof. In certain embodiments, the apricoxib compound has the formula:

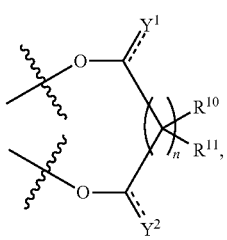

wherein:

$R^{14}$ and $R^{15}$ independently are $C_1$-$C_6$ alkyl or $C_1$-$C_6$ haloalkyl;

$R^{16}$ is $C_1$-$C_6$ alkyl or —NR$^{17}$R$^{18}$, wherein $R^{17}$ and $R^{18}$ independently are —H or $C_1$-$C_6$ alkyl, or $R^{17}$ and $R^{18}$, together with the nitrogen atom to which they are attached, form a heterocyclyl group; and the apricoxib compound can be connected to the remainder of the conjugate at the 3 position or the 5 position of the pyrrolyl ring.

In some embodiments, the platinum-containing antitumor agent is of Formula I or a pharmaceutically acceptable salt thereof:

(I)

wherein:

$X^1$ and $X^2$ independently are —Cl, —OH, optionally substituted —O-(alkyl or cyclyl), optionally substituted —O-(alkyl or cyclyl)-C(═O)OR$^7$, optionally substituted —O-(alkyl or cyclyl)-C(═O)NR$^8$R$^9$, optionally substituted —OC(═O)-(alkyl or cyclyl), optionally substituted —OC(═O)-(alkyl or cyclyl)-C(═O)OR$^7$, optionally substituted —OC(═O)-(alkyl or cyclyl)-C(═O)NR$^8$R$^9$, or optionally substituted thiourea, wherein:

cyclyl is an optionally substituted cycloalkyl, heterocyclyl, aryl or heteroaryl group;

$R^7$ is —H, optionally substituted alkyl, optionally substituted cycloalkyl or optionally substituted heterocyclyl; and $R^8$ and $R^9$ independently are —H, optionally substituted alkyl, optionally substituted cycloalkyl or optionally substituted heterocyclyl; or $R^8$ and $R^9$, together with the nitrogen atom to which they are attached, form an optionally substituted heterocyclyl group; and $X^1$ and $X^2$ can be cis or trans relative to each other; or $X^1$ and $X^2$ together are part of a sulfate (SO$_4^{-2}$) group; or $X^1$ and $X^2$ together form wherein:

$Y^1$ and $Y^2$ independently are —H, —OH, oxo (forming a carbonyl group with the adjacent carbon atom), or optionally substituted alkyl;

$R^{10}$ and $R^{11}$ independently are —H, —OH, —NH$_2$, optionally substituted alkyl, optionally substituted —O-alkyl, optionally substituted —O-alkyl-C(═O)OR$^7$, optionally substituted —O-alkyl-C(═O)NR$^8$R$^9$, optionally substituted —OC(═O)-alkyl, optionally substituted —OC(═O)-alkyl-C(═O)OR$^7$, optionally substituted —OC(═O)-alkyl-C(═O)NR$^8$R$^9$, —NR$^{12}$R$^{13}$, optionally substituted —NH-alkyl-C(═O)OR$^7$, optionally substituted —NH-alkyl-C(═O)NR$^8$R$^9$, optionally substituted —NHC(═O)-alkyl, —NHC(=O)-alkyl-C(=O)OR$^7$, or optionally substituted —NHC(=O)-alkyl-C(=O)NR$^8$R$^9$, wherein:
R$^7$ is —H, optionally substituted alkyl, optionally substituted cycloalkyl or optionally substituted heterocyclyl;
R$^8$ and R$^9$ independently are —H, optionally substituted alkyl, optionally substituted cycloalkyl or optionally substituted heterocyclyl; or
R$^8$ and R$^9$, together with the nitrogen atom to which they are attached, form an optionally substituted heterocyclyl group; and
R$^{12}$ and R$^{13}$ independently are —H, optionally substituted alkyl, optionally substituted cycloalkyl, optionally substituted heterocyclyl, optionally substituted aryl or optionally substituted heteroaryl; or
R$^{12}$ and R$^{13}$, together with the nitrogen atom to which they are attached, form an optionally substituted heterocyclyl or heteroaryl group; or
R$^{10}$ and R$^{11}$, together with the carbon atom to which they are attached, form an optionally substituted cycloalkyl ring; and
n is 0 or 1;
X$^3$ and X$^4$ independently are absent or are —Cl, —OH, optionally substituted —O-(alkyl or cyclyl), optionally substituted —O-(alkyl or cyclyl)-C(=O)OR$^7$, optionally substituted —O-(alkyl or cyclyl)-C(=O)NR$^8$R$^9$, optionally substituted —OC(=O)-(alkyl or cyclyl), optionally substituted —OC(=O)-(alkyl or cyclyl)-C(=O)OR$^7$, optionally substituted —OC(=O)-(alkyl or cyclyl)-C(=O)NR$^8$R$^9$, or optionally substituted thiourea, wherein:
cyclyl is an optionally substituted cycloalkyl, heterocyclyl, aryl or heteroaryl group;
R$^7$ is —H, optionally substituted alkyl, optionally substituted cycloalkyl or optionally substituted heterocyclyl; and
R$^8$ and R$^9$ independently are —H, optionally substituted alkyl, optionally substituted cycloalkyl or optionally substituted heterocyclyl; or
R$^8$ and R$^9$, together with the nitrogen atom to which they are attached, form an optionally substituted heterocyclyl group;
R$^1$, R$^2$, R$^3$, R$^4$, R$^5$ and R$^6$ independently are —H, optionally substituted alkyl, optionally substituted cycloalkyl, optionally substituted heterocyclyl, optionally substituted aryl or optionally substituted heteroaryl; or
NR$^1$R$^2$R$^3$ and NR$^4$R$^5$R$^6$ independently are optionally substituted heterocyclyl or optionally substituted heteroaryl; or
NR$^1$R$^2$R$^3$ and NR$^4$R$^5$R$^6$ together are part of an optionally substituted alkyldiamine, cycloalkyldiamine, heterocyclyldiamine, aryldiamine or heteroaryldiamine group, or part of a nitrogen-containing heterocyclyl or heteroaryl group substituted with an aminoalkyl group, or part of a cycloalkyl, heterocyclyl, aryl or heteroaryl group substituted with at least two aminoalkyl groups.

In some embodiments, the platinum metal of the platinum-containing antitumor agent is Pt$^{+2}$ [Pt(II)]. In certain embodiments, the antitumor agent is of Formula I and comprises Pt(II) having no axial ligand X$^3$ or X$^4$, wherein X$^1$ and X$^2$ are lipophilic groups, such as optionally substituted —O-alkyl, optionally substituted —O-alkyl-C(=O)O-alkyl, optionally substituted —OC(=O)-alkyl and optionally substituted —OC(=O)-alkyl-C(=O)O-alkyl, wherein each occurrence of alkyl independently contains 2 to 15 or more carbon atoms and is straight-chain or branched. In other embodiments, the platinum metal of the antitumor agent is Pt$^{+4}$ [Pt(IV)]. In certain embodiments, the antitumor agent is of Formula I and comprises Pt(IV) having axial ligands X$^3$ and X$^4$, wherein X$^3$ and X$^4$ are lipophilic groups, such as optionally substituted —O-alkyl, optionally substituted —O-alkyl-C(=O)O-alkyl, optionally substituted —OC(=O)-alkyl and optionally substituted —OC(=O)-alkyl-C(=O)O-alkyl, wherein each occurrence of alkyl independently contains 2 to 15 or more carbon atoms and is straight-chain or branched. Increased lipophilicity of the platinum-containing antitumor agent (or any other component of the conjugate) can increase the accumulation of the conjugate in tumor/cancer cells (e.g., by promoting passive permeation of the conjugate across the plasma membrane of tumor/cancer cells) and thereby can enhance the efficacy of the conjugate. Platinum(IV) complexes can be reduced to platinum(II) complexes without an axial ligand by a redox-active molecule (e.g., glutathione or ascorbic acid/ascorbate) inside tumor/cancer cells, and can overcome any tumor/cancer resistance to platin compounds, e.g., by being converted to antitumor-active platinum(II) complexes intracellularly.

In certain embodiments, the platinum-containing antitumor agent is selected from the group consisting of cisplatin, carboplatin, dicycloplatin, enloplatin, eptaplatin (heptaplatin), ethacraplatin, iproplatin, kiteplatin, lobaplatin, miboplatin, miriplatin, nedaplatin, ormaplatin (tetraplatin), oxaliplatin, oxoplatin [cis-diamminedichloro-trans-dihydroxo-platinum(IV)], phenanthriplatin, picazoplatin, picoplatin (AMD473), pyriplatin, satraplatin (JM216), spiroplatin, triplatin, zeniplatin, cis-diamminedihydroxoplatinum(II), cis-diammine(2-aminomalonate)platinum(II), cis-diammine(2-hydroxymalonate)platinum(II), chloro(1,2-ethanediamine)(N,N'-dimethylthiourea)platinum(II), chloro(1,2-ethanediamine)(tetramethylthiourea)-platinum(II), cis-dichloro(1,2-ethanediamine)platinum(II), cis-dichloro(1,2-ethanediamine)-trans-dihydroxo-platinum(IV), cis-dichloro(1,2-ethanediamine)-trans-bis(acetato)-platinum(IV), cis-dichloro(1,2-ethanediamine)-trans-bis(succinic acid)-platinum(IV), cis-dichloro[1,1-bis(aminomethyl)cyclohexane]-platinum(II), cis-dichloro[1,1-bis(aminomethyl)cyclohexane]-trans-dihydroxo-platinum(IV), cis-dichloro[1,1-bis(aminomethyl)cyclohexane]-trans-bis(acetato)-platinum(IV), cis-dichloro[1,1-bis(aminomethyl)cyclohexane]-trans-bis(succinic acid)-platinum(IV), JM118 [cis-amminedichloro(cyclohexylamine)platinum(II)], JM149 [cis-amminedichloro(cyclohexylamine)-trans-dihydroxo-platinum(IV)], JM335 [trans-amminedichloro(cyclohexylamine)-trans-dihydroxo-platinum(IV)], cis-diamminedichloro-trans-bis(acetato)-platinum(IV), cis-diamminedichloro-trans-bis(succinic acid)-platinum(IV), cis-diammine(1,1-cyclobutanedicarboxylato)-trans-dihydroxo-platinum(IV), cis-diammine(1,1-cyclobutanedicarboxylato)-trans-bis(succinic acid)-platinum(IV), LA-12 [(OC-6-43)-bis(acetato)(1-adamantylamine)amminedichloroplatinum(IV)], and analogs, derivatives, residues and salts thereof.

In further embodiments, the platinum-containing antitumor agent is selected from the group consisting of:

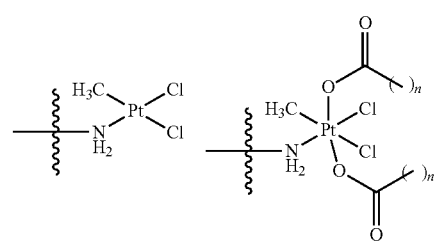

-continued
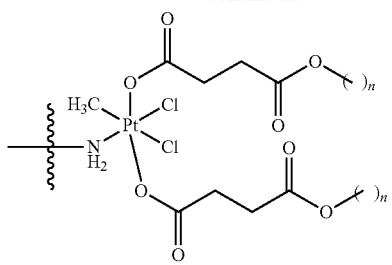
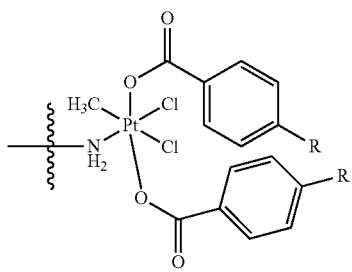
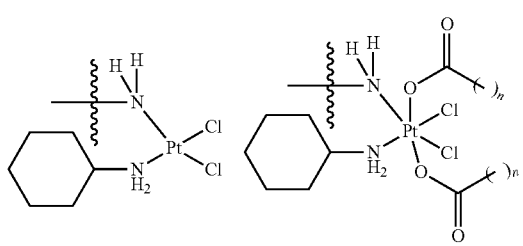
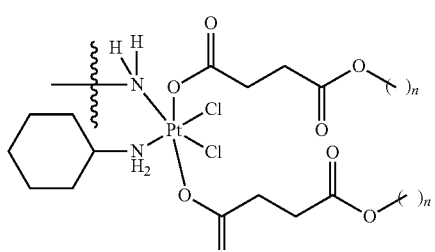
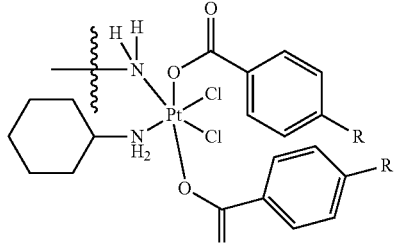
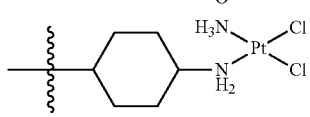
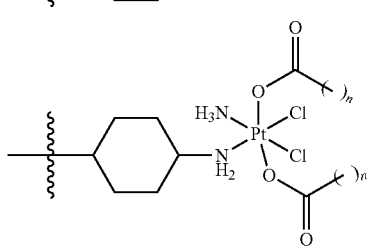
-continued
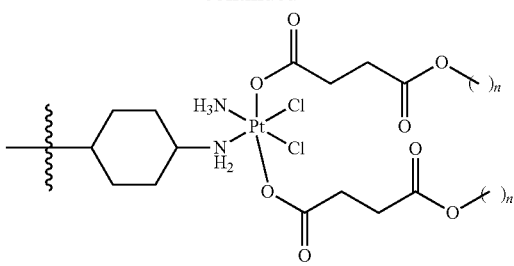
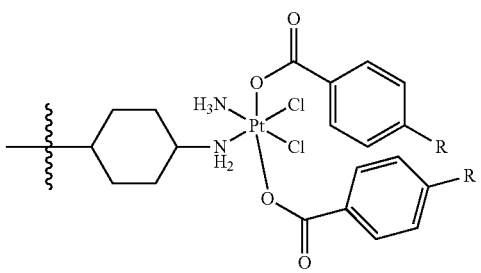
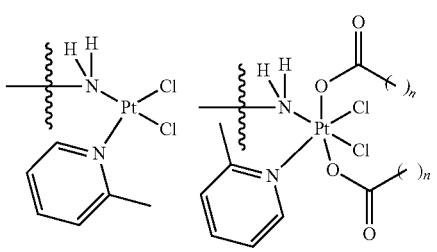
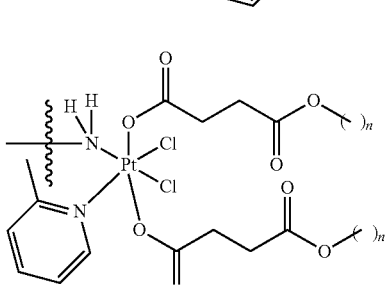
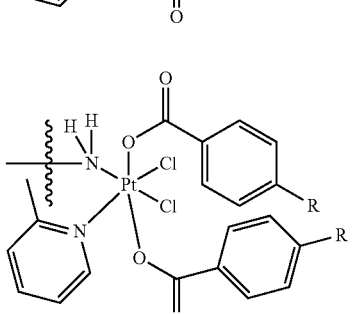
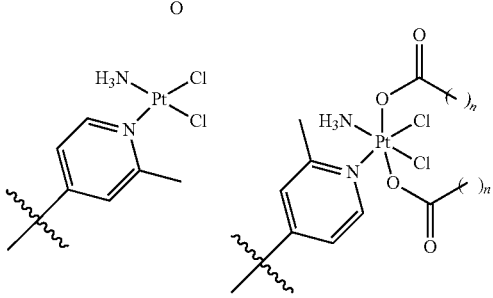

-continued
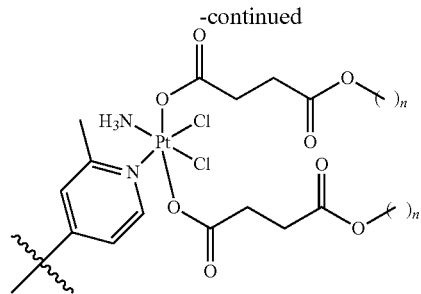
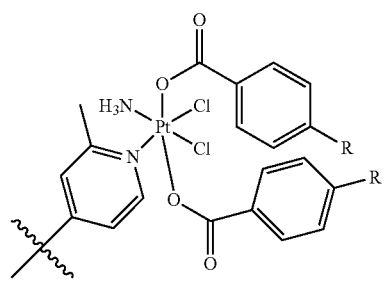
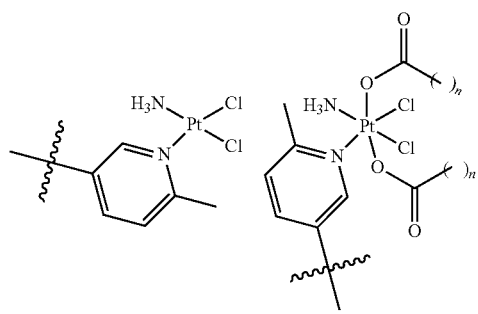
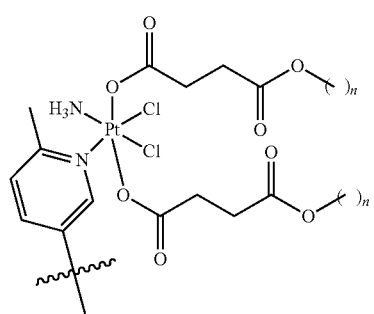
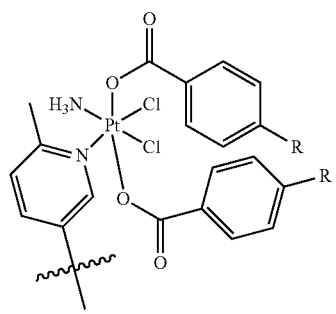
-continued
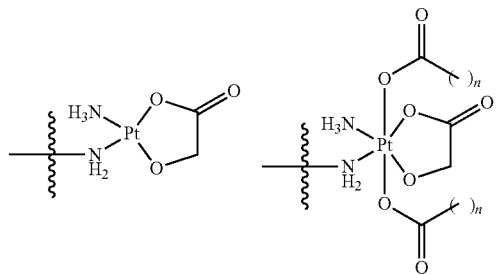
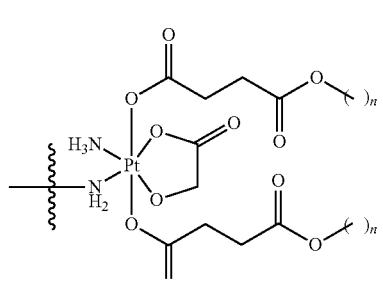
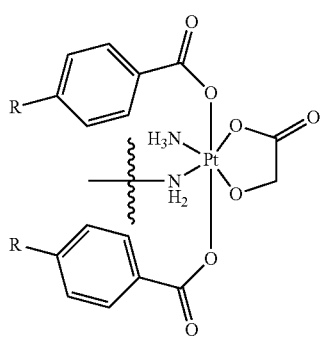
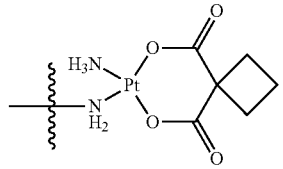
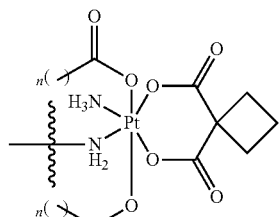
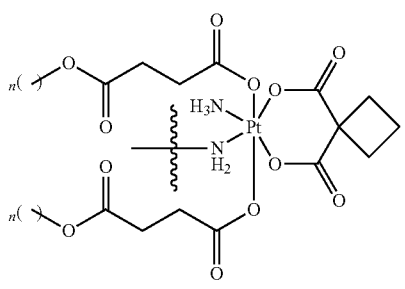

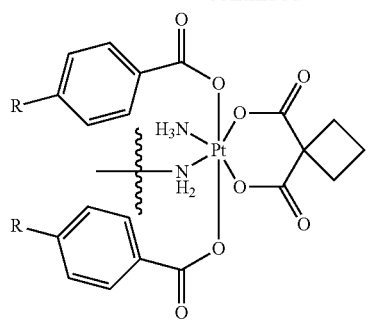
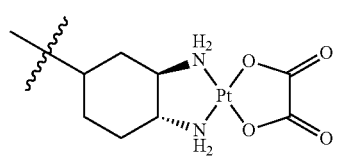
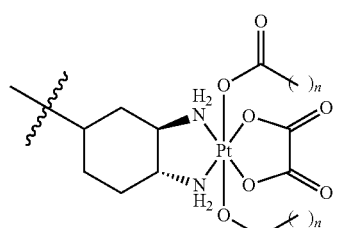
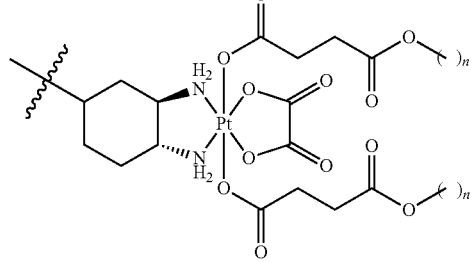
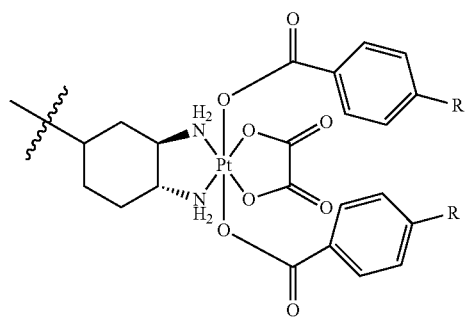
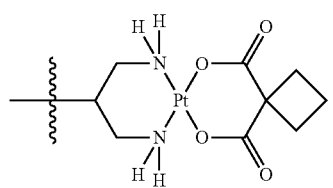
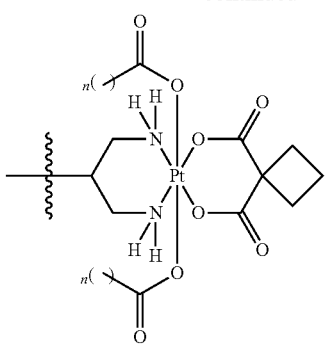
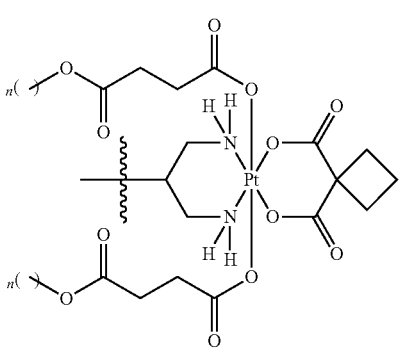
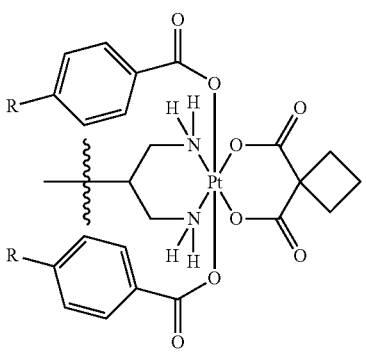
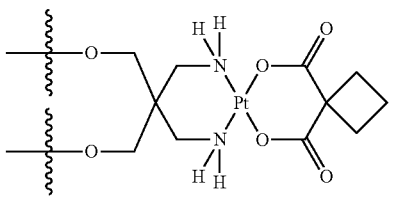
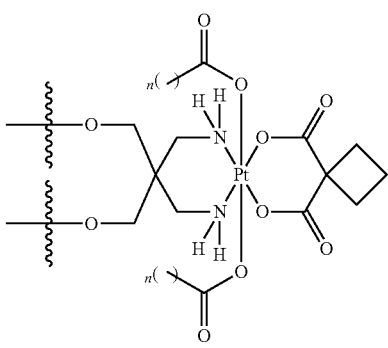

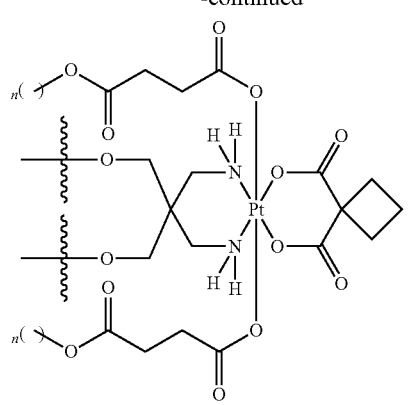
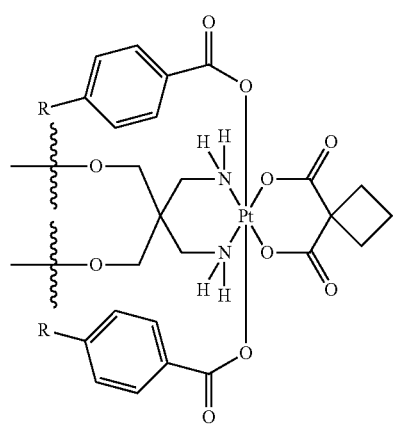
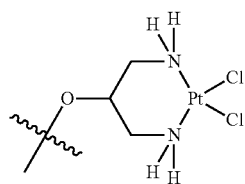
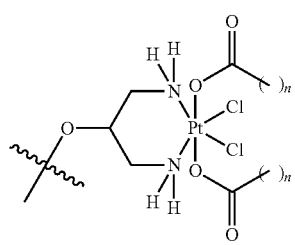
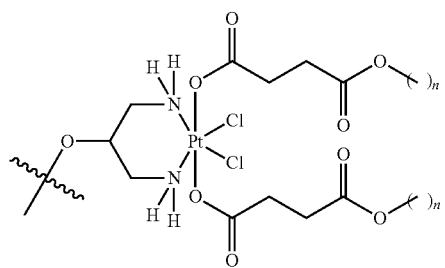
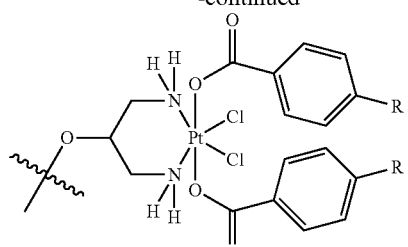
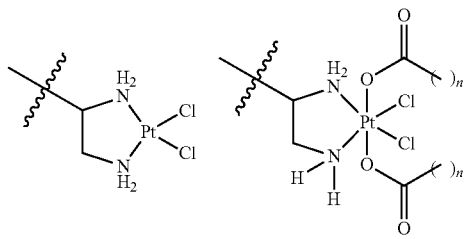
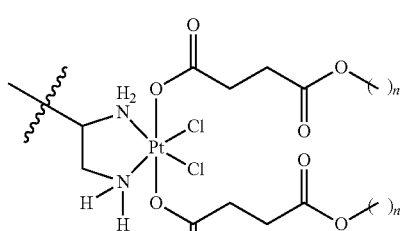
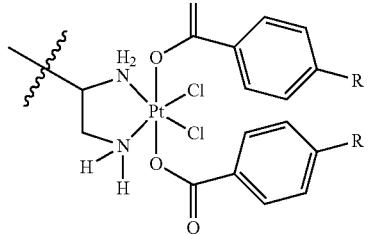
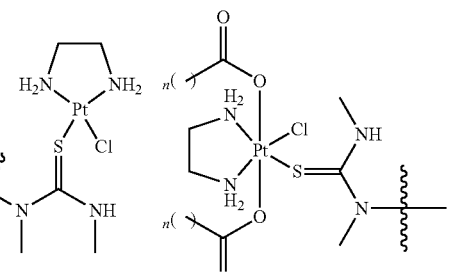
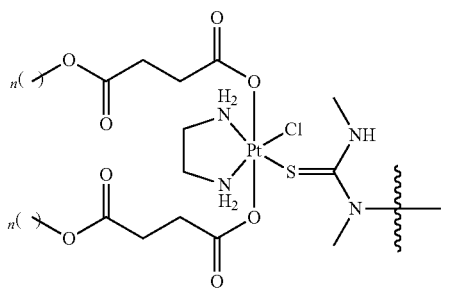

-continued
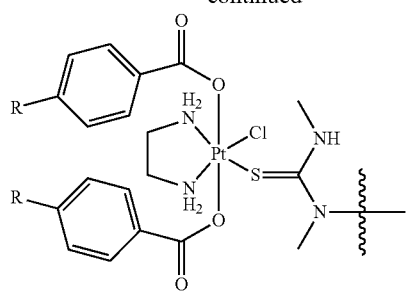
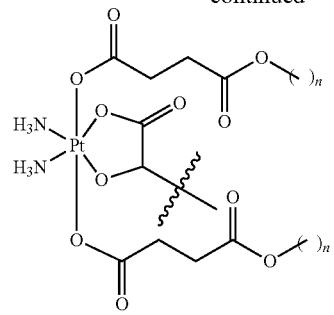
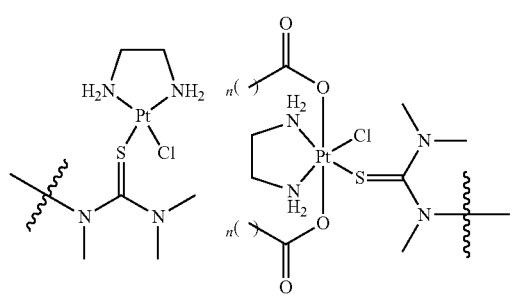
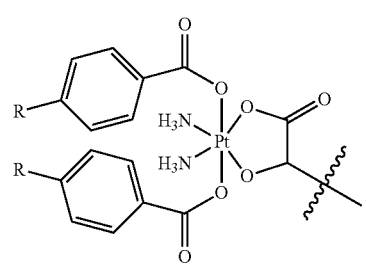
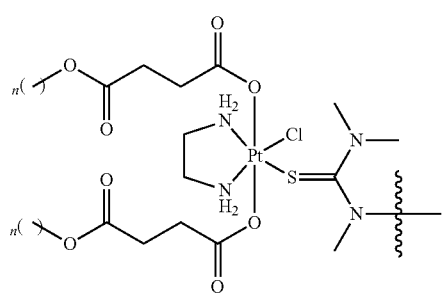
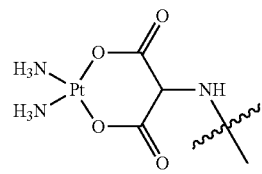
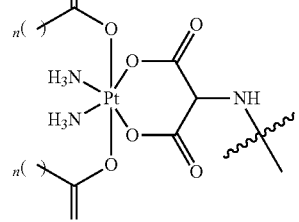
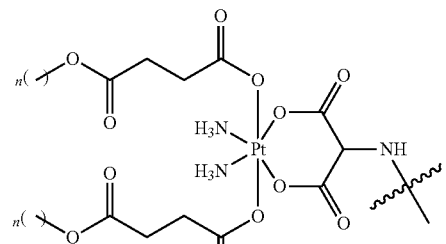
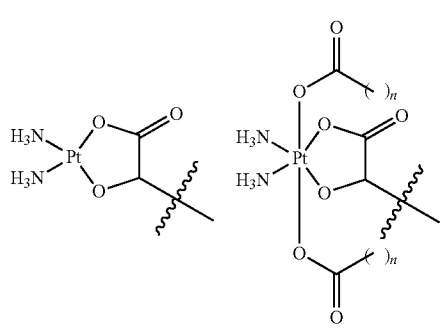
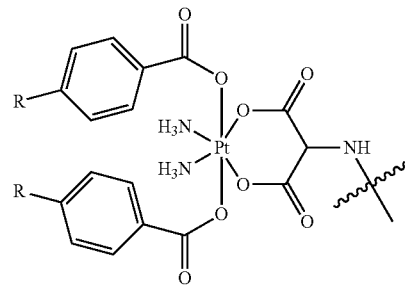

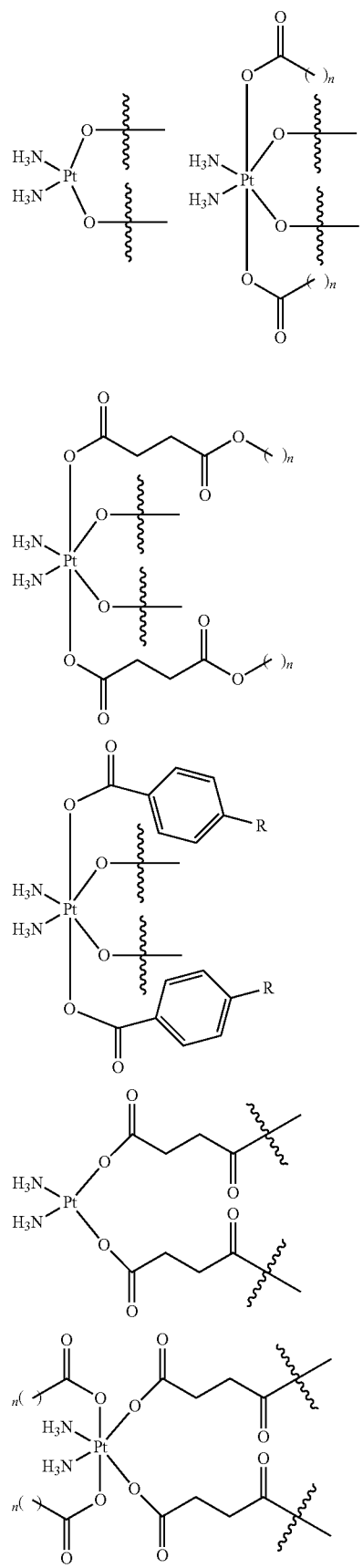
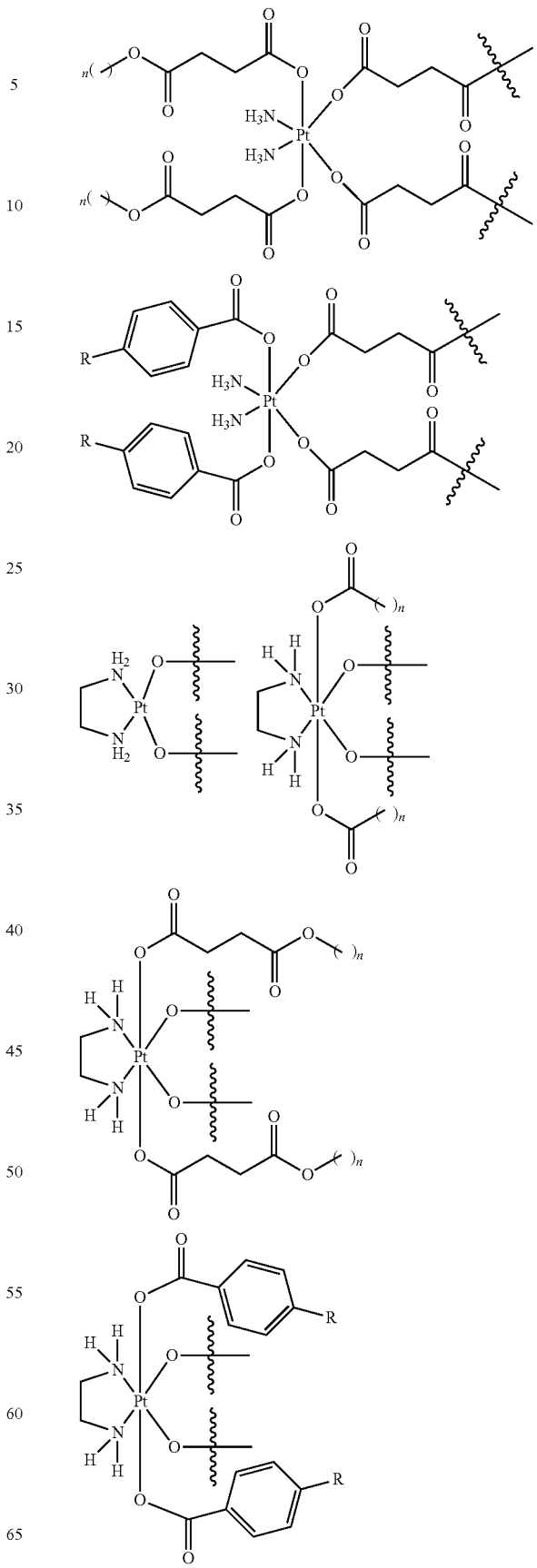

-continued
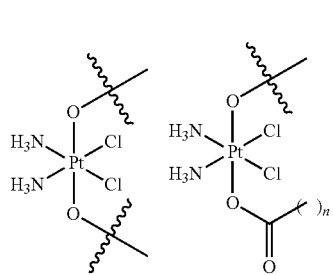 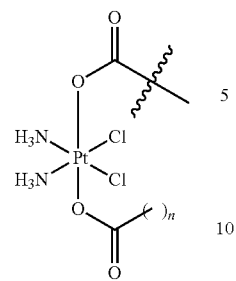
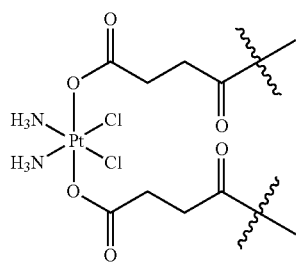
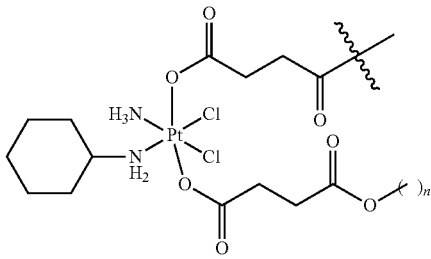
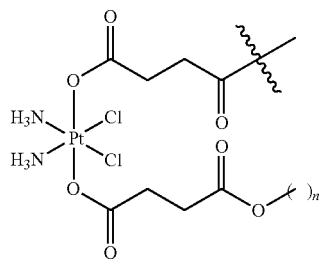
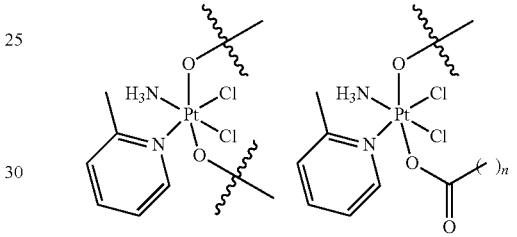
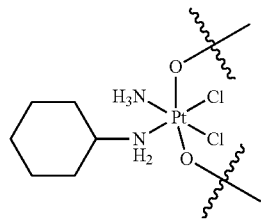
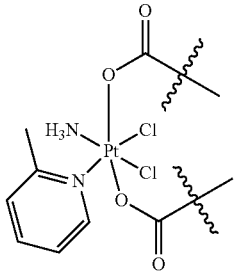
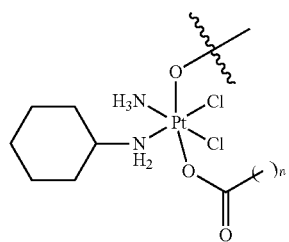
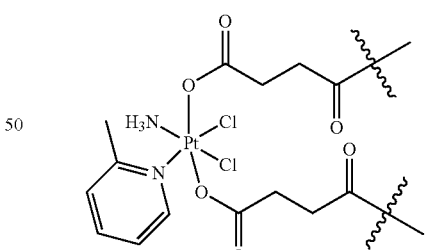
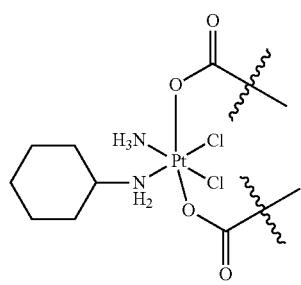
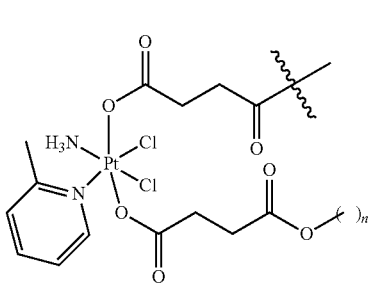

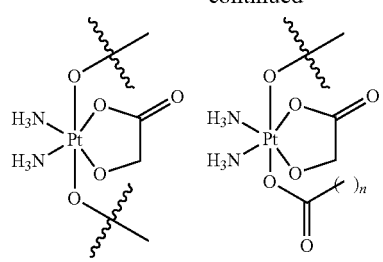
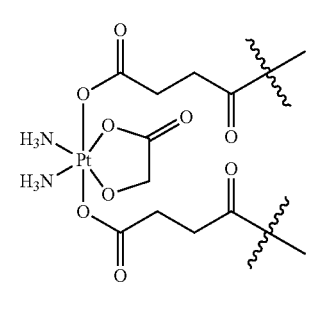
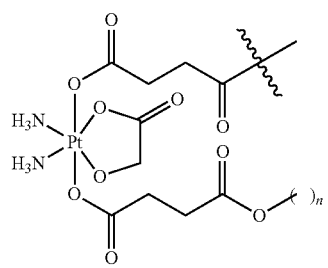
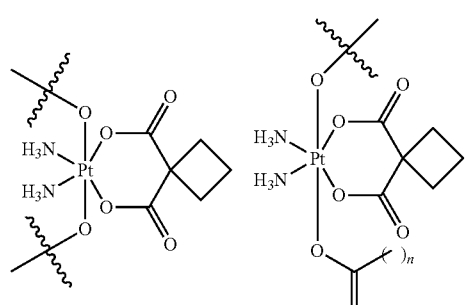
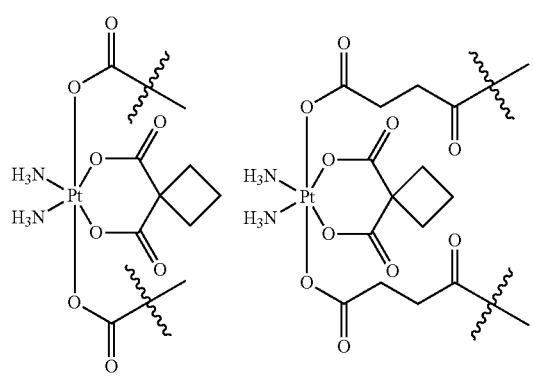
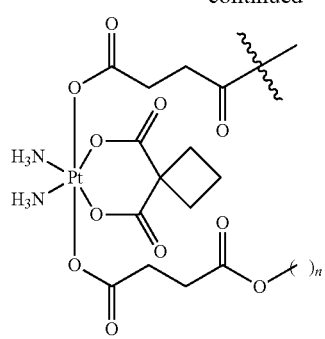
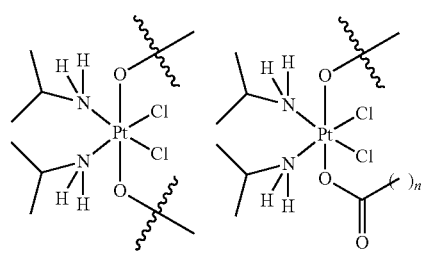
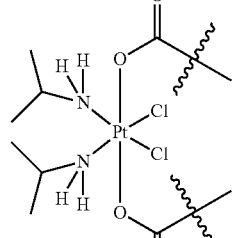
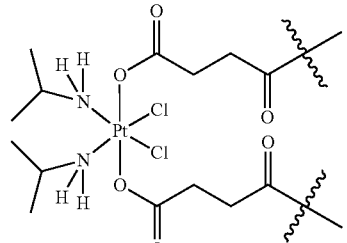
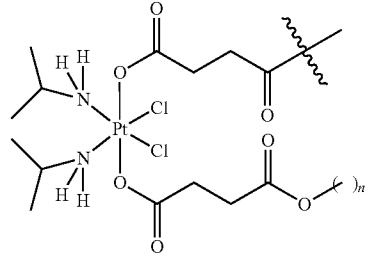
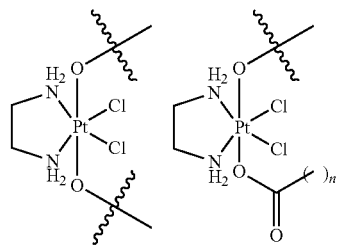

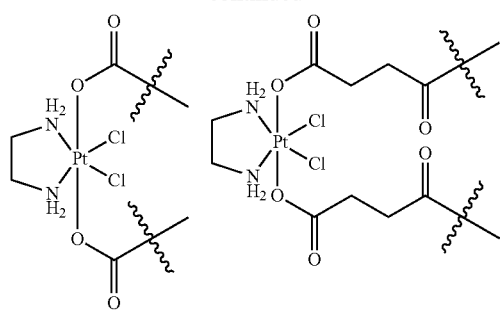
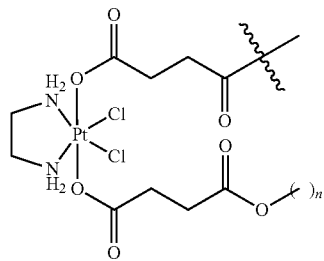
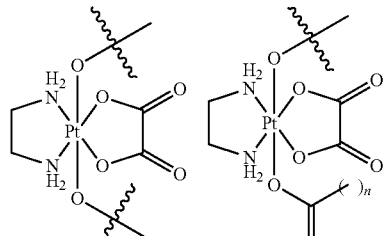
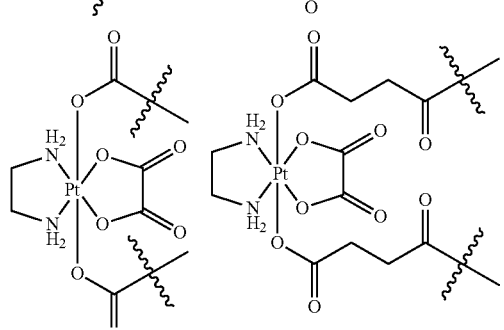
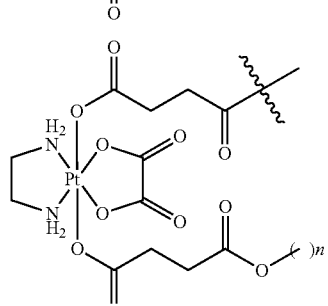
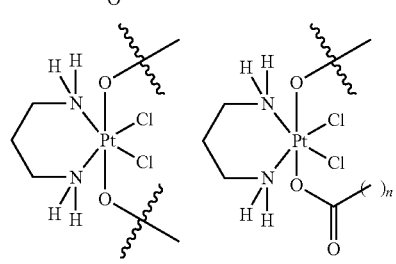
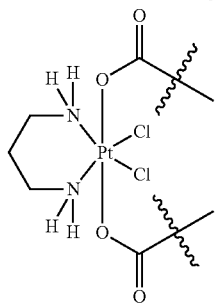
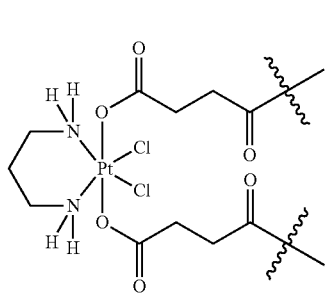
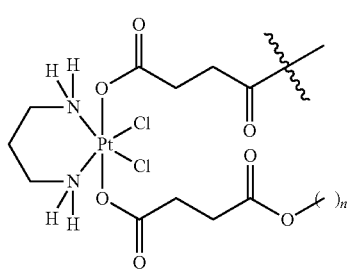
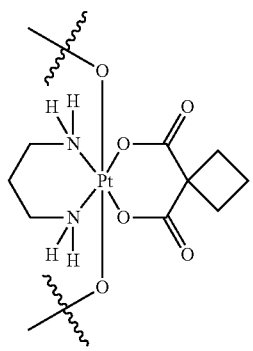
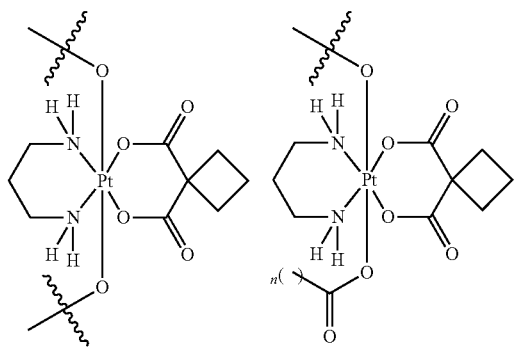
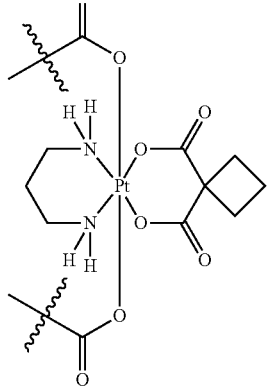

-continued
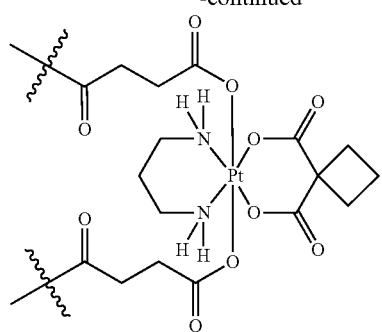
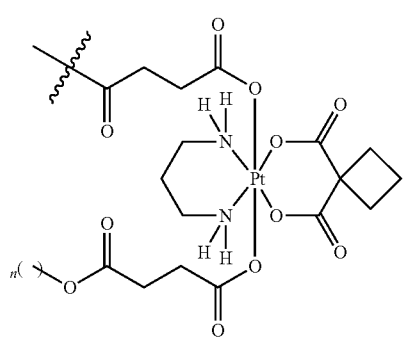
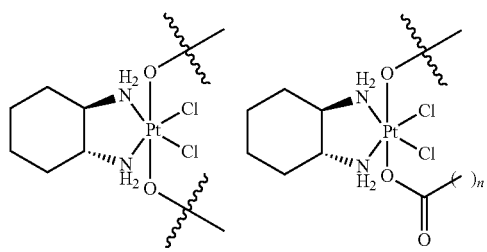
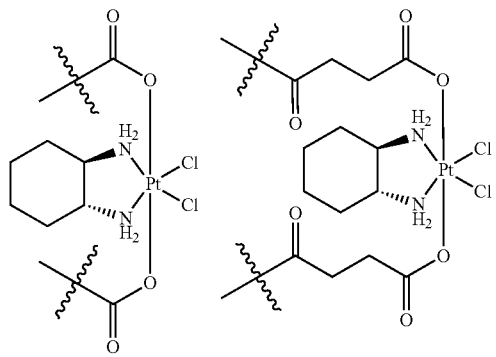
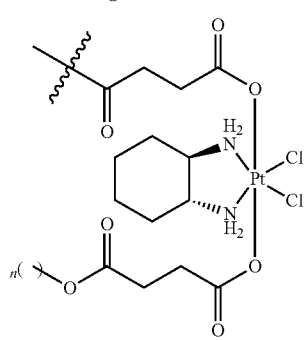
-continued
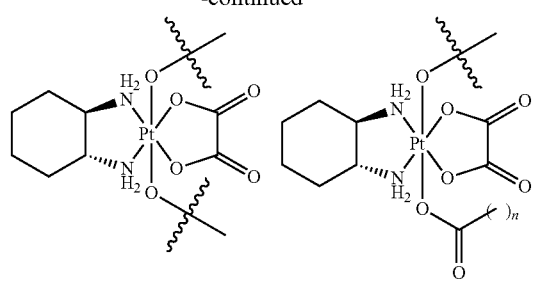
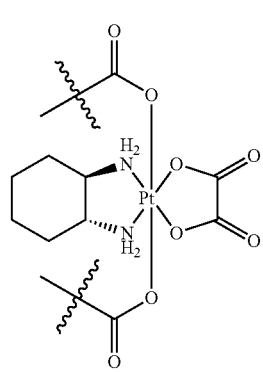
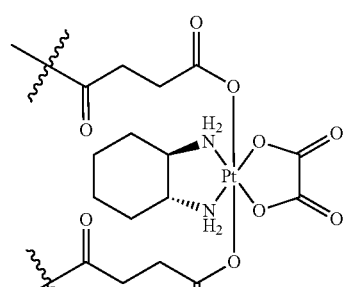
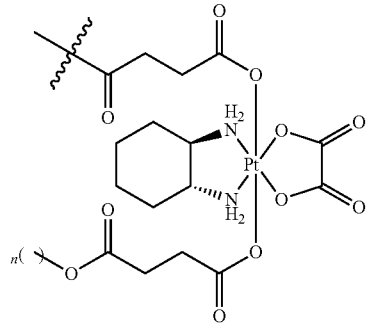
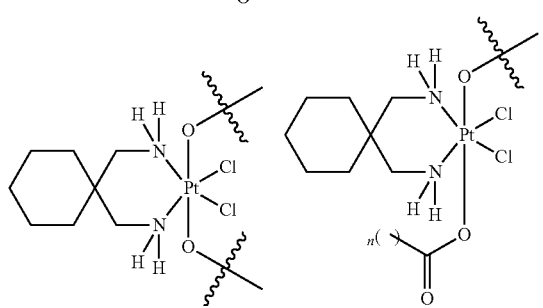

-continued

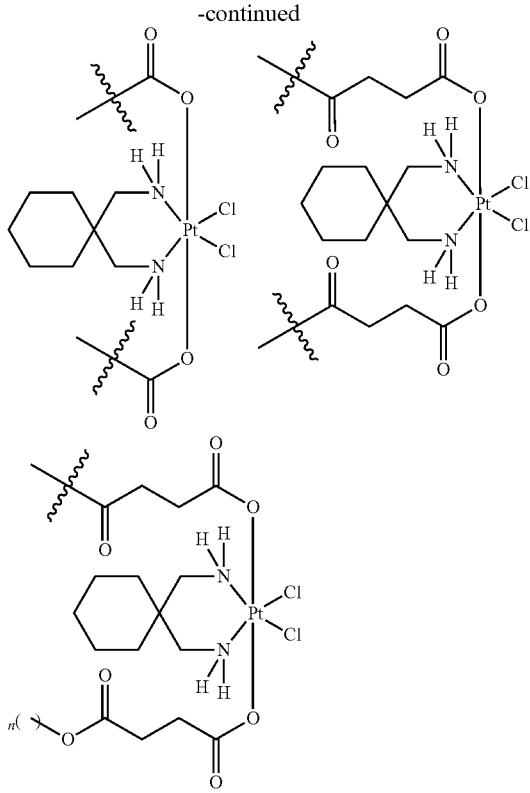

and corresponding platinum complexes that can be directly or indirectly connected to a COX-2-targeting moiety at one axial position and have a —OC(=O)-(4-phenyl-R) ligand at the other axial position, and pharmaceutically acceptable salts thereof, wherein:

R is —H or $C_1$-$C_6$ alkyl;

n is an integer from 1 to 15 or more; and an atom adjacent to a wavy line is a site where the platinum-containing antitumor agent is connected to the remainder of the conjugate.

In some embodiments, the COX-2-targeting moiety and the platinum-containing antitumor agent are directly associated with each other. The targeting moiety and the antitumor agent can be directly associated with each other in any suitable manner, such as by covalent or non-covalent (e.g., ionic) bonding, complexation or coordination.

In other embodiments, the conjugates described herein further comprise a linker, and the COX-2-targeting moiety and the platinum-containing antitumor agent are associated with each other via the linker. The linker independently can be associated with the COX-2-targeting moiety and the platinum-containing antitumor agent in any suitable manner, such as by covalent or non-covalent (e.g., ionic) bonding, complexation or coordination (i.e., the nature of the association between the linker and the targeting moiety is independent of the nature of the association between the linker and the antitumor agent).

A conjugate can comprise one or more COX-2-targeting moieties, one or more linkers, and one or more platinum-containing antitumor agents. In some embodiments, a conjugate comprises a single COX-2-targeting moiety, a single linker, and a single platinum-containing antitumor agent. In other embodiments, a conjugate comprises a plurality of COX-2-targeting moieties, a plurality of linkers, and a plurality of platinum-containing antitumor agents. In further embodiments, a conjugate comprises a single COX-2-targeting moiety, a plurality of linkers, and a plurality of platinum-containing antitumor agents. In additional embodiments, a conjugate comprises a single platinum-containing antitumor agent, a plurality of linkers, and a plurality of COX-2-targeting moieties. In certain embodiments, a conjugate has the formula:

[CTM-linker]$_n$-PAA wherein CTM denotes COX-2-targeting moiety, PAA denotes platinum-containing antitumor agent, and n is an integer from 1 to 6 or more.

The COX-2-targeting moiety and the platinum-containing antitumor agent can be directly or indirectly (e.g., via a linker) associated with each other at any chemically possible location on the targeting moiety and the antitumor agent that results in a stable and biologically active conjugate.

The COX-2-targeting moiety can be part of one or more equatorial ligands, and/or one or more axial ligands [if the platinum complex is, e.g., Pt(IV)], on the platinum metal of the platin agent. Furthermore, the COX-2-targeting moiety can be part of an equatorial or axial ligand by means of a linker or can directly coordinate to the platinum metal (e.g., a carboxylate group, a hydroxyl group or an amino [e.g., a primary or secondary amino] group of the targeting moiety coordinating to the platinum metal). If the COX-2-targeting moiety is part of one or more axial ligands of a Pt(IV) complex that has a suitable reduction potential [e.g., carboxylato ligand(s)], reduction of the Pt(IV) complex by a redox-active molecule (e.g., glutathione or ascorbic acid/ascorbate) inside tumor/cancer cells converts Pt(IV) to Pt(II) and releases the axial ligand(s) containing the COX-2-targeting moiety.

In some embodiments, the linker(s) are selected from the group consisting of:

1) optionally substituted $C_1$-$C_{40}$ hydrocarbylene;
2) optionally substituted $C_2$-$C_{40}$ heterohydrocarbylene;
3) -$L_E$-$R_4$-$L_F$-, wherein:
   $L_E$ is absent or is —N($R^8$)—, wherein $R^8$ is —H or optionally substituted $C_1$-$C_6$ alkyl;
   $R^4$ is optionally substituted $C_1$-$C_{40}$ hydrocarbylene or optionally substituted $C_2$-$C_{40}$ heterohydrocarbylene; and
   $L_F$ is absent or is selected from the group consisting of —O—, —N($R^9$)—, —C(=O)—, —C(=O)N($R^9$)—, —N($R^9$)C(=O)—, —S(O)N($R^9$)—, —N($R^9$)S(O)—, —S(O)$_2$N($R^9$)—, —N($R^9$)S(O)$_2$—, —N($R^9$)C(=O)N($R^9$)—, —N($R^9$)C(=O)O—, —OC(=O)N($R^9$)—, —(CH=CH)—, and divalent cycloalkyl and heterocyclic groups (e.g., 1,2,3-triazole and 1,2,4-triazole), wherein each occurrence of $R^9$ independently is —H or optionally substituted $C_1$-$C_6$ alkyl; and
4) —C≡N(CH$_2$)$_m$X—,

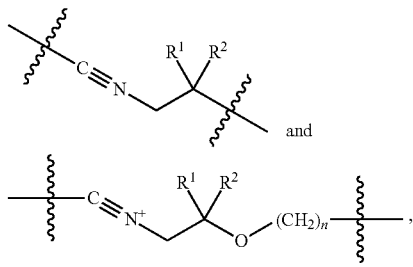

wherein:
X is absent or is —O— or —N(R³)—, wherein R³ is —H or $C_1$-$C_6$ alkyl;
R¹ and R² independently are —H, —F, $C_1$-$C_6$ alkyl, hydroxyl-substituted $C_1$-$C_6$ alkyl, —O—$C_1$-$C_6$ alkyl, or $C_3$-$C_6$ cycloalkyl; or
R¹ and R², together with the carbon atom to which they are attached, form a $C_3$-$C_8$ cycloalkyl ring or heterocyclyl ring;
m is an integer from 1 to 12; and
n is an integer from 0 to 4.

In further embodiments, the linker(s) are selected from the group consisting of:
1) —$(CH_2)_n$—, —$O(CH_2)_n$—, —$O(CH_2)_nO$—, —$N(R^1)(CH_2)_n$—, —$N(R^1)(CH_2)_n$—, —$N(R^2)$—, and $N(R^1)(CH_2)_nO$—, wherein R¹ and R² independently are —H or $C_1$-$C_6$ alkyl, and n is an integer from 2 to 20;
2) —$(CX^1X^2)_m(CH_2)_n$—, wherein each occurrence of X¹ and X² independently is —H or —F, m is an integer from 1 to 6, and n is an integer from 0 to 20;
3) (—$CH_2CH_2O$—)$_n$ and (—$CH_2CH(CH_3)O$—)$_n$, wherein n is an integer from 1 to 12;
4) —$X^1CH_2CH_2OCH_2CH_2X^2$— and —$X^1CH_2CH_2O$(—$CH_2CH_2O$—)$_nCH_2CH_2X^2$—, wherein X¹ and X² independently are absent or are —O— or —N(R)—, each occurrence of R independently is —H or $C_1$-$C_6$ alkyl, and n is an integer from 1 to 12;
5) —$X^1CH_2$(—$CH_2CH_2O$—)$_n(CH_2)_3X^2$—, wherein X¹ and X² independently are absent or are —O— or —N(R)—, each occurrence of R independently is —H or $C_1$-$C_6$ alkyl, and n is an integer from 1 to 12;
6) —$C(=O)(CH_2)_nX$—, wherein X is absent or is —O— or —N(R)—, R is —H or $C_1$-$C_6$ alkyl, and n is an integer from 1 to 20;
7) —$C(=O)(CH_2)_nC(=O)$—, wherein n is an integer from 2 to 20;
8) —$C(=O)CH_2CH_2C(=O)N(R)(CH_2)_nC(=O)$—, wherein R is —H or $C_1$-$C_6$ alkyl, and n is an integer from 1 to 20;
9) —$C(=O)CH_2CH_2C(=O)N(R^1)CH_2$(—$CH_2CH_2O$—)$_n(CH_2)_3X$—, wherein X is —O—, —$N(R^2)$— or —C(=O)—, R¹ and R² independently are —H or $C_1$-$C_6$ alkyl, and n is an integer from 1 to 12;
10) —$C(=O)CH_2$(—$OCH_2CH_2$—)$_nO$— and —$C(=O)CH_2$(—$OCH_2CH_2$—)$_nOCH_2C(=O)$—, wherein n is an integer from 1 to 12; and
11) —$X^1(CH_2)_m$-cyclyl-$(CH_2)$—$X^2$—, wherein X¹ and X² independently are absent or are —O— or —N(R)—, each occurrence of R independently is —H or $C_1$-$C_6$ alkyl, cyclyl is cycloalkyl, aryl, heterocyclyl or heteroaryl, and m and n independently are integers from 0 to 6.

In certain embodiments, the linker(s) are selected from the group consisting of:
1) —$(CH_2)_n$—, —$(CH_2)_nO$— and —$(CH_2)_nN(R)$—, wherein R is —H or $C_1$-$C_6$ alkyl and n is an integer from 4 to 10 or more;
2) —$(CF_2)$—$(CH_2)_n$—, wherein m is an integer from 1 to 4 or more, and n is an integer from 1 to 15 or more;
3) —$CH_2CH_2OCH_2CH_2$—, —$CH_2CH_2O$(—$CH_2CH_2O$—)$_n$, —$CH_2CH_2O$(—$CH_2CH_2O$—)$_nCH_2CH_2$—, and —$NH$(—$CH_2CH_2O$—)$_nX$, wherein X is absent or is —$CH_2$— or —$CH_2CH_2$—, and n is an integer from 1 to 4 or more;
4) —$NHCH_2CH_2OCH_2CH_2NH$— and —$NHCH_2CH_2O$(—$CH_2CH_2O$—)$_nCH_2CH_2NH$—, wherein n is an integer from 1 to 4 or more;

5) —$NH(CH_2)_nNH$—, —$NH(CH_2)$—$NMe$-, and —$NMe(CH_2)$—$NMe$-, wherein n is an integer from 2 or 4 to 10 or more;
6) —$O(CH_2)_n$—, —$NHX(CH_2)_n$—, —$NHX(CH_2)_nNH$—, and —$NHX(CH_2)_nO$—, wherein X is absent or is —$S(=O)_2$—, and n is an integer from 4 to 10 or more;
7) —$C(=O)(CH_2)_n$— and —$C(=O)(CH_2)_nX$—, wherein X is —O— or —N(R)—, R is —H or $C_1$-$C_6$ alkyl, and n is an integer from 4 to 10 or more;
8) —$C(=O)(CH_2)$—$C(=O)$—, wherein n is an integer from 2 or 4 to 10 or more;
9) —$C\equiv N(CH_2)_mX$—, wherein X is absent or is —O— or —NH—, and m is an integer from 4 to 10 or more;
10) 1,2-cyclopropyldimethylene, 1,2-cyclobutyldimethylene, 1,3-cyclobutyldimethylene, 1,2-cyclopentyldimethylene, 1,3-cyclopentyldimethylene, 1,2-cyclohexyldimethylene, 1,3-cyclohexyldimethylene, and 1,4-cyclohexyldimethylene; and
11)

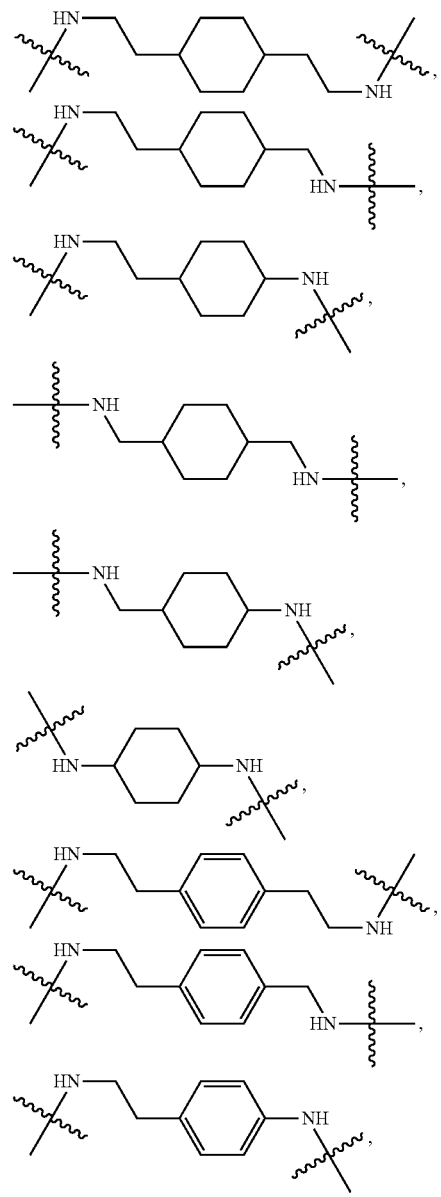

-continued

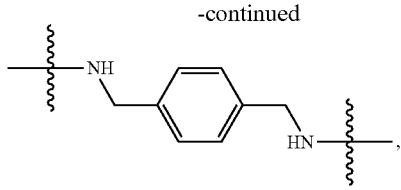

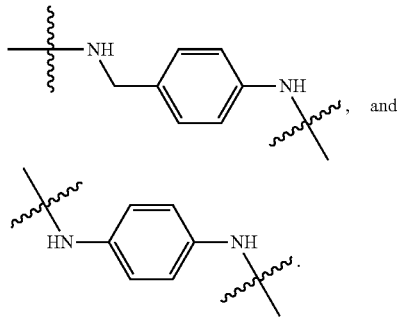

The linker(s) can have one or more sulfur atoms in place of one or more oxygen atoms of the linkers described herein, as appropriate. Furthermore, the linker(s) can have one or more carbon-carbon triple bonds, which can be incorporated to reduce the flexibility of the linker(s).

It is understood that one of the nitrogen atoms of a diamine linker can optionally coordinate to the platinum metal of a platinum-containing antitumor agent—e.g, in place of an amine group on, e.g., cisplatin, carboplatin, nedaplatin, picoplatin or satraplatin.

In further embodiments, the COX-2-targeting moiety comprises indomethacin, or an analog, derivative, residue or salt thereof, and the linker(s) are —N(R$^1$)(CH$_2$)$_n$— or —N(R$^1$)(CH$_2$)$_n$N(R$^2$)—, wherein R$^1$ and R$^2$ independently are —H or methyl, and n is an integer from 2 or 4 to 10 (e.g., n is 6). In certain embodiments, the COX-2-targeting moiety comprises

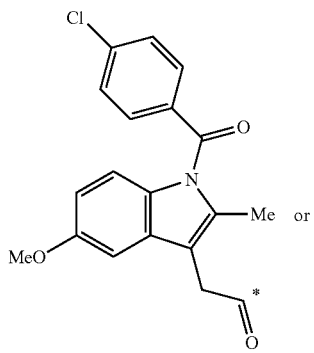

or

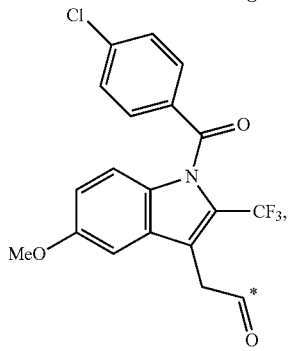

the linker(s) are —NH(CH$_2$)$_n$— or —NH(CH$_2$)$_n$NH—, wherein n is an integer from 4 to 10 (e.g., n is 6), and the platinum-containing antitumor agent (PAA) can be any PAA described herein. The present disclosure specifically discloses, e.g., conjugates comprising one or two units of

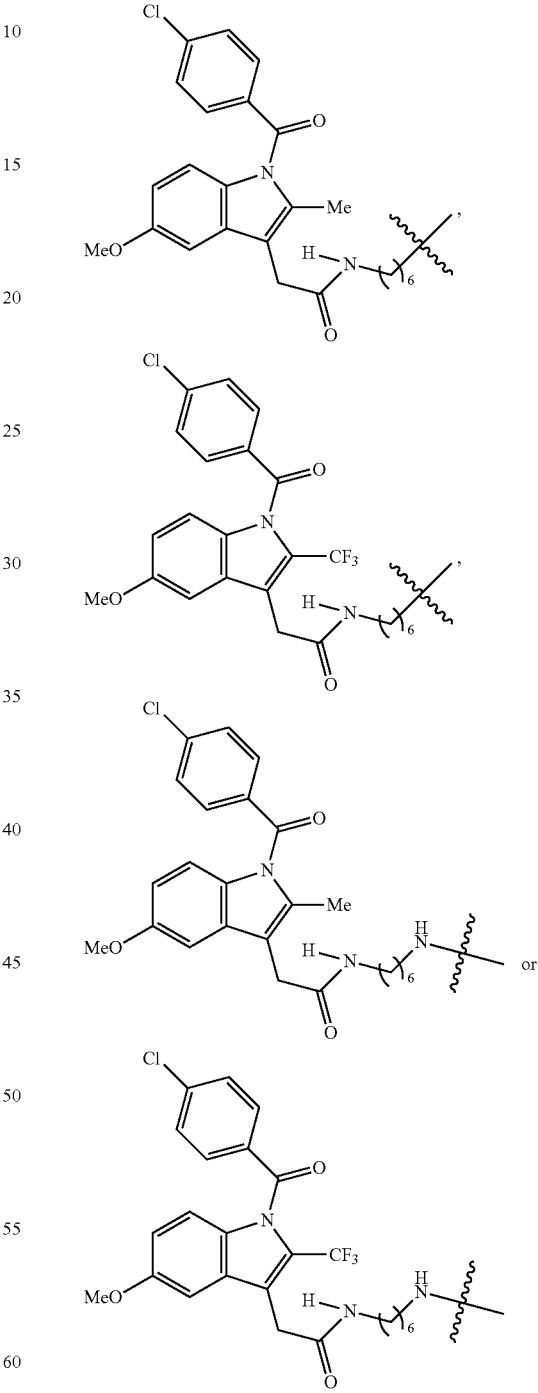

attached to each of the platinum-containing antitumor agents described herein.

In some embodiments, the conjugates are selected from the group consisting of:

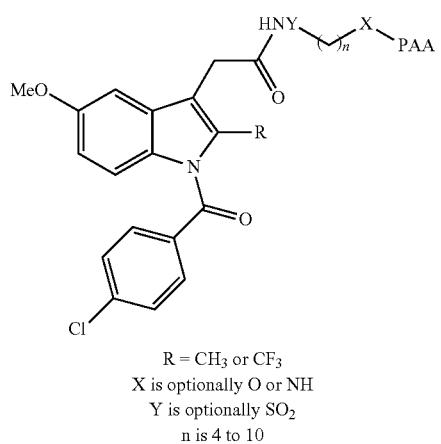

R = CH₃ or CF₃
X is optionally O or NH
Y is optionally SO₂
n is 4 to 10

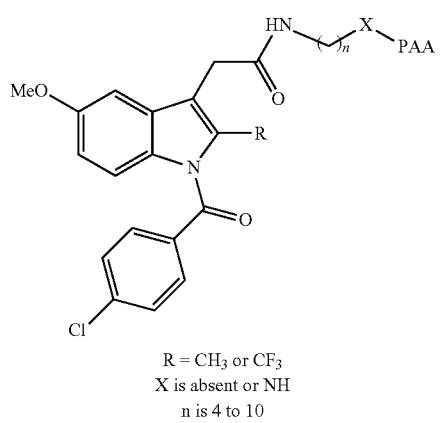

R = CH₃ or CF₃
X is absent or NH
n is 4 to 10

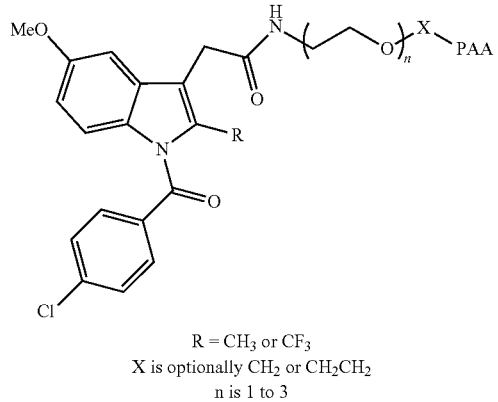

R = CH₃ or CF₃
X is optionally CH₂ or CH₂CH₂
n is 1 to 3

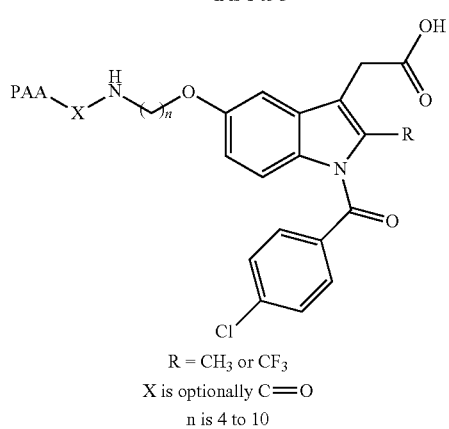

R = CH₃ or CF₃
X is optionally C=O
n is 4 to 10

-continued

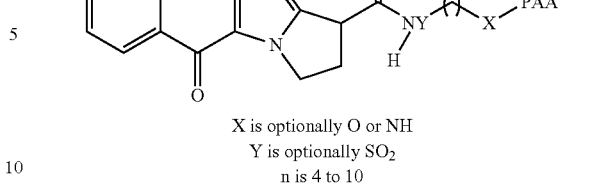

X is optionally O or NH
Y is optionally SO₂
n is 4 to 10

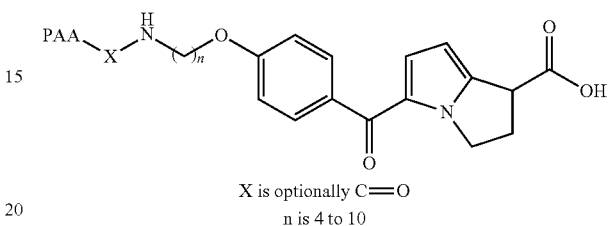

X is optionally C=O
n is 4 to 10

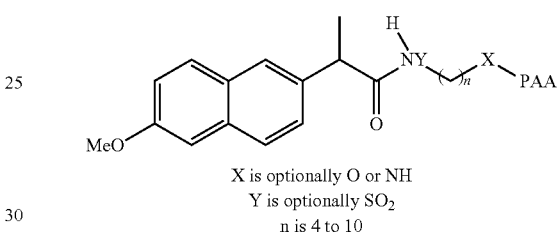

X is optionally O or NH
Y is optionally SO₂
n is 4 to 10

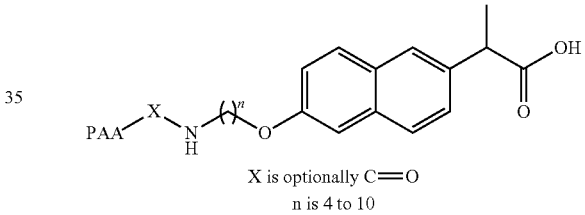

X is optionally C=O
n is 4 to 10

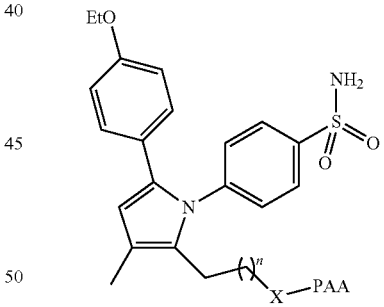

X is optionally O or NH
n is 3 to 10

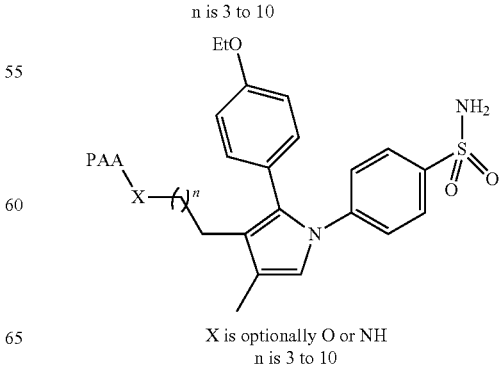

X is optionally O or NH
n is 3 to 10

-continued
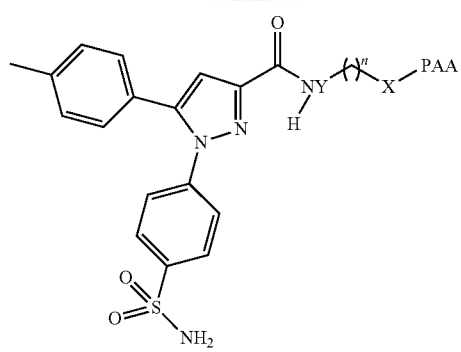
X is optionally O or NH
Y is optionally SO₂
n is 4 to 10
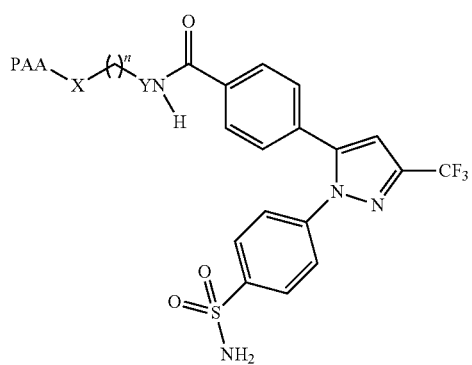
X is optionally O or NH
Y is optionally SO₂
n is 4 to 10
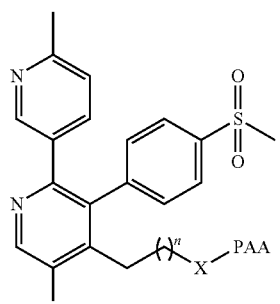
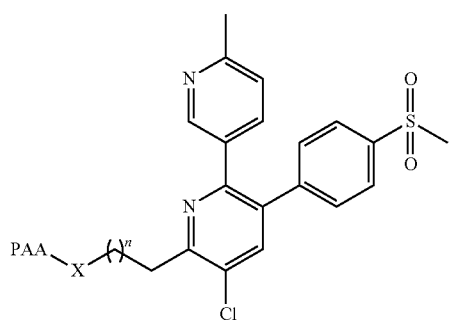
X is optionally O or NH
n is 3 to 10
-continued
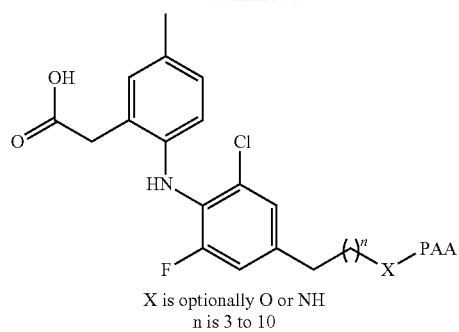
X is optionally O or NH
n is 3 to 10
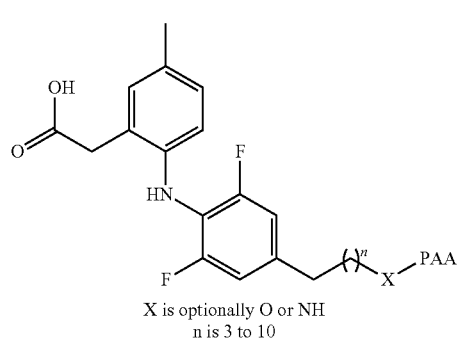
X is optionally O or NH
n is 3 to 10
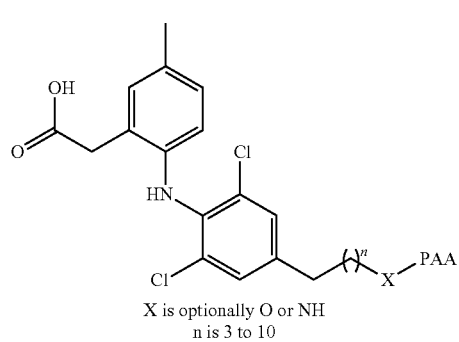
X is optionally O or NH
n is 3 to 10
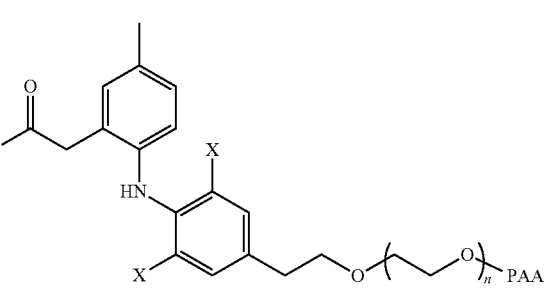
X is F or Cl
n is 1 to 3
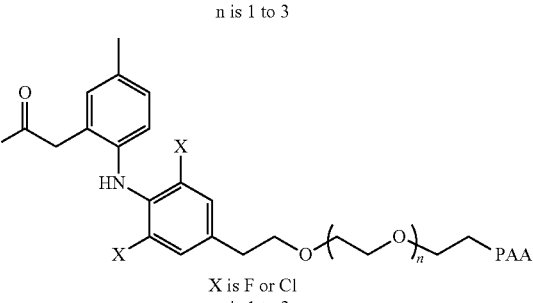
X is F or Cl
n is 1 to 2

49
-continued

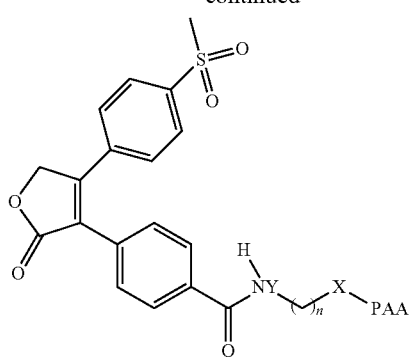

X is optionally O or NH
Y is optionally SO$_2$
n is 4 to 10

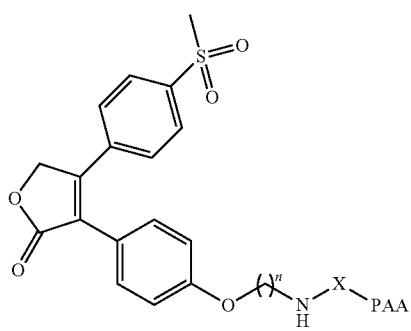

X is optionally C=O
n is 4 to 10

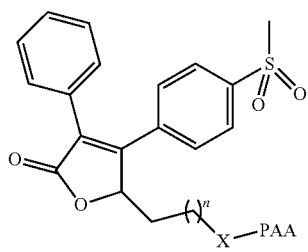

X is optionally O or NH
n is 3 to 10

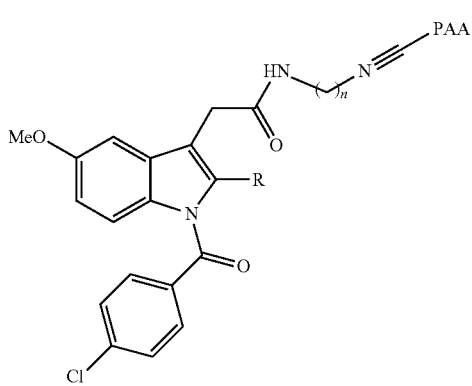

R = CH$_3$ or CF$_3$
n is 4 to 10

50
-continued

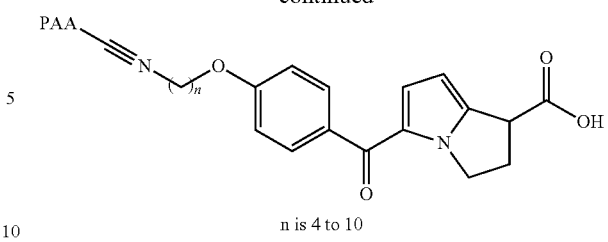

n is 4 to 10 and pharmaceutically acceptable salts thereof, wherein PAA denotes platinum-containing antitumor agent and the COX-2-targeting moiety can be part of an equatorial ligand or an axial ligand on the platinum metal.

In additional embodiments, the conjugates are selected from the group consisting of:

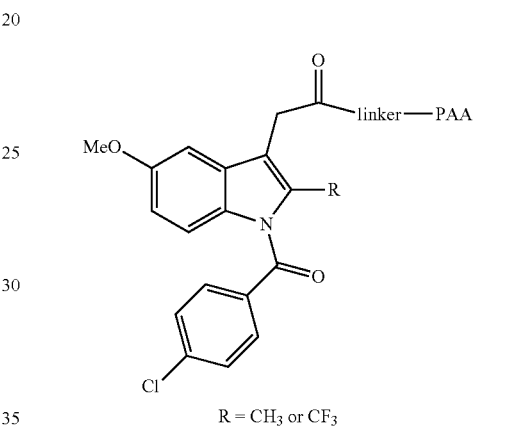

R = CH$_3$ or CF$_3$

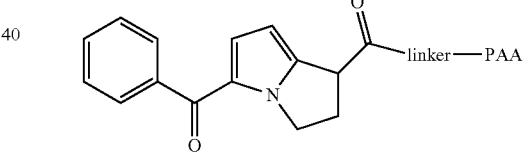

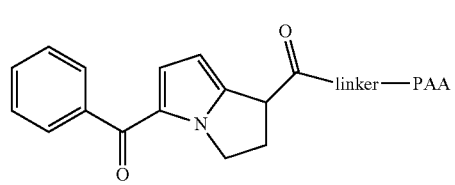

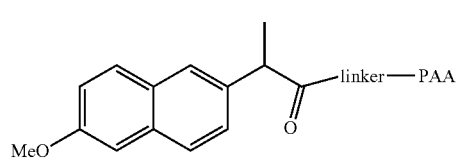

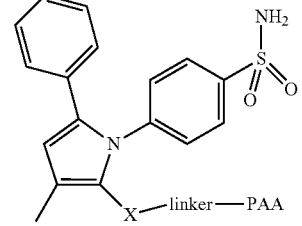

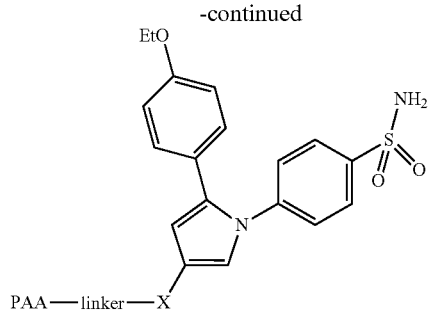
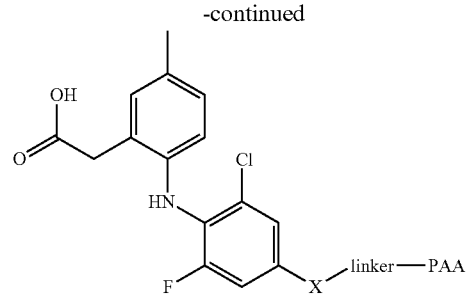
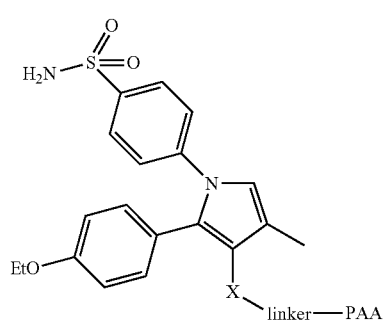
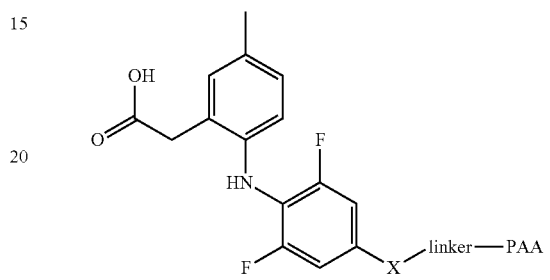
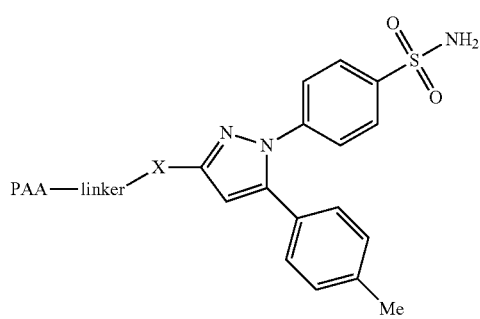
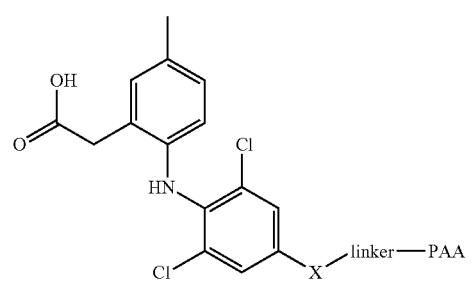
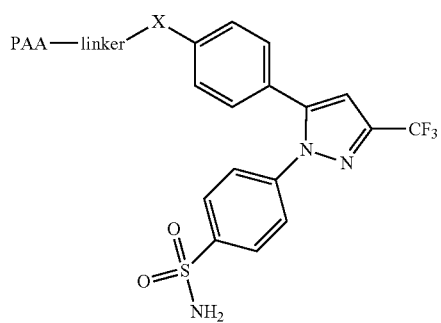
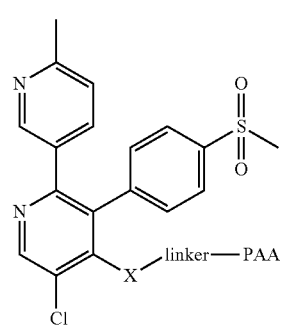
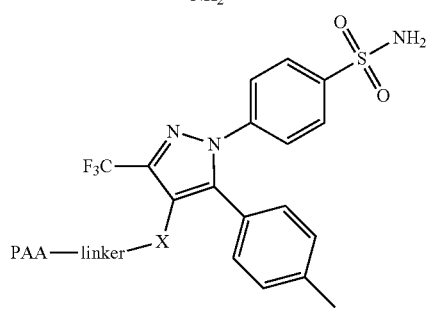
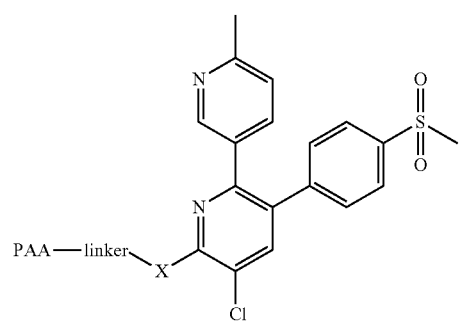

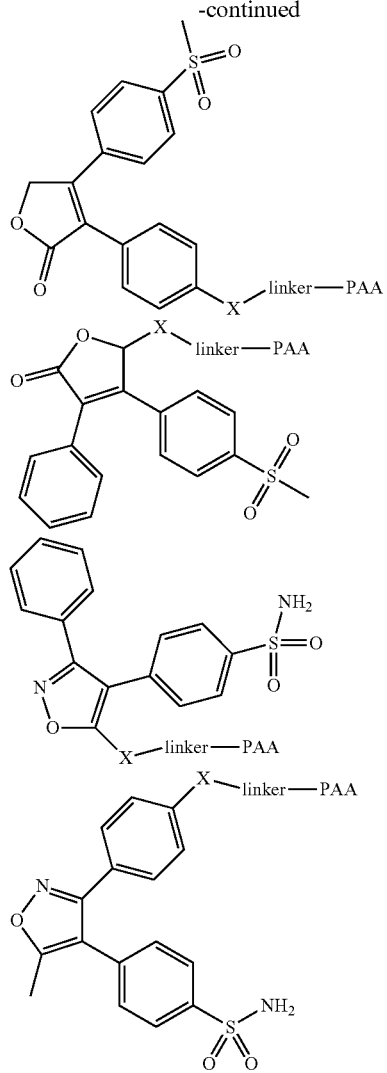

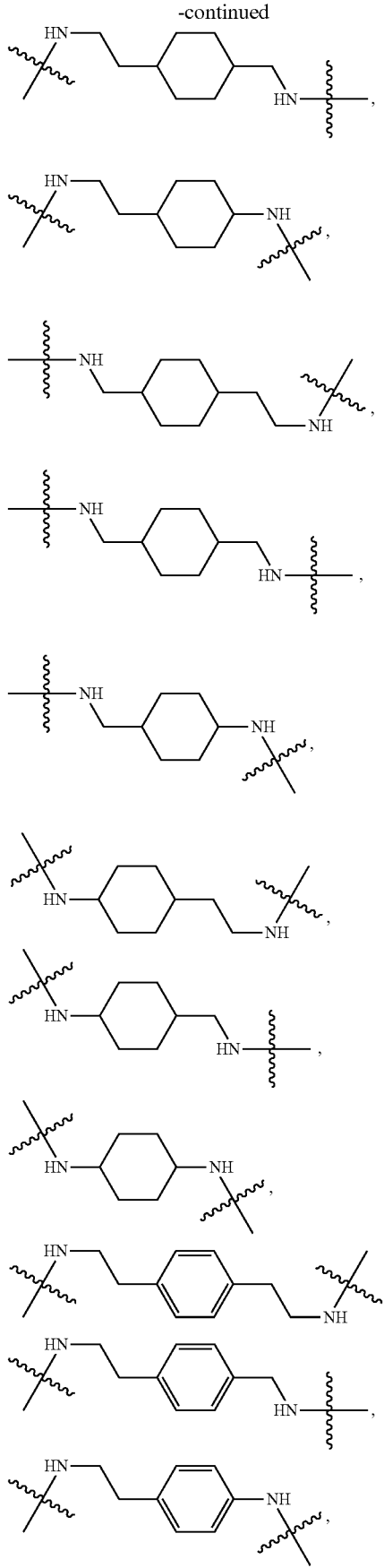

and pharmaceutically acceptable salts thereof, wherein:

PAA denotes platinum-containing antitumor agent;

the COX-2-targeting moiety can be part of an equatorial ligand or an axial ligand on the platinum metal;

X is absent or is —C(=O)—, —OC(=O)— (capable of forming a carbamate bond), or —S(=O)$_2$—; and the linker, in the direction from the COX-2-targeting moiety to the PAA, is selected from the group consisting of:

1) —NH(CH$_2$)$_n$NH— and —NH(CH$_2$)$_n$NMe-, wherein n is an integer from 2 or 4 to 10;

2) —NHCH$_2$CH$_2$OCH$_2$CH$_2$NH— and —NHCH$_2$CH$_2$O(—CH$_2$CH$_2$O—)$_n$CH$_2$CH$_2$NH—, wherein n is 1 or 2; and

3)

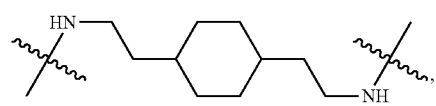

55

-continued

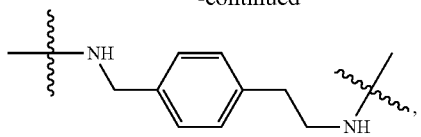

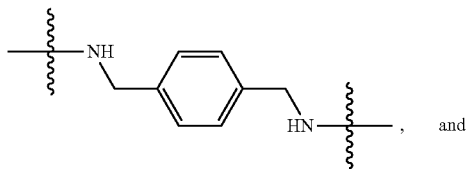, and

56

-continued

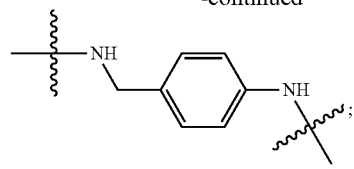;

wherein the nitrogen atom at the right end of the linker can optionally coordinate to the platinum metal of the PAA (e.g., in place of an ammine group on cisplatin, carboplatin, nedaplatin, picoplatin or satraplatin).

In certain embodiments, the conjugates are selected from the group consisting of:

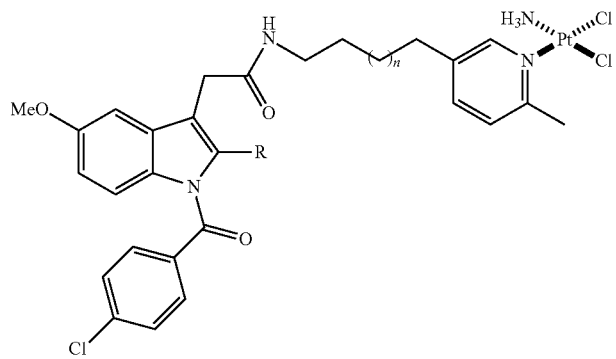

R = CH$_3$ or CF$_3$
n = 1 to 5 (e.g., 3)

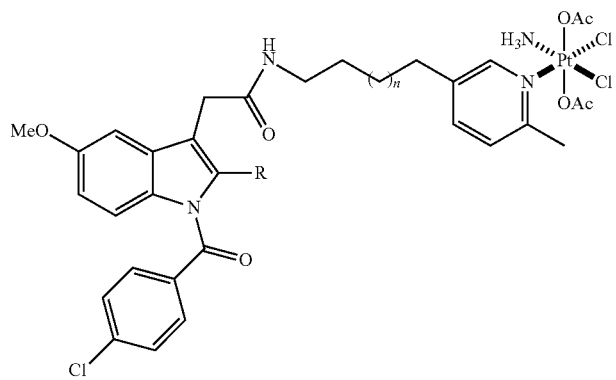

R = CH$_3$ or CF$_3$
n = 1 to 5 (e.g., 3)

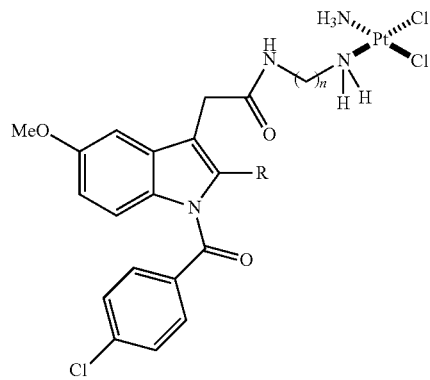

R = CH$_3$ or CF$_3$
n = 2 to 8 (e.g., 6)

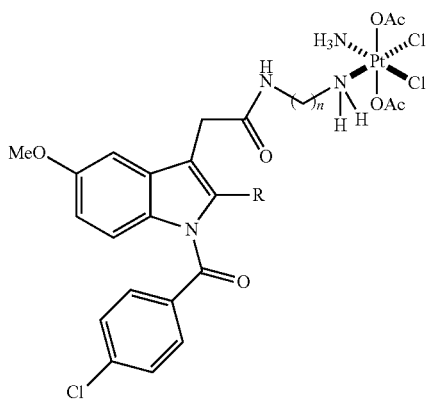
R = CH₃ or CF₃
n = 2 to 8 (e.g., 6)
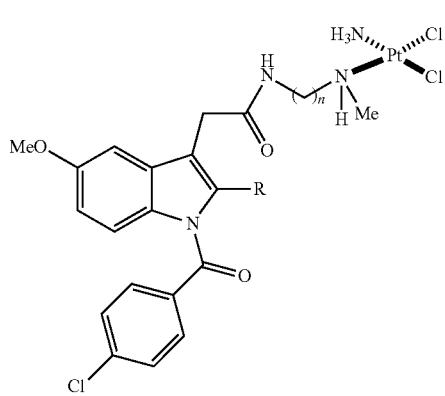
R = CH₃ or CF₃
n = 2 to 8 (e.g., 6)
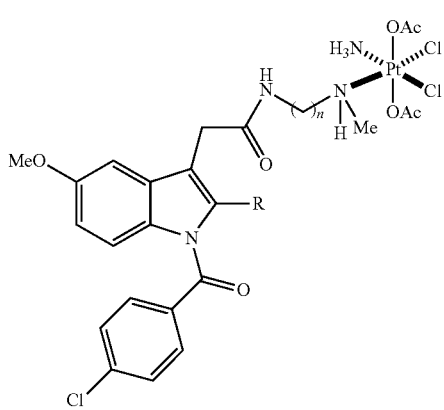
R = CH₃ or CF₃
n = 2 to 8 (e.g., 6)
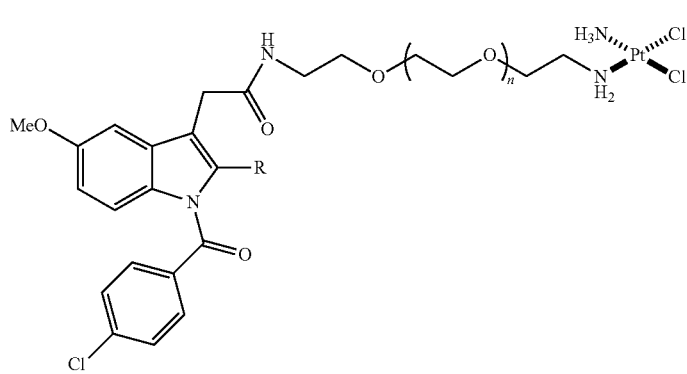
R = CH₃ or CF₃
n = 0, 1 or 2
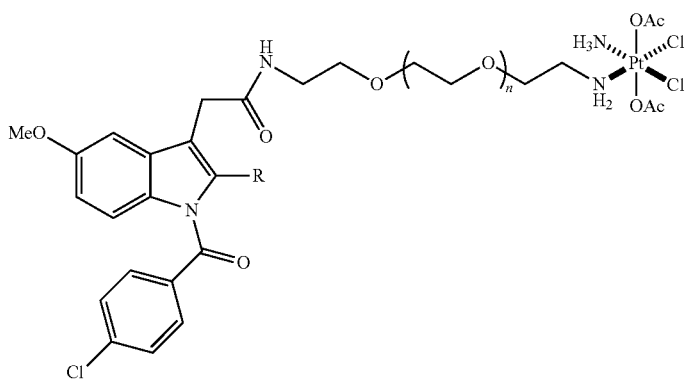
R = CH₃ or CF₃
n = 0, 1 or 2

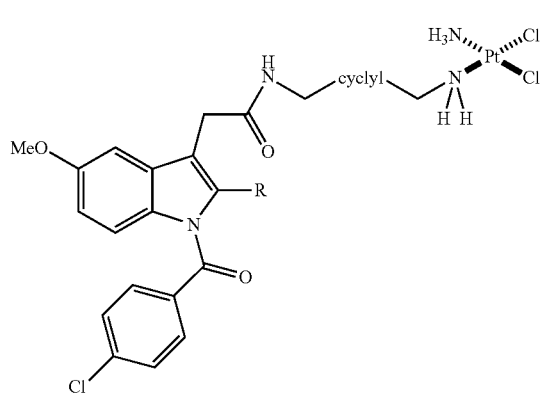
R = CH₃ or CF₃
cyclyl = 1,4-cyclohexyl or 1,4-phenyl
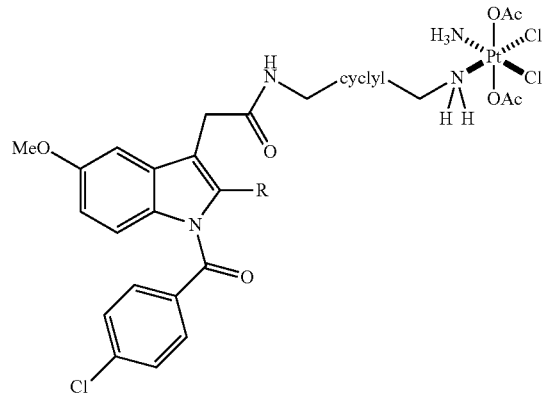
R = CH₃ or CF₃
cyclyl = 1,4-cyclohexyl or 1,4-phenyl
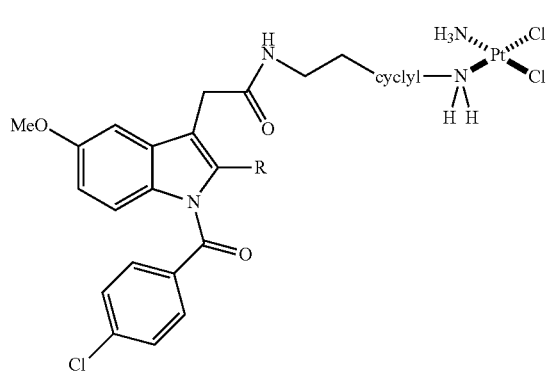
R = CH₃ or CF₃
cyclyl = 1,4-cyclohexyl or 1,4-phenyl
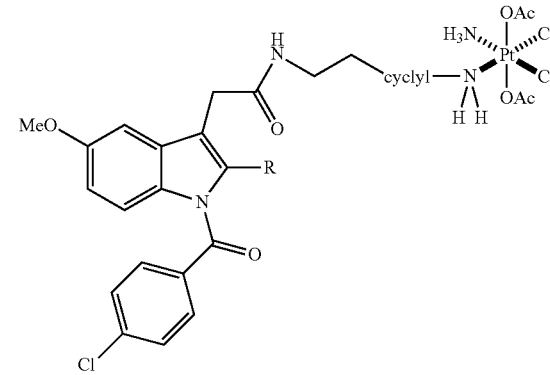
R = CH₃ or CF₃
cyclyl = 1,4-cyclohexyl or 1,4-phenyl
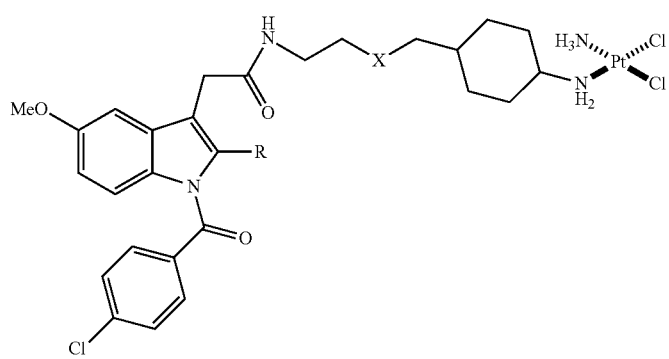
1) R = Me & X = CH₂; or
2) R = Me & X = O; or
3) R = CF₃ & X = CH₂; or
4) R = CF₃ & X = O -continued
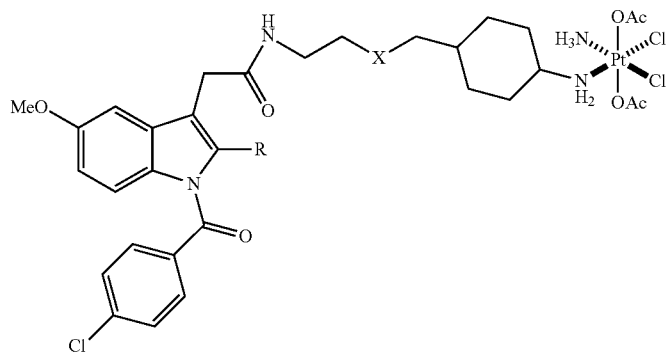
1) R = Me & X = CH$_2$; or
2) R = Me & X = O; or
3) R = CF$_3$ & X = CH$_2$; or
4) R = CF$_3$ & X = O
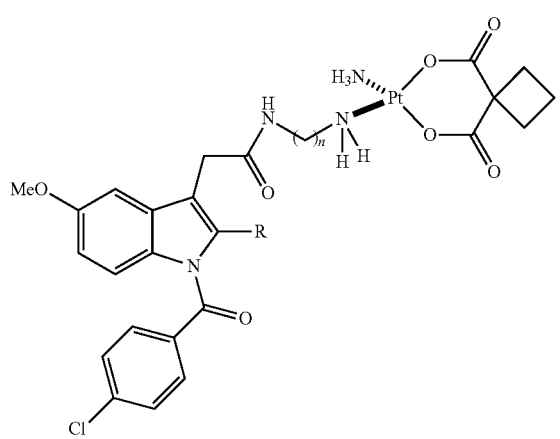
R = CH$_3$ or CF$_3$
n = 2 to 8 (e.g., 6)
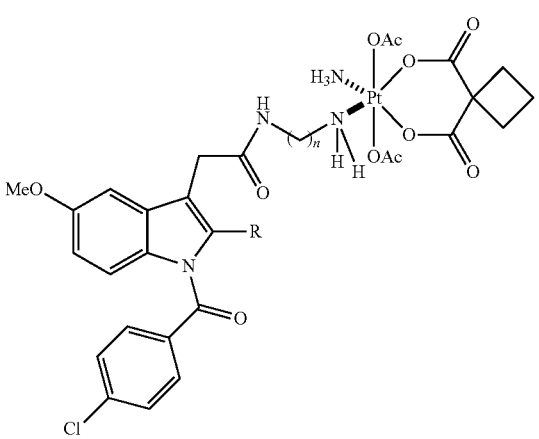
R = CH$_3$ or CF$_3$
n = 2 to 8 (e.g., 6)
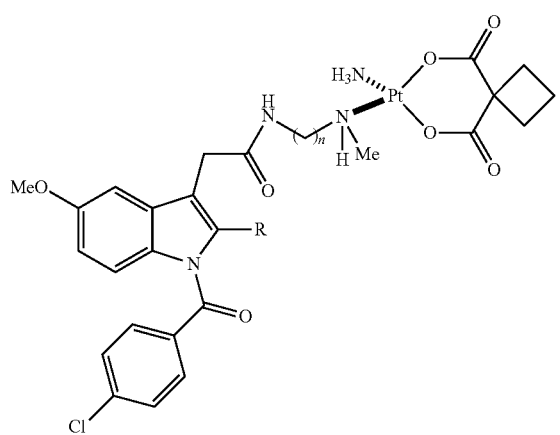
R = CH$_3$ or CF$_3$
n = 2 to 8 (e.g., 6)
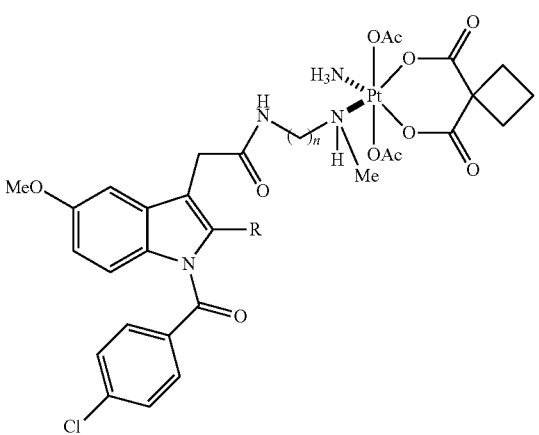
R = CH$_3$ or CF$_3$
n = 2 to 8 (e.g., 6)

-continued
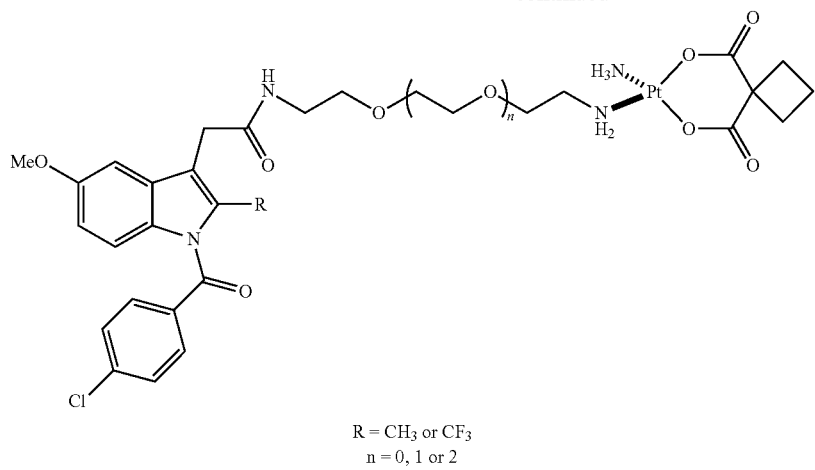
R = CH₃ or CF₃
n = 0, 1 or 2
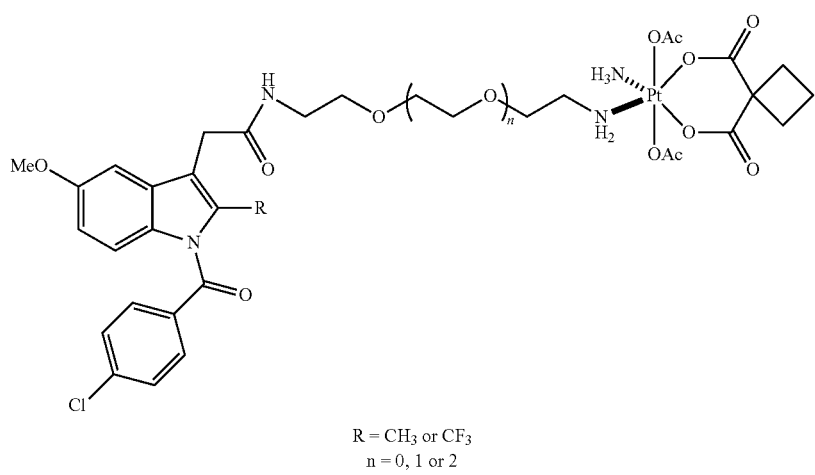
R = CH₃ or CF₃
n = 0, 1 or 2
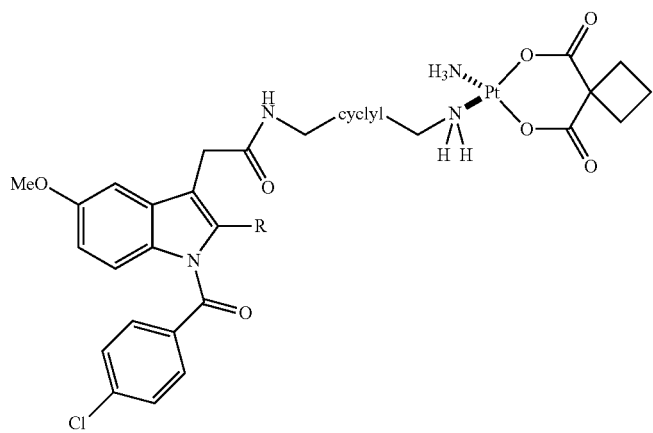
R = CH₃ or CF₃
cyclyl = 1,4-cyclohexyl or 1,4-phenyl -continued
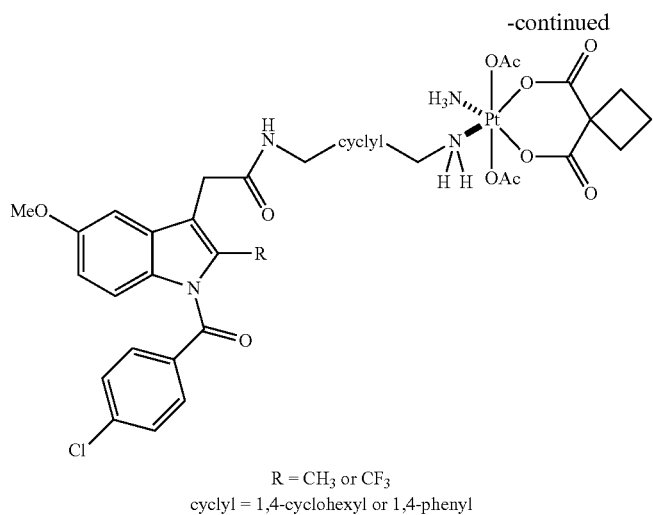
R = CH₃ or CF₃
cyclyl = 1,4-cyclohexyl or 1,4-phenyl
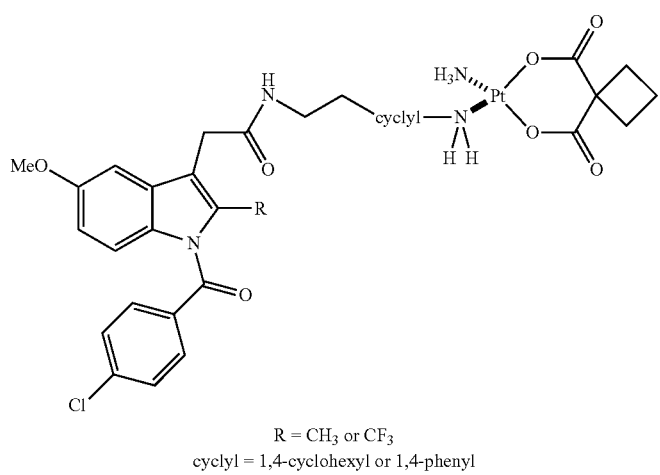
R = CH₃ or CF₃
cyclyl = 1,4-cyclohexyl or 1,4-phenyl
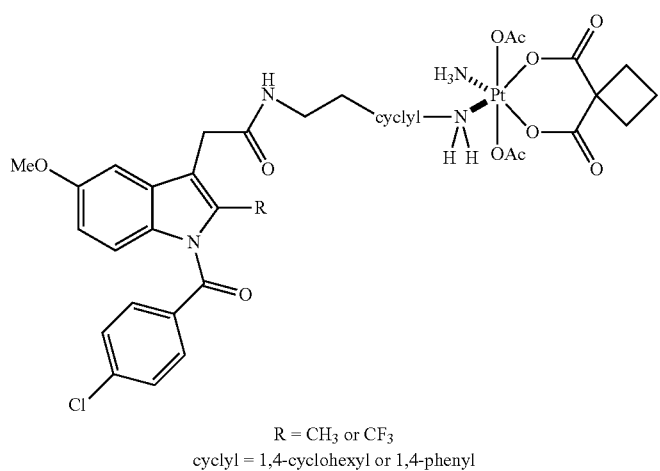
R = CH₃ or CF₃
cyclyl = 1,4-cyclohexyl or 1,4-phenyl

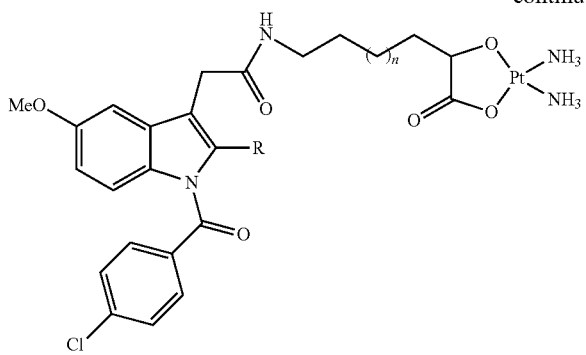
R = CH₃ or CF₃
n = 1 to 5 (e.g., 3)
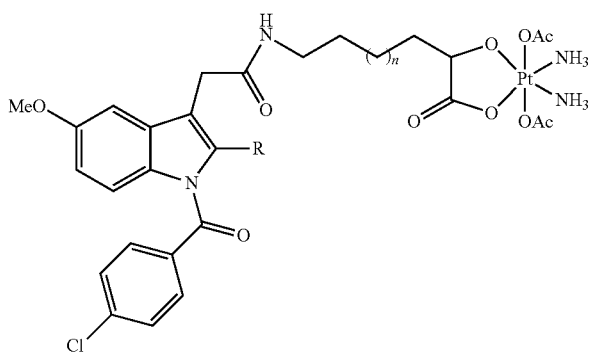
R = CH₃ or CF₃
n = 1 to 5 (e.g., 3)
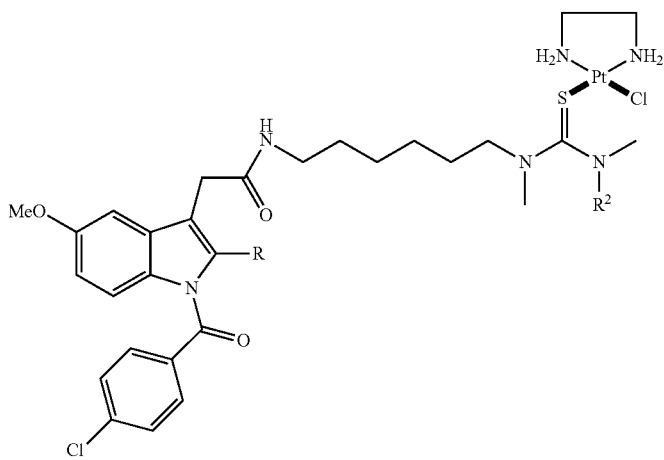
1) $R^1$ = Me & $R^2$ = H; or
2) $R^1$ = Me & $R^2$ = Me; or
3) $R^1$ = CF₃ & $R^2$ = H; or
4) $R^1$ = CF₃ & $R^2$ = Me 69
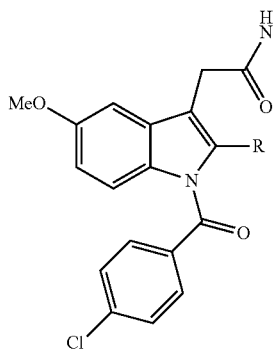
-continued
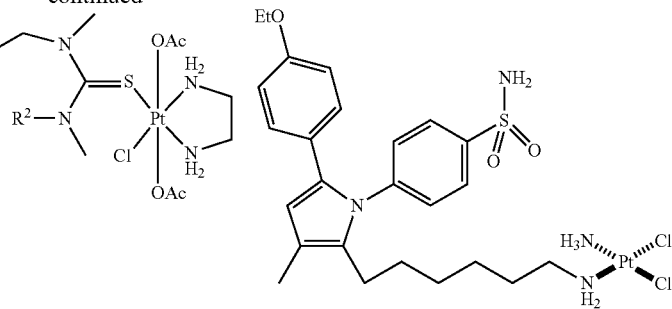
1) R¹ = Me & R² = H; or
2) R¹ = Me & R² = Me; or
3) R¹ = CF₃ & R² = H; or
4) R¹ = CF₃ & R² = Me
70
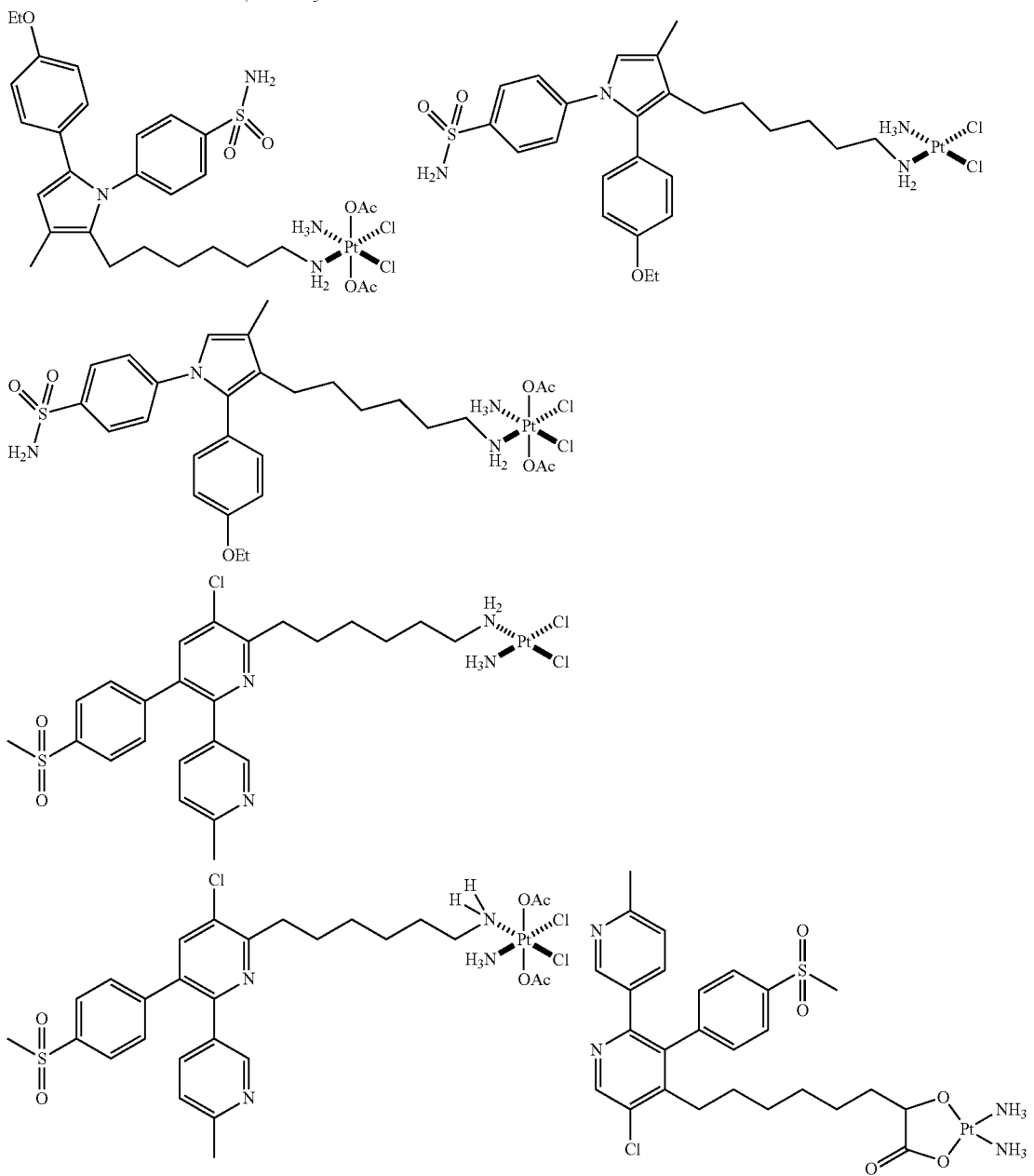

-continued
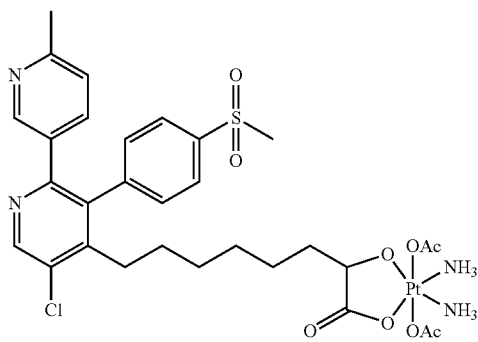
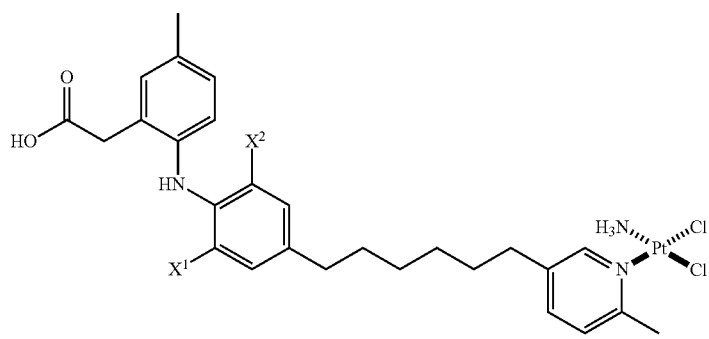
1) X¹ = F & X² = Cl; or
2) X¹ = X² = F; or
3) X¹ = X² = Cl
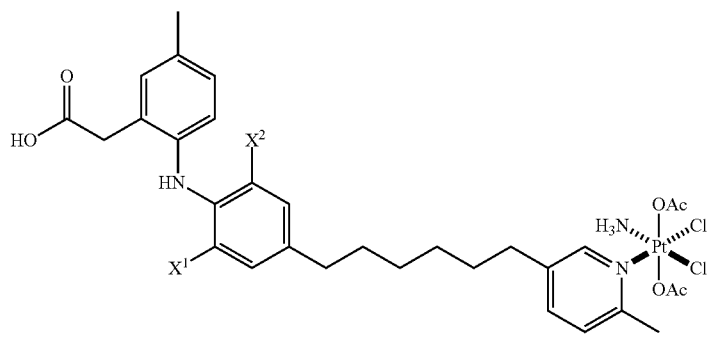
1) X¹ = F & X² = Cl; or
2) X¹ = X² = F; or
3) X¹ = X² = Cl
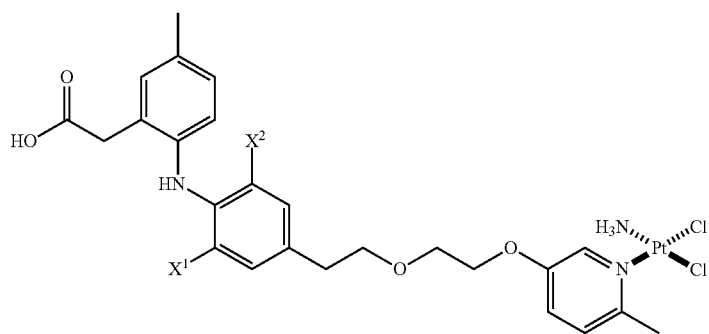
1) X¹ = F & X² = Cl; or
2) X¹ = X² = F; or
3) X¹ = X² = Cl -continued
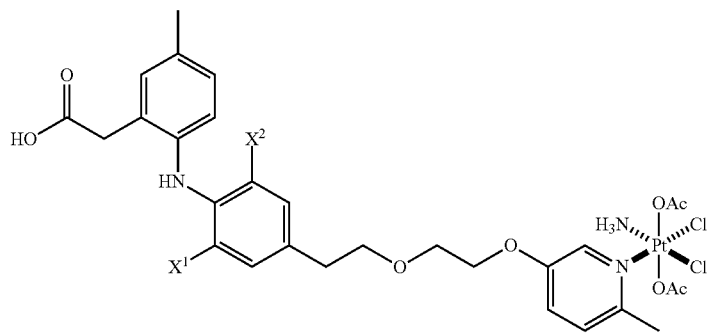
1) $X^1$ = F & $X^2$ = Cl; or
2) $X^1$ = $X^2$ = F; or
3) $X^1$ = $X^2$ = Cl
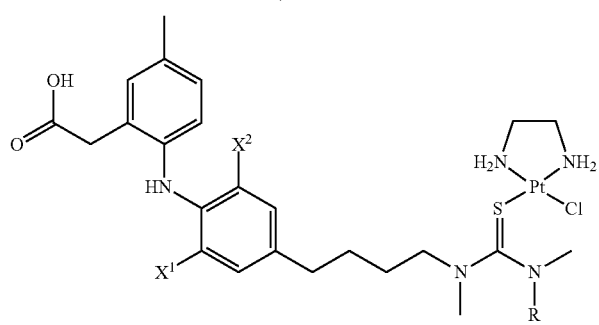
1) $X^1$ = F, $X^2$ = Cl, & R = H; or
2) $X^1$ = F, $X^2$ = Cl, & R = Me; or
3) $X^1$ = $X^2$ = F & R = H; or
4) $X^1$ = $X^2$ = F & R = Me; or
5) $X^1$ = $X^2$ = Cl & R = H; or
5) $X^1$ = $X^2$ = Cl & R = Me
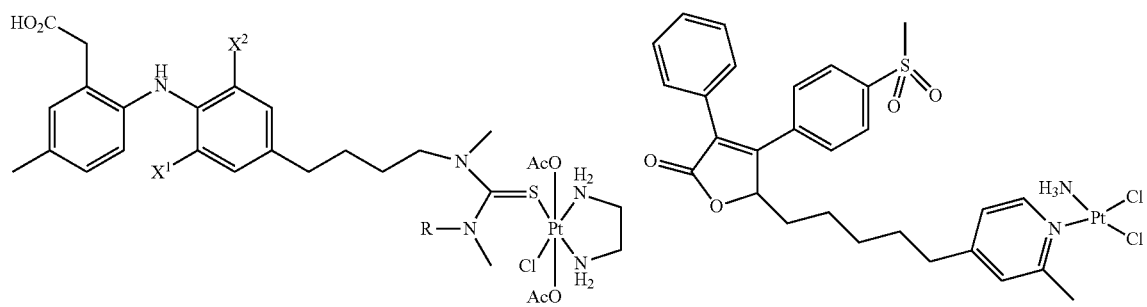
1) $X^1$ = F, $X^2$ = Cl, & R = H; or
2) $X^1$ = F, $X^2$ = Cl, & R = Me; or
3) $X^1$ = $X^2$ = F & R = H; or
4) $X^1$ = $X^2$ = F & R = Me; or
5) $X^1$ = $X^2$ = Cl & R = H; or
5) $X^1$ = $X^2$ = Cl & R = Me
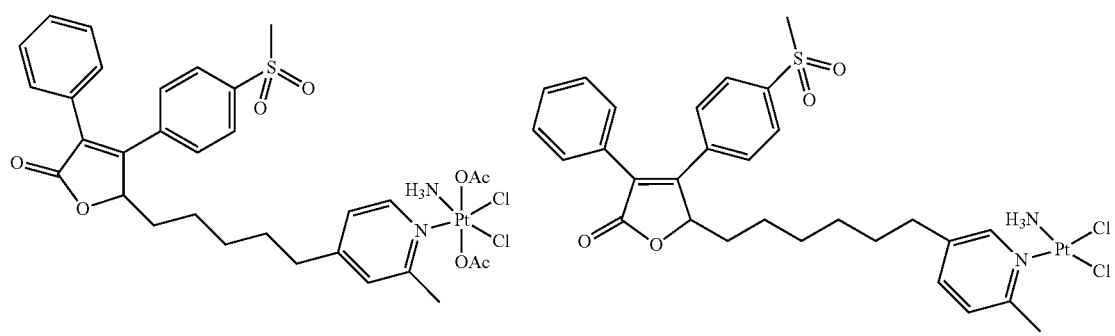

-continued
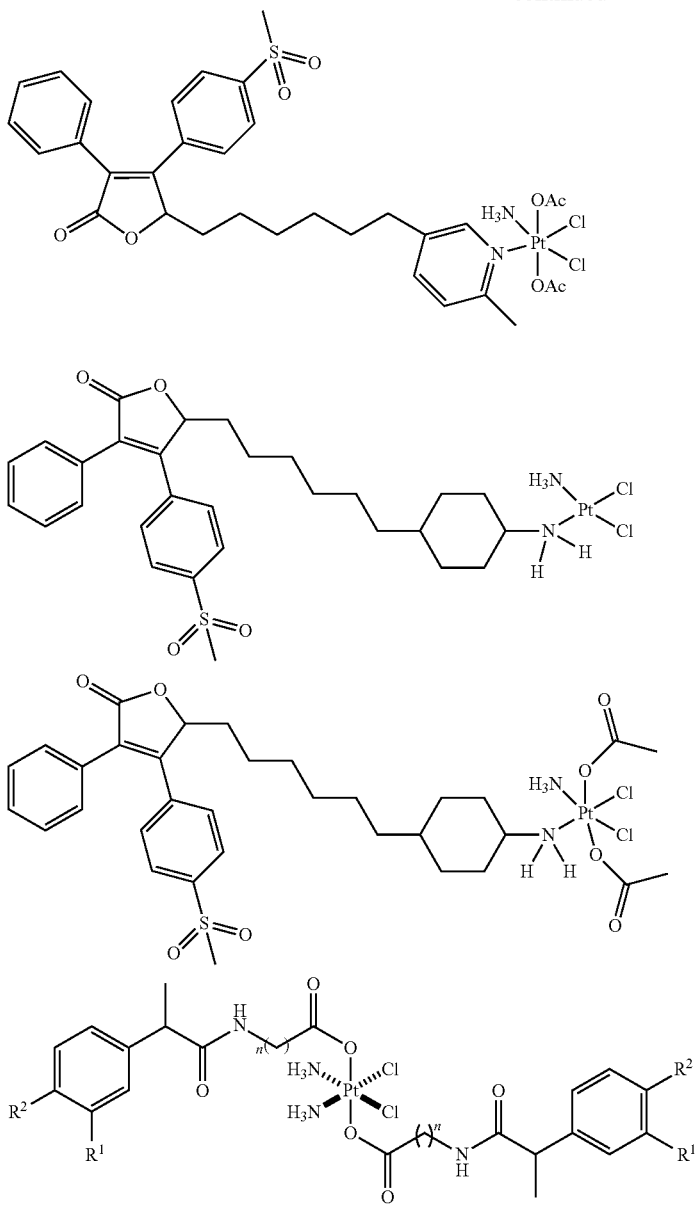
1) R¹ = H & R² = —CH₂CHMe₂
2) R¹ = H & R² = —CH₂—(2-cyclopentanone)
3) R¹ = F & R² = phenyl
   n = 4 to 8
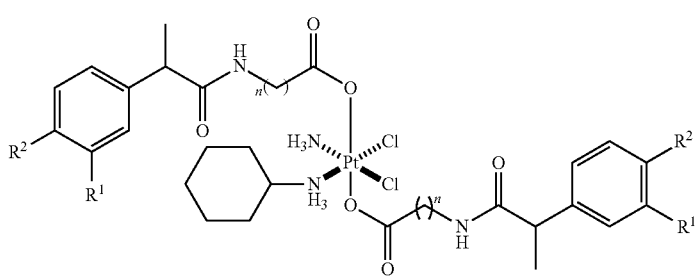
1) R¹ = H & R² = —CH₂CHMe₂
2) R¹ = H & R² = —CH₂—(2-cyclopentanone)
3) R¹ = F & R² = phenyl
   n = 4 to 8

-continued
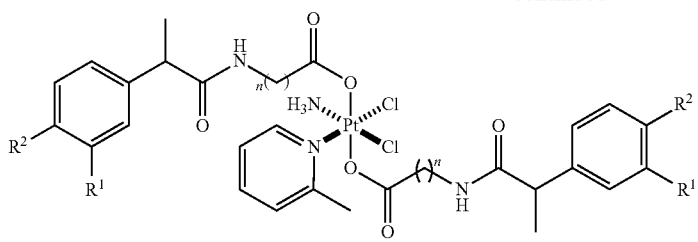
1) R¹ = H & R² = —CH₂CHMe₂
2) R¹ = H & R² = —CH₂—(2-cyclopentanone)
3) R¹ = F & R² = phenyl
n = 4 to 8
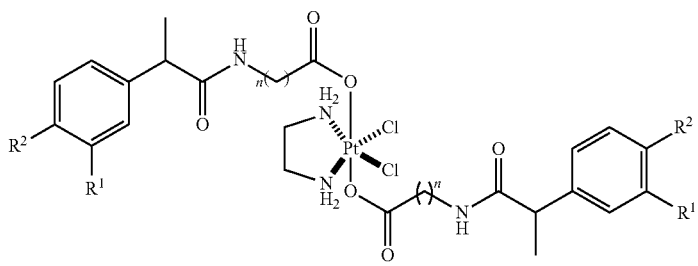
1) R¹ = H & R² = —CH₂CHMe₂
2) R¹ = H & R² = —CH₂—(2-cyclopentanone)
3) R¹ = F & R² = phenyl
n = 4 to 8
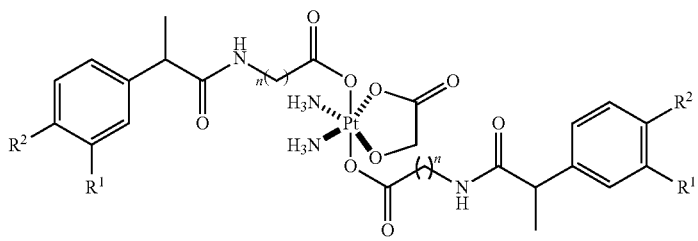
1) R¹ = H & R² = —CH₂CHMe₂
2) R¹ = H & R² = —CH₂—(2-cyclopentanone)
3) R¹ = F & R² = phenyl
n = 4 to 8
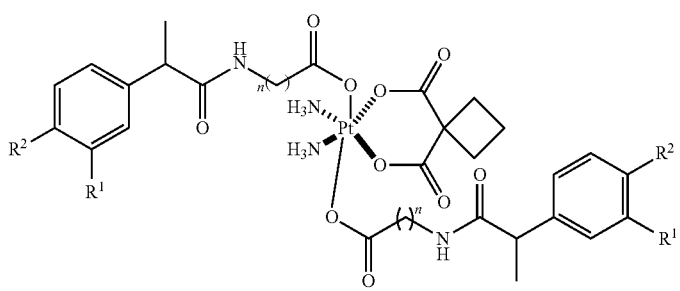
1) R¹ = H & R² = —CH₂CHMe₂
2) R¹ = H & R² = —CH₂—(2-cyclopentanone)
3) R¹ = F & R² = phenyl
n = 4 to 8

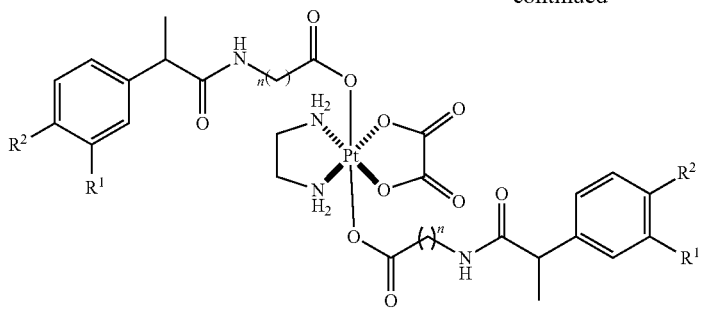
1) R¹ = H & R² = —CH₂CHMe₂
2) R¹ = H & R² = —CH₂—(2-cyclopentanone)
3) R¹ = F & R² = phenyl
   n = 4 to 8
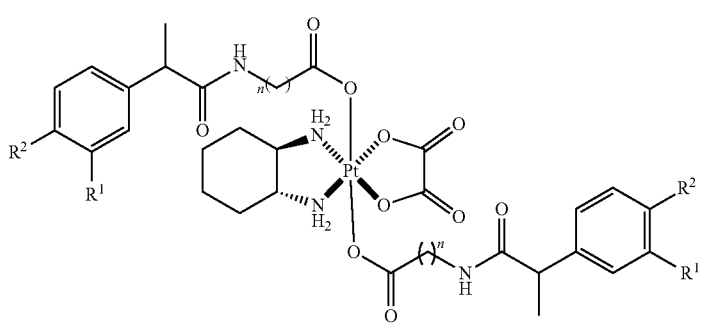
1) R¹ = H & R² = —CH₂CHMe₂
2) R¹ = H & R² = —CH₂—(2-cyclopentanone)
3) R¹ = F & R² = phenyl
   n = 4 to 8
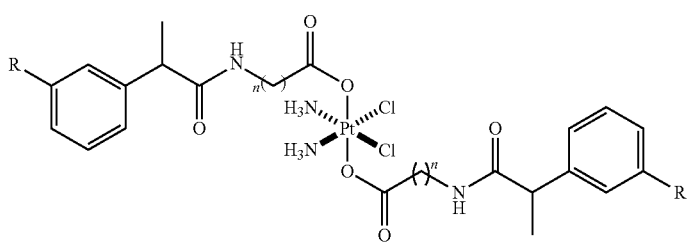
1) R = —O—phenyl
2) R = —C(=O)—phenyl
   n = 4 to 8
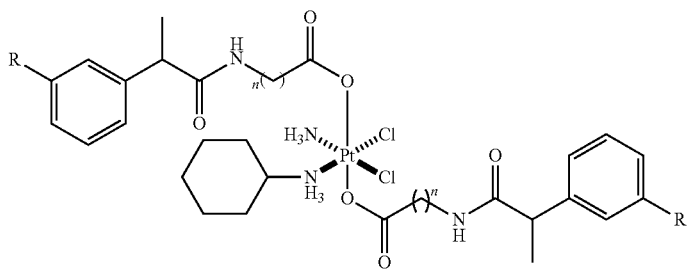
1) R = —O—phenyl
2) R = —C(=O)—phenyl
   n = 4 to 8

-continued
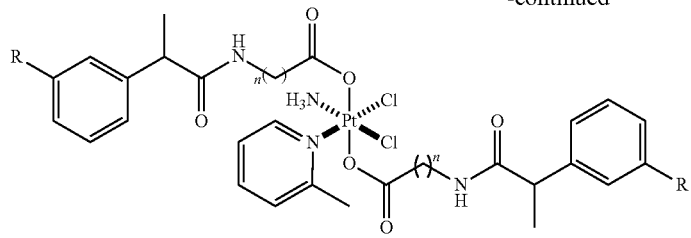
1) R = —O—phenyl
2) R = —C(=O)—phenyl
n = 4 to 8
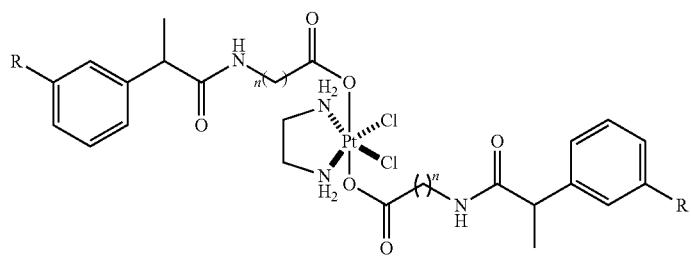
1) R = —O—phenyl
2) R = —C(=O)—phenyl
n = 4 to 8
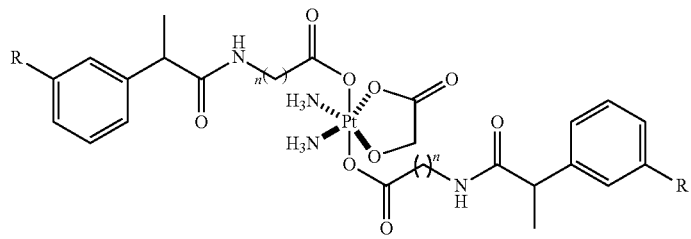
1) R = —O—phenyl
2) R = —C(=O)—phenyl
n = 4 to 8
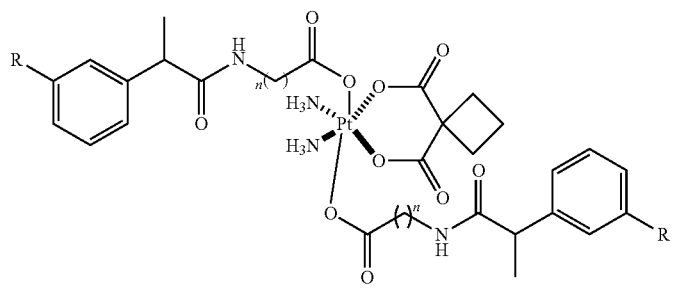
1) R = —O—phenyl
2) R = —C(=O)—phenyl
n = 4 to 8
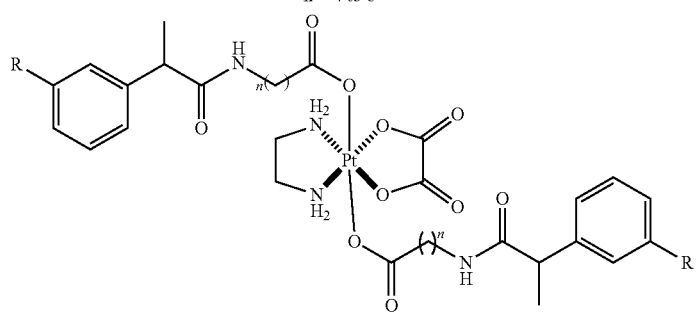
1) R = —O—phenyl
2) R = —C(=O)—phenyl
n = 4 to 8

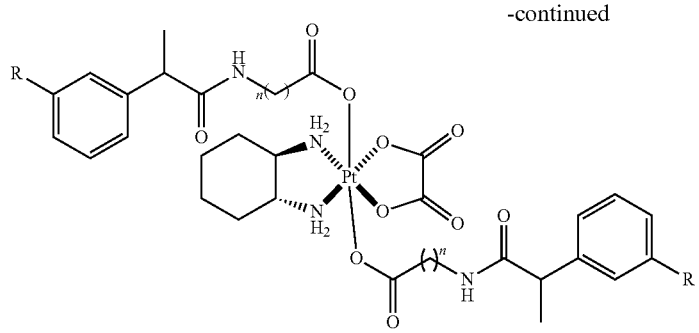
1) R = —O—phenyl
2) R = —C(=O)—phenyl
n = 4 to 8
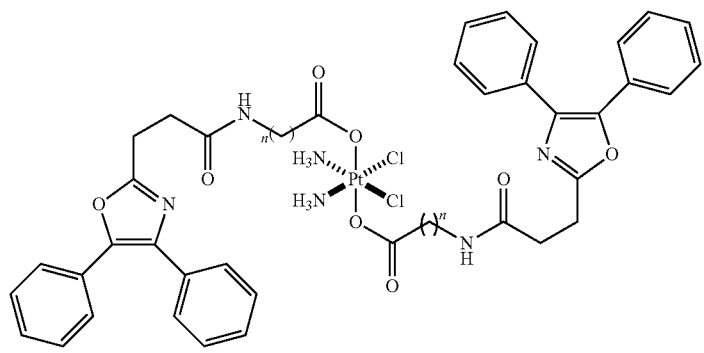
n = 4 to 8
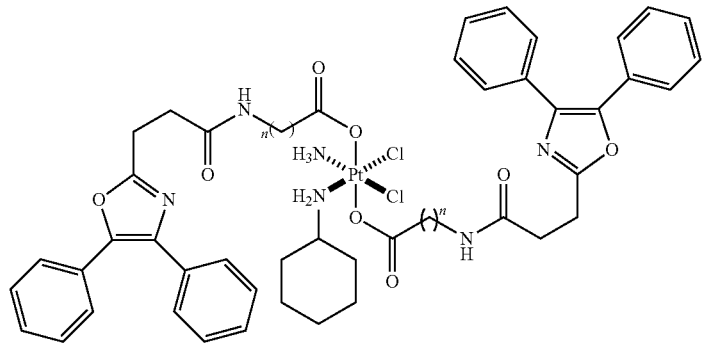
n = 4 to 8
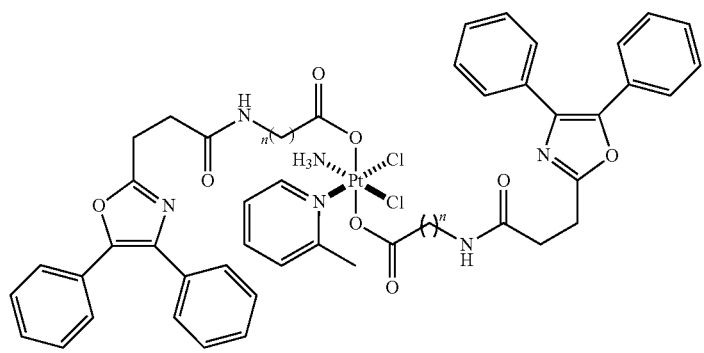
n = 4 to 8

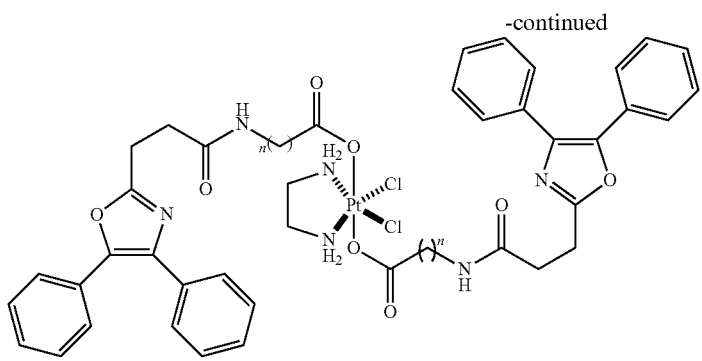
n = 4 to 8
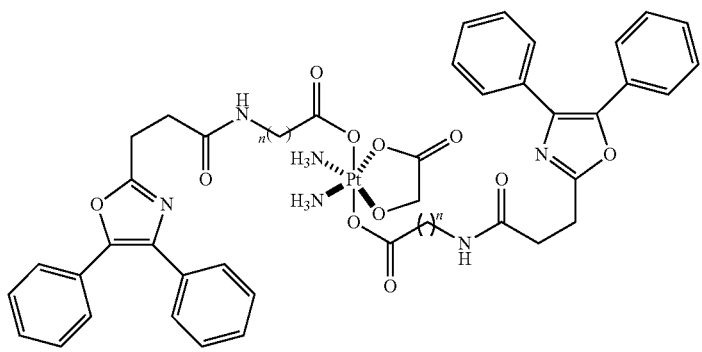
n = 4 to 8
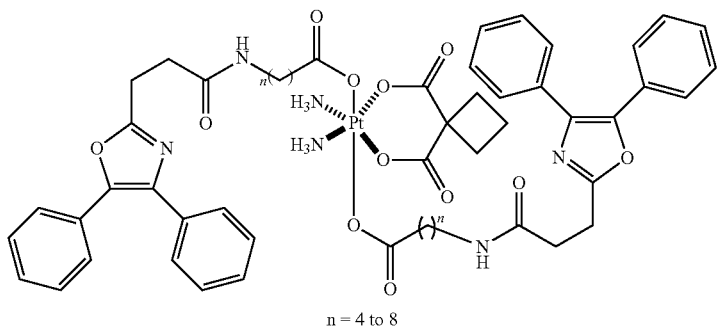
n = 4 to 8
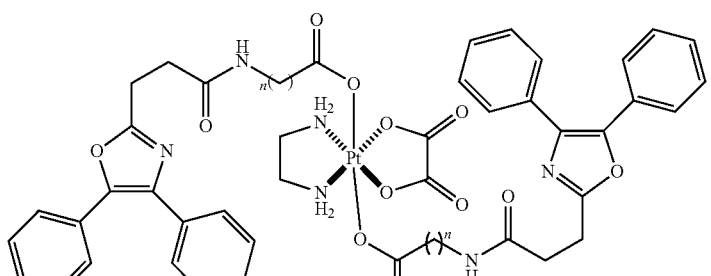
n = 4 to 8

-continued
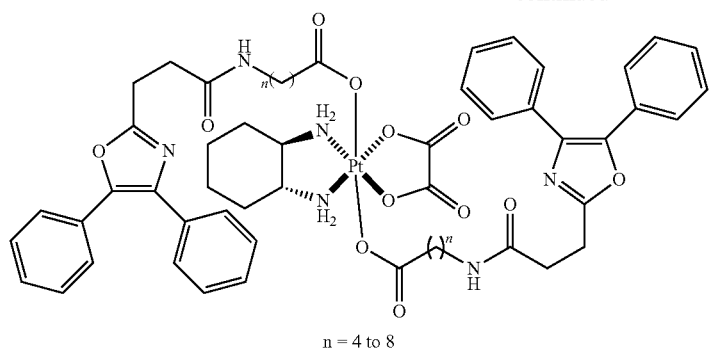
n = 4 to 8
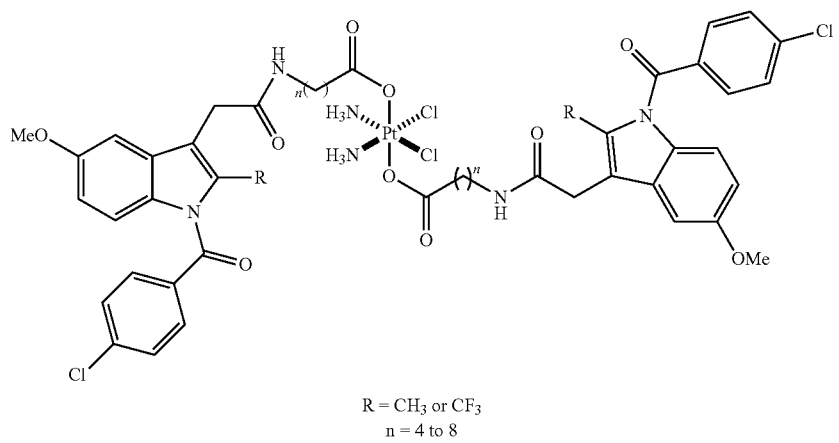
R = CH₃ or CF₃
n = 4 to 8
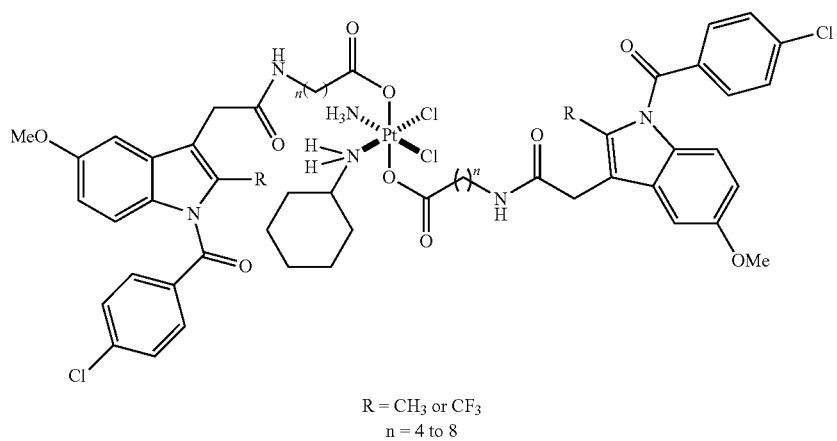
R = CH₃ or CF₃
n = 4 to 8
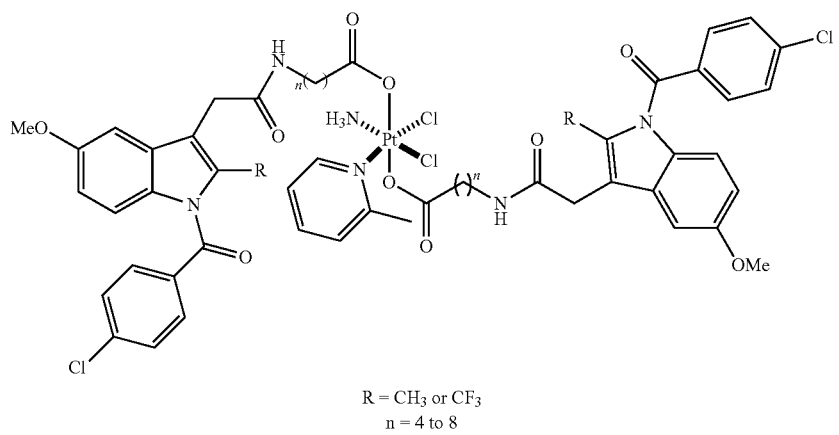
R = CH₃ or CF₃
n = 4 to 8

-continued
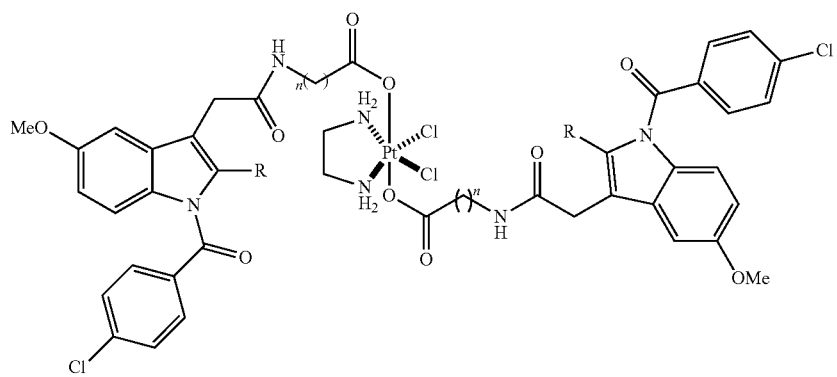
R = CH₃ or CF₃
n = 4 to 8
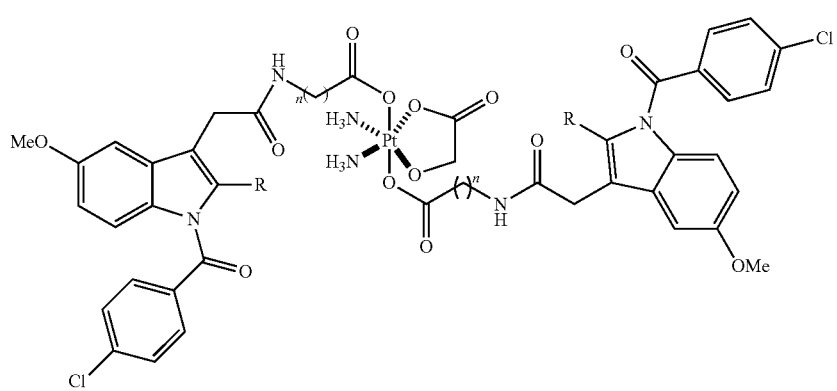
R = CH₃ or CF₃
n = 4 to 8
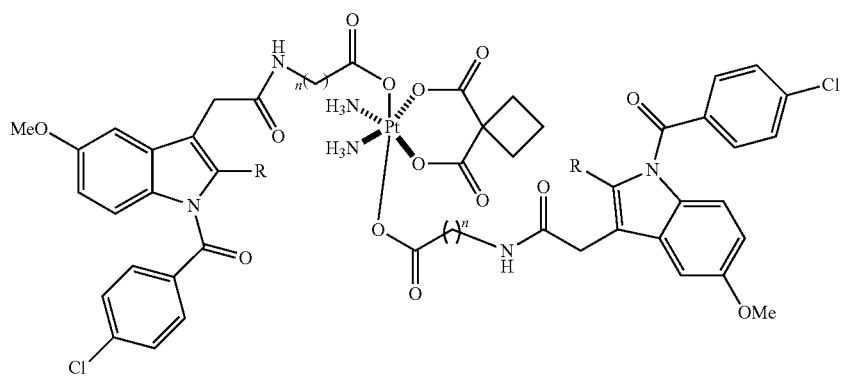
R = CH₃ or CF₃
n = 4 to 8

-continued
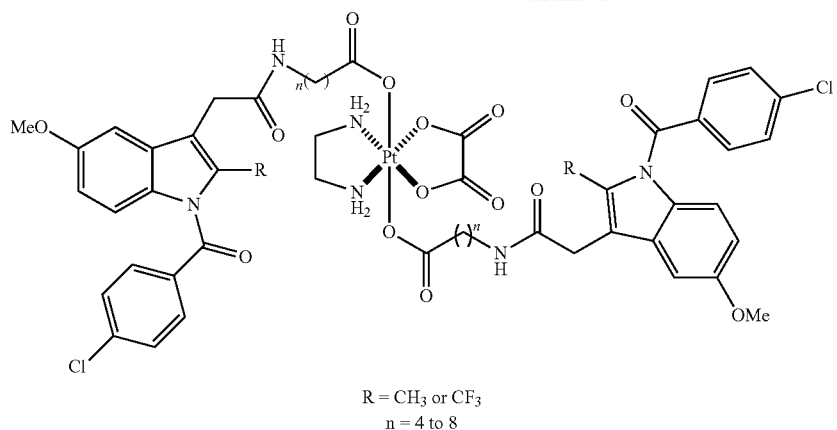
R = CH₃ or CF₃
n = 4 to 8
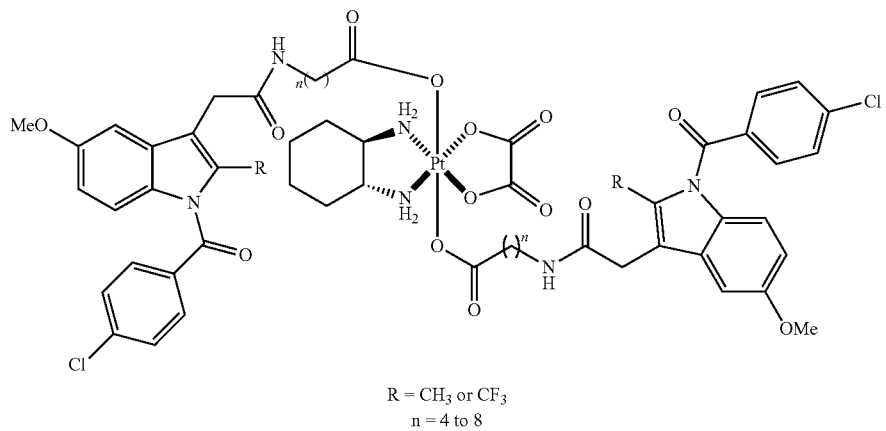
R = CH₃ or CF₃
n = 4 to 8
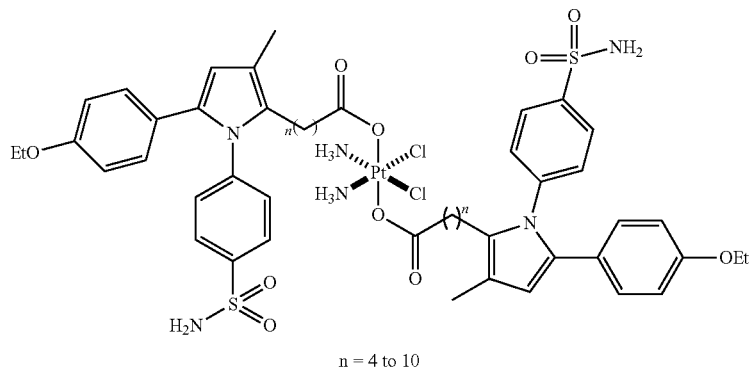
n = 4 to 10
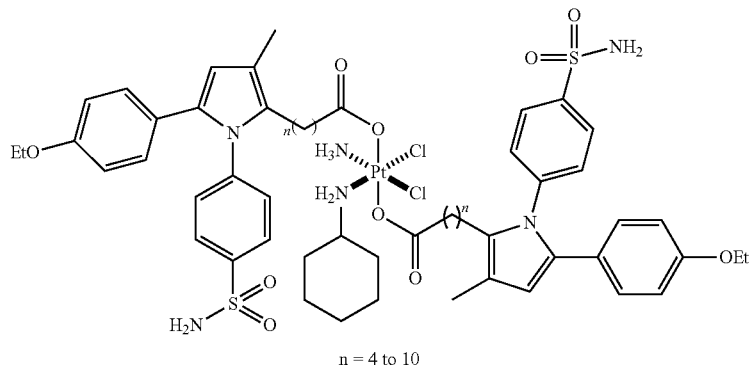
n = 4 to 10

-continued
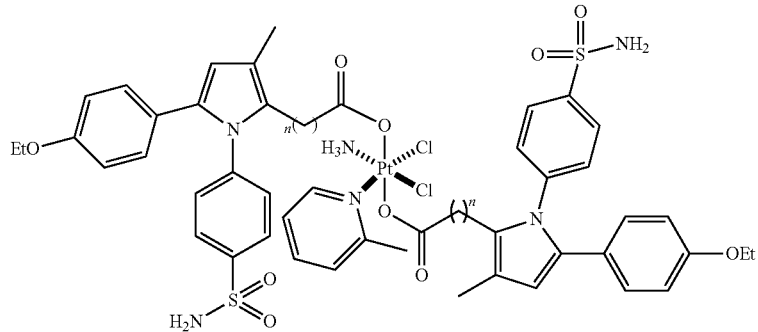
n = 4 to 10
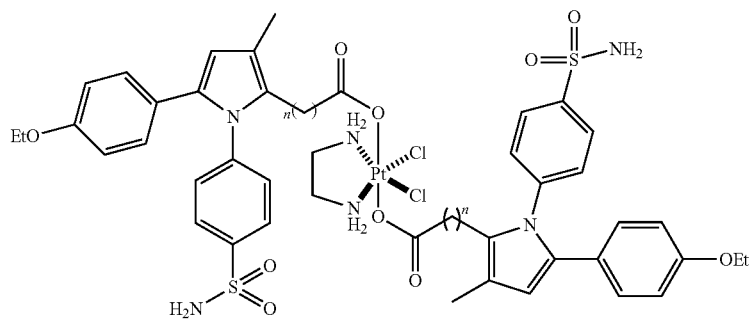
n = 4 to 10
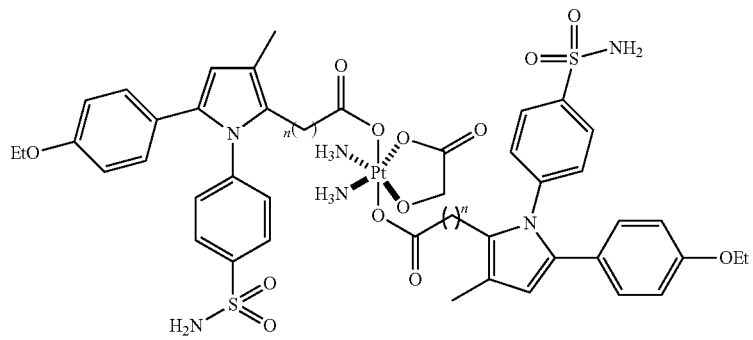
n = 4 to 10
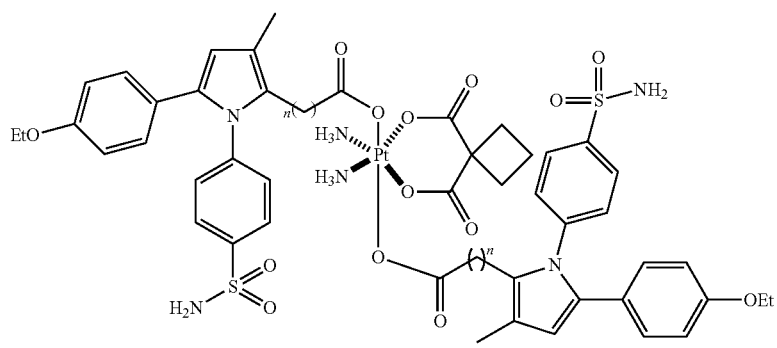
n = 4 to 10

-continued
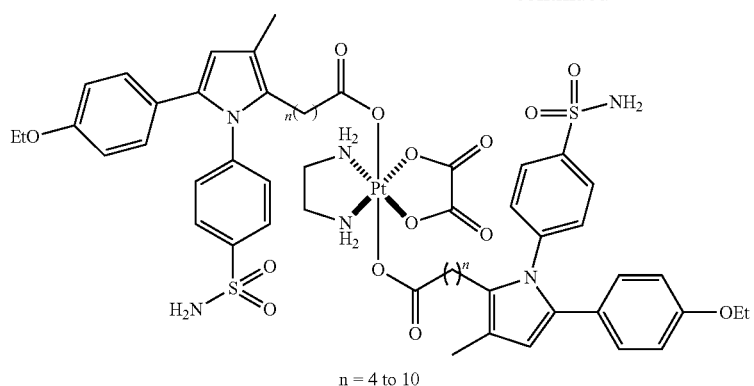
n = 4 to 10
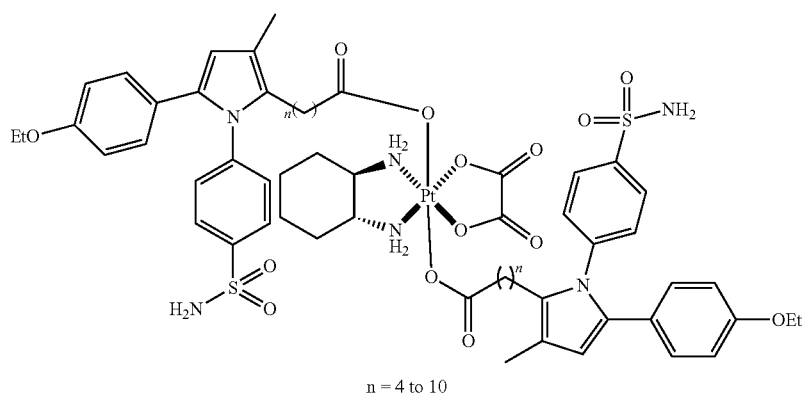
n = 4 to 10
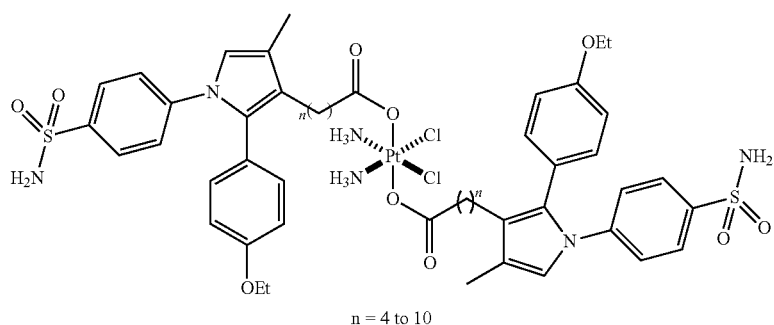
n = 4 to 10
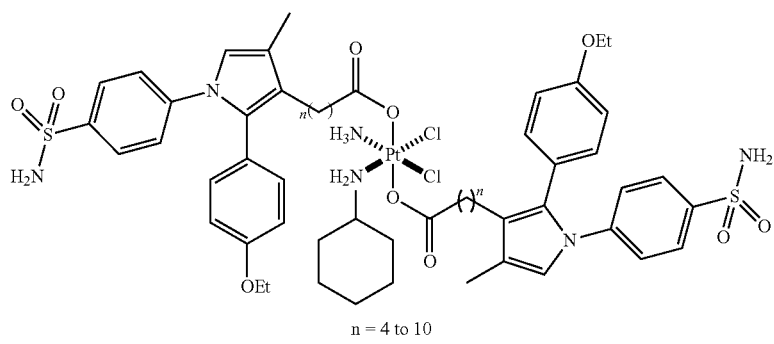
n = 4 to 10

-continued
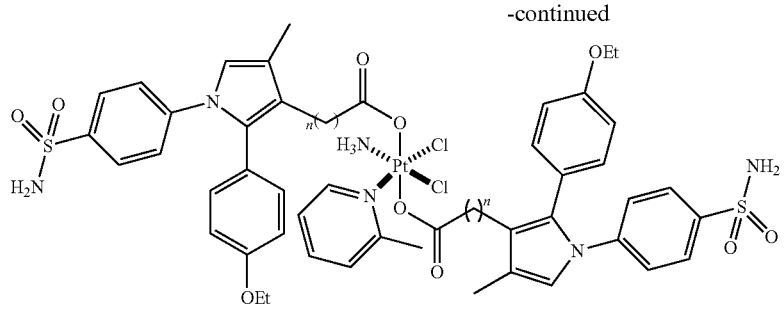
n = 4 to 10
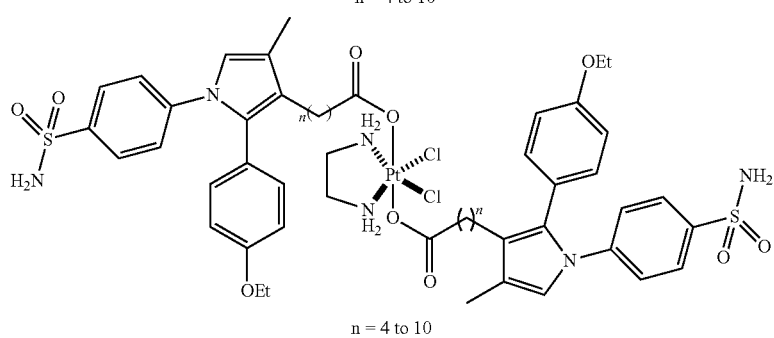
n = 4 to 10
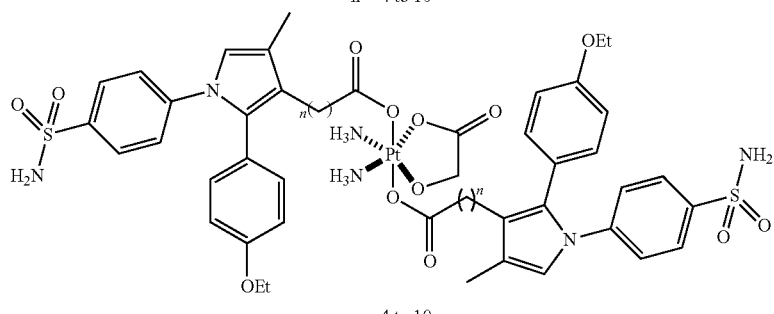
n = 4 to 10
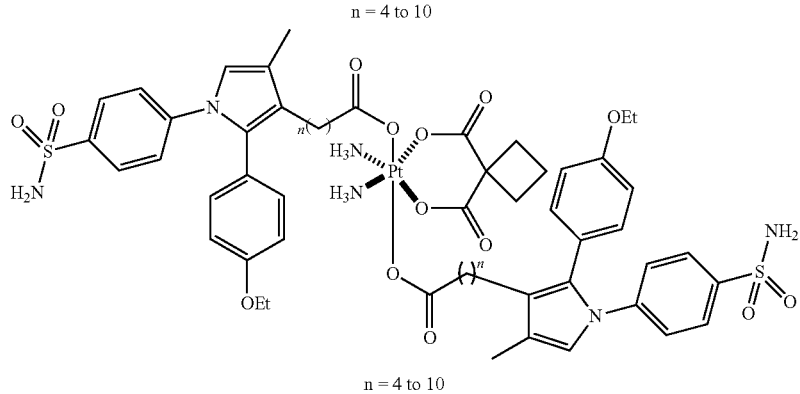
n = 4 to 10
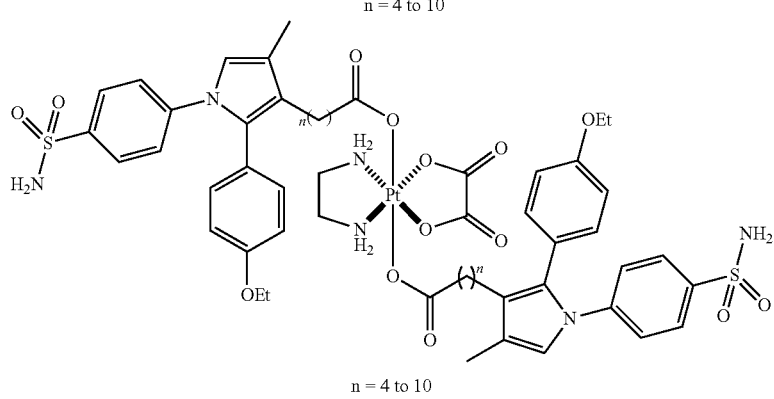
n = 4 to 10

-continued
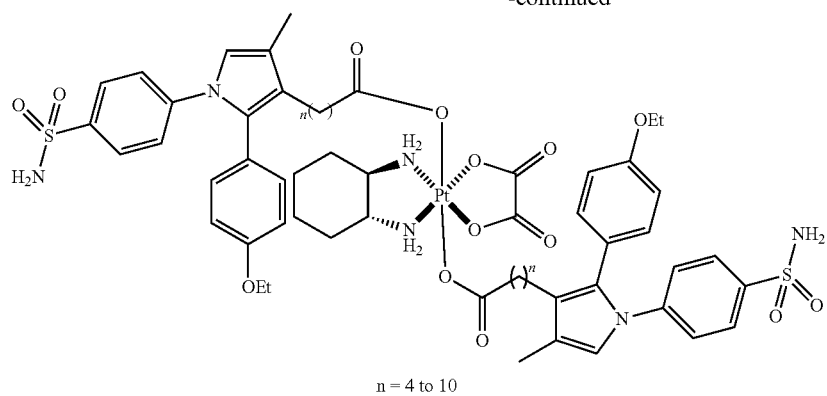
n = 4 to 10
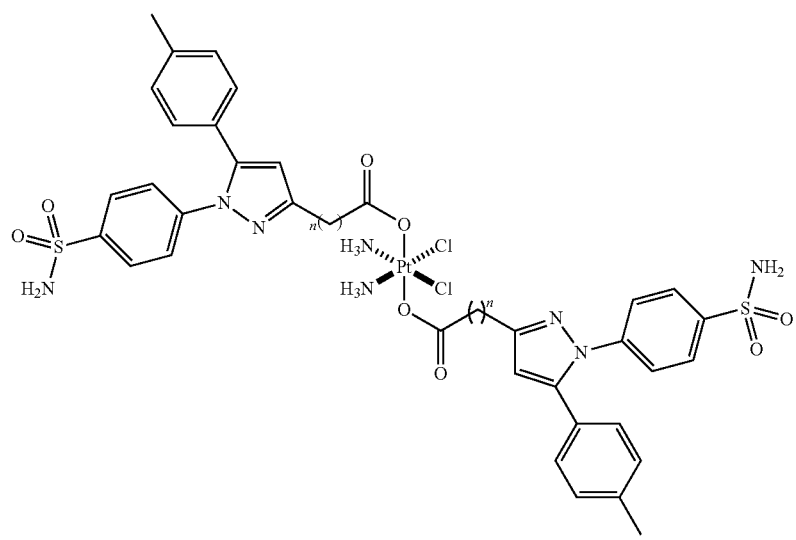
n = 4 to 10
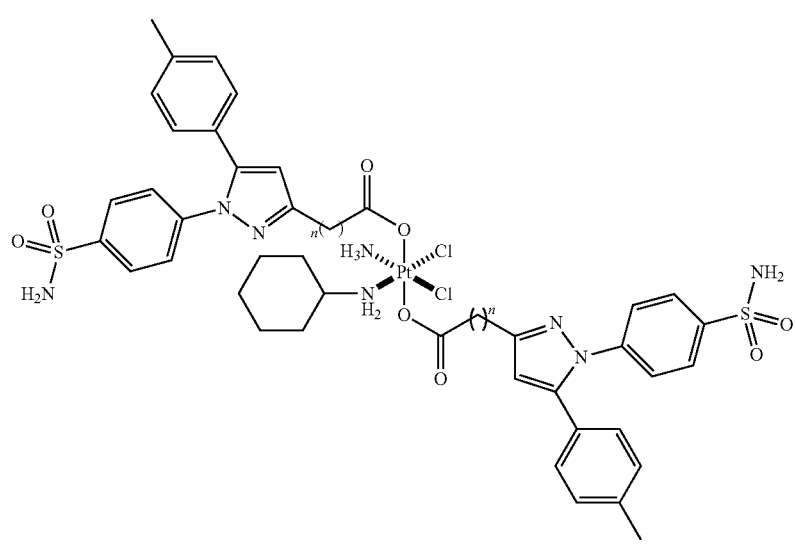
n = 4 to 10

-continued
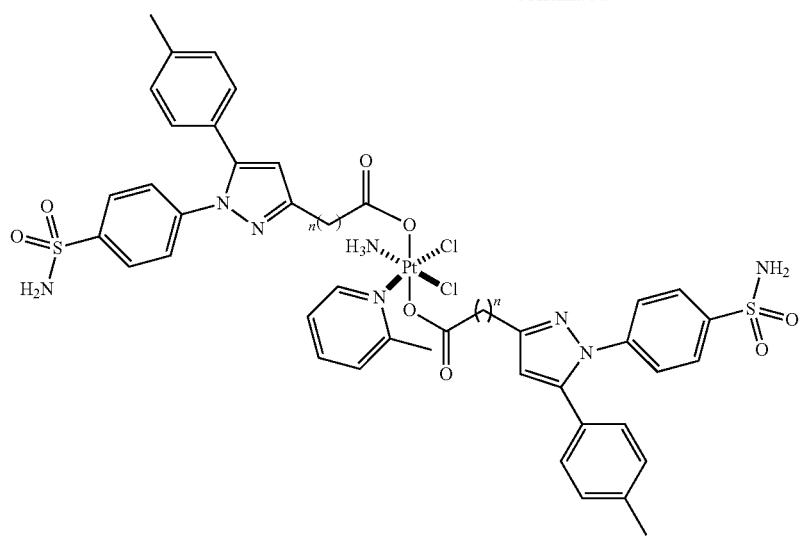
n = 4 to 10
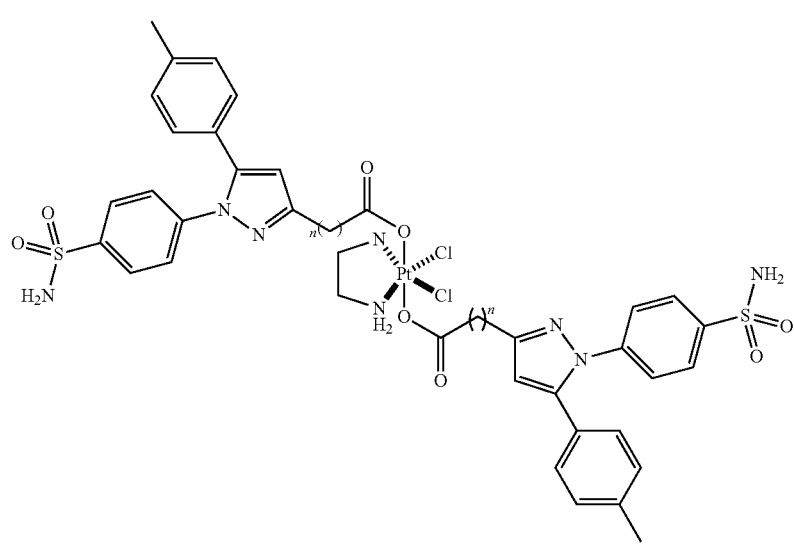
n = 4 to 10
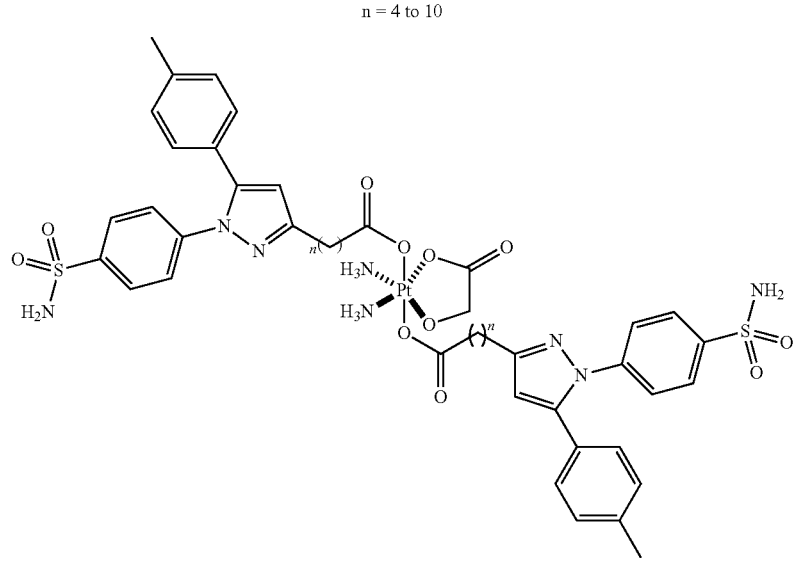
n = 4 to 10

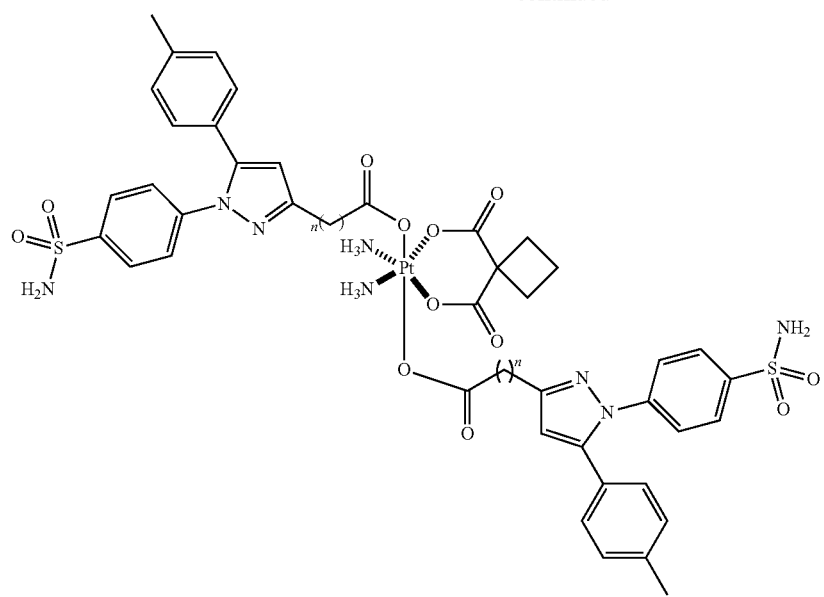
n = 4 to 10
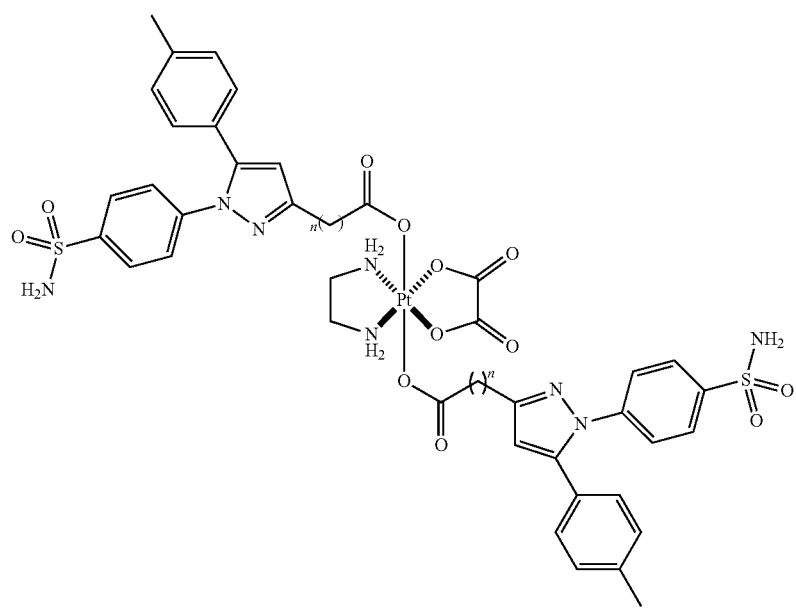
n = 4 to 10

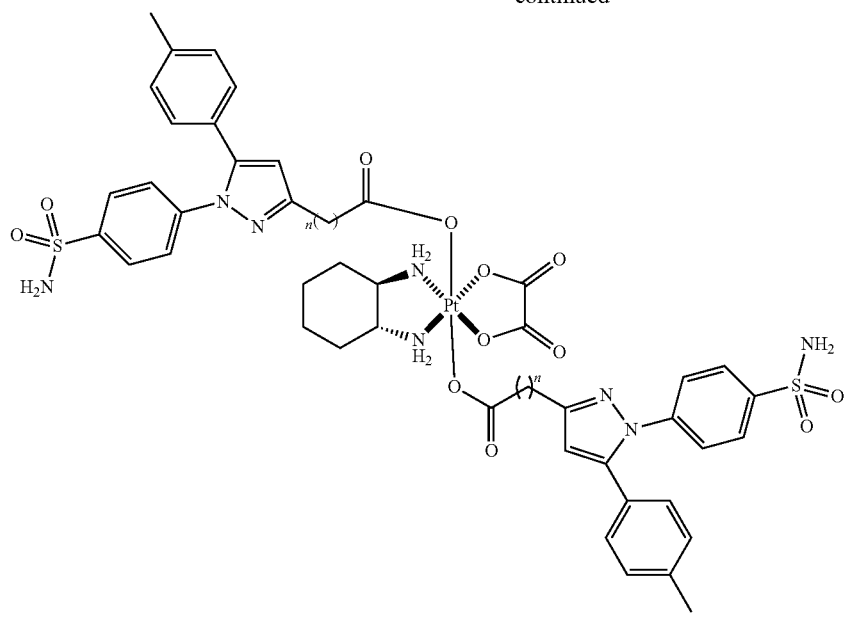
n = 4 to 10
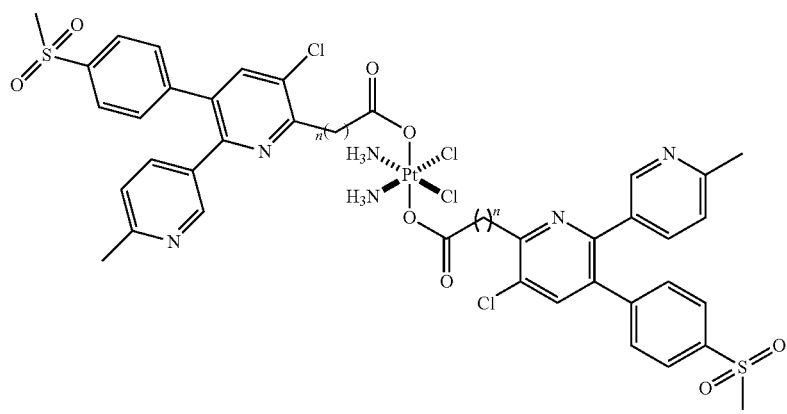
n = 4 to 10
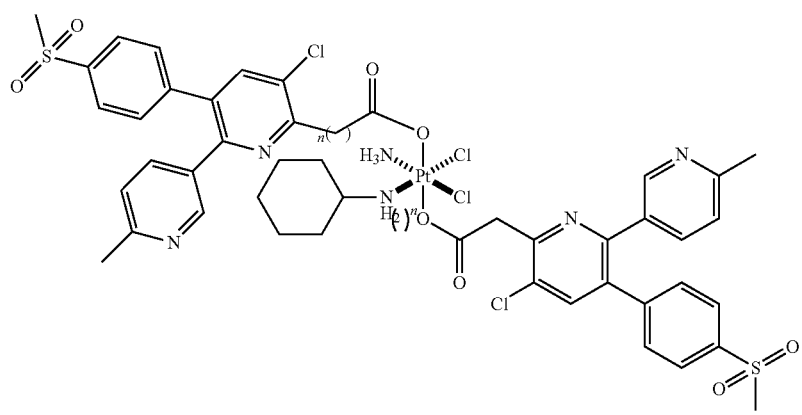
n = 4 to 10

-continued
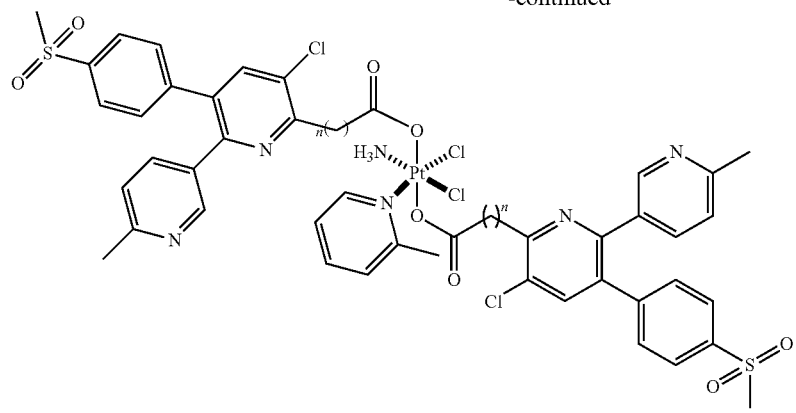
n = 4 to 10
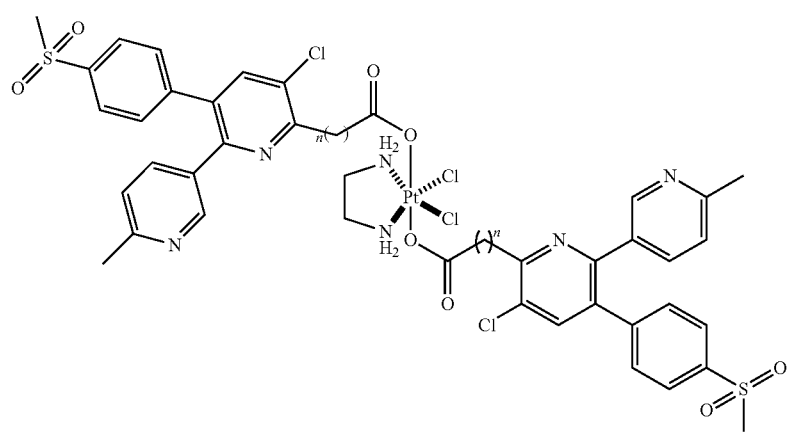
n = 4 to 10
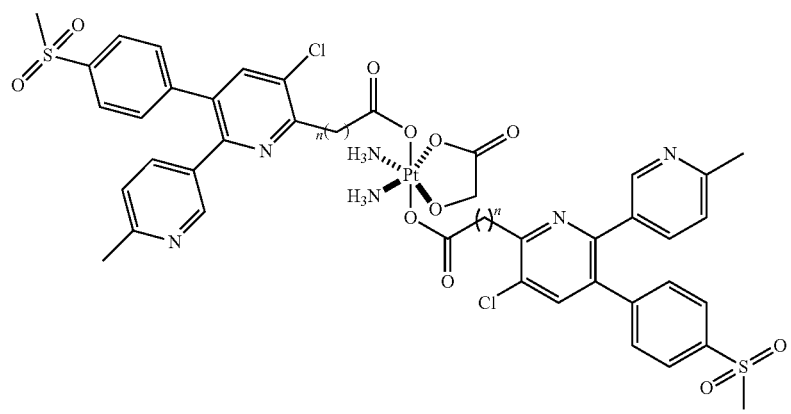
n = 4 to 10

-continued
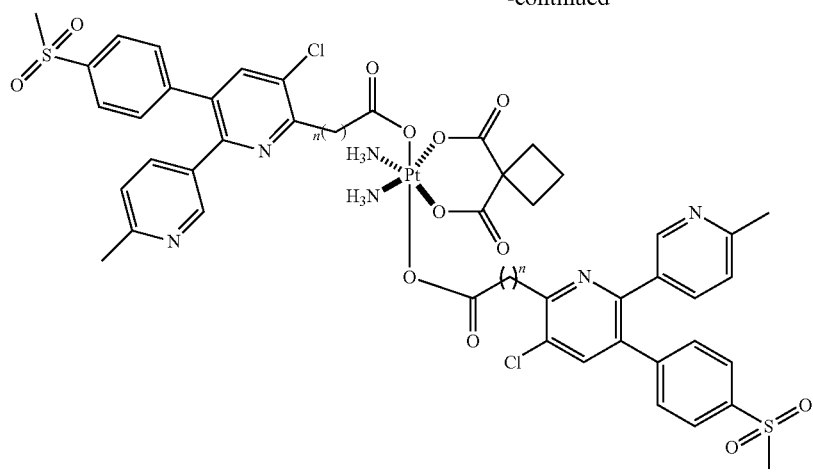
n = 4 to 10
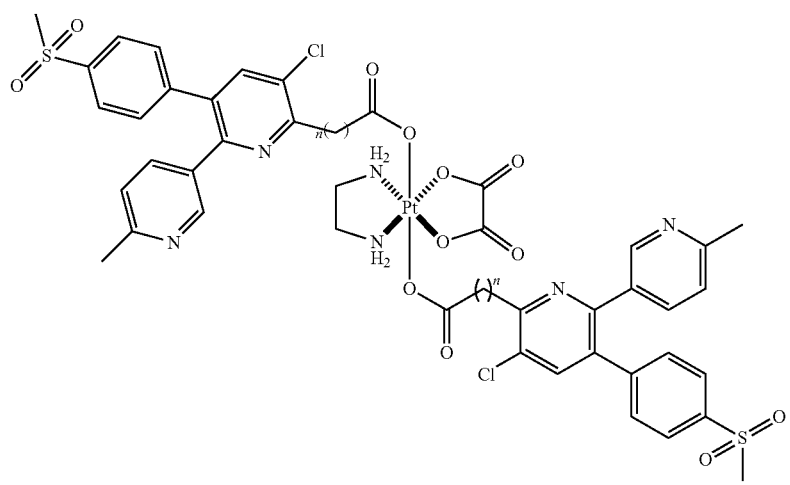
n = 4 to 10
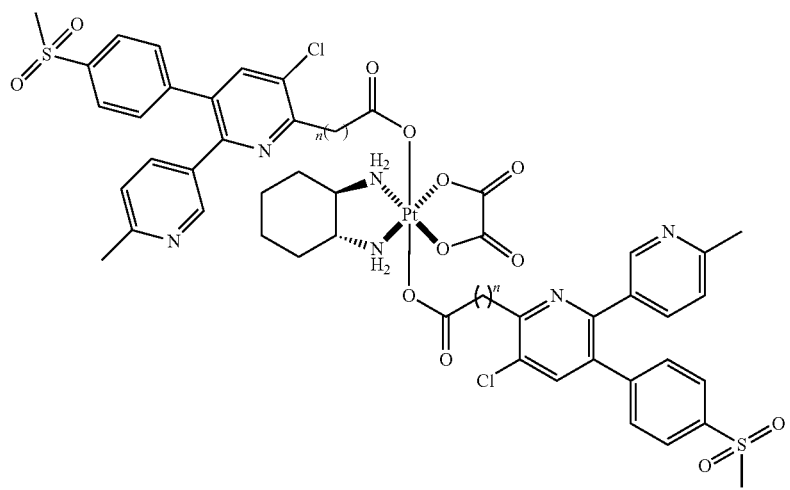
n = 4 to 10

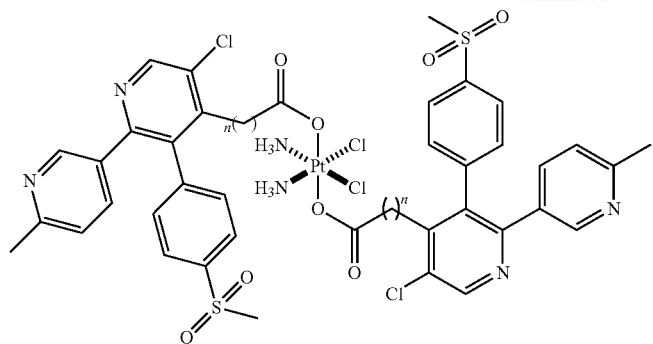
n = 4 to 10
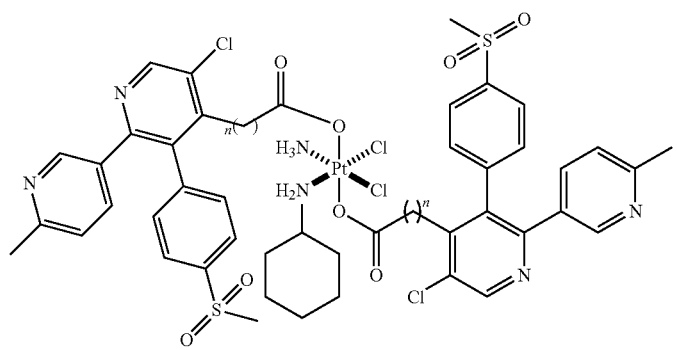
n = 4 to 10
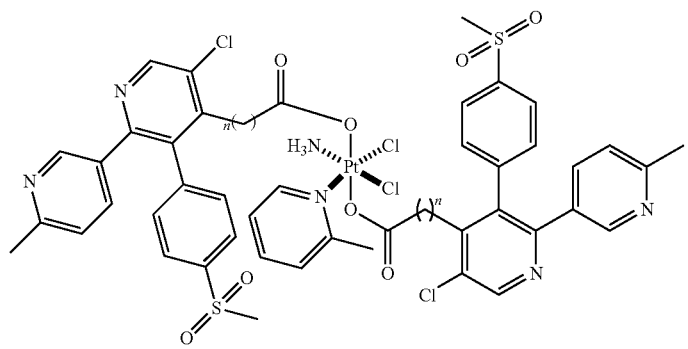
n = 4 to 10
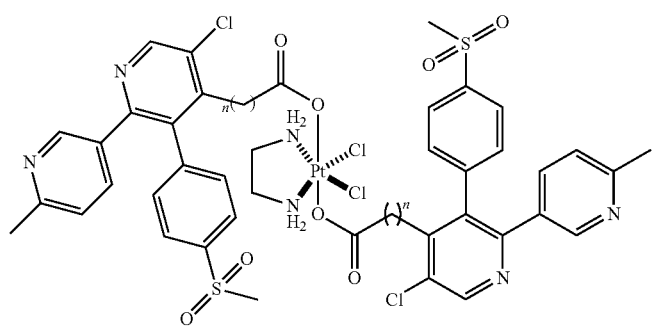
n = 4 to 10

-continued
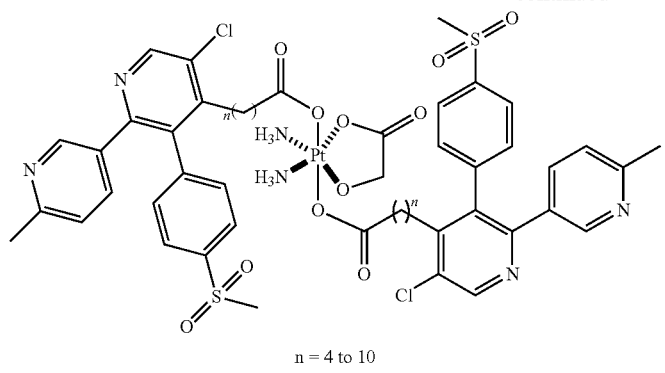
n = 4 to 10
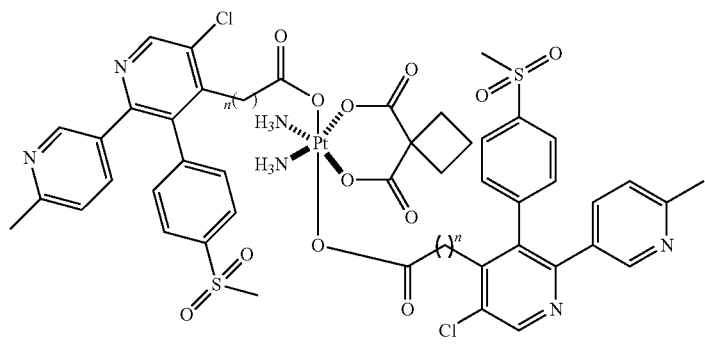
n = 4 to 10
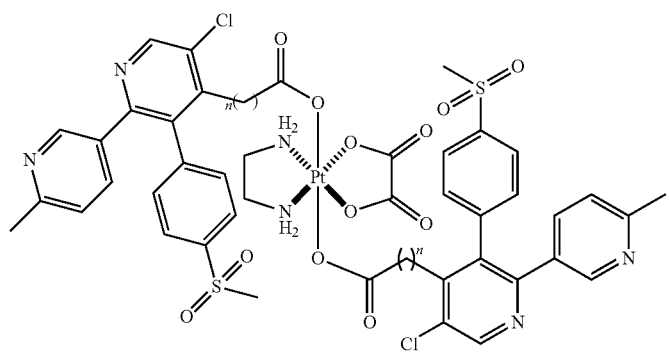
n = 4 to 10
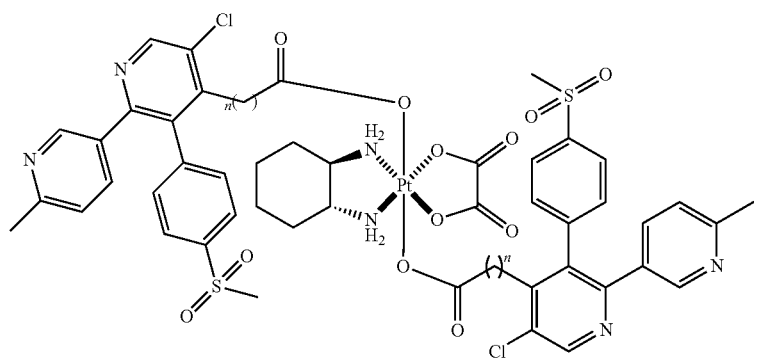
n = 4 to 10

-continued
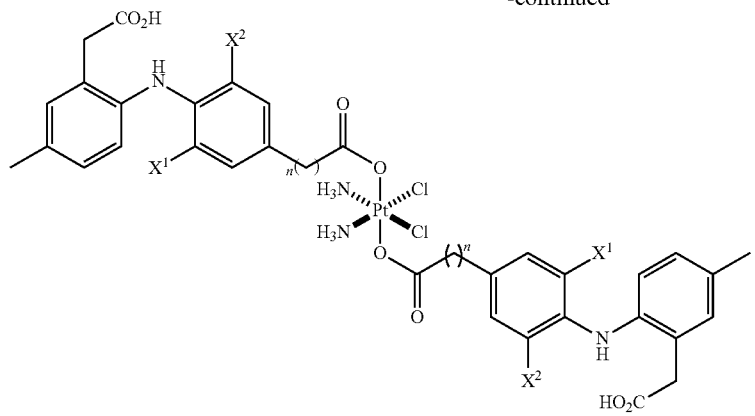
1) $X^1 = F$ & $X^2 = Cl$;
2) $X^1 = X^2 = F$; or
3) $X^1 = X^2 = Cl$
n = 4 to 10
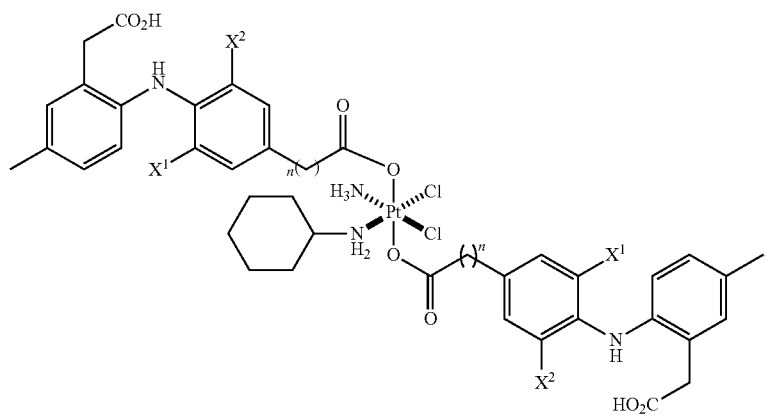
1) $X^1 = F$ & $X^2 = Cl$;
2) $X^1 = X^2 = F$; or
3) $X^1 = X^2 = Cl$
n = 4 to 10
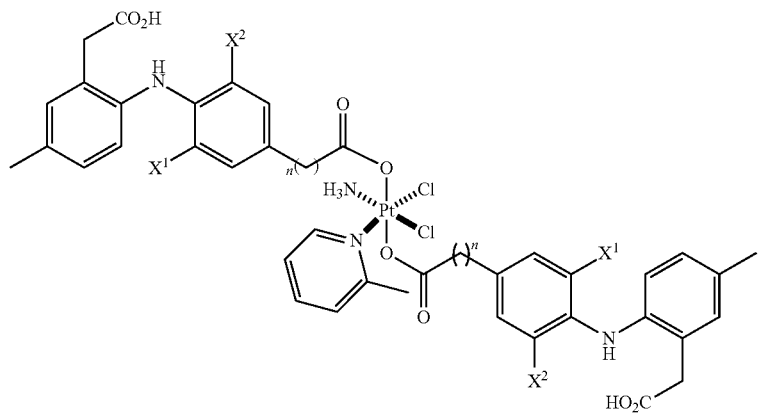
1) $X^1 = F$ & $X^2 = Cl$;
2) $X^1 = X^2 = F$; or
3) $X^1 = X^2 = Cl$
n = 4 to 10

-continued
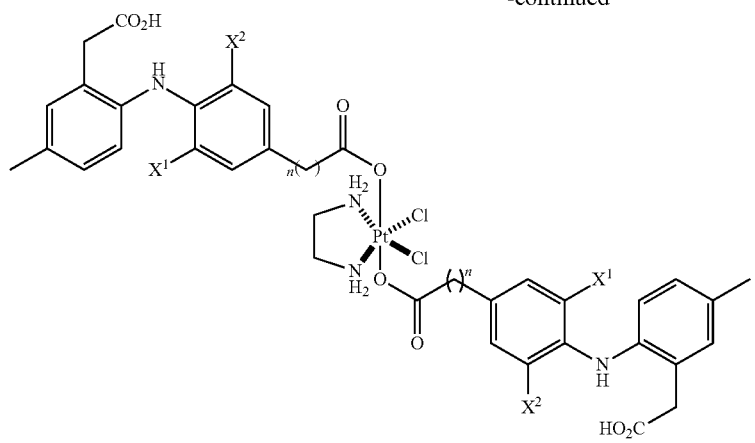
1) $X^1$ = F & $X^2$ = Cl;
2) $X^1$ = $X^2$ = F; or
3) $X^1$ = $X^2$ = Cl
n = 4 to 10
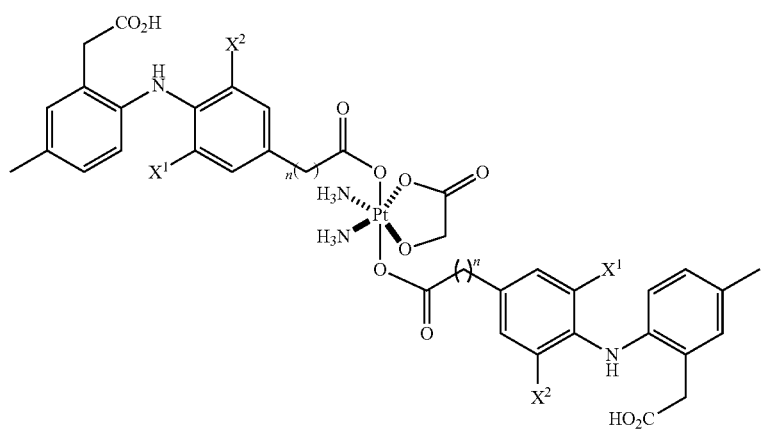
1) $X^1$ = F & $X^2$ = Cl;
2) $X^1$ = $X^2$ = F; or
3) $X^1$ = $X^2$ = Cl
n = 4 to 10
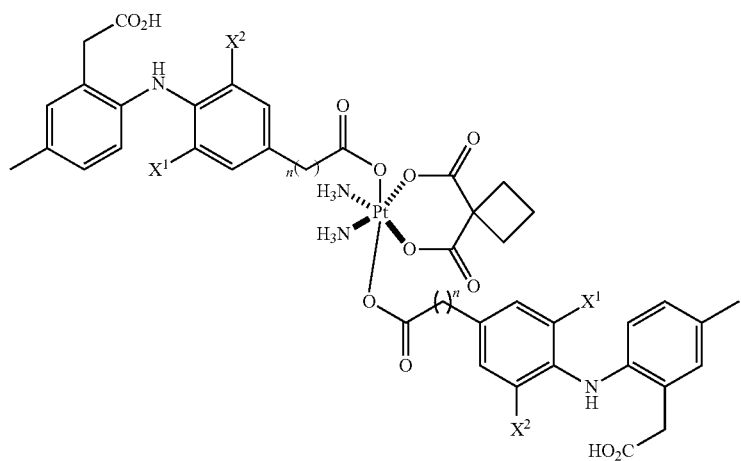
1) $X^1$ = F & $X^2$ = Cl;
2) $X^1$ = $X^2$ = F; or
3) $X^1$ = $X^2$ = Cl
n = 4 to 10

-continued
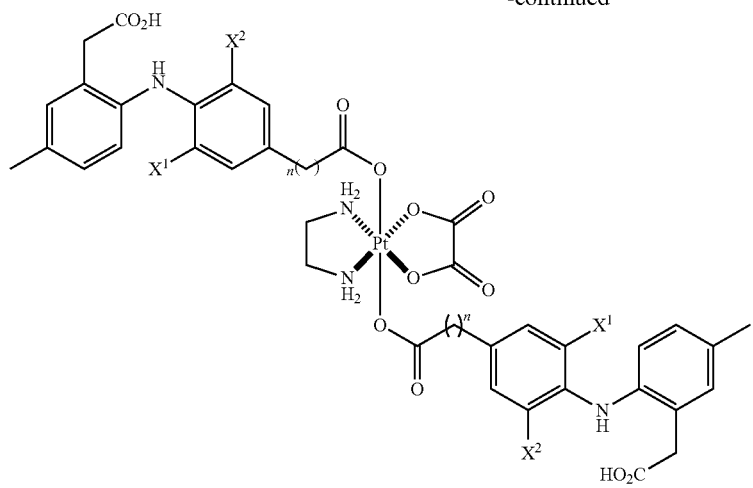
1) $X^1$ = F & $X^2$ = Cl;
2) $X^1$ = $X^2$ = F; or
3) $X^1$ = $X^2$ = Cl
n = 4 to 10
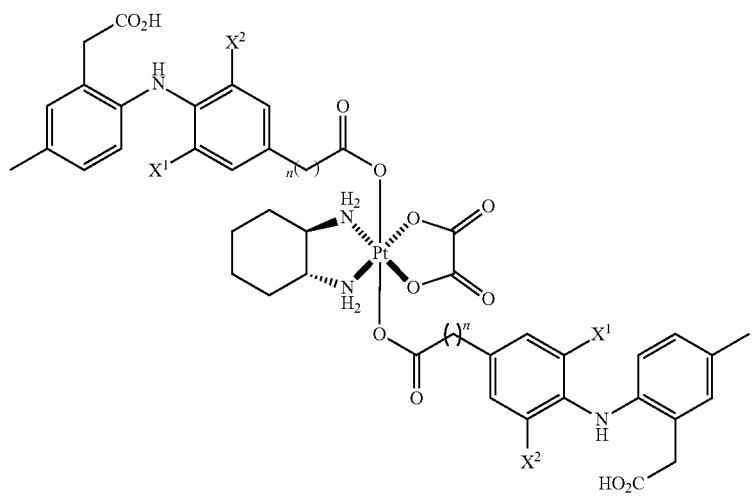
1) $X^1$ = F & $X^2$ = Cl;
2) $X^1$ = $X^2$ = F; or
3) $X^1$ = $X^2$ = Cl
n = 4 to 10
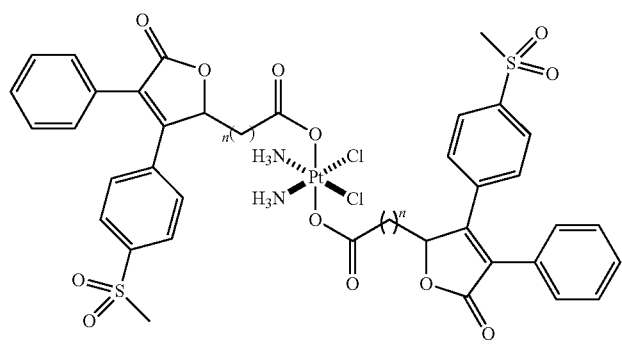
n = 4 to 10

-continued
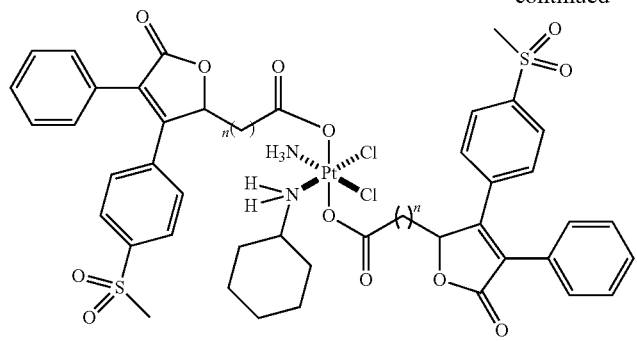
n = 4 to 10
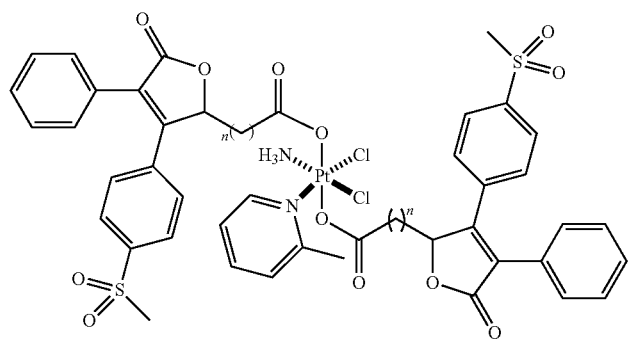
n = 4 to 10
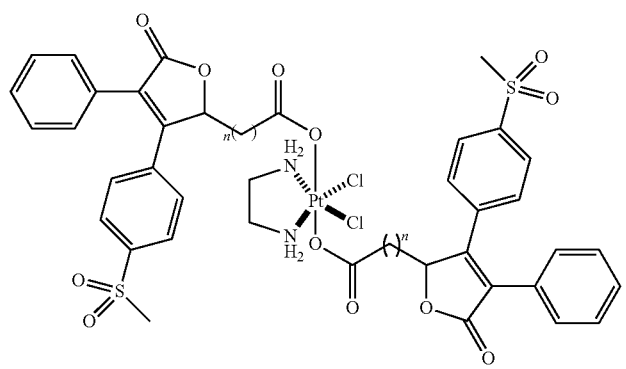
n = 4 to 10
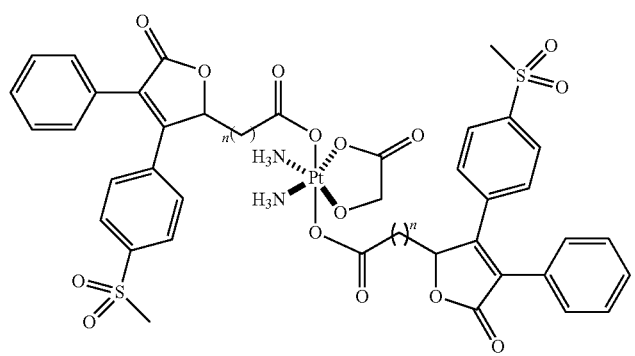
n = 4 to 10

-continued
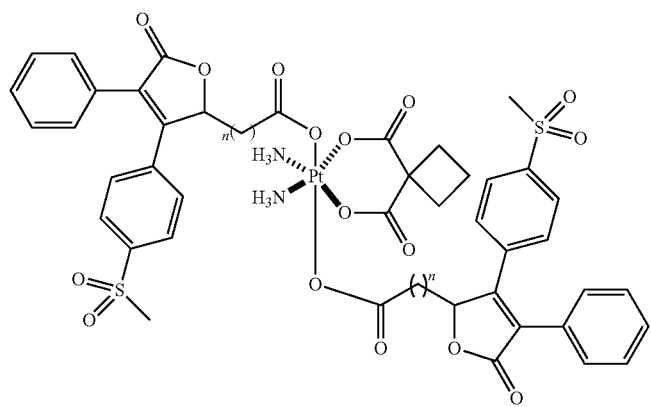
n = 4 to 10
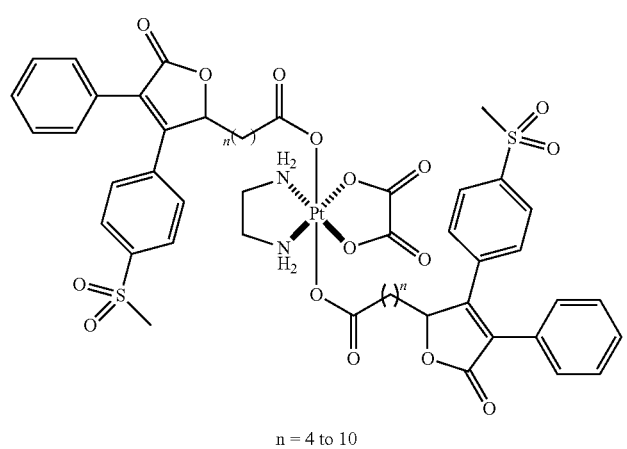
n = 4 to 10
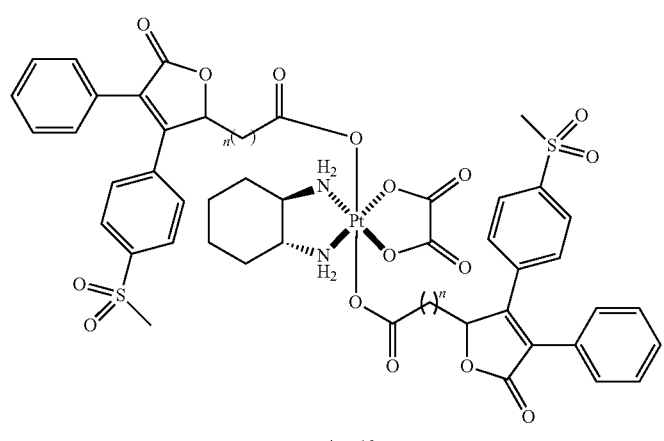
n = 4 to 10
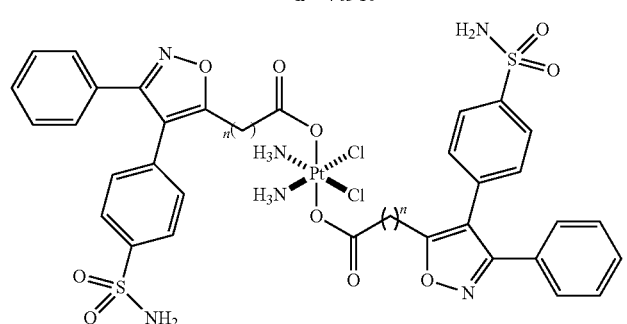
n = 4 to 10

-continued
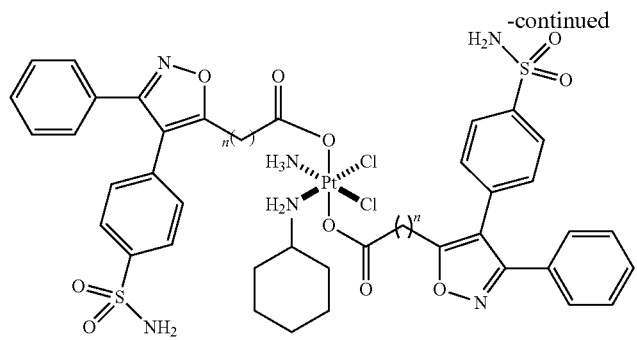
n = 4 to 10
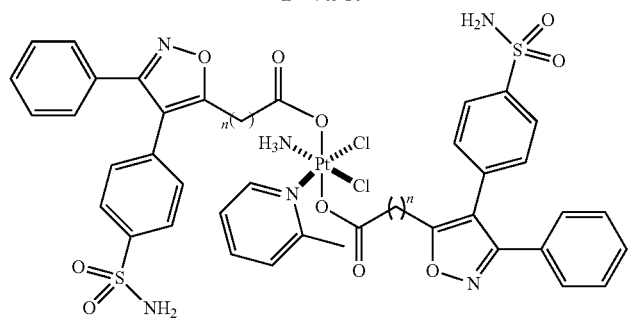
n = 4 to 10
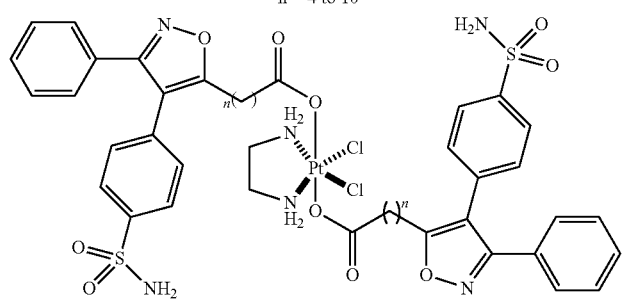
n = 4 to 10
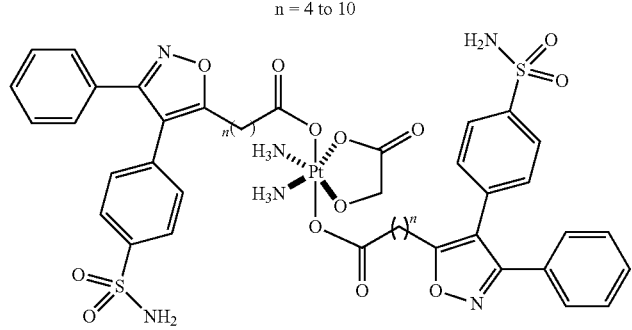
n = 4 to 10
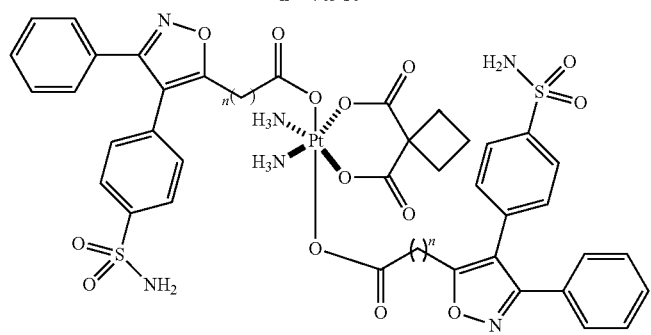
n = 4 to 10

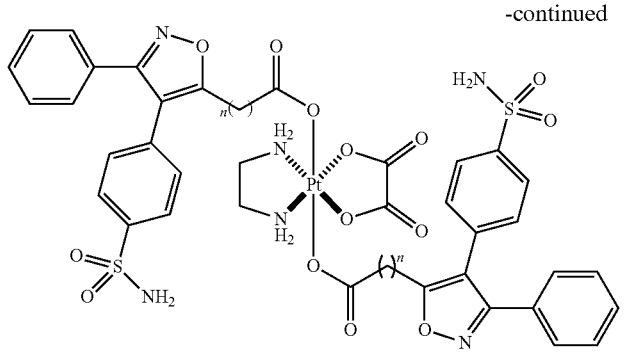

n = 4 to 10

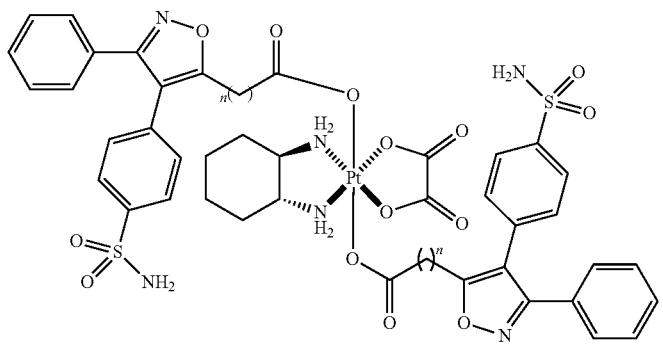

n = 4 to 10 and corresponding conjugates in which the platinum metal is connected to a COX-2-targeting moiety at one axial position and has a —OC(=O)$R^{10}$ or —OC(=O)-(4-phenyl-$R^{11}$) ligand at the other axial position, wherein $R^{10}$ is $C_1$-$C_{10}$ alkyl and $R^{11}$ is —H or $C_1$-$C_6$ alkyl, and pharmaceutically acceptable salts thereof.

The conjugates described herein can bind to COX-2 with high affinity. In certain embodiments, the conjugates have a dissociation constant ($K_d$) with COX-2 of no more than about 100 nM, 50 nM, 10 nM or 1 nM.

In additional embodiments, the conjugates inhibit COX-2. In certain embodiments, the conjugates have a half maximal inhibitory concentration ($IC_{50}$) of no more than about 1000 nM, 500 nM, 250 nM, 100 nM, 50 nM or 10 nM (e.g., no more than about 250 nM or 100 nM) for inhibition of COX-2 (e.g., in an enzyme assay or a cell-based assay).

In further embodiments, the conjugates, whether comprising a linker or no linker, target COX-2 selectively or preferentially (e.g., target COX-2 selectively or preferentially over COX-1). In additional embodiments, the linker(s) increase the selectivity or preference of the conjugates for COX-2 (e.g., increase the selectivity or preference of the conjugates for COX-2 over COX-1).

The present disclosure encompasses all possible stereoisomers and geometric isomers, including all possible diastereomers, enantiomers and geometric isomers of the COX-2-targeting moieties, platinum-containing antitumor agents, linkers and conjugates described herein, and not only the specific stereoisomers and geometric isomers as indicated by drawn structure or nomenclature. Some embodiments of the disclosure relate to the specific stereoisomers and geometric isomers indicated by drawn structure or nomenclature. The disclosure further encompasses all possible stereoisomers and geometric isomers of the conjugates described herein in substantially pure form or as mixtures thereof in any ratio (e.g., racemic mixtures).

The conjugates described herein can exist or be used in the form of a pharmaceutically acceptable salt. In some embodiments, the salt is an addition salt formed with an acid (e.g., a mineral acid [such as HCl, HBr, HI, nitric acid, phosphoric acid or sulfuric acid] or an organic acid [such as a carboxylic acid or a sulfonic acid]), e.g., if the conjugate has a basic nitrogen atom. Suitable acids for use in the preparation of pharmaceutically acceptable salts include without limitation acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, D-gluconic acid, D-glucuronic acid, L-glutamic acid, alpha-oxoglutaric acid, glycolic acid, hippuric acid, hydrobromic acid, hydrochloric acid, hydroiodic acid, (±)-DL-lactic acid, (+)-L-lactic acid, lactobionic acid, lauric acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, propionic acid, L-pyroglutamic acid, pyruvic acid, saccharic acid, salicylic acid, 4-amino-salicylic acid, sebacic acid, stearic acid, succinic acid, sulfuric acid, tannic acid, (±)-DL-tartaric acid, (+)-L-tartaric acid, thiocyanic acid, p-toluenesulfonic acid, undecylenic acid, and valeric acid.

If the conjugate has an acidic group (e.g., a carboxyl group), an addition salt can be formed with a base. Pharmaceutically acceptable base addition salts can be formed with, e.g., metals (e.g., alkali metals or alkaline earth metals) or amines (e.g., organic amines). Non-limiting examples of metals useful as cations include alkali metals (e.g., lithium, sodium, potassium and cesium), alkaline earth metals (e.g., magnesium and calcium), aluminum and zinc. Metal cations can be provided by way of, e.g., inorganic bases, such as hydroxides, carbonates and hydrogen carbonates. Non-limiting examples of organic amines useful for forming base addition salts include chloroprocaine, choline, cyclohexylamine, dibenzylamine, N,N'-dibenzylethylenediamine, dicyclohexylamine, diethanolamine, ethylenediamine, N-ethylpiperidine, histidine, isopropylamine, N-methylglucamine, procaine, pyrazine, triethylamine and trimethylamine. Pharmaceutically acceptable salts are discussed in detail in Handbook of Pharmaceutical Salts, Properties, Selection and Use, P. Stahl and C. Wermuth, Eds., Wiley-VCH (2011).

III. Pharmaceutical Compositions Comprising The Conjugates

To treat a tumor or cancer, the conjugates described herein can be administered alone or in the form of a pharmaceutical composition. In some embodiments, a pharmaceutical composition comprises a conjugate described herein and one or more pharmaceutically acceptable carriers or excipients. The composition can optionally contain an additional antitumor agent as described herein.

Pharmaceutically acceptable carriers and excipients include pharmaceutically acceptable materials, vehicles and substances. Non-limiting examples of excipients include liquid and solid fillers, diluents, binders, lubricants, glidants, surfactants, dispersing agents, disintegration agents, emulsifying agents, wetting agents, suspending agents, thickeners, solvents, isotonic agents, buffers, pH adjusters, absorption-delaying agents, sweetening agents, flavoring agents, coloring agents, stabilizers, preservatives, antioxidants, antimicrobial agents, antibacterial agents, antifungal agents, adjuvants, encapsulating materials and coating materials. The use of such excipients in pharmaceutical formulations is known in the art. Except insofar as any conventional carrier or excipient is incompatible with a conjugate, the disclosure encompasses the use of conventional carriers and excipients in formulations containing the conjugates described herein. See, e.g., Remington: The Science and Practice of Pharmacy, 21st Ed., Lippincott Williams & Wilkins (Philadelphia, Pa. [2005]); Handbook of Pharmaceutical Excipients, 5th Ed., Rowe et al., Eds., The Pharmaceutical Press and the American Pharmaceutical Association (2005); Handbook of Pharmaceutical Additives, 3rd Ed., Ash and Ash, Eds., Gower Publishing Co. (2007); and Pharmaceutical Preformulation and Formulation, Gibson, Ed., CRC Press LLC (Boca Raton, Fla. [2004]).

Proper formulation can depend on various factors, such as the route of administration chosen. Potential routes of administration of pharmaceutical compositions comprising the conjugates described herein include without limitation oral, parenteral (including intramuscular, subcutaneous, intradermal, intravascular, intravenous, intraarterial, intramedullary and intrathecal), intracavitary, intraperitoneal, and topical (including dermal/epicutaneous, transdermal, mucosal, transmucosal, intranasal [e.g., by nasal spray or drop], intraocular [e.g., by eye drop], pulmonary [e.g., by inhalation], buccal, sublingual, rectal and vaginal).

As an example, formulations of the conjugates suitable for oral administration can be presented as, e.g., capsules (including push-fit capsules and soft capsules), cachets or tablets; as powders or granules; as boluses, electuaries or pastes; as solutions or suspensions in an aqueous liquid and/or a non-aqueous liquid; or as oil-in-water liquid emulsions or water-in-oil liquid emulsions. For example, push-fit capsules can contain a conjugate in admixture with, e.g., a filler (e.g., lactose), a binder (e.g., a starch) and a lubricant (e.g., talc or magnesium stearate), and optionally a stabilizer. For soft capsules, a conjugate can be dissolved or suspended in a suitable liquid (e.g., a fatty oil, liquid paraffin or liquid polyethylene glycol), and a stabilizer can be added. As another example, dispersible powder or granules of a conjugate can be mixed with any suitable combination of an aqueous liquid, an organic solvent and/or an oil and any suitable excipients (e.g., any combination of a dispersing agent, a wetting agent, a suspending agent, an emulsifying agent and/or a preservative) to form a solution, suspension or emulsion.

The conjugates described herein can also be formulated for parenteral administration by injection or infusion. Formulations for injection or infusion can be in the form of, e.g., solutions, suspensions or emulsions in oily or aqueous vehicles, and can contain excipients such as suspending agents, dispersing agents and/or stabilizing agents. For example, aqueous or non-aqueous (e.g., oily) sterile injection solutions can contain a conjugate along with excipients such as an antioxidant, a buffer, a bacteriostat and solutes that render the formulation isotonic with the blood of the subject. Aqueous or non-aqueous sterile suspensions can contain a conjugate along with excipients such as a suspending agent and a thickening agent, and optionally a stabilizer and an agent that increases the solubility of the conjugate to allow for the preparation of a more concentrated solution or suspension.

Pharmaceutical compositions of the conjugates described herein can also be in the form of nanoparticles, microparticles or liposomes comprising one or more lipids and a conjugate. In some embodiments, the nanoparticles, microparticles or liposomes are composed of one or more phospholipids. Examples of phospholipids include without limitation phosphatidic acids (e.g., DMPA, DPPA and DSPA), phosphatidylcholines (e.g., DDPC, DEPC, DLPC, DMPC, DOPC, DPPC, DSPC and POPC), phosphatidylethanolamines (e.g., DMPE, DOPE, DPPE and DSPE), phosphatidylglycerols (e.g., DMPG, DPPG, DSPG and POPG), and phosphatidylserines (e.g., DOPS). Nanoparticles, microparticles or liposomes composed of a fusogenic lipid (e.g., DPPG) in the lipid bilayer can fuse with the plasma membrane of tumor/cancer cells and thereby deliver an antitumor conjugate inside those cells.

The pharmaceutical compositions can be manufactured in any suitable manner known in the art, e.g., by means of conventional mixing, dissolving, suspending, granulating, dragee-making, levigating, emulsifying, encapsulating, entrapping or compressing processes.

The compositions can be presented in unit dosage form as a single dose wherein all active and inactive ingredients are combined in a suitable system, and components do not need to be mixed to form the composition to be administered. The unit dosage form can contain an effective dose, or an appropriate fraction thereof, of a conjugate described herein. A representative example of a unit dosage form is a tablet, capsule, or pill for oral administration.

Alternatively, the compositions can be presented as a kit, wherein the active ingredient, excipients and carriers (e.g., solvents) are provided in two or more separate containers (e.g., ampules, vials, tubes, bottles or syringes) and need to be combined to form the composition to be administered. The kit can contain instructions for preparing and administering the composition (e.g., a solution to be injected intravenously).

IV. Preparation Of The Conjugates

Figure 2:
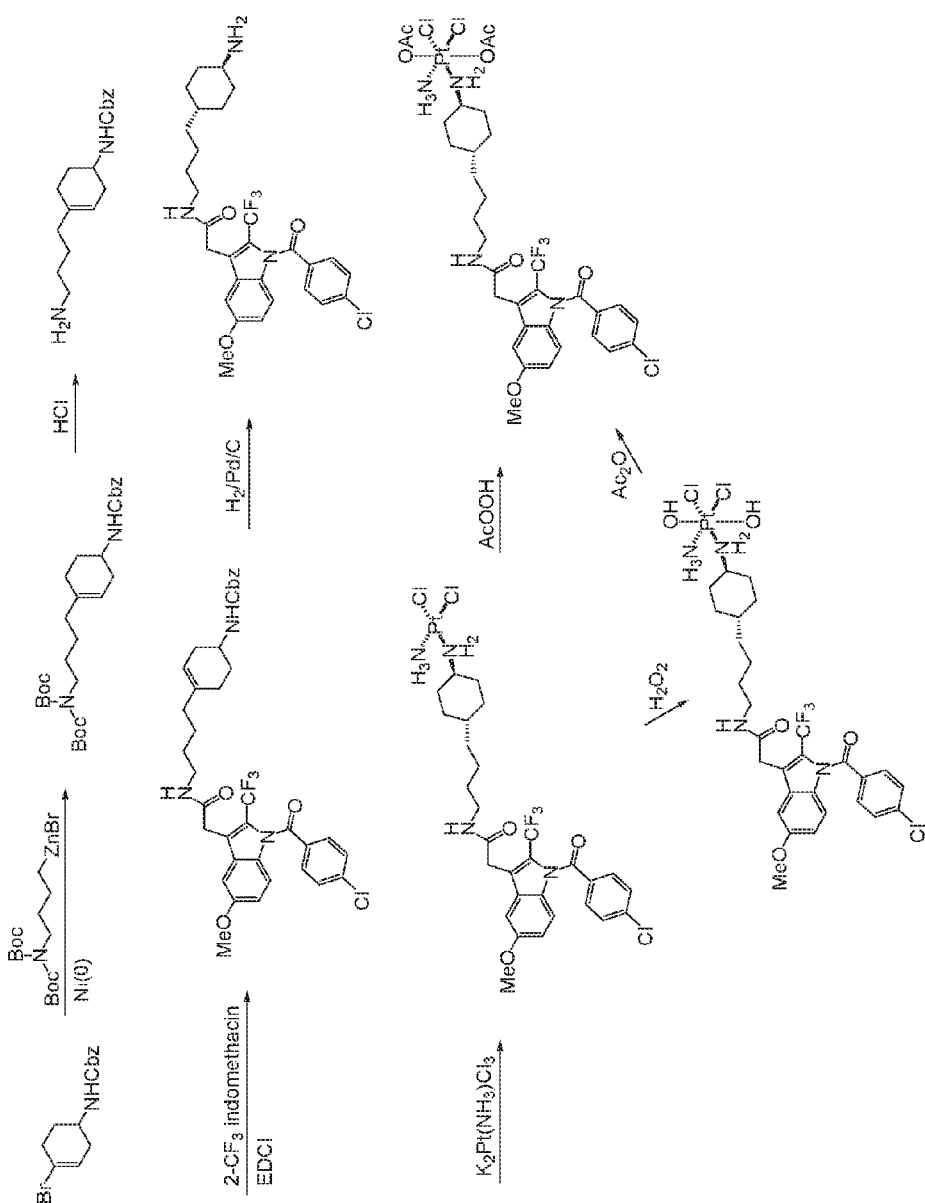
Figure 3:
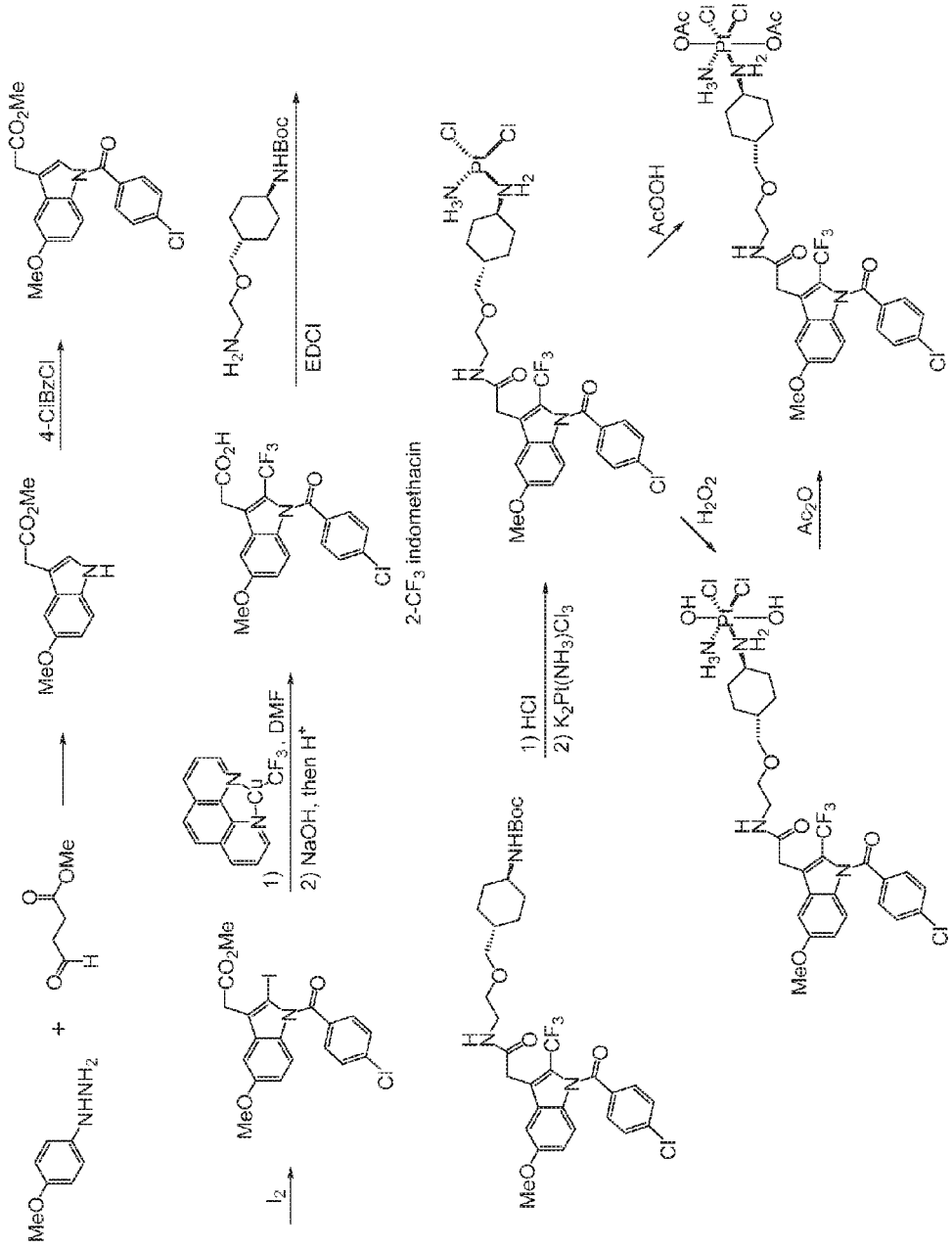
Figure 4:
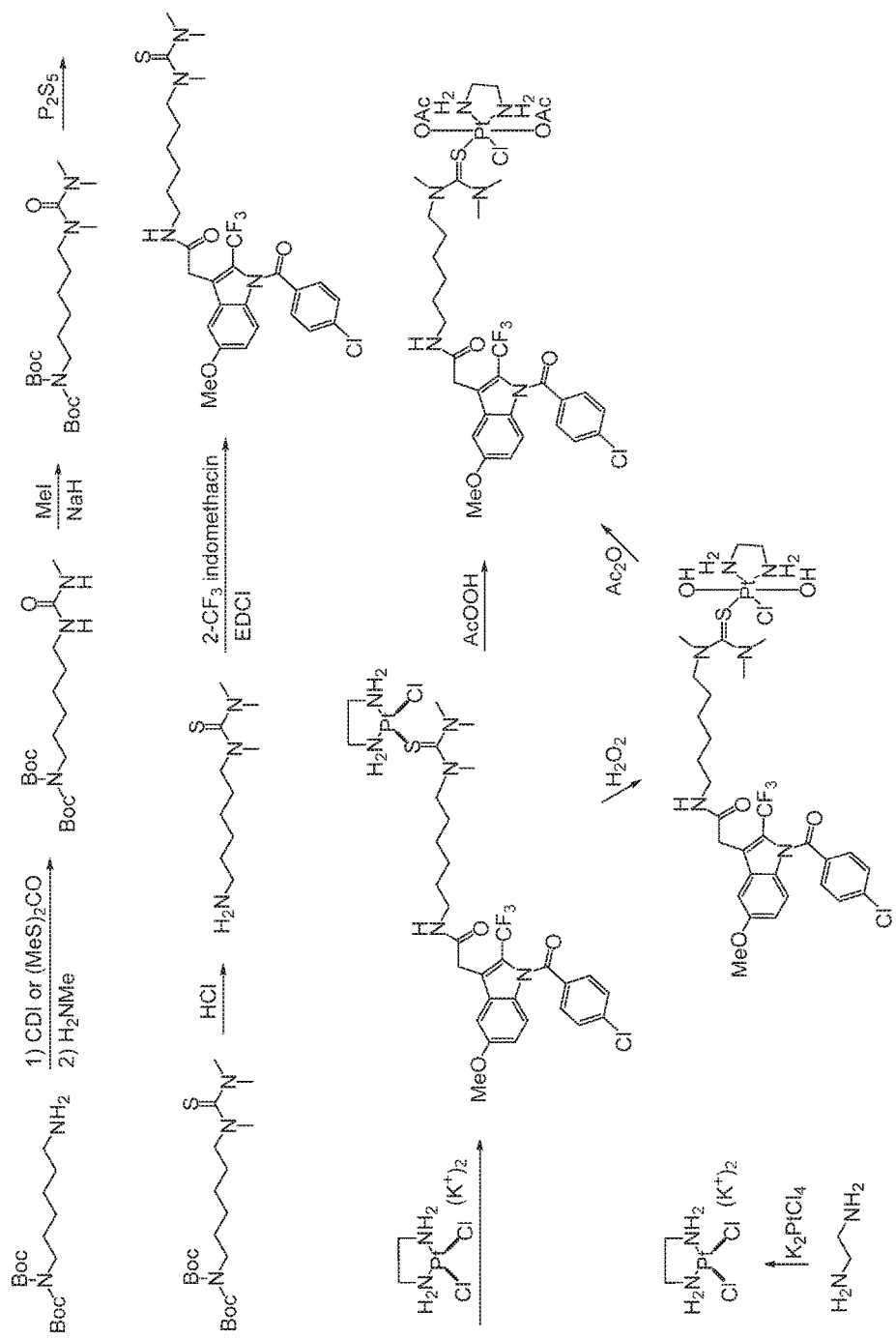
Figure 5:
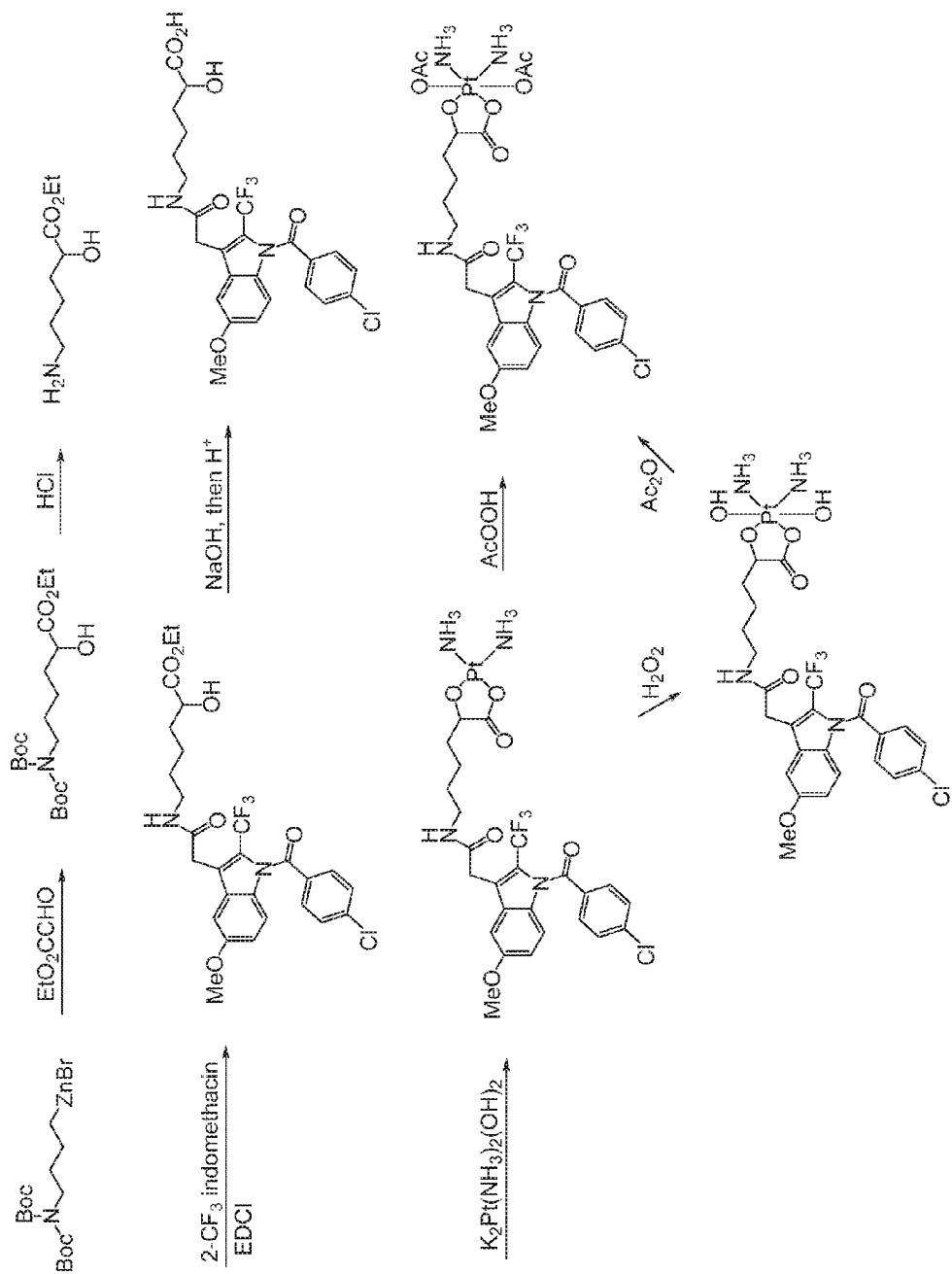
Figure 6:
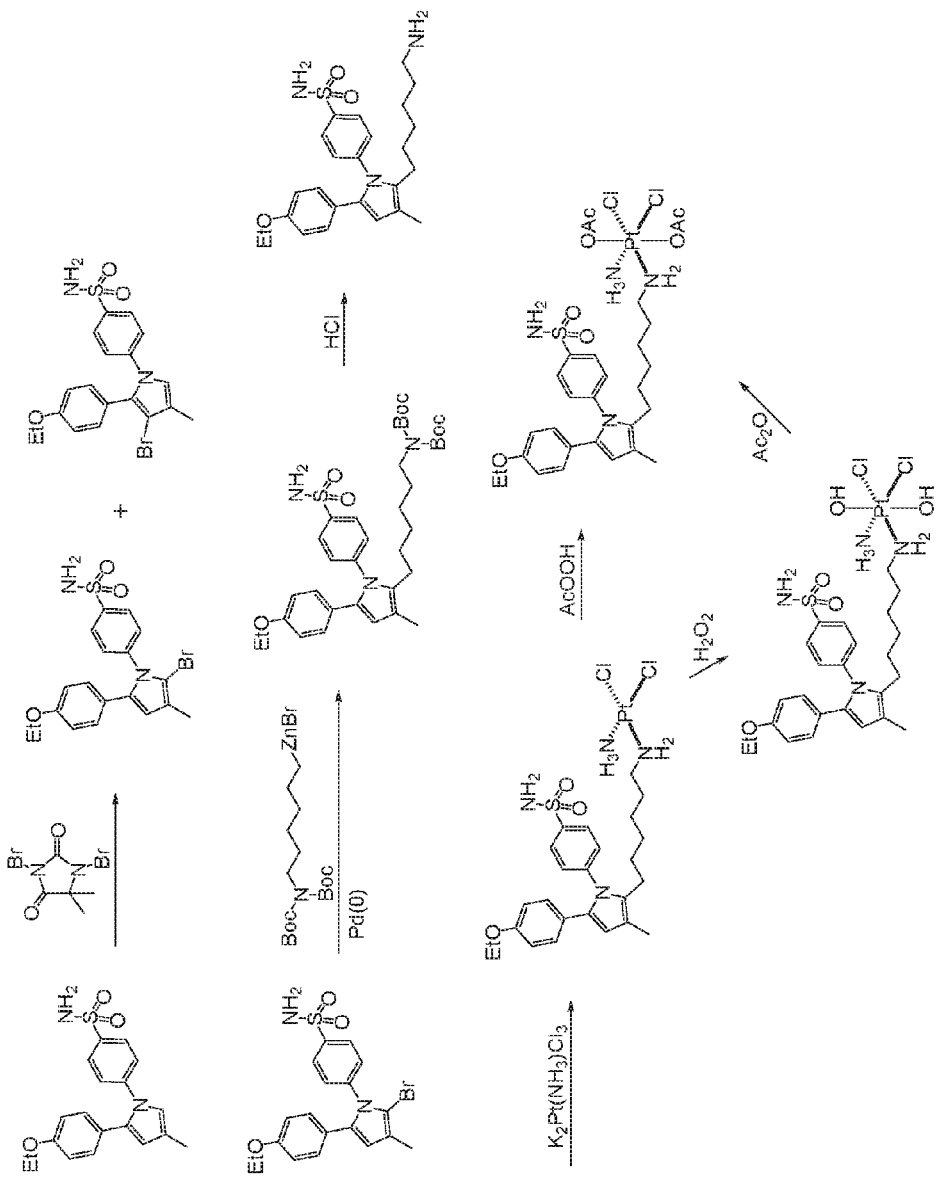
Figure 7:
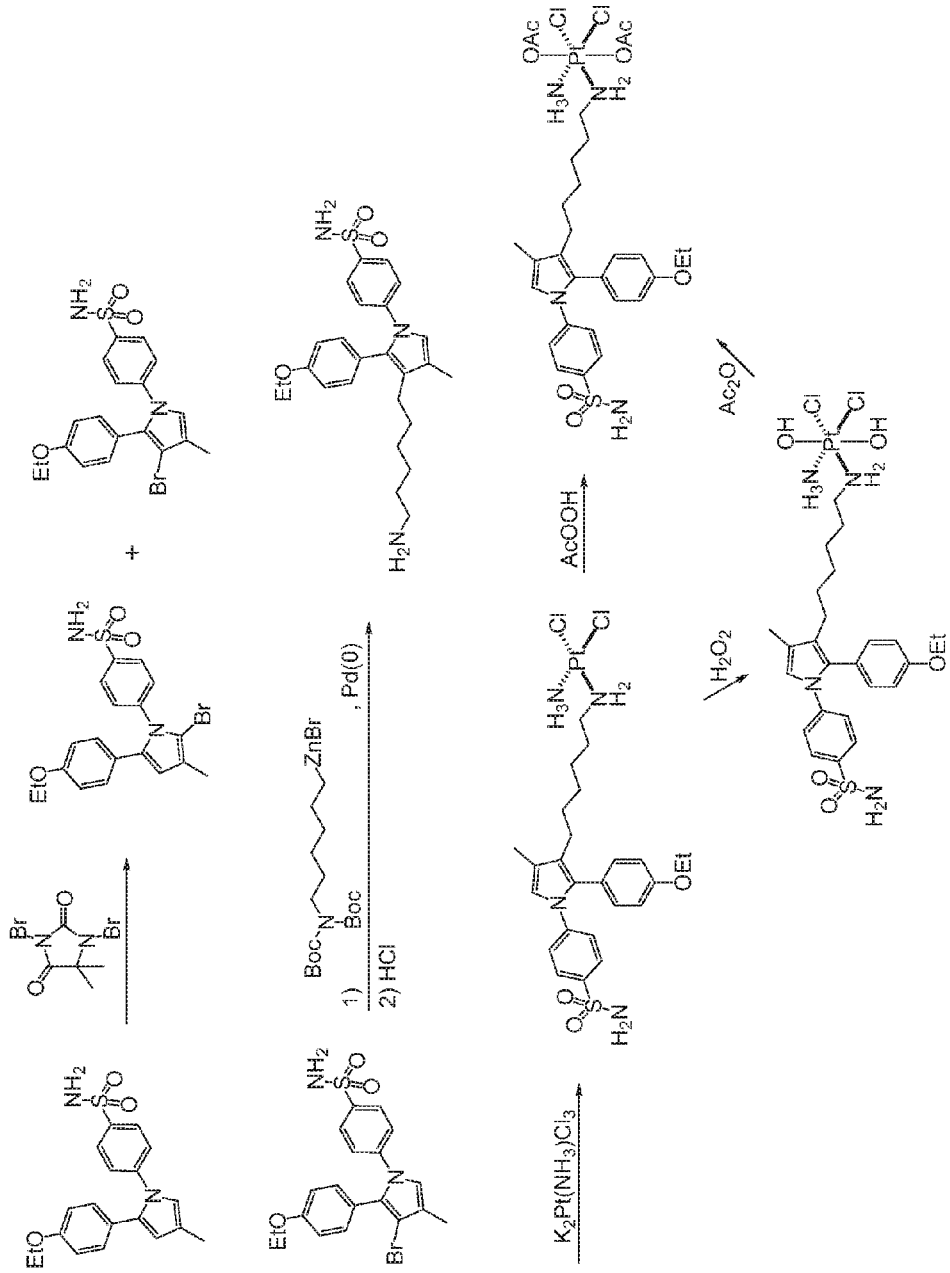
Figure 8:
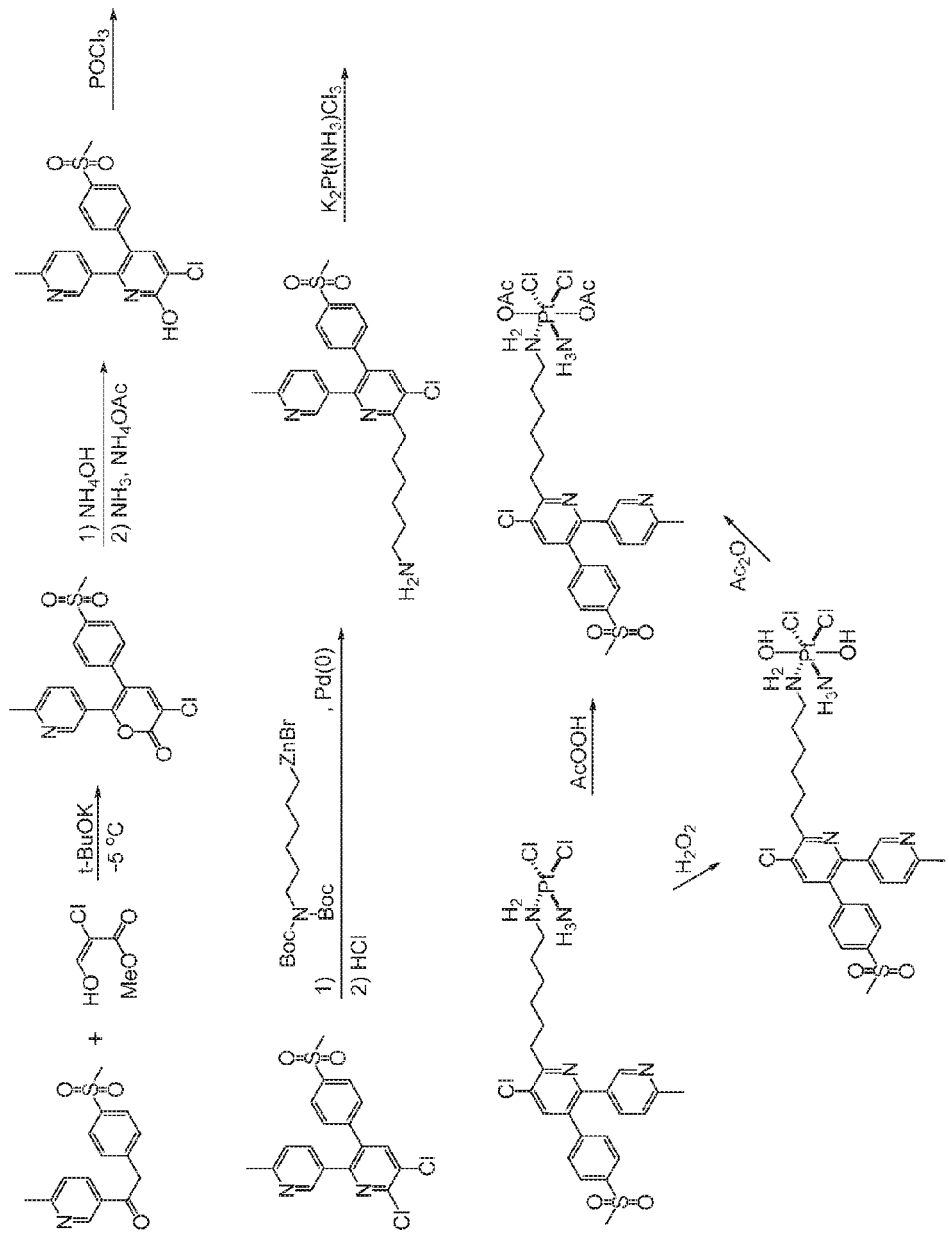
Figure 9:
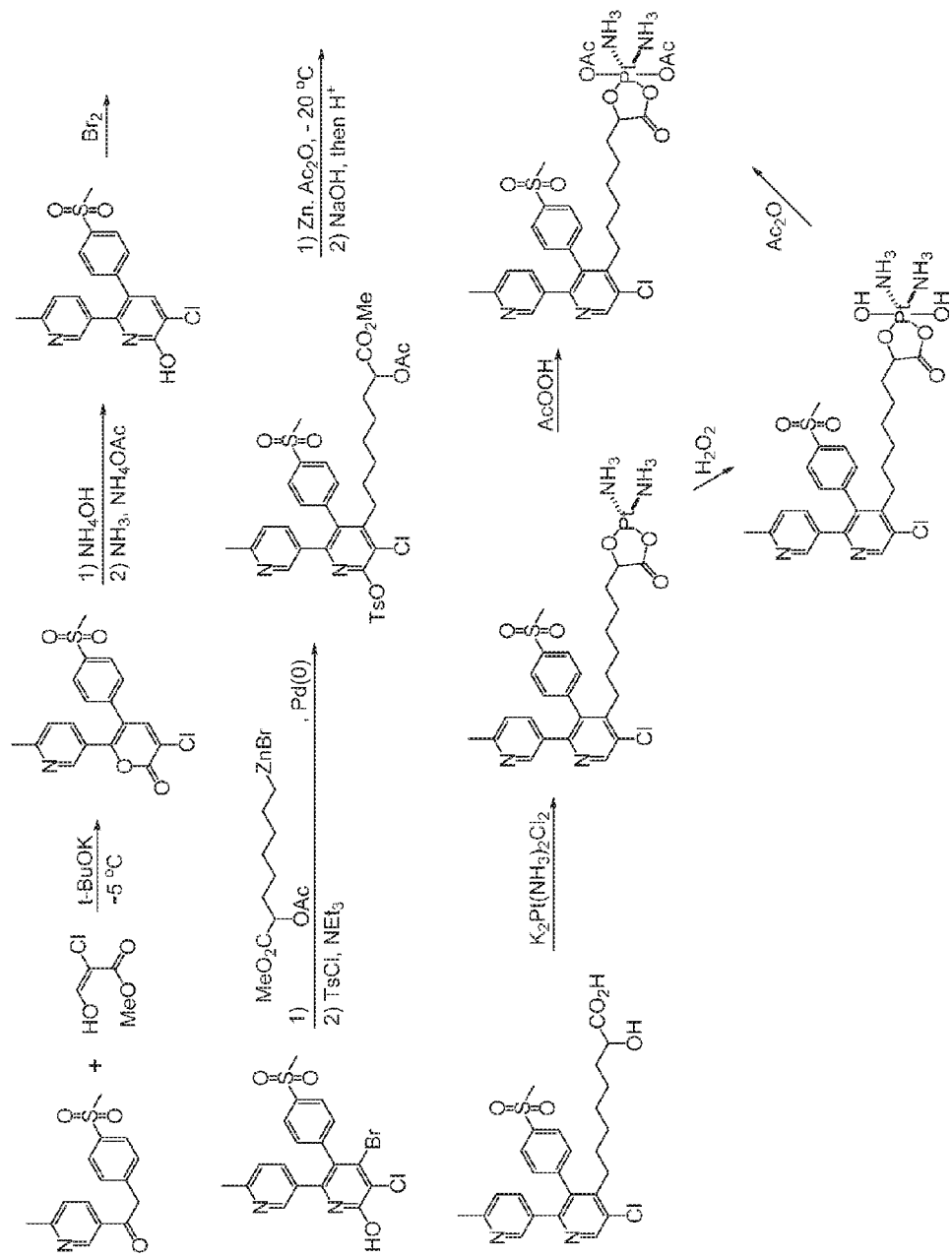
Figure 10:
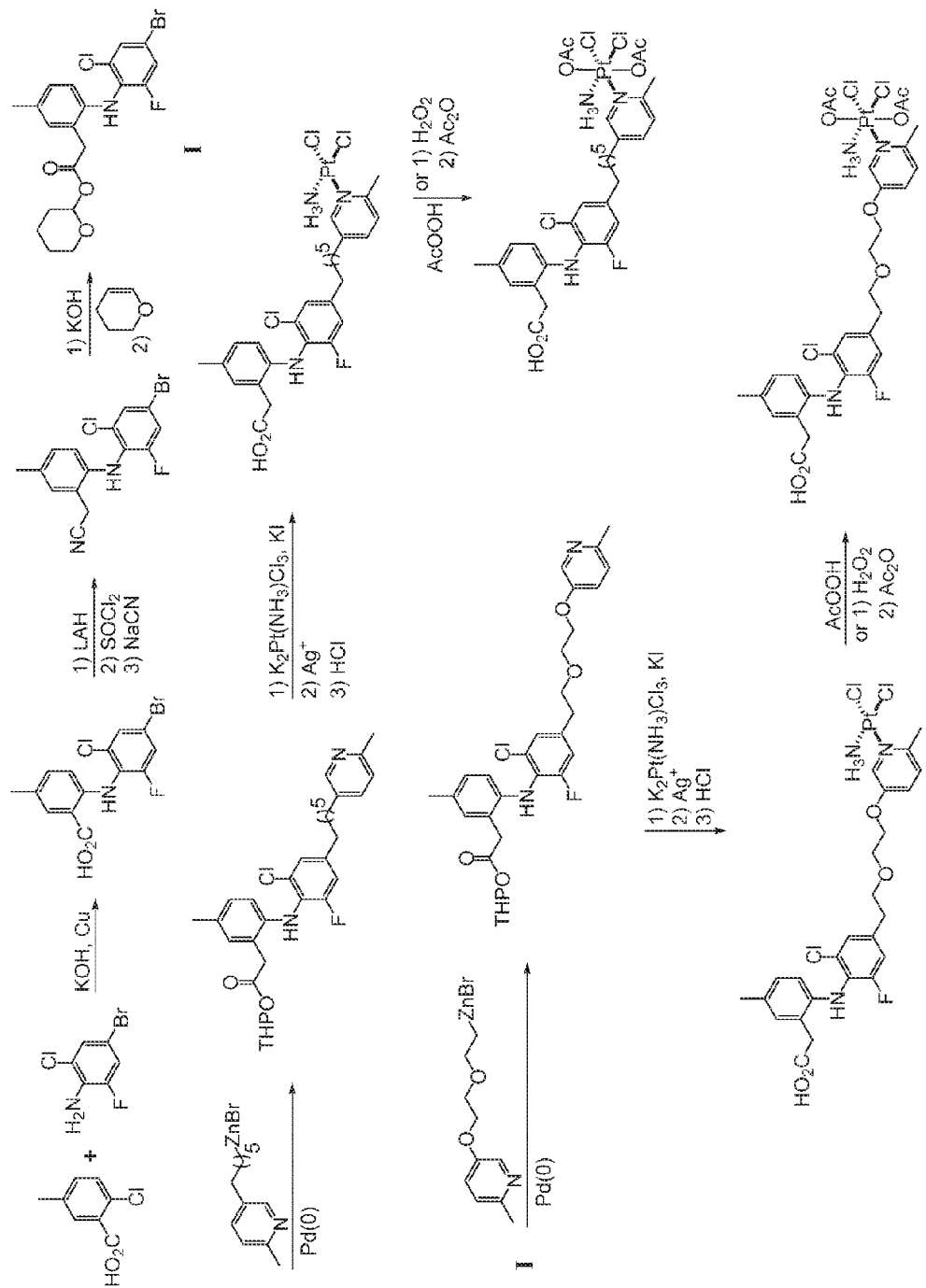
Figure 11:
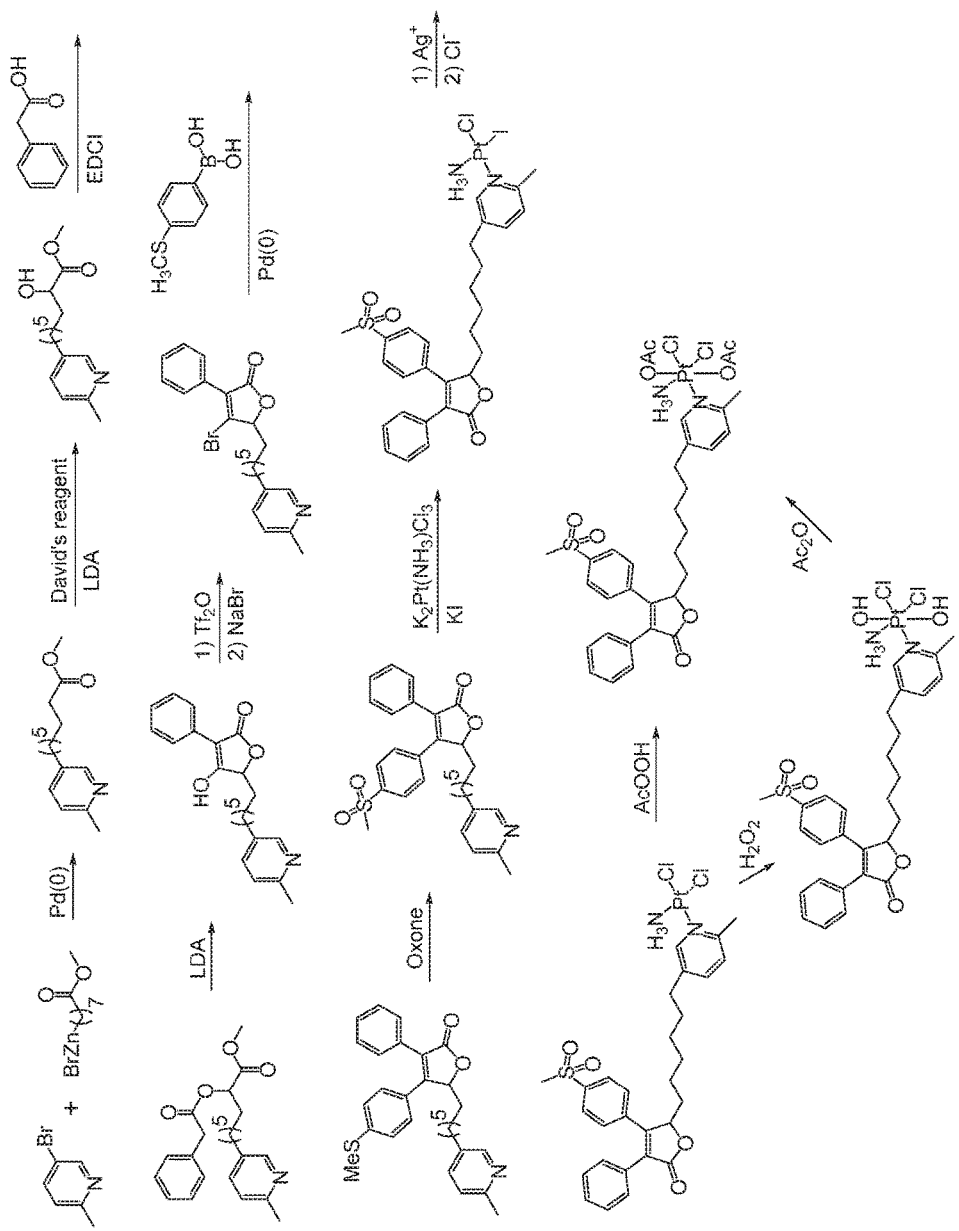
Figure 12:
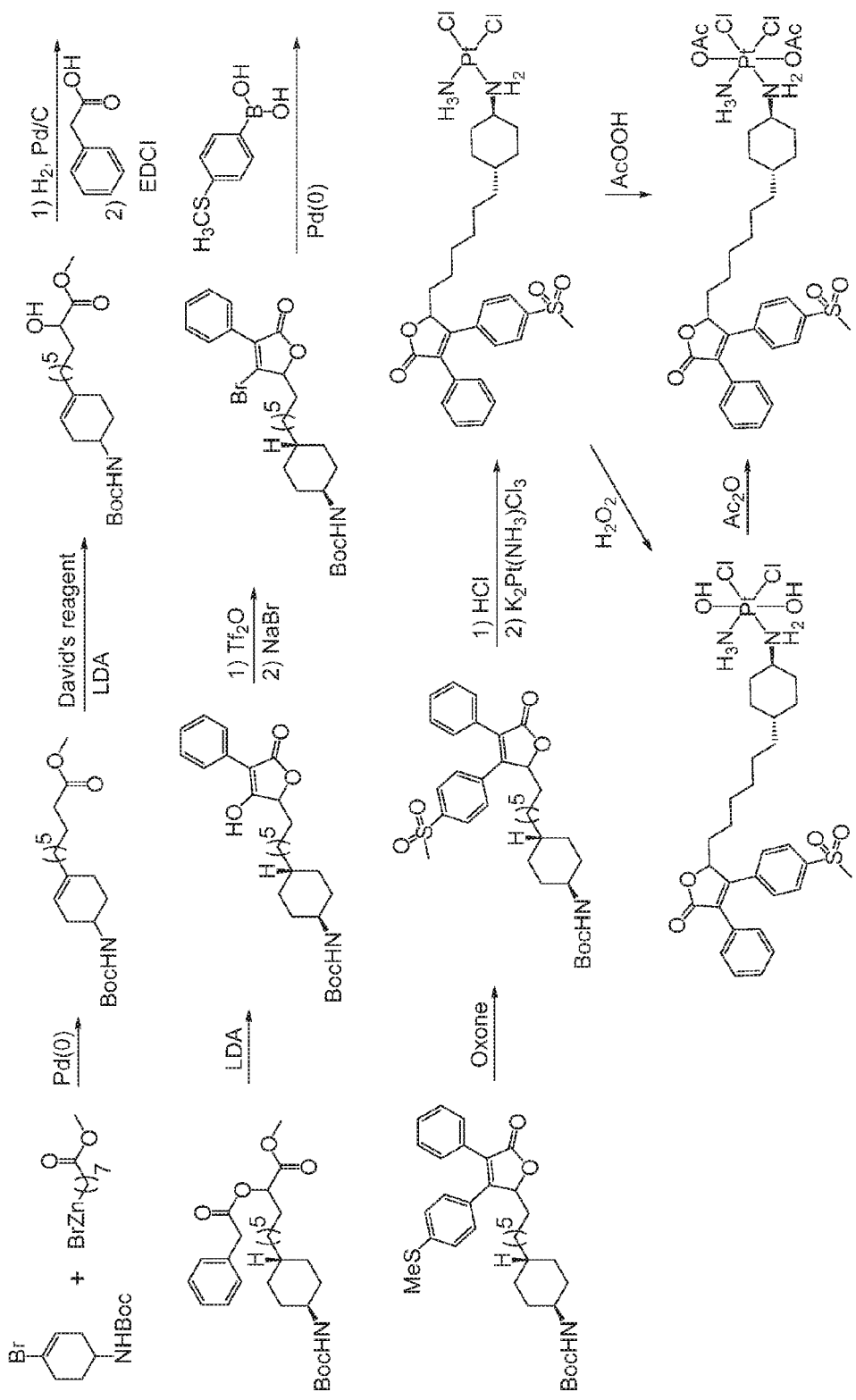
Figure 13:
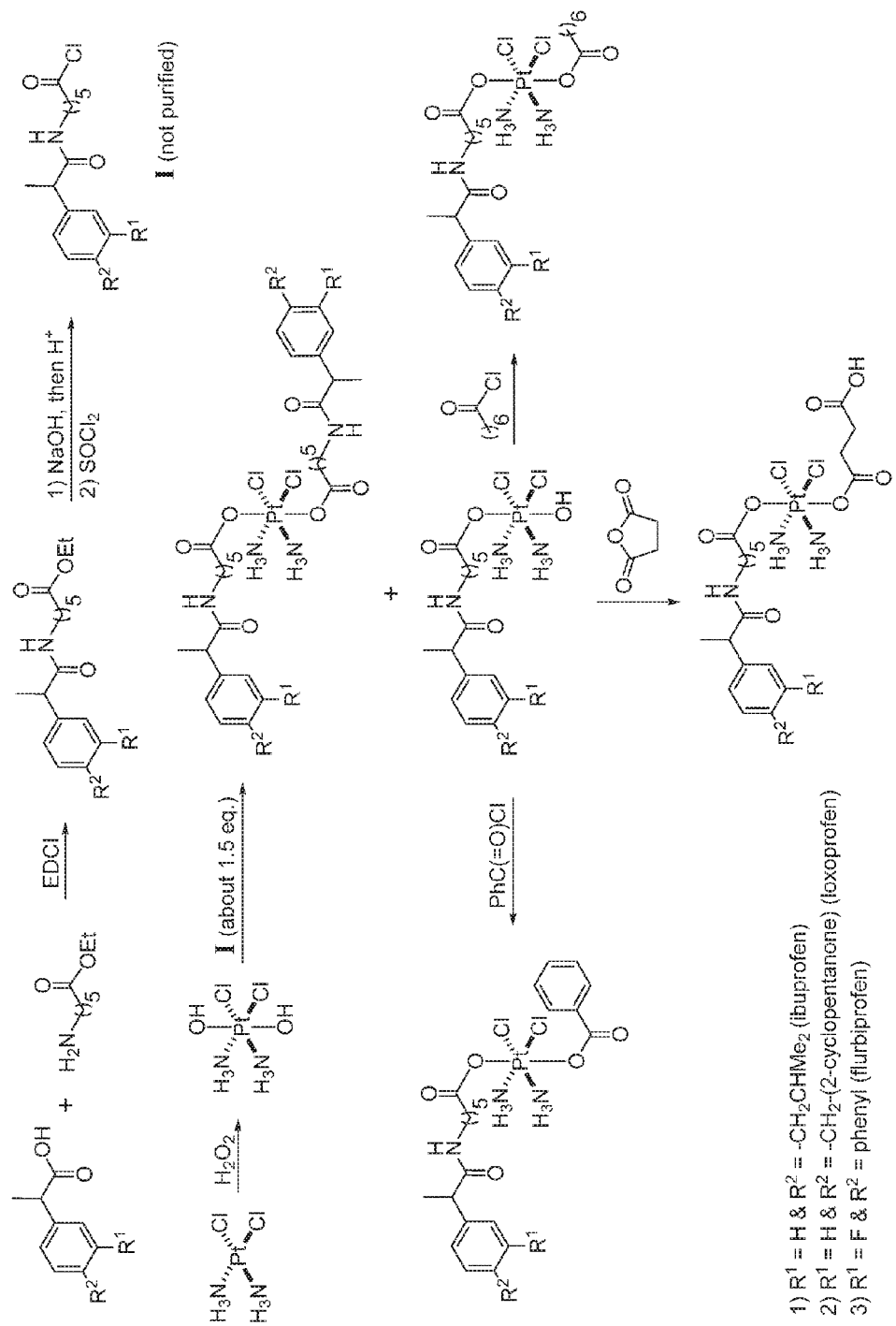
Figure 14:
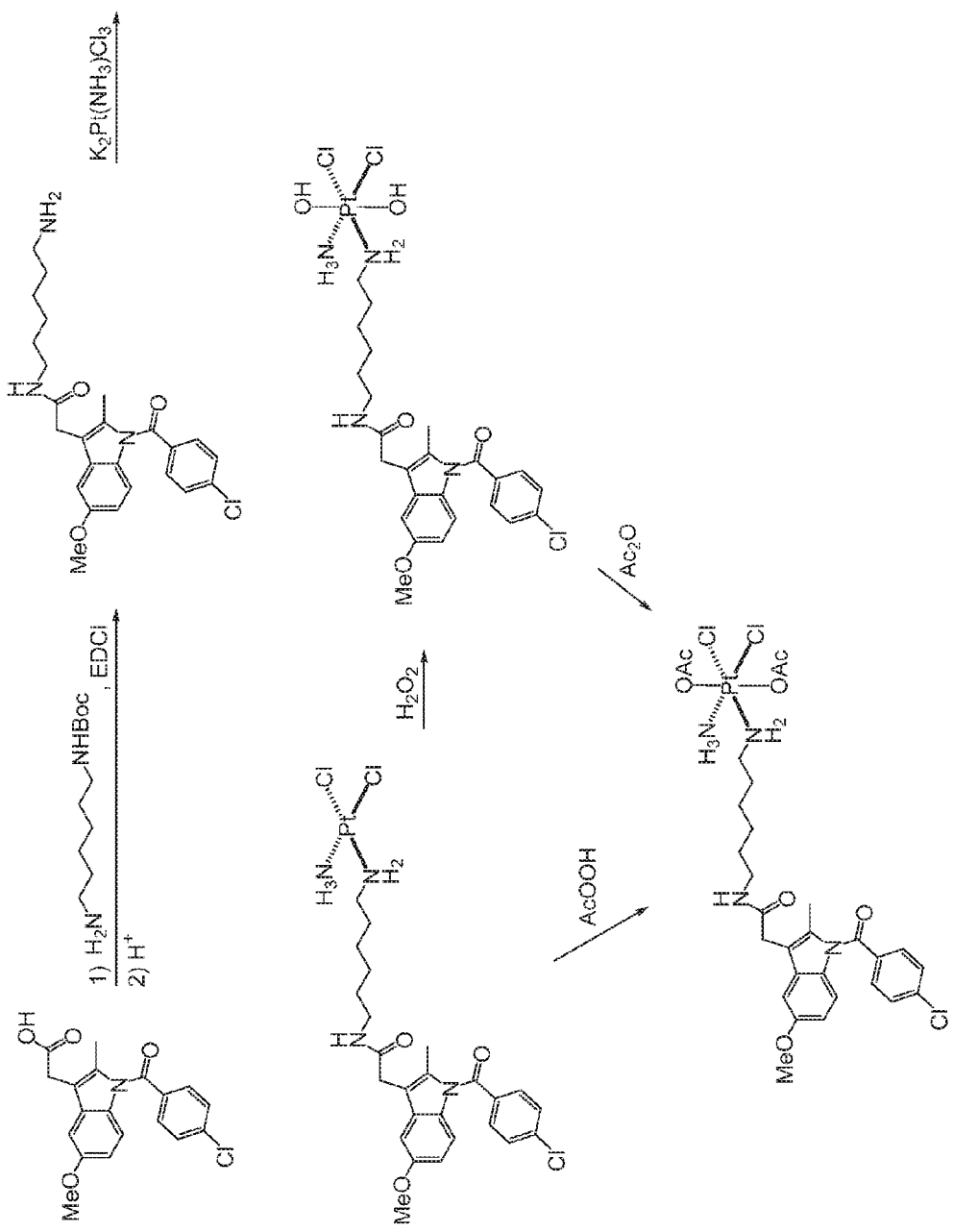
Figure 15:
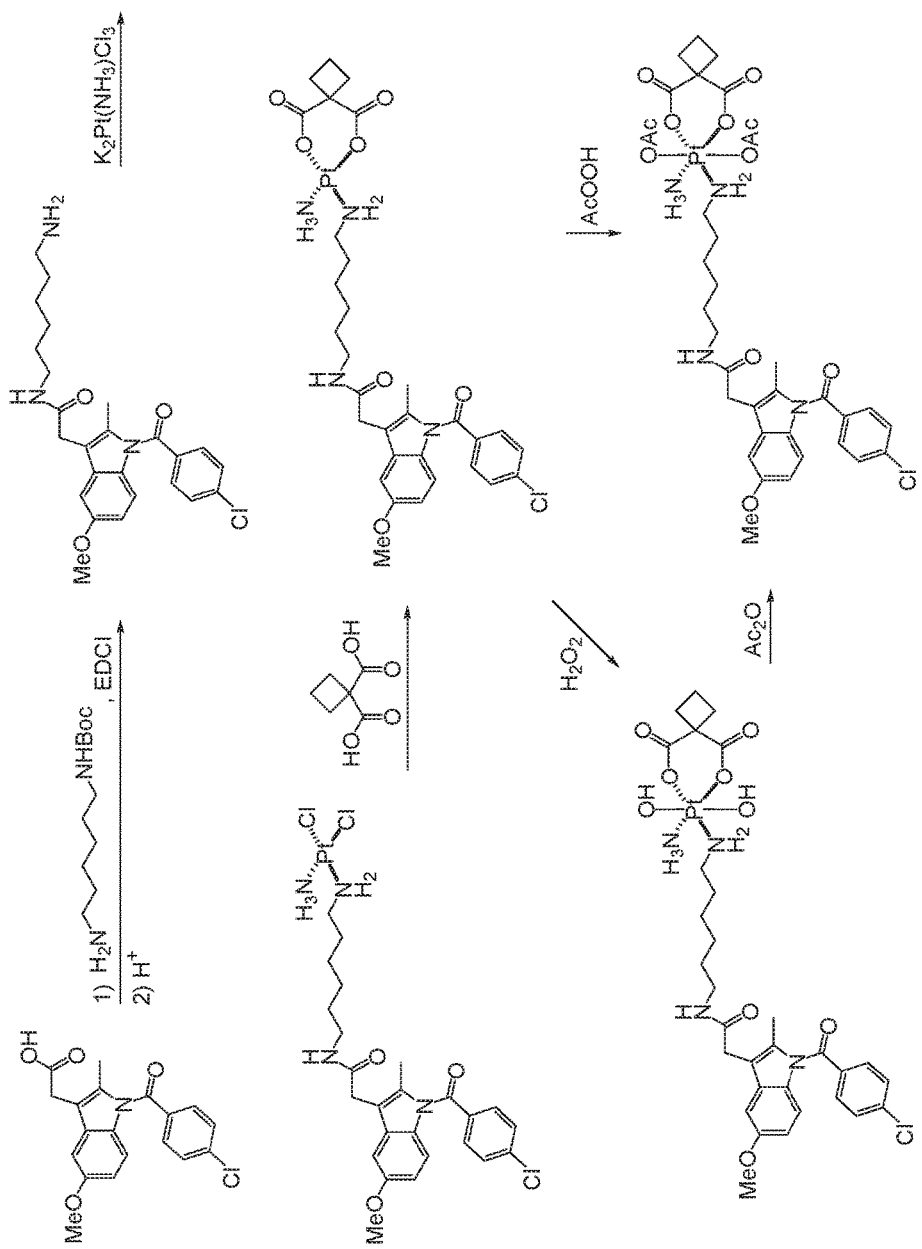
Figure 16:
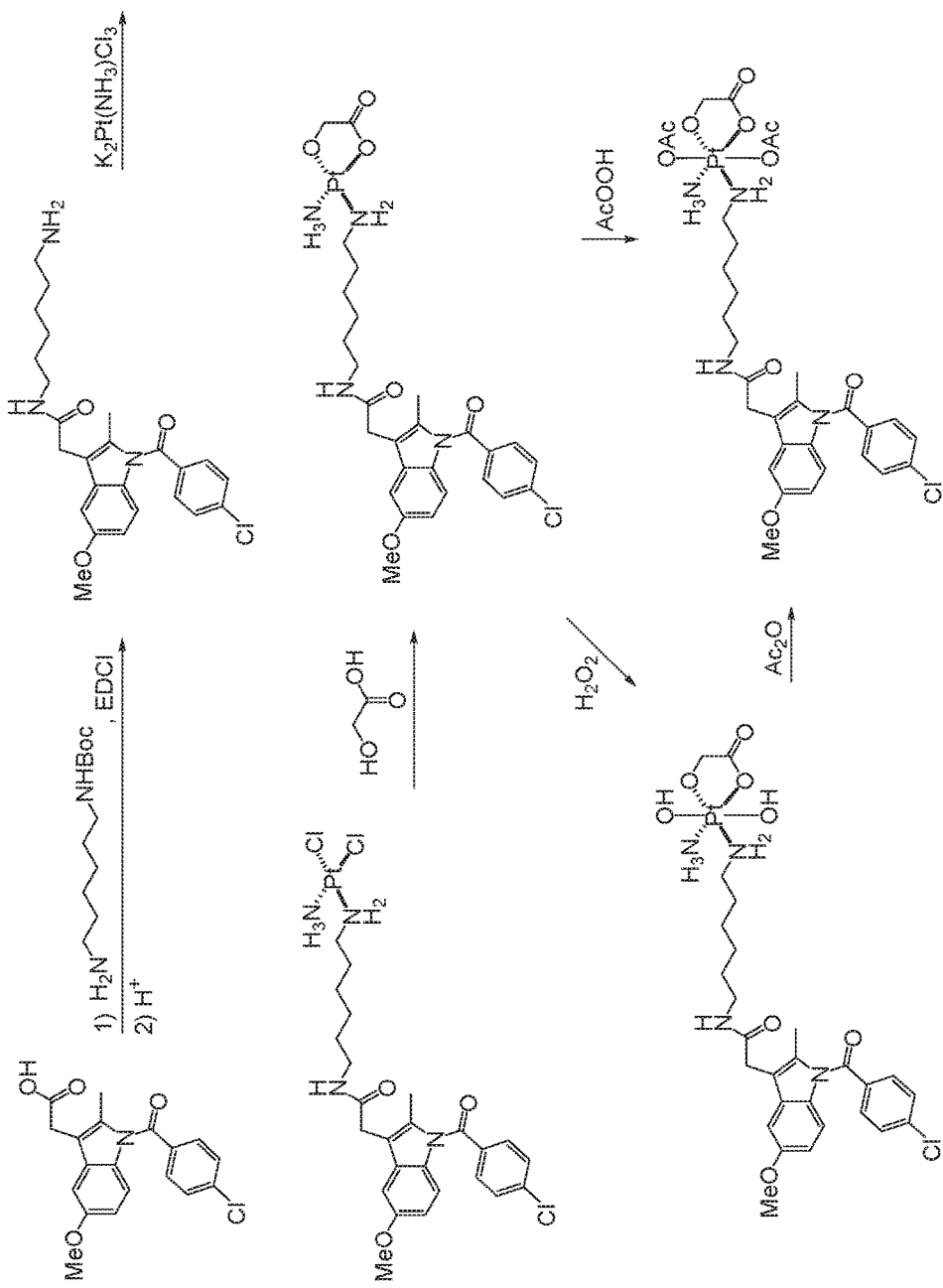

FIGS. 1-16 describe exemplary synthesis of representative conjugates comprising a COX-2-targeting moiety, a linker and a platinum-[e.g., platinum(II)- or platinum(IV)-] containing antitumor agent. Other reactions, reagents and conditions can be employed in the synthesis of those conjugates as known in the art. Furthermore, other conjugates comprising other COX-2-targeting moieties, other platinum-containing antitumor agents, and other linkers or no linker can be prepared according to methodologies described herein and those known in the art.

V. Use Of The Conjugates To Treat Tumors And Cancers

The conjugates described herein can be used to inhibit the growth or proliferation of cells characterized by abnormal growth or proliferation, or to kill such cells, such as tumor and cancer cells. The expression of COX-2 is upregulated in a wide variety of tumor/cancer cells, including many benign (tumor), in situ (potentially malignant), malignant, metastatic, primary and secondary tumor and cancer cells. The COX-2-targeting conjugates described herein can be used to selectively target tumor/cancer cells and treat the sites of tumor/cancer pathology in a subject, including benign, in situ, malignant, metastatic, primary and secondary tumors and cancers. Accordingly, some embodiments of the disclosure relate to a method of treating a tumor or cancer, comprising administering to a subject in need of treatment a therapeutically effective amount of a conjugate described herein. An additional antitumor agent can optionally be administered to treat the tumor or cancer.

In some embodiments, the conjugates have a half maximal effective concentration ($EC_{50}$), or a half maximal inhibitory concentration ($IC_{50}$), of no more than about 500 nM, 250 nM, 100 nM, 50 nM, 10 nM or 1 nM (e.g., no more than about 100 nM) for inhibition of cell growth or proliferation. In further embodiments, the cells are tumor or cancer cells that overexpress COX-2.

The COX-2-targeting conjugates can be employed to treat any kind of tumor or cancer characterized by overexpression of COX-2. In some embodiments, the tumor or cancer is a tumor or cancer of the nervous system (e.g., myelin), central nervous system (e.g., brain and meninges), head or neck (e.g. mouth, tongue, nasal cavity, paranasal sinus, nasopharynx, hypopharynx, throat, parathyroid or thyroid), gastrointestinal tract (e.g., esophagus, stomach, duodenum, small or large intestine, colon or rectum), lung, pancreas, gallbladder, liver, kidney, bladder, breast, uterus (e.g., endometrium), cervix, ovary, prostate, testicle, skin (e.g., melanoma), smooth muscle (e.g., leiomyoma or leiomyosarcoma), epithelial tissue or cells (e.g., adenoma, adenocarcinoma or carcinoma of the head or neck, pituitary gland, gastrointestinal tract, appendix, lung, bronchi, pancreas, gallbladder, liver, kidney, adrenal gland, bladder, urothelium, breast, uterus [e.g., endometrium], cervix, ovary, prostate, skin, or squamous cells), connective tissue (e.g., bone [e.g., adamantinoma, Ewing's sarcoma or osteosarcoma], cartilage [e.g., chondrosarcoma], nerve [e.g., neurofibrosarcoma] or fat [e.g., liposarcoma]), hematopoietic or lymphoid tissue or cells (e.g., leukemia, lymphoma, myeloma or myeloproliferative neoplasm [e.g., polycythemia vera]), germ cells (e.g., of the testicle or ovary), or immature/precursor cells (e.g., glioblastoma, hepatoblastoma, neuroblastoma or retinoblastoma).

In further embodiments, COX-2-overexpressing tumors and cancers are selected from the group consisting of tumors and cancers of the nervous system (including nerve sheath tumors, such as peripheral nerve sheath tumors), central nervous system (including meningioma), brain (including glioblastoma), head and neck (including mouth, tongue, nasal cavity, paranasal sinuses, nasopharynx, hypopharynx, throat, parathyroid and thyroid), gastrointestinal tract (including esophagus, stomach, duodenum, small and large intestine, colon and rectum), lung, pancreas, gallbladder, liver, kidney, bladder, breast, uterus (including endometrium), cervix, ovary, prostate, skin (including melanoma), epithelial tissues and cells (including adenomas, adenocarcinomas and carcinomas of the head and neck [including mouth, nasopharynx, hypopharynx and thyroid], gastrointestinal tract [including esophagus, stomach, duodenum, small and large intestine, colon and rectum], lung, bronchi, pancreas, gallbladder, liver, kidney, bladder, urothelium, breast, uterus [including endometrium], cervix, ovary, prostate, skin, squamous cells, and mesothelial cells [including mesothelioma]), mesenchymal cells (including chondrosarcoma and osteosarcoma), and hematopoietic and lymphoid tissues and cells (including chronic lymphocytic leukemia, chronic myeloid leukemia, Hodgkin's lymphoma, non-Hodgkin's lymphoma and multiple myeloma). See, e.g., S. Zha et al., Cancer Lett., 215:1-20 (2004); and M. Bernard et al., Curr. Pharm. Des., 14:2051-2060 (2008).

In some embodiments, the platinum-containing antitumor agent of the conjugates described herein exerts its antitumor/anticancer (e.g., cytotoxic or pro-apoptotic) effect while being directly or indirectly (e.g., via a linker) associated with the COX-2-targeting moiety. In other embodiments, the platinum-containing antitumor agent exerts its antitumor/anticancer effect after being dissociated from the COX-2-targeting moiety. In certain embodiments, the platinum-containing antitumor agent exerts its antitumor/anticancer effect after being cleaved from the linker connecting the antitumor agent to the COX-2-targeting moiety. The platinum-containing antitumor agent can have an antitumor/anticancer effect regardless of whether or not the COX-2-targeting moiety or the conjugate has an effect (e.g., an inhibitory effect) on COX-2.

In addition to targeting the conjugates to tumor/cancer cells overexpressing COX-2, the COX-2-targeting moiety may have an antitumor/anticancer (e.g., anti-proliferative, pro-apoptotic or anti-angiogenic) effect. COX-2 promotes malignancy, angiogenesis and metastasis. See, e.g., Bernard et al., Curr. Pharm. Des. (supra). The COX-2-targeting moiety may have an antitumor/anticancer effect regardless of whether or not the moiety has an inhibitory effect on COX-2. Furthermore, the COX-2-targeting moiety may have an antitumor/anticancer effect while being directly or indirectly (e.g., via a linker) associated with the platinum-containing antitumor agent, or after being dissociated from the platinum agent (e.g., after being cleaved from the linker connecting the targeting moiety to the platinum agent).

The conjugates described herein can be administered by any suitable mode. Potential modes of administration include without limitation oral and parenteral (including intramuscular, subcutaneous, intradermal, intravascular, intravenous, intraarterial, intramedullary and intrathecal), intracavitary, intraperitoneal, and topical (including dermal/epicutaneous, transdermal, mucosal, transmucosal, intranasal [e.g., by nasal spray or drop], intraocular [e.g., by eye drop], pulmonary [e.g., by inhalation], buccal, sublingual, rectal and vaginal). In some embodiments, the conjugates are administered orally. In certain embodiments, conjugates comprising a platinum(IV)-containing antitumor agent are administered orally. In other embodiments, the conjugates are administered intravenously. In certain embodiments, conjugates comprising a platinum(II)-containing antitumor agent are administered intravenously.

The conjugates can be delivered into tumor/cancer cells by any suitable means. For example, the conjugates can be taken up by tumor/cancer cells by passive permeation through the plasma membrane of the cells. As another example, the conjugates can be taken up by tumor/cancer cells by active transport, e.g., via an organic cation transporter (e.g., organic cation transporter 1, 2 or 3) or a copper transporter (e.g., CTR1). As a further example, the conjugates can be delivered into tumor/cancer cells by fusion of nanoparticles, microparticles or liposomes containing the conjugates with the plasma membrane of tumor/cancer cells.

In some embodiments, an additional antitumor agent is administered in combination with a conjugate described herein to treat a tumor or cancer. Use of the conjugate could lower the dose of the additional antitumor agent that would otherwise be required, thereby reducing any side-effect caused by the additional antitumor agent. The additional antitumor agent can be administered concurrently with or sequentially to (before or after) administration of the conjugate. If administered concurrently with the conjugate, the additional antitumor agent can be contained in the same composition as the conjugate or in separate compositions.

In certain embodiments, the additional antitumor agent is selected from the group consisting of:

1) cytotoxic agents, including without limitation:
    i) alkylating agents, such as aziridines (e.g., diaziquone, mytomycin and thiotepa), nitrogen mustards (e.g., mannomustine, mustine [mechlorethamine], aniline mustard, bendamustine, benzoic acid mustard, chlorambucil, C6-galactose mustard, melphalan, ossichlorin [nitromin], prednimustine, uramustine, nitrogen mustard carbamates [e.g., estramustine], and oxazaphosphorines [e.g., cyclophosphamide, ifosfamide, mafosfamide, and trofosfamide]), nitrosoureas (e.g., carmustine, fotemustine, lomustine, nimustine, N-nitroso-N-methylurea, ranimustine, semustine and streptozotocin), alkylsulfonates (e.g., busulfan, mannosulfan and treosulfan), hydrazines (e.g., dacarbazine and procarbazine), imidazotetrazines (e.g., mitozolomide and temozolomide), and triazines (e.g., hexamethylmelamine [altretamine]);
    ii) cytotoxic antibiotics, such as anthracyclines (e.g., daunorubicin, doxorubicin, epirubicin, idarubicin, aclarubicin, mitoxantrone, pirarubicin and valrubicin), actinomycins (e.g., actinomycin D), bleomycins (e.g., bleomycins $A_2$ and $B_2$), mitomycins (e.g., mitomycin C) and plicamycins;
    iii) anti-metabolites, such as anti-folates (e.g., aminopterin, methotrexate and pemetrexed), deoxynucleoside analogs (e.g., 5-azacytidine [azacitidine], 5-aza-2'-deoxycytidine [decitabine], cladribine, clofarabine, cytarabine, decitabine, fludarabine, gemcitabine, nelarabine and pentostatin), fluoropyrimidines (e.g., 5-fluorouracil, 5-fluoro-5'-deoxyuridine [doxifluridine] and capecitabine), and thiopurines (e.g., thioguanine, azathioprine and mercaptopurine);
    iv) anti-microtubule agents, such as dolastatins (e.g., dolastatin 15), epothilones (e.g., epothilones A-F), taxanes (e.g., paclitaxel and docetaxel), vinca alkaloids (e.g., vinblastine, vincristine, vindesine, vinflunine and vinorelbine), colchicine, nocodazole, podophyllotoxin and rhizoxin;
    v) histone deacetylase inhibitors, such as trichostatins (e.g., trichostatin A), romidepsin and vorinostat;
    vi) kinase inhibitors, such as curcumin, cyclocreatine, deguelin, fostriecin, hispidin, tyrphostins (e.g., tyrphostins AG 34 and AG 879), bortezomib, erlotinib, gefitinib, imatinib, vemurafenib and vismodegib;
    vii) topoisomerase I inhibitors, such as camptothecin, irinotecan and topotecan;
    viii) topoisomerase II-targeting agents, such as topoisomerase II poisons (e.g., etoposide, tafluposide, teniposide, doxorubicin and mitoxantrone) and topoisomerase II inhibitors (e.g., novobiocin, merbarone and aclarubicin);
    ix) DNA or RNA synthesis inhibitors, such as 3-amino-1,2,4-benzotriazine 1,4-dioxide, cytosine β-D-arabinofuranoside, 5,6-dichlorobenzimidazole 1-β-D-ribofuranoside, ganciclovir and hydroxyurea;
    x) protein synthesis inhibitors, such as homoharringtonine;
    xi) cell growth and differentiation regulators, such as retinoids (e.g., retinol [vitamin A], all-trans retinal [vitamin A aldehyde], all-trans retinoic acid [tretinoin], 9-cis-retinoic acid [alitretinoin], 13-cis-retinoic acid [isotretinoin], etretinate, acitretin, adapalene, bexarotene and tazarotene);
    xii) cell proliferation inhibitors, such as mTOR inhibitors (e.g., rapamycin [sirolimus]), apigenin, cholecalciferol (vitamin $D_3$) and sex hormone-binding globulin;
    xiii) apoptosis inducers, such as 17-allylamino-17-demethoxygeldanamycin, melatonin, mevinolin, psoralen, thapsigargin and troglitazone; and
    analogs, derivatives and salts thereof;

2) agents that stimulate the immune system, including without limitation:
    i) agonists/activators of tumor necrosis factor receptor superfamily member 4 (TNFRSF4, OX40 or CD134), such as OX40-targeting antibodies (e.g., MEDI-6469 and 9B12) and ligands for OX40 (e.g., OX40L);
    ii) agonists/activators of TNFRSF member 5 (TNFRSF5 or CD40), such as CD40-targeting antibodies (e.g., dacetuzumab and CP-870,893) and ligands for CD40 (e.g., CD40L [CD154]);
    iii) agonists/activators of TNFRSF member 9 (TNFRSF9, 4-1BB or CD137), such as 4-1BB-targeting antibodies (e.g., urelumab [BMS-663513] and PF-05082566) and ligands for 4-1BB (e.g., 4-1BBL);
    iv) agonists/activators of TNFRSF member 18 (TNFRSF18, glucocorticoid-induced TNFR-related protein [GITR] or CD357), such as GITR-targeting antibodies (e.g., DTA-1 and TRX518) and ligands for GITR (e.g., GITRL);
    v) agonists/activators of toll-like receptors (TLRs), such as ligands for TLR9 (e.g., unmethylated CpG oligodeoxynucleotides [CpG ODNs], such as agatolimod); and
    analogs, derivatives, fragments and salts thereof;

3) agents that block immune checkpoints, including without limitation:
    i) inhibitors of programmed cell death 1 (PD-1) receptor or ligands thereof (e.g., PD-L1 and PD-L2), such as anti-PD-1 antibodies (e.g., nivolumab [BMS-936558, MDX-1106 or ONO-4538], pembrolizumab [lambrolizumab or MK-3475], pidilizumab [CT-011] and MEDI-0680 [AMP-514]), anti-PD-1 fusion proteins (e.g., AMP-224 [containing an $F_c$ Ab domain and PD-L2]), and anti-PD-L1 antibodies (e.g., BMS-936559 [MDX-1105], MEDI-4736, MPDL3280A [RG7446] and MSB0010718C);
    ii) inhibitors of cytotoxic T lymphocyte-associated protein 4 (CTLA-4) receptor or ligands thereof, such as anti-CTLA-4 antibodies (e.g., ipilimumab and tremelimumab);

iii) inhibitors of killer cell immunoglobulin-like receptors (KIRs) or ligands thereof, such as anti-KIR antibodies (e.g., lirilumab [IPH2102 or BMS-986015]);
iv) inhibitors of lymphocyte activation gene 3 (LAG-3) receptor or ligands thereof, such as anti-LAG-3 antibodies (e.g., BMS-986016);
v) inhibitors of indoleamine 2,3-dioxygenase (IDO or IDO1), such as indoximod (1-methyl-D-tryptophan or NLG-8189), NLG-919, INCB024360, α-methyl-tryptophan, β-carboline (9H-pyrido[3,4-b]indole or norharmane), and COX-2 inhibitors (e.g., coxibs, which down-regulate the expression of IDO); and
analogs, derivatives, fragments and salts thereof;

4) angiogenesis inhibitors, including without limitation inhibitors of vascular endothelial growth factors (VEGFs) (e.g., squalamine and anti-VEGF antibodies such as bevacizumab) or receptors therefor (VEGFRs) (e.g., axitinib, pazopanib, sorafenib and sunitinib), inhibitors of platelet-derived growth factors (PDGFs) (e.g., squalamine) or receptors therefor (PDGFRs) (e.g., axitinib, pazopanib, sorafenib and sunitinib), inhibitors of fibroblast growth factors (FGFs) (e.g., squalamine) or receptors therefor (FGFRs), inhibitors of angiopoietins (e.g., anti-angiopoietin antibodies such as nesvacumab) or receptors therefor, inhibitors of integrins (e.g., ALG-1001 and JSM-6427), anecortave (anecortave acetate), angiostatin (e.g., angiostatin K1-3), $\alpha_v\beta_3$ inhibitors (e.g., etaracizumab), berberine, bleomycins, borrelidin, carboxyamidotriazole, cartilage-derived angiogenesis inhibitors (e.g., chondromodulin I and troponin I), castanospermine, CM101, cyclopropene fatty acids (e.g., sterculic acid), α-difluoromethylornithine, endostatin, everolimus, fumagillin, genistein, interferon-α, interleukin-12, itraconazole, linomide, matrix metalloproteinase (MMP) inhibitors (e.g., batimastat, cipemastat, ilomastat, marimastat, prinomastat, rebimastat, tanomastat, and tetracyclines [e.g., doxycycline, incyclinide and minocycline]), 2-methoxyestradiol, pigment epithelium-derived factor (PEDF), platelet factor-4, PPAR-γ agonists (e.g., thiazolidinediones, such as ciglitazone, lobeglitazone, netoglitazone, pioglitazone, rivoglitazone, rosiglitazone and troglitazone), prolactin, sphingosine-1-phosphate inhibitors (e.g., sonepcizumab), squalene, staurosporine, angiostatic steroids (e.g., tetrahydrocortisol) plus heparin, stilbenoids, suramin, SU5416, tasquinimod, tecogalan, tetrathiomolybdate, thalidomide and derivatives thereof (e.g., lenalidomide and pomalidomide), thiabendazole, thrombospondins (e.g., thrombospondin 1), TNP-470, tranilast, Withaferin A, and analogs, derivatives, fragments and salts thereof; and 5) other kinds of antitumor agents, including without limitation:
i) drug-efflux pump inhibitors, such as P-glycoprotein inhibitors (e.g., mifepristone and verapamil);
ii) cell adhesion inhibitors, such as cimetidine;
iii) Golgi apparatus disruptors, such as brefeldins (e.g., brefeldin A);
iv) ionizing radiation, such as X-ray;
v) radiation sensitizers of tumor/cancer cells, such as poly(ADP-ribose) polymerase (PARP) inhibitors (e.g., 4-amino-1,8-naphthalimide) and berberine;
vi) enhancers of cell survival after treatment with cytotoxic drugs or radiation, such as pifithrin-α;
vii) vaccines, such as those that stimulate the immune system to recognize proteins produced by tumor/cancer cells and thereby to attack tumor/cancer cells; and
analogs, derivatives and salts thereof.

A particular antitumor agent may have more than one mechanism of action and may be classified in more than one category.

The additional antitumor agent used in combination with a conjugate described herein can also be selected for more directed therapy of tumors and cancers. Table 1 lists non-limiting examples of antitumor agents employed in directed therapy of tumors and cancers.

TABLE 1

| Tumor/Cancer | Directed Antitumor Therapeutics |
| --- | --- |
| Breast cancer | selective estrogen receptor antagonists (e.g., tamoxifen, 4-hydroxytamoxifen, raloxifene, toremifene, fulvestrant) |
| Breast cancer (post-menopausal) | aromatase inhibitors (e.g., anastrozole, letrozole, exemestane, formestane, megestrol acetate) |
| Breast cancer | androgens (testosterone-like) (e.g., fluoxymesterone) |
| Breast cancer | anti-Her2/neu receptor monoclonal antibodies (e.g., trastuzumab) |
| Breast cancer and other solid tumors | dual inhibitors of Her2/neu receptor and epidermal growth factor receptor (EGFR) (e.g., lapatinib, neratinib) |
| Ovarian cancer | poly(ADP-ribose) polymerase (PARP) inhibitors (e.g., olaparib) |
| Prostate cancer | gonadotropin-releasing hormone (GnRH) analogs (e.g., leuprolide, goserelin) |
| Prostate cancer | androgen receptor inhibitors (e.g., flutamide, bicalutamide, estrace) |
| Prostate cancer | estrogen agonists (e.g., diethylstilbestrol, estrace, polyestradiol phosphate) |
| Breast, endometrial and prostate cancers | progestins (progesterone-like) (e.g., megestrol acetate, medroxyprogesterone acetate) |
| Breast, colorectal, renal and non-small cell lung cancers, and brain tumors | anti-VEGF monoclonal antibodies (e.g., bevacizumab) |
| Non-small cell lung cancer | EGFR tyrosine kinase inhibitors (e.g., afatinib, gefitinib, erlotinib, osimertinib) |
| Non-small cell lung cancer | anaplastic lymphoma kinase (ALK) inhibitors (e.g., alectinib, ceritinib, crizotinib) |
| Colorectal, non-small cell lung, and squamous cell head and neck cancers | anti-EGFR monoclonal antibodies (e.g., cetuximab, necitumumab, nimotuzumab, panitumumab) |
| Colorectal, gastric and non-small cell lung cancers | anti-VEGFR monoclonal antibodies (e.g., ramucirumab) |

TABLE 1-continued

| Tumor/Cancer | Directed Antitumor Therapeutics |
|---|---|
| Colorectal, gastric, renal, bladder, non-small cell lung, and squamous cell head and neck cancers and melanoma | anti-PD-1 or anti-PD-L1 monoclonal antibodies (e.g., nivolumab, pembrolizumab); and/or anti-CTLA-4 monoclonal antibodies (e.g., ipilimumab, tremelimumab) |
| Melanoma | B-Raf inhibitors (e.g., vemurafenib, dabrafenib) and/or MEK inhibitors (e.g., cobimetinib, trametinib) |
| Basal cell carcinoma | Hedgehog signaling pathway inhibitors (e.g., sonidegib [erismodegib]) |
| Thyroid cancer | VEGFR inhibitors (e.g., lenvatinib) |
| Acute myelogenous leukemia | anti-CD33 antibody-drug conjugates (e.g., gemtuzumab ozogamicin) |
| Chronic myelogenous leukemia & gastrointestinal stromal tumor | Bcr-Abl tyrosine kinase inhibitors (e.g., bafetinib, bosutinib, dasatinib, imatinib, nilotinib, ponatinib) |
| Chronic lymphocytic leukemia & non-Hodgkin's lymphoma | anti-CD20 monoclonal antibodies (e.g., obinutuzumab, ofatumumab, rituximab, tositumomab, $^{90}$Y- or $^{111}$In-ibritumomab tiuxetan); and/or anti-CD52 monoclonal antibodies (e.g., alemtuzumab) |
| Acute lymphoblastic leukemia & non-Hodgkin's lymphoma | anti-CD19 monoclonal antibodies (e.g., blinatumomab) |
| Hodgkin's lymphoma and anaplastic large-cell lymphoma | anti-CD30 antibody-drug conjugates (e.g., brentuximab vedotin) |
| Multiple myeloma | antibodies targeting CD38 (e.g., daratumumab) or signaling lymphocytic activation molecule F7 (SLAMF7) (e.g., elotuzumab) |
| Multiple myeloma | proteasome inhibitors (e.g., bortezomib, carfilzomib); and/or histone deacetylase inhibitors (e.g., panobinostat) |
| Multiple myeloma | anti-angiogenic & anti-proliferative (e.g., lenalidomide, pomalidomide) |
| Cancer stem cells | salinomycin |

VI. Representative Embodiments

The following embodiments of the disclosure are provided by way of example only:

1. A conjugate comprising a moiety that targets cyclooxygenase II (COX-2), a platinum-containing antitumor agent, and a linker connecting the COX-2-targeting moiety to the platinum-containing antitumor agent.
2. The conjugate of embodiment 1, wherein the COX-2-targeting moiety comprises a non-steroidal anti-inflammatory drug (NSAID), or an analog, derivative, residue or salt thereof.
3. The conjugate of embodiment 2, wherein the NSAID is selected from the group consisting of acetic acid derivatives, anthranilic acid derivatives (fenamates), enolic acid derivatives (oxicams), propionic acid derivatives, salicylates, COX-2-selective inhibitors, other kinds of NSAIDs, and analogs, derivatives, residues and salts thereof.
4. The conjugate of embodiment 3, wherein:
   the acetic acid derivatives include aceclofenac, diclofenac, etodolac, indomethacin, ketorolac, nabumetone, sulindac, sulindac sulfide, sulindac sulfone, tolmetin, and analogs, derivatives, residues and salts thereof;
   the anthranilic acid derivatives (fenamates) include flufenamic acid, meclofenamic acid, mefenamic acid, tolfenamic acid, and analogs, derivatives, residues and salts thereof;
   the enolic acid derivatives (oxicams) include droxicam, isoxicam, lornoxicam, meloxicam, piroxicam, tenoxicam, and analogs, derivatives, residues and salts thereof;
   the propionic acid derivatives include fenoprofen, flurbiprofen, ibuprofen, dexibuprofen, ketoprofen, dexketoprofen, loxoprofen, naproxen, oxaprozin, and analogs, derivatives, residues and salts thereof;
   the salicylates include diflunisal, salicylic acid, acetylsalicylic acid, choline magnesium trisalicylate, salsalate, and analogs, derivatives, residues and salts thereof;
   the COX-2-selective inhibitors include apricoxib, celecoxib, etoricoxib, firocoxib, fluorocoxibs (e.g., fluorocoxibs A-C), lumiracoxib, mavacoxib, parecoxib, rofecoxib, tilmacoxib (JTE-522), valdecoxib, 4-O-methylhonokiol, DuP-697, CG100649, NS-398, SC-58125, benzothieno[3,2-d]pyrimidin-4-one sulfonamide thio-derivatives, COX-2 inhibitors derived from *Tribulus terrestris*, and analogs, derivatives, residues and salts thereof; and
   the other kinds of NSAIDs include anilinopyridinecarboxylic acids (e.g., clonixin), sulfonanilides (e.g., nimesulide), dual inhibitors of lipooxygenase (e.g., 5-LOX) and cyclooxygenase (e.g., COX-2) (e.g., chebulagic acid, licofelone, 2-(3,4,5-trimethoxyphenyl)-4-(N-methylindol-3-yl)thiophene, and di-tert-butylphenol-based compounds [e.g., DTPBHZ, DTPINH, DTPNHZ and DTPSAL]), and analogs, derivatives, residues and salts thereof.
5. The conjugate of embodiment 4, wherein the NSAID is selected from the group consisting of indomethacin, ketorolac, naproxen, ibuprofen, fenoprofen, flurbiprofen, ketoprofen, loxoprofen, oxaprozin, apricoxib, celecoxib, etoricoxib, lumiracoxib, rofecoxib, valdecoxib, and analogs, derivatives, residues and salts thereof.
6. The conjugate of embodiment 5, wherein the COX-2-targeting moiety is selected from the group consisting of:

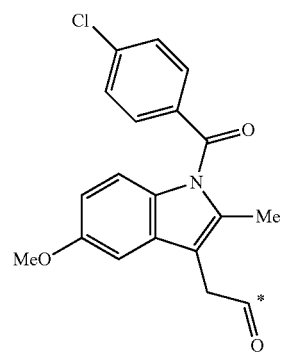

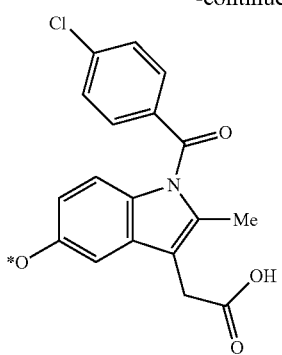
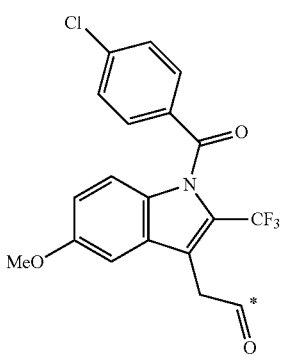
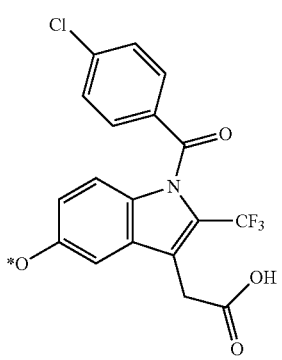
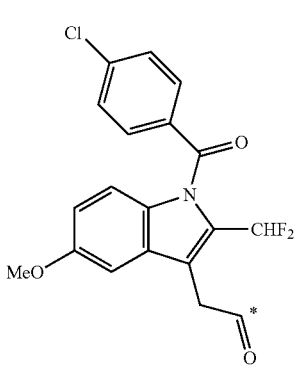
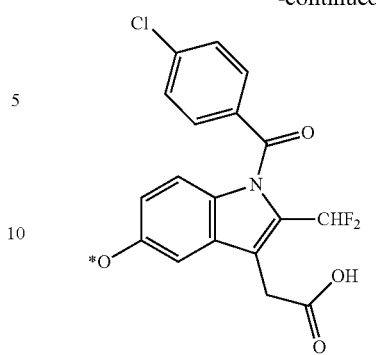
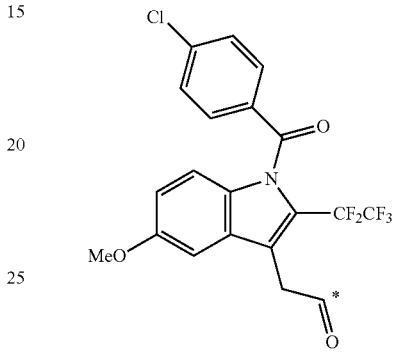
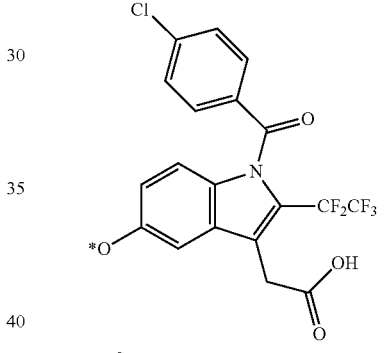
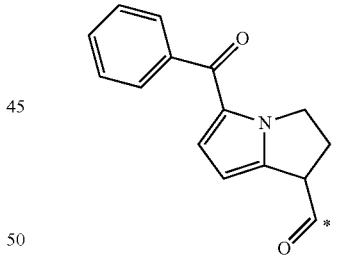
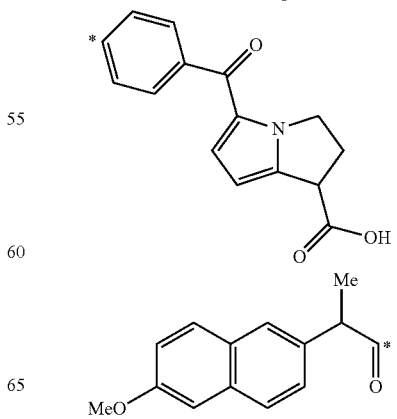

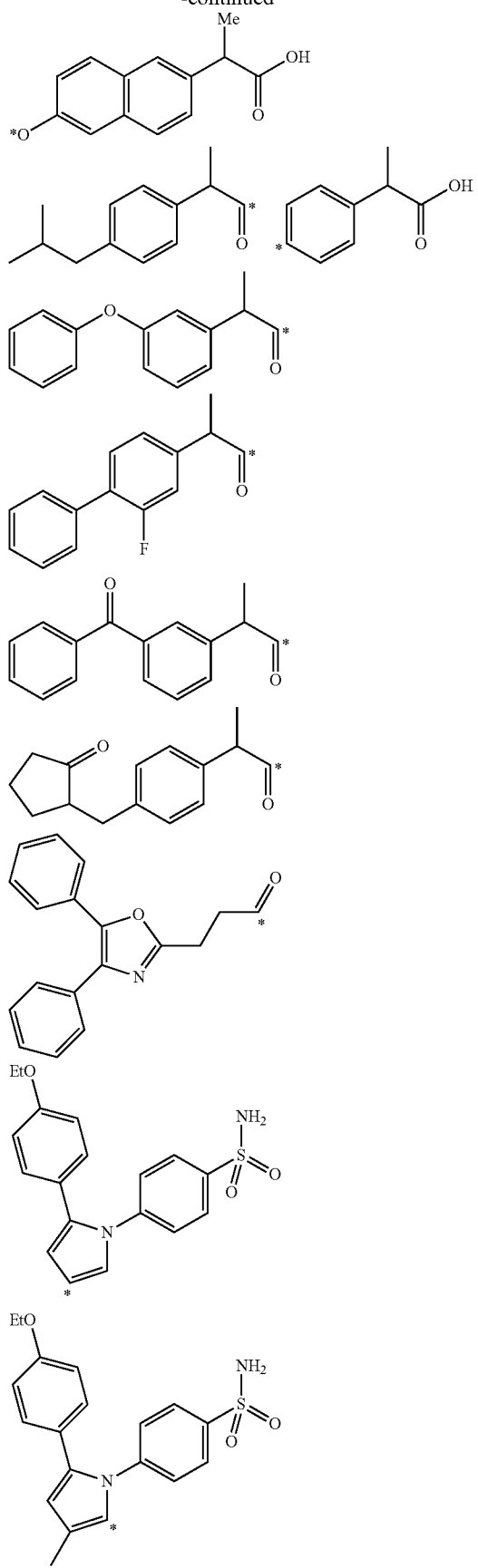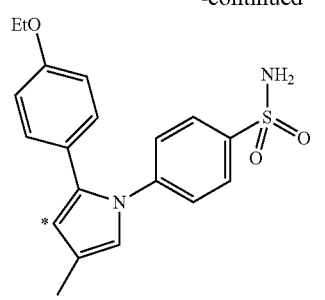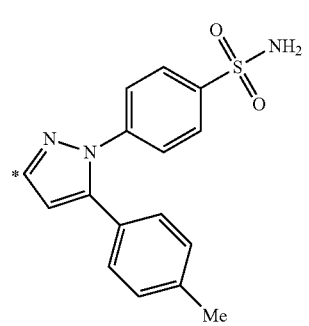

143
-continued

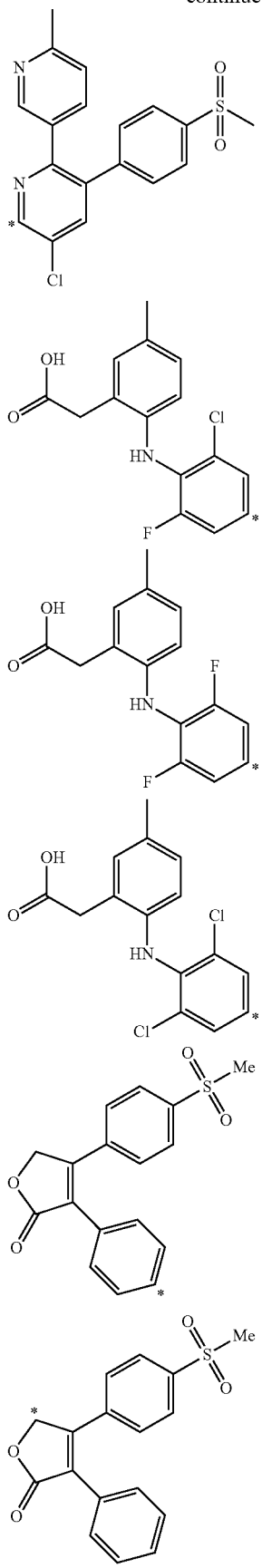

144
-continued

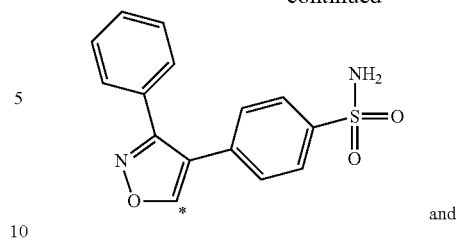

and

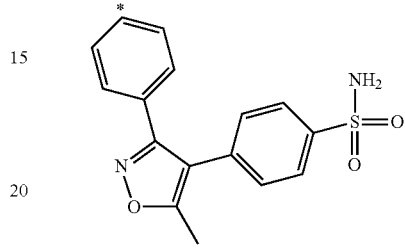

and pharmaceutically acceptable salts thereof, wherein the methyl group of any methyl-containing COX-2-targeting moiety can optionally be replaced with —CF$_3$, and an atom marked with an asterisk (*) is a site where the COX-2-targeting moiety is connected to the remainder of the conjugate.

7. The conjugate of embodiment 5, wherein the NSAID is indomethacin, or an analog, derivative, residue or salt thereof.

8. The conjugate of embodiment 7, wherein the COX-2-targeting moiety is

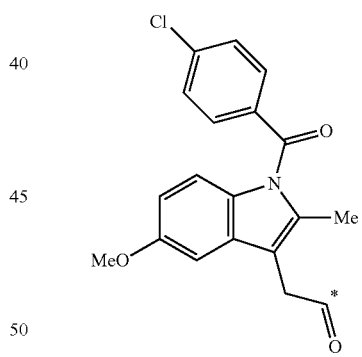

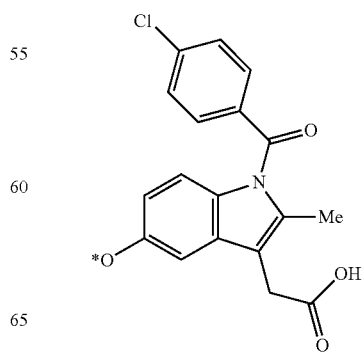

145
-continued

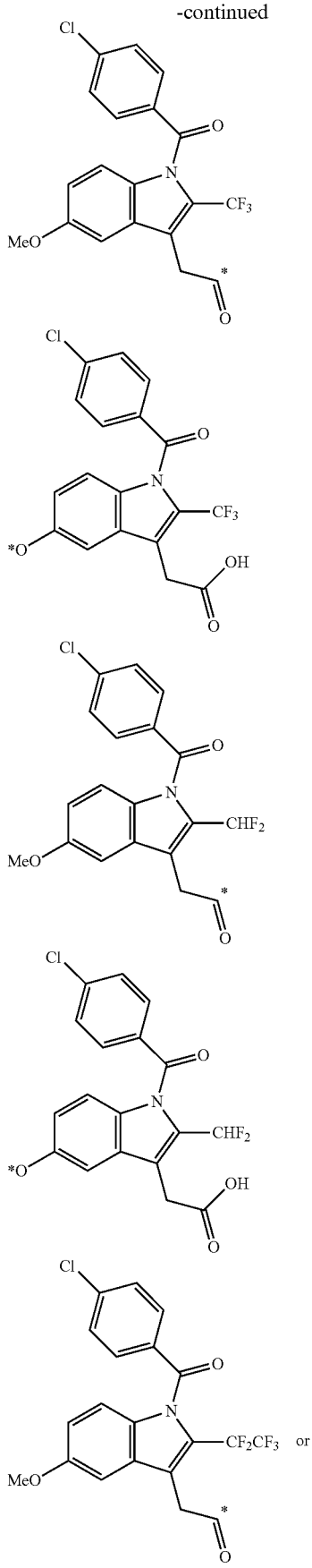

146
-continued

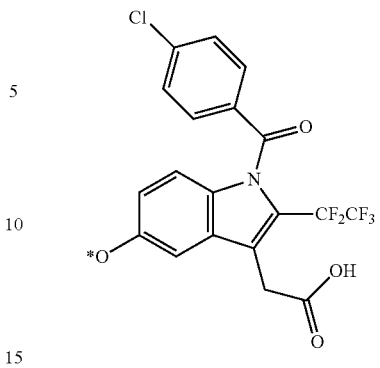

or a pharmaceutically acceptable salt thereof, wherein an atom marked with an asterisk (*) is a site where the COX-2-targeting moiety is connected to the remainder of the conjugate.

9. The conjugate of any one of embodiments 1 to 6, wherein the COX-2-targeting moiety comprises a COX-2-selective inhibitor, or an analog, derivative, residue or salt thereof.

10. The conjugate of embodiment 9, wherein the COX-2-selective inhibitor is selected from the group consisting of apricoxib, celecoxib, etoricoxib, firocoxib, fluorocoxibs (e.g., fluorocoxibs A-C), lumiracoxib, mavacoxib, parecoxib, rofecoxib, tilmacoxib (JTE-522), valdecoxib, 4-O-methylhonokiol, DuP-697, CG100649, NS-398, SC-58125, benzothieno[3,2-d]pyrimidin-4-one sulfonamide thio-derivatives, COX-2 inhibitors derived from *Tribulus terrestris*, and analogs, derivatives, residues and salts thereof.

11. The conjugate of any one of the preceding embodiments, wherein the platinum-containing antitumor agent is of Formula I or a pharmaceutically acceptable salt thereof:

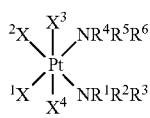

(I)

wherein:

$X^1$ and $X^2$ independently are —Cl, —OH, optionally substituted —O-(alkyl or cyclyl), optionally substituted —O-(alkyl or cyclyl)-C(=O)OR$^7$, optionally substituted —O-(alkyl or cyclyl)-C(=O)NR$^8$R$^9$, optionally substituted —OC(=O)-(alkyl or cyclyl), optionally substituted —OC(=O)-(alkyl or cyclyl)-C(=O)OR$^7$, optionally substituted —OC(=O)-(alkyl or cyclyl)-C(=O)NR$^8$R$^9$, or optionally substituted thiourea, wherein:

cyclyl is an optionally substituted cycloalkyl, heterocyclyl, aryl or heteroaryl group;

R$^7$ is —H, optionally substituted alkyl, optionally substituted cycloalkyl or optionally substituted heterocyclyl; and R$^8$ and R$^9$ independently are —H, optionally substituted alkyl, optionally substituted cycloalkyl or optionally substituted heterocyclyl; or R⁸ and R⁹, together with the nitrogen atom to which they are attached, form an optionally substituted heterocyclyl group; and X¹ and X² can be cis or trans relative to each other; or X¹ and X² together are part of a sulfate (SO₄⁻²) group; or X¹ and X² together form

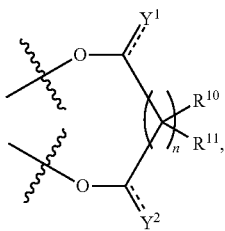

wherein:

Y¹ and Y² independently are —H, —OH, oxo (forming a carbonyl group with the adjacent carbon atom), or optionally substituted alkyl;

R¹⁰ and R¹¹ independently are —H, —OH, —NH₂, optionally substituted alkyl, optionally substituted —O-alkyl, optionally substituted —O-alkyl-C(=O)OR⁷, optionally substituted —O-alkyl-C(=O)NR⁸R⁹, optionally substituted —OC(=O)-alkyl, optionally substituted —OC(=O)-alkyl-C(=O)OR⁷, optionally substituted —OC(=O)-alkyl-C(=O)NR⁸R⁹, —NR¹²R¹³, optionally substituted —NH-alkyl-C(=O)OR⁷, optionally substituted —NH-alkyl-C(=O)NR⁸R⁹, optionally substituted —NHC(=O)-alkyl, —NHC(=O)-alkyl-C(=O)OR⁷, or optionally substituted —NHC(=O)-alkyl-C(=O)NR⁸R⁹, wherein:

R⁷ is —H, optionally substituted alkyl, optionally substituted cycloalkyl or optionally substituted heterocyclyl;

R⁸ and R⁹ independently are —H, optionally substituted alkyl, optionally substituted cycloalkyl or optionally substituted heterocyclyl; or R⁸ and R⁹, together with the nitrogen atom to which they are attached, form an optionally substituted heterocyclyl group; and R¹² and R¹³, independently are —H, optionally substituted alkyl, optionally substituted cycloalkyl, optionally substituted heterocyclyl, optionally substituted aryl or optionally substituted heteroaryl; or R¹² and R¹³, together with the nitrogen atom to which they are attached, form an optionally substituted heterocyclyl or heteroaryl group; or R¹⁰ and R¹¹, together with the carbon atom to which they are attached, form an optionally substituted cycloalkyl ring; and n is 0 or 1;

X³ and X⁴ independently are absent or are —Cl, —OH, optionally substituted —O-(alkyl or cyclyl), optionally substituted —O-(alkyl or cyclyl)-C(=O)OR⁷, optionally substituted —O-(alkyl or cyclyl)-C(=O)NR⁸R⁹, optionally substituted —OC(=O)-(alkyl or cyclyl), optionally substituted —OC(=O)-(alkyl or cyclyl)-C(=O)OR⁷, optionally substituted —OC(=O)-(alkyl or cyclyl)-C(=O)NR⁸R⁹, or optionally substituted thiourea, wherein: cyclyl is an optionally substituted cycloalkyl, heterocyclyl, aryl or heteroaryl group;

R⁷ is —H, optionally substituted alkyl, optionally substituted cycloalkyl or optionally substituted heterocyclyl; and R⁸ and R⁹ independently are —H, optionally substituted alkyl, optionally substituted cycloalkyl or optionally substituted heterocyclyl; or R⁸ and R⁹, together with the nitrogen atom to which they are attached, form an optionally substituted heterocyclyl group;

R¹, R², R³, R⁴, R⁵ and R⁶ independently are —H, optionally substituted alkyl, optionally substituted cycloalkyl, optionally substituted heterocyclyl, optionally substituted aryl or optionally substituted heteroaryl; or NR¹R²R³ and NR⁴R⁵R⁶ independently are optionally substituted heterocyclyl or optionally substituted heteroaryl; or NR¹R²R³ and NR⁴R⁵R⁶ together are part of an optionally substituted alkyldiamine, cycloalkyldiamine, heterocyclyldiamine, aryldiamine or heteroaryldiamine group, or part of a nitrogen-containing heterocyclyl or heteroaryl group substituted with an aminoalkyl group, or part of a cycloalkyl, heterocyclyl, aryl or heteroaryl group substituted with at least two aminoalkyl groups.

12. The conjugate of any one of the preceding embodiments, wherein the platinum-containing antitumor agent is selected from the group consisting of cisplatin, carboplatin, dicycloplatin, enloplatin, eptaplatin (heptaplatin), ethacraplatin, iproplatin, kiteplatin, lobaplatin, miboplatin, miriplatin, nedaplatin, ormaplatin (tetraplatin), oxaliplatin, oxoplatin [cis-diamminedichloro-trans-dihydroxoplatinum(IV)], phenanthriplatin, picazoplatin, picoplatin (AMD473), pyriplatin, satraplatin (JM216), spiroplatin, triplatin, zeniplatin, cis-diamminedihydroxoplatinum(II), cis-diammine(2-aminomalonate)platinum(II), cis-diammine(2-hydroxymalonate)platinum(II), chloro(1,2-ethanediamine)(N,N'-dimethylthiourea)platinum(II), chloro(1,2-ethanediamine)-(tetramethylthiourea)platinum(II), cis-dichloro(1,2-ethanediamine)platinum(II), cis-dichloro(1,2-ethanediamine)-trans-dihydroxo-platinum(IV), cis-dichloro(1,2-ethanediamine)-trans-bis(acetato)-platinum(IV), cis-dichloro(1,2-ethanediamine)-trans-bis(succinic acid)-platinum(IV), cis-dichloro[1,1-bis(aminomethyl)cyclohexane]-platinum(II), cis-dichloro[1,1-bis(aminomethyl)cyclohexane]-trans-dihydroxo-platinum(IV), cis-dichloro[1,1-bis(aminomethyl)cyclohexane]-trans-bis(acetato)-platinum(IV), cis-dichloro[1,1-bis(aminomethyl)cyclohexane]-trans-bis(succinic acid)-platinum(IV), JM118 [cis-amminedichloro(cyclohexylamine)platinum(II)], JM149 [cis-amminedichloro(cyclohexylamine)-trans-dihydroxo-platinum(IV)], JM335 [trans-amminedichloro(cyclohexylamine)-trans-dihydroxo-platinum(IV)], cis-diamminedichloro-trans-bis(acetato)-platinum(IV), cis-diamminedichloro-trans-bis(succinic acid)-platinum(IV), cis-diammine(1,1-cyclobutanedicarboxylato)-trans-dihydroxo-platinum(IV), cis-diammine(1,1-cyclobutanedicarboxylato)-trans-bis(succinic acid)-platinum(IV), LA-12 [(OC-6-43)-bis(acetato)(1-adamantylamine)amminedichloroplatinum(IV)], and analogs, derivatives, residues and salts thereof.

13. The conjugate of embodiment 11 or 12, wherein the platinum-containing antitumor agent is selected from the group consisting of:

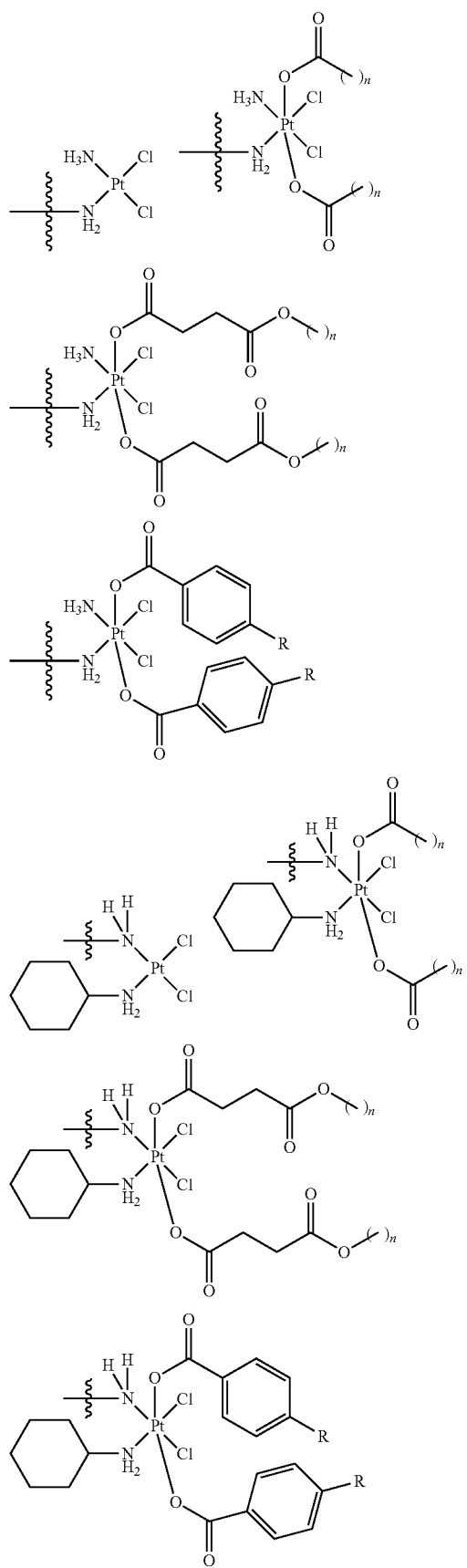
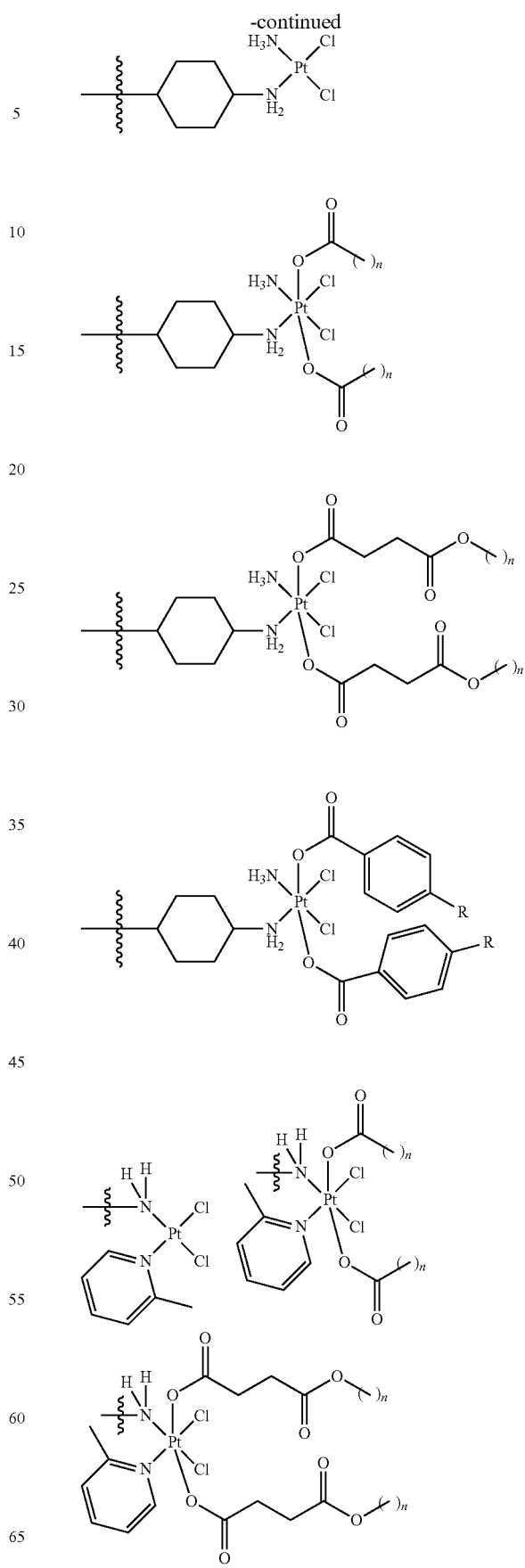

151
-continued
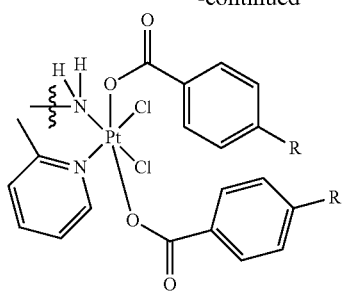
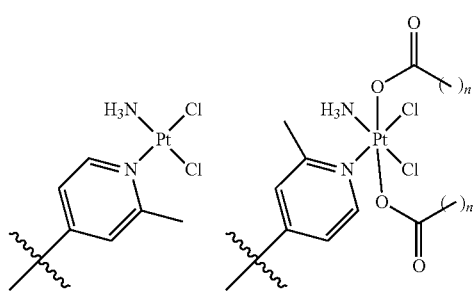
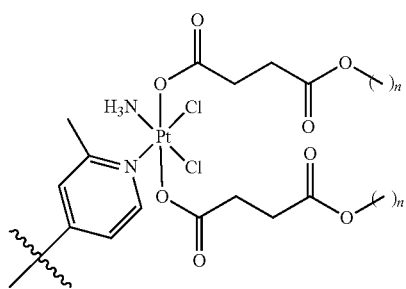
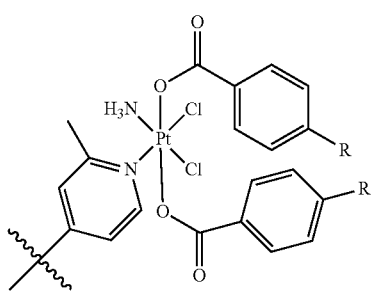
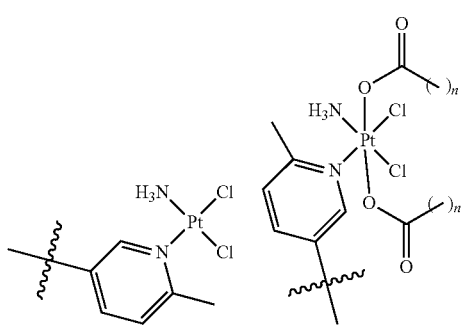
152
-continued
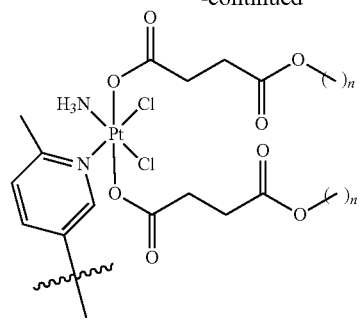
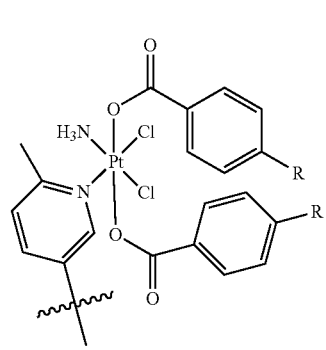
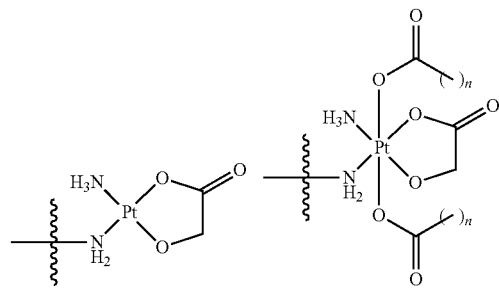
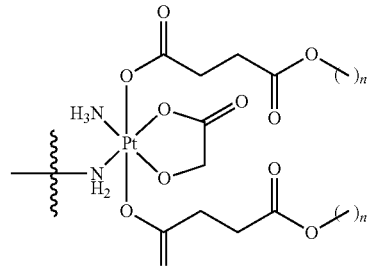
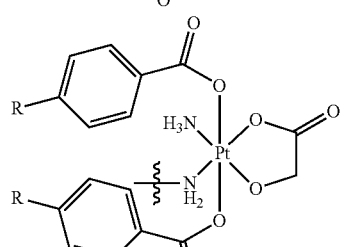
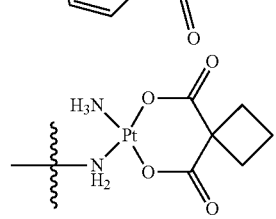

153
-continued
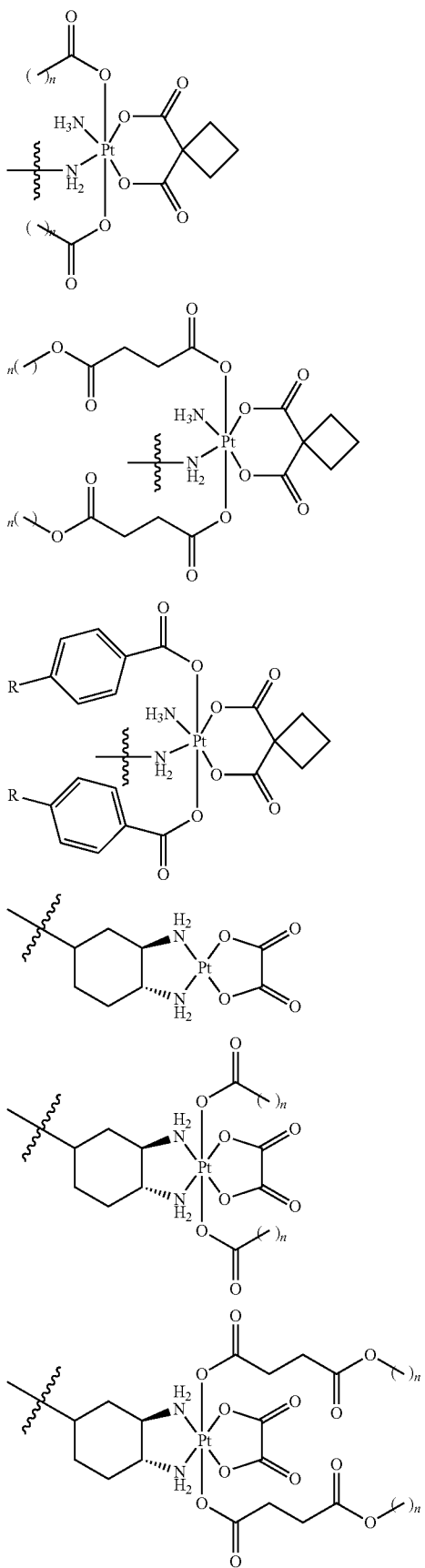
154
-continued
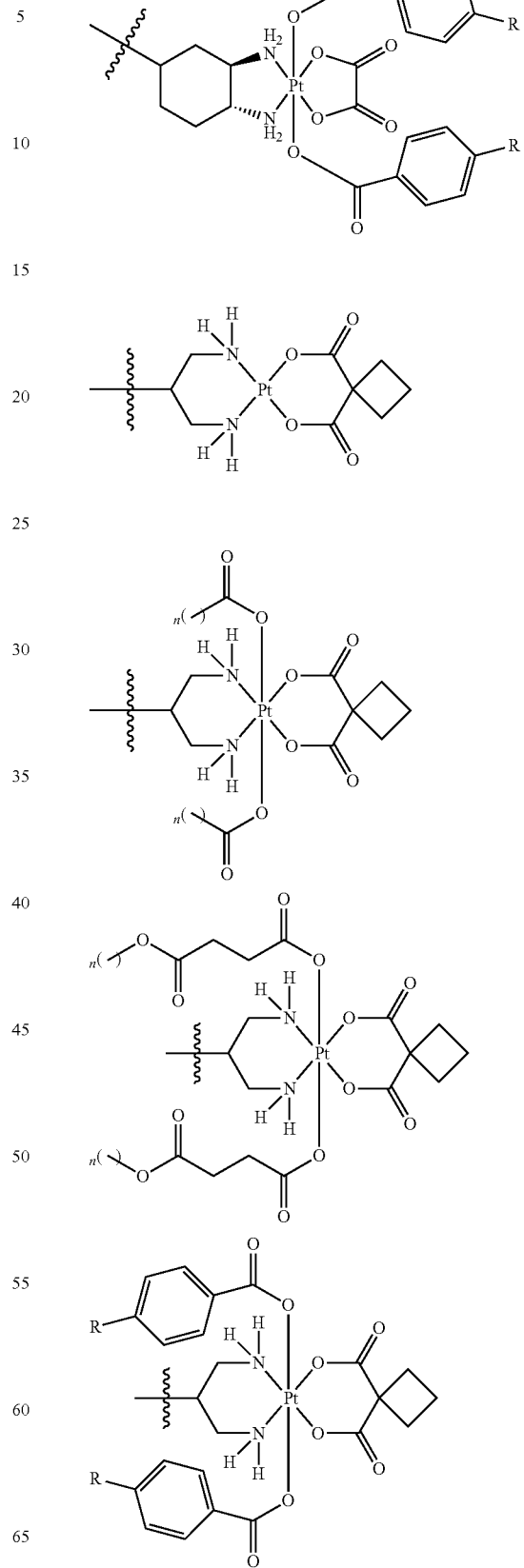

155
-continued
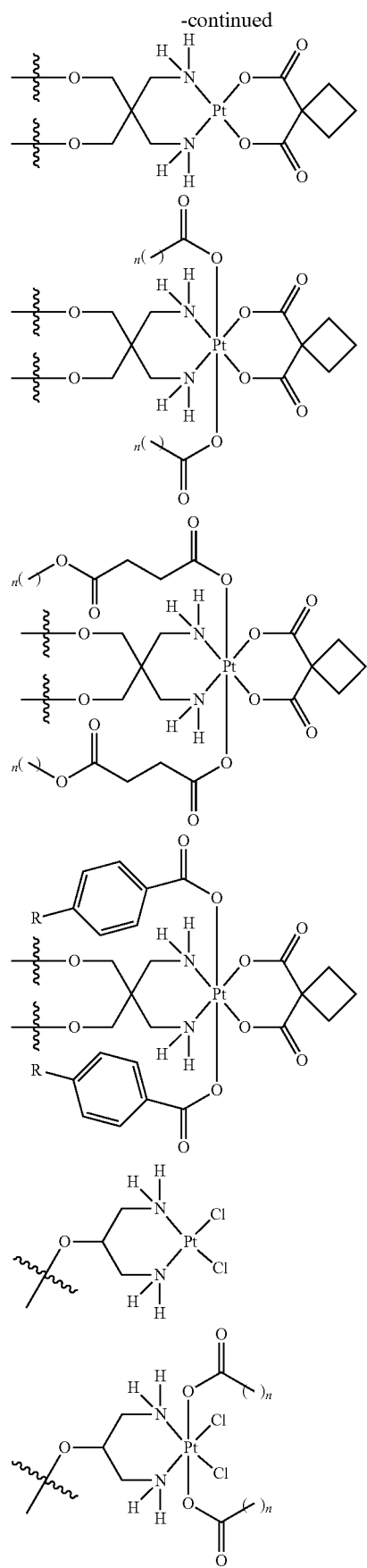
156
-continued
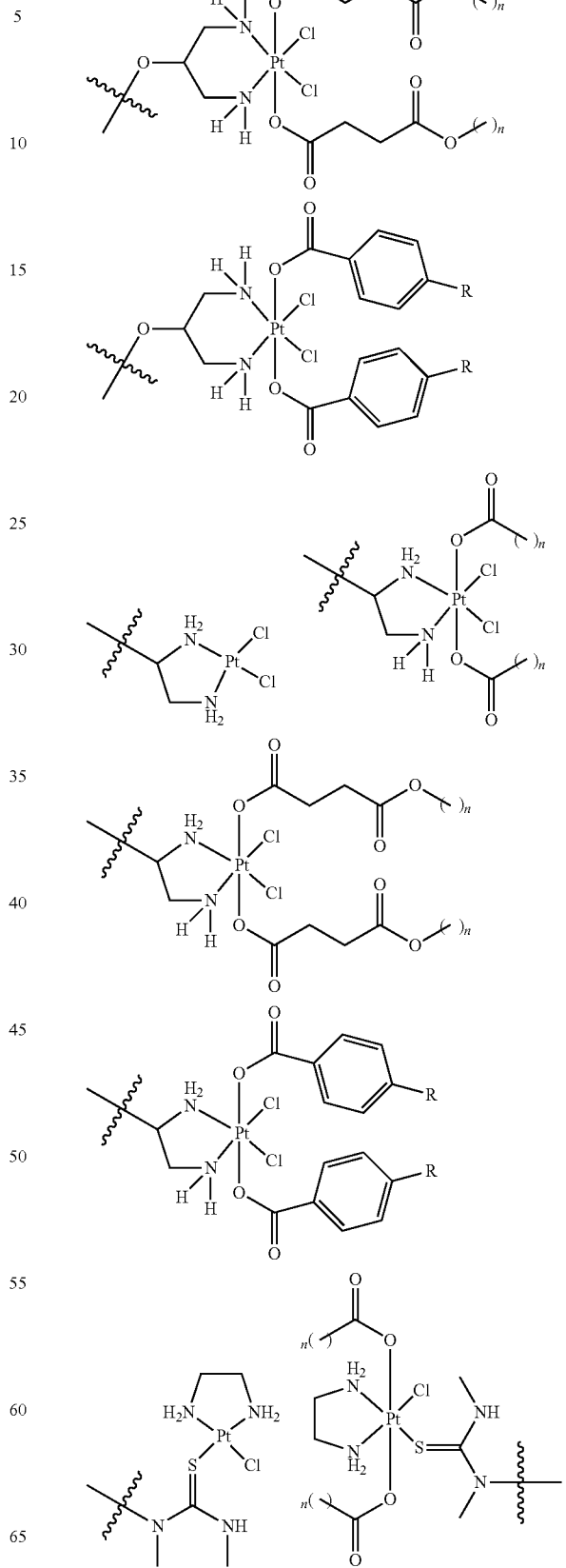

157
-continued
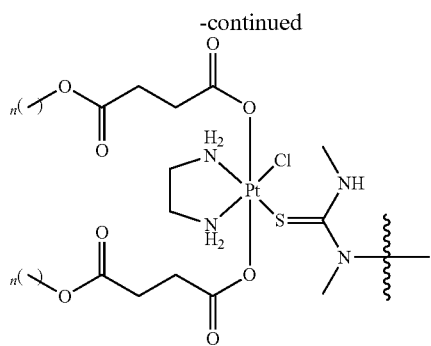
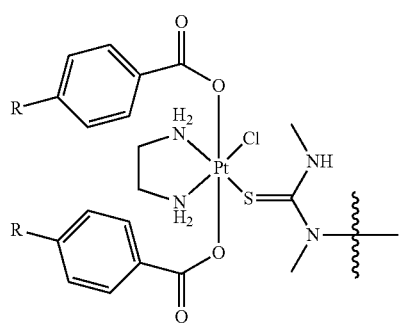
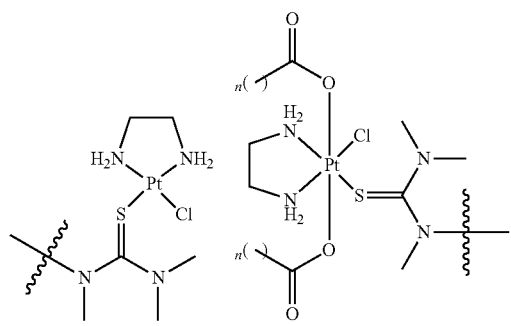
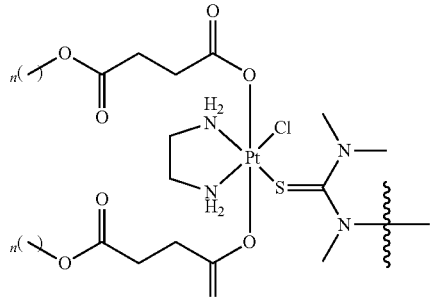
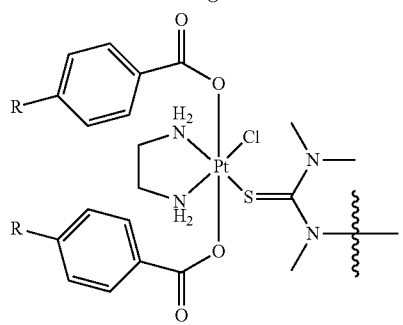
158
-continued
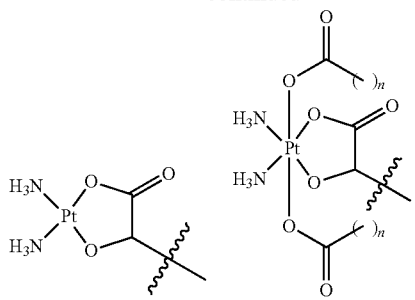
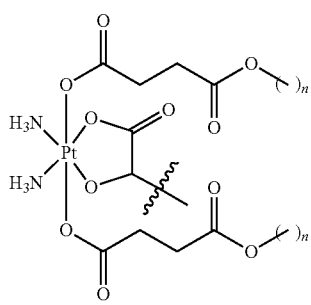
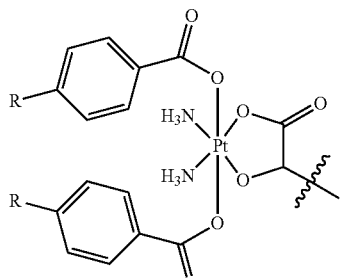
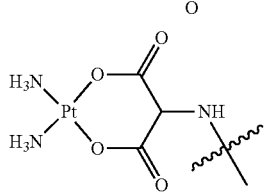
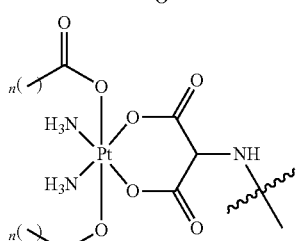
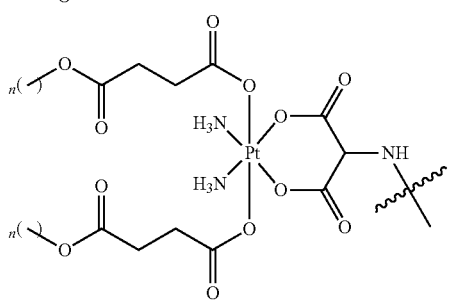

159
-continued
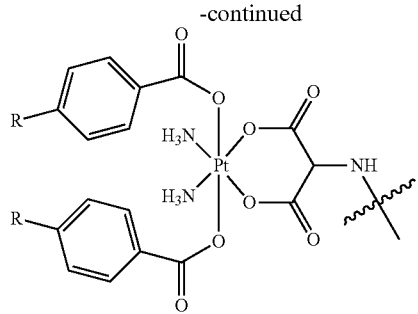
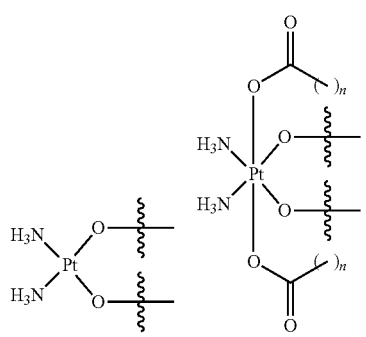
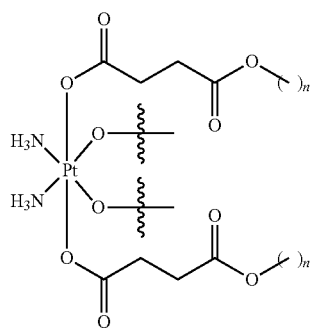
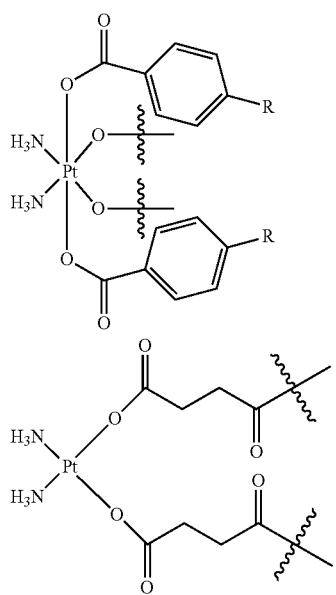
160
-continued
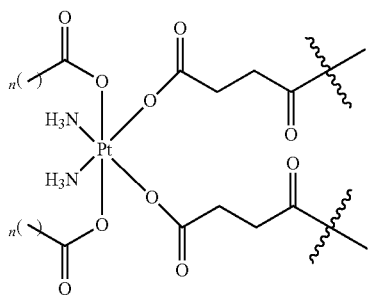
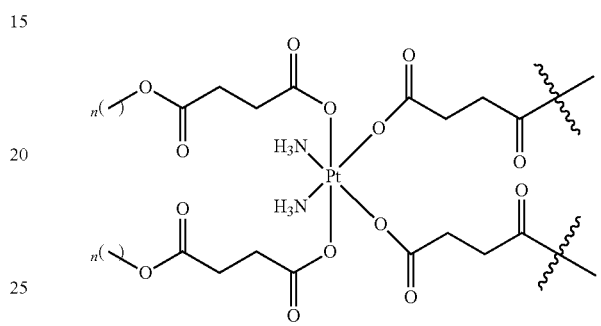
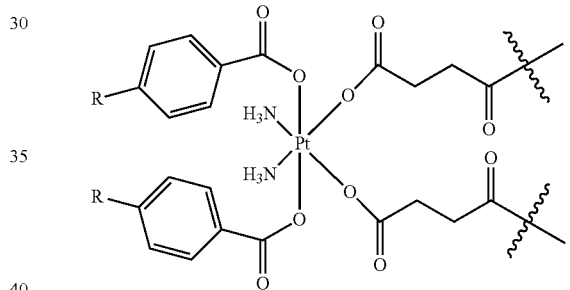
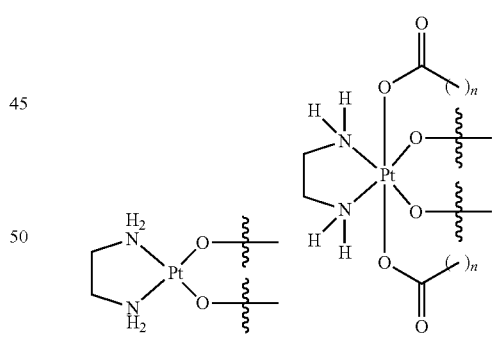
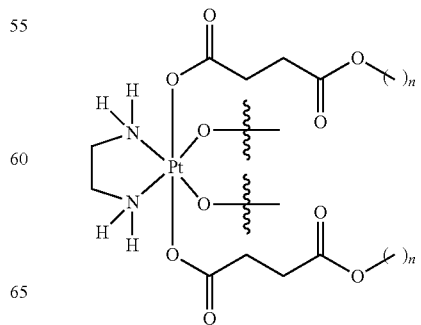

-continued
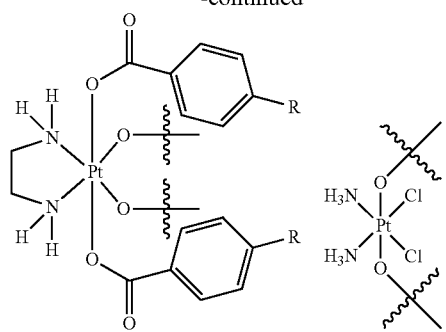
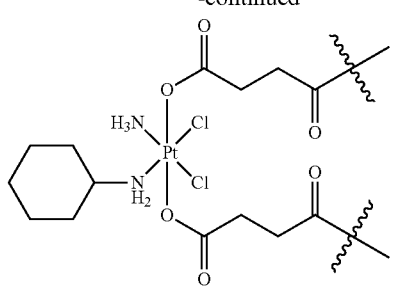
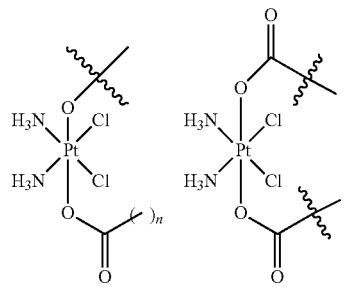
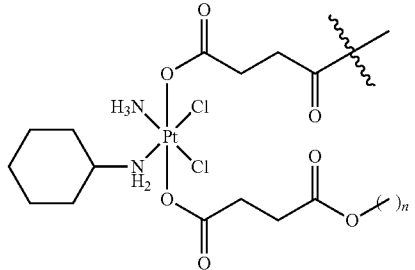
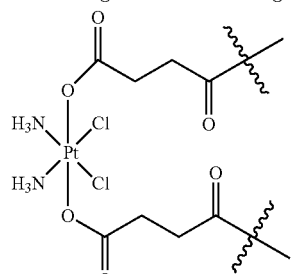
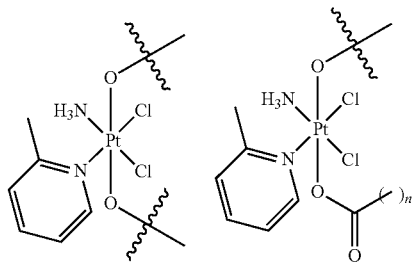
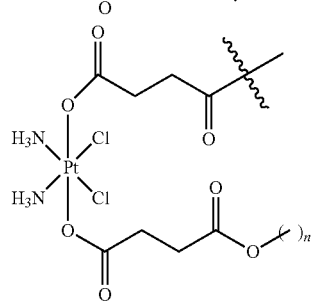
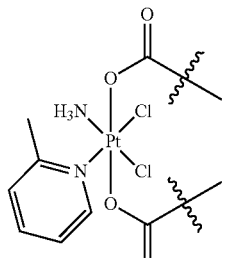
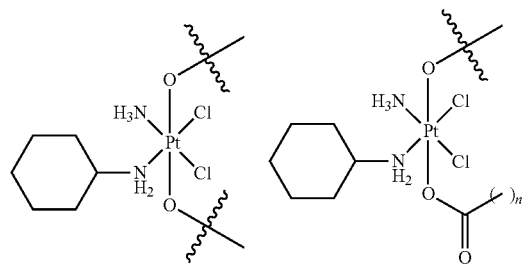
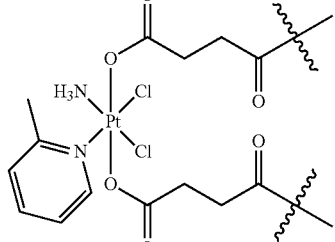
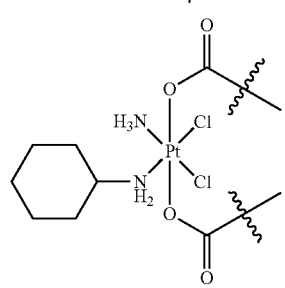
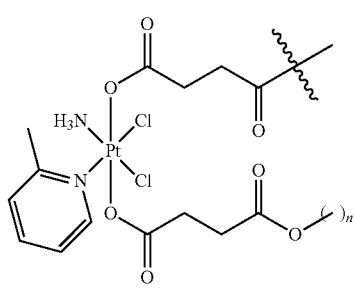

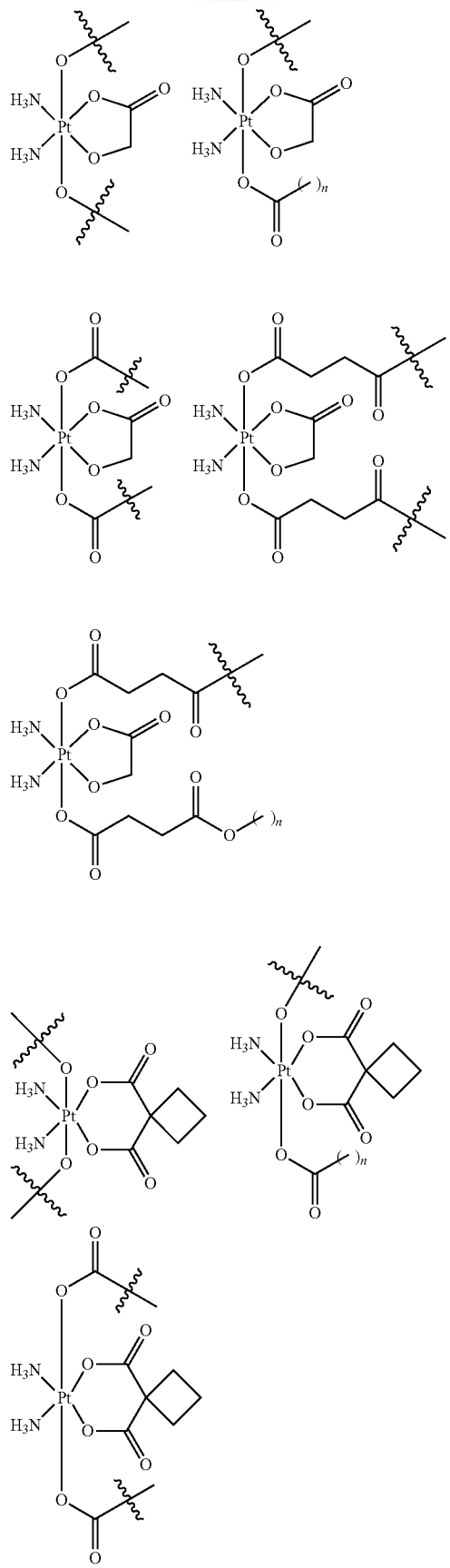
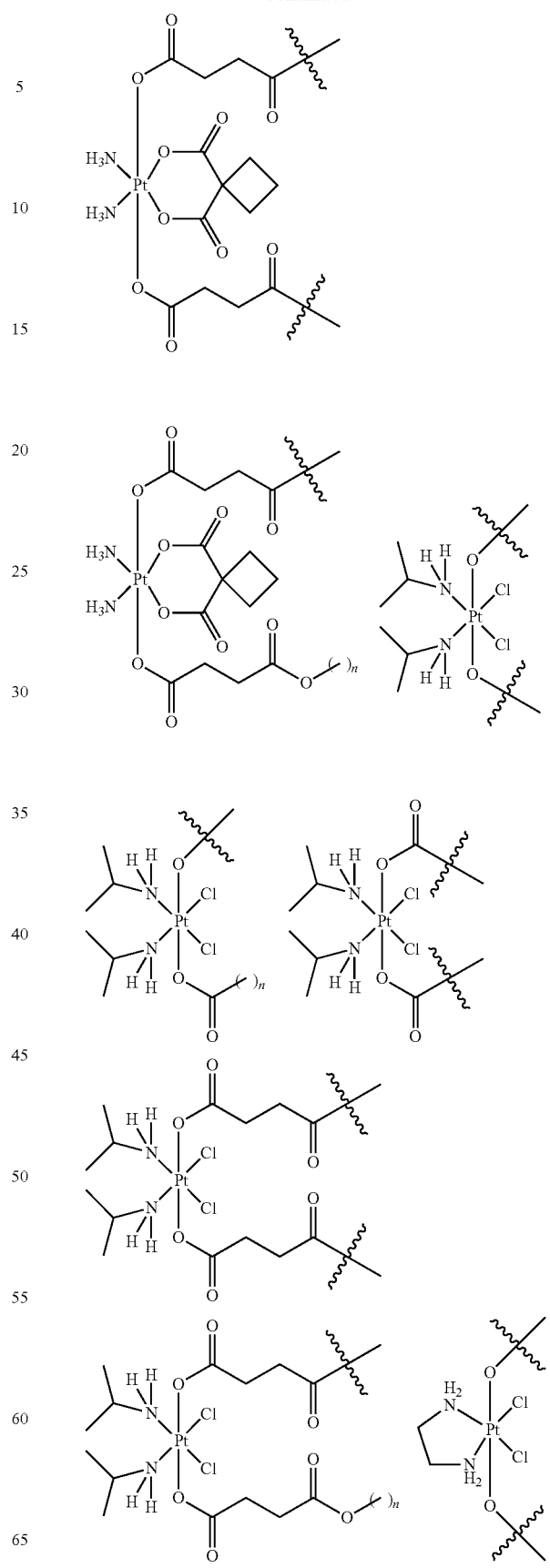

165
-continued
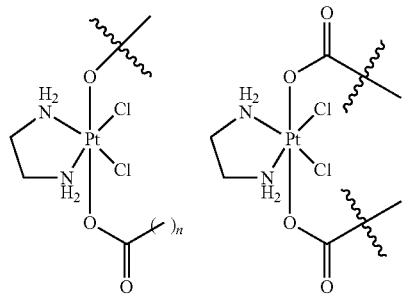
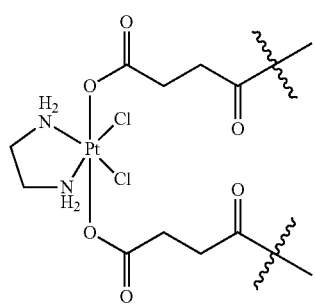
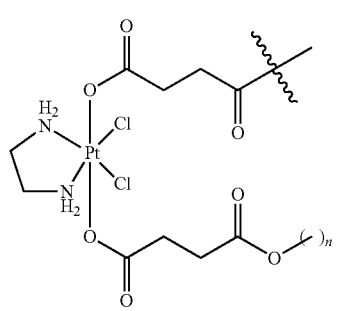
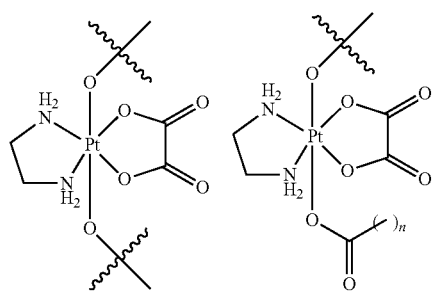
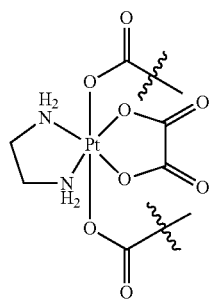
166
-continued
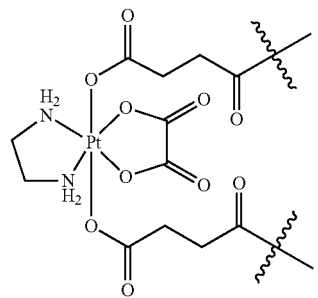
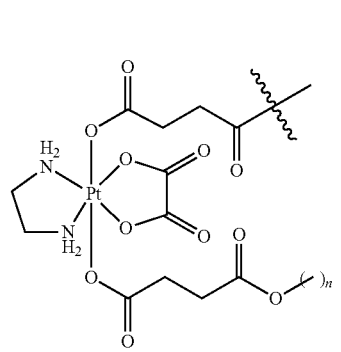
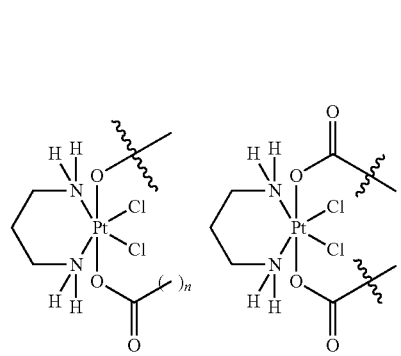
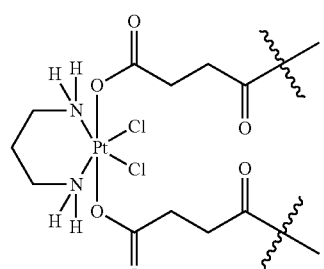
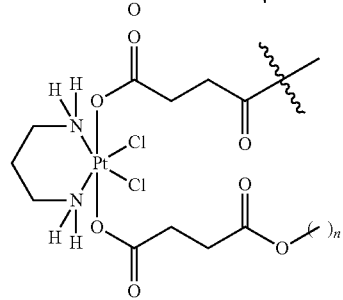

-continued
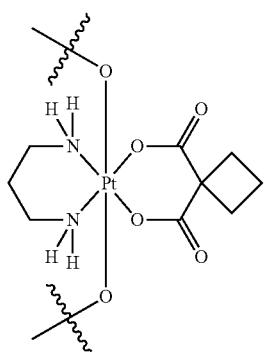
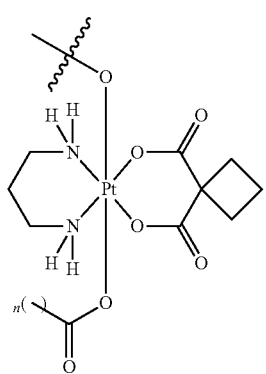
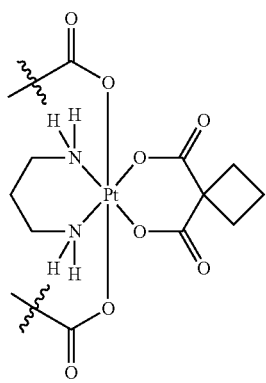
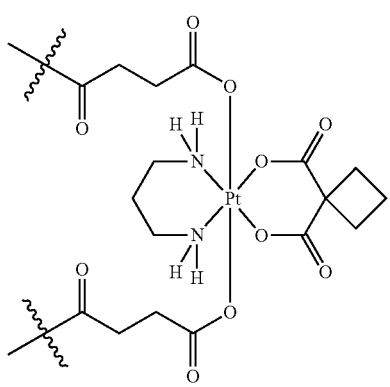
-continued
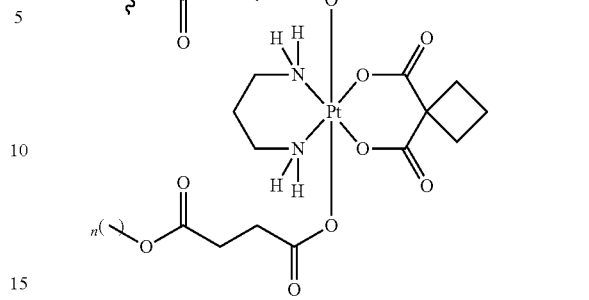
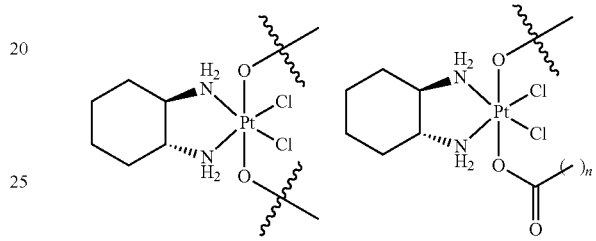
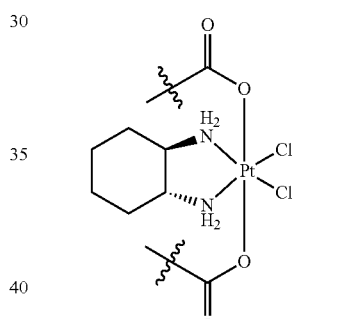
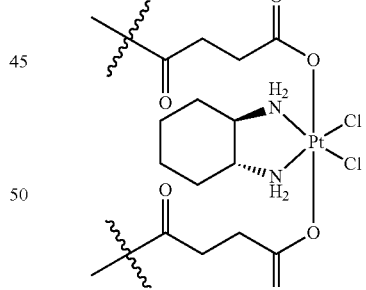
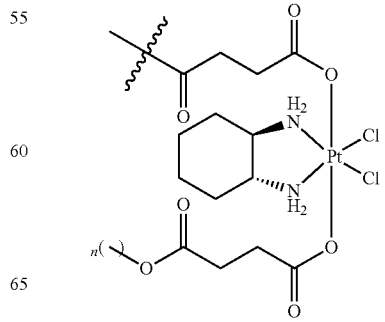

169
-continued

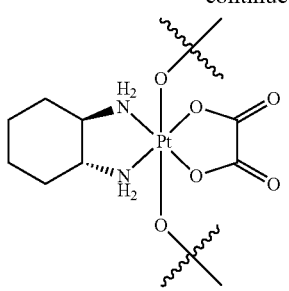

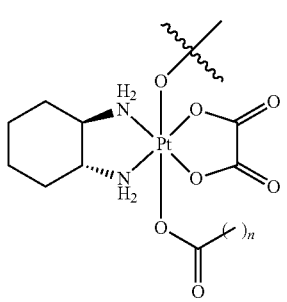

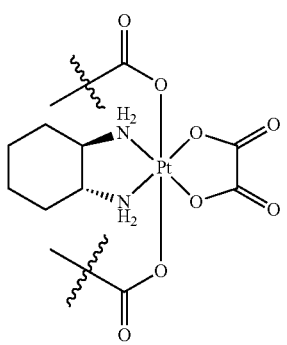

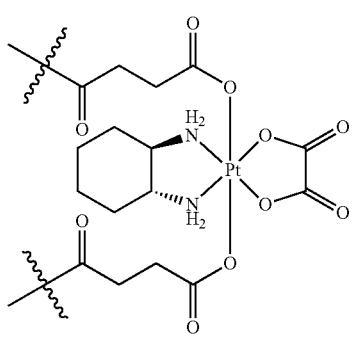

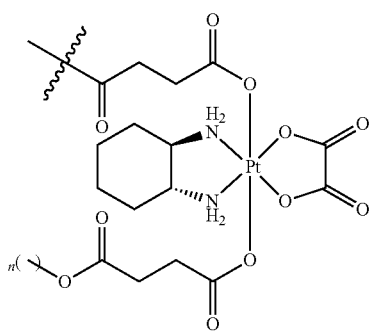

170
-continued

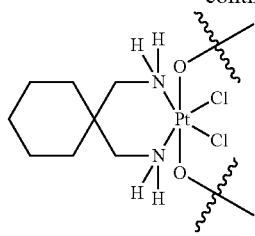

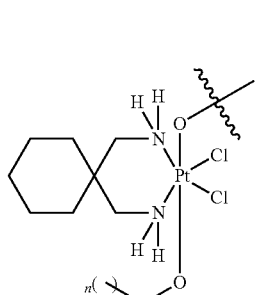
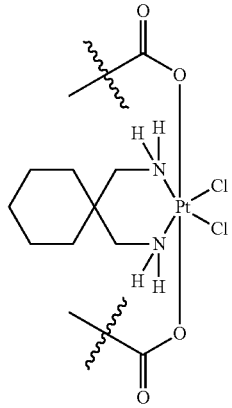

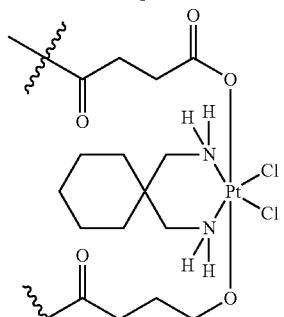

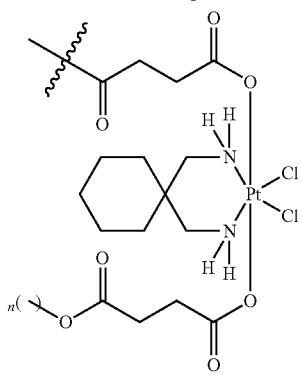

and corresponding platinum complexes that can be connected to a COX-2-targeting moiety at one axial position and have a —OC(=O)-(4-phenyl-R) ligand at the other axial position, and pharmaceutically acceptable salts thereof, wherein:

R is —H or $C_1$-$C_6$ alkyl;

n is an integer from 1 to 15; and an atom adjacent to a wavy line is a site where the platinum-containing antitumor agent is connected to the remainder of the conjugate.

14. The conjugate of any one of the preceding embodiments, wherein the linker independently is associated with the COX-2-targeting moiety and the platinum-containing antitumor agent by covalent or non-covalent (e.g., ionic) bonding, complexation or coordination.

15. The conjugate of any one of the preceding embodiments, which is of the formula:

[CTM-linker]$_n$-PAA wherein CTM denotes COX-2-targeting moiety, PAA denotes platinum-containing antitumor agent, and n is an integer from 1 to 6.

16. The conjugate of any one of the preceding embodiments, wherein the linker is selected from the group consisting of:
1) optionally substituted $C_1$-$C_{40}$ hydrocarbylene;
2) optionally substituted $C_2$-$C_{40}$ heterohydrocarbylene;
3) -$L_E$-$R_4$-$L_F$-, wherein:
   $L_E$ is absent or is —N($R^8$)—, wherein $R^8$ is —H or optionally substituted $C_1$-$C_6$ alkyl;
   $R^4$ is optionally substituted $C_1$-$C_{40}$ hydrocarbylene or optionally substituted $C_2$-$C_{40}$ heterohydrocarbylene; and
   $L_F$ is absent or is selected from the group consisting of —O—, —N($R^9$)—, —C(=O)—, —C(=O)N($R^9$)—, —N($R^9$)C(=O)—, —S(O)N($R^9$)—, —N($R^9$)S(O)—, —S(O)$_2$N($R^9$)—, —N($R^9$)S(O)$_2$—, —N($R^9$)C(=O)N($R^9$)—, —N($R^9$)C(=O)O—, —OC(=O)N($R^9$)—, —(CH=CH)—, and divalent cycloalkyl and heterocyclic groups (e.g., 1,2,3-triazole and 1,2,4-triazole), wherein each occurrence of $R^9$ independently is —H or optionally substituted $C_1$-$C_6$ alkyl; and
4) —C≡N(CH$_2$)$_m$X—,

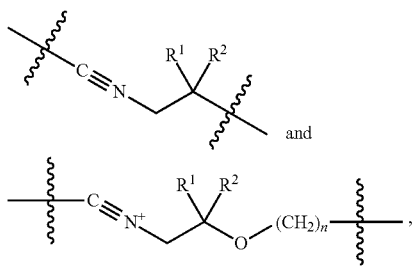

and wherein:
X is absent or is —O— or —N($R^3$)—, wherein $R^3$ is —H or $C_1$-$C_6$ alkyl;
$R^1$ and $R^2$ independently are —H, —F, $C_1$-$C_6$ alkyl, hydroxyl-substituted $C_1$-$C_6$ alkyl, —O—$C_1$-$C_6$ alkyl, or $C_3$-$C_6$ cycloalkyl; or
$R^1$ and $R^2$, together with the carbon atom to which they are attached, form a $C_3$-$C_8$ cycloalkyl ring or heterocyclyl ring;
m is an integer from 1 to 12; and
n is an integer from 0 to 4.

17. The conjugate of any one of the preceding embodiments, wherein the linker is selected from the group consisting of:
1) —(CH$_2$)$_n$—, —O(CH$_2$)$_n$—, —O(CH$_2$)$_n$O—, —N($R^1$)(CH$_2$)$_n$—, —N($R^1$)(CH$_2$)$_n$N($R^2$)—, and —N($R^1$)(CH$_2$)$_n$O—, wherein $R^1$ and $R^2$ independently are —H or $C_1$-$C_6$ alkyl, and n is an integer from 2 to 20;
2) —(CX$^1$X$^2$)$_m$(CH$_2$)$_n$—, wherein each occurrence of X$^1$ and X$^2$ independently is —H or —F, m is an integer from 1 to 6, and n is an integer from 0 to 20;
3) (—CH$_2$CH$_2$O—)$_n$ and (—CH$_2$CH(CH$_3$)O—)$_n$, wherein n is an integer from 1 to 12;
4) —X$^1$CH$_2$CH$_2$OCH$_2$CH$_2$X$^2$— and —X$^1$CH$_2$CH$_2$O(—CH$_2$CH$_2$O—)$_n$CH$_2$CH$_2$X$^2$—, wherein X$^1$ and X$^2$ independently are absent or are —O— or —N(R)—, each occurrence of R independently is —H or $C_1$-$C_6$ alkyl, and n is an integer from 1 to 12;
5) —X$^1$CH$_2$(—CH$_2$CH$_2$O—)$_n$(CH$_2$)$_3$X$^2$—, wherein X$^1$ and X$^2$ independently are absent or are —O— or —N(R)—, each occurrence of R independently is —H or $C_1$-$C_6$ alkyl, and n is an integer from 1 to 12;
6) —C(=O)(CH$_2$)$_n$X—, wherein X is absent or is —O— or —N(R)—, R is —H or $C_1$-$C_6$ alkyl, and n is an integer from 1 to 20;
7) —C(=O)(CH$_2$)$_n$C(=O)—, wherein n is an integer from 2 to 20;
8) —C(=O)CH$_2$CH$_2$C(=O)N(R)(CH$_2$)$_n$C(=O)—, wherein R is —H or $C_1$-$C_6$ alkyl, and n is an integer from 1 to 20;
9) —C(=O)CH$_2$CH$_2$C(=O)N($R^1$)CH$_2$(—CH$_2$CH$_2$O—)$_n$(CH$_2$)$_3$X—, wherein X is —O—, —N($R^2$)— or —C(=O)—, $R^1$ and $R^2$ independently are —H or $C_1$-$C_6$ alkyl, and n is an integer from 1 to 12;
10) —C(=O)CH$_2$(—OCH$_2$CH$_2$—)$_n$O— and —C(=O)CH$_2$(—OCH$_2$CH$_2$—)$_n$OCH$_2$C(=O)—, wherein n is an integer from 1 to 12; and
11) —X$^1$(CH$_2$)$_m$-cyclyl-(CH$_2$)$_n$X$^2$—, wherein X$^1$ and X$^2$ independently are absent or are —O— or —N(R)—, each occurrence of R independently is —H or $C_1$-$C_6$ alkyl, cyclyl is cycloalkyl, aryl, heterocyclyl or heteroaryl, and m and n independently are integers from 0 to 6.

18. The conjugate of any one of the preceding embodiments, wherein the linker is selected from the group consisting of:
1) —(CH$_2$)$_n$—, —(CH$_2$)$_n$O— and —(CH$_2$)$_n$N(R)—, wherein R is —H or $C_1$-$C_6$ alkyl and n is an integer from 4 to 10;
2) —(CF$_2$)$_m$(CH$_2$)$_n$—, wherein m is an integer from 1 to 4, and n is an integer from 1 to 15;
3) —CH$_2$CH$_2$OCH$_2$CH$_2$—, —CH$_2$CH$_2$O(—CH$_2$CH$_2$O—)$_n$, —CH$_2$CH$_2$O(—CH$_2$CH$_2$O—)$_n$CH$_2$CH$_2$—, and —NH(—CH$_2$CH$_2$O—)$_n$X, wherein X is absent or is —CH$_2$— or —CH$_2$CH$_2$—, and n is an integer from 1 to 4;
4) —NHCH$_2$CH$_2$OCH$_2$CH$_2$NH— and —NHCH$_2$CH$_2$O(—CH$_2$CH$_2$O—)$_n$CH$_2$CH$_2$NH—, wherein n is an integer from 1 to 4;
5) —NH(CH$_2$)$_n$NH—, —NH(CH$_2$)$_n$NMe-, and —NMe(CH$_2$)$_n$NMe-, wherein n is an integer from 2 or 4 to 10;
6) —O(CH$_2$)$_n$—, —O(CH$_2$)$_n$O—, —NHX(CH$_2$)$_n$—, —NHX(CH$_2$)$_n$NH—, and —NHX(CH$_2$)$_n$O—, wherein X is absent or is —S(=O)$_2$—, and n is an integer from 4 to 10;
7) —C(=O)(CH$_2$)$_n$— and —C(=O)(CH$_2$)$_n$X—, wherein X is —O— or —N(R)—, R is —H or $C_1$-$C_6$ alkyl, and n is an integer from 4 to 10;
8) —C(=O)(CH$_2$)$_n$C(=O)—, wherein n is an integer from 2 or 4 to 10;
9) —C≡N(CH$_2$)$_m$X—, wherein X is absent or is —O— or —NH—, and m is an integer from 4 to 10;
10) 1,2-cyclopropyldimethylene, 1,2-cyclobutyldimethylene, 1,3-cyclobutyldimethylene, 1,2-cyclopentyldimethylene, 1,3-cyclopentyldimethylene, 1,2-cyclohexyldimethylene, 1,3-cyclohexyldimethylene, and 1,4-cyclohexyldimethylene; and

11)

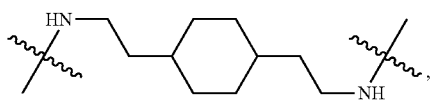

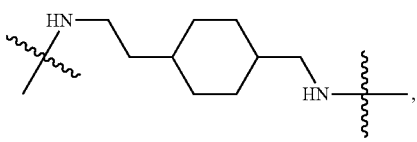

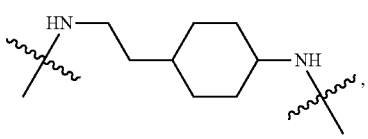

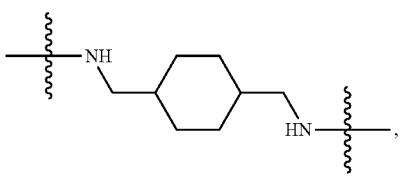

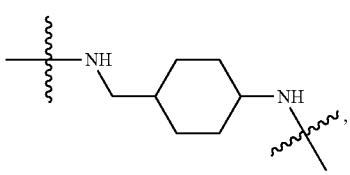

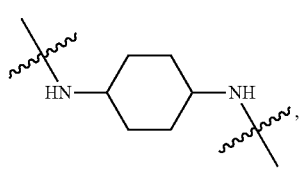

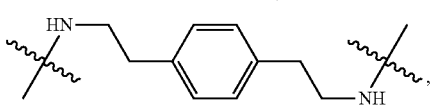

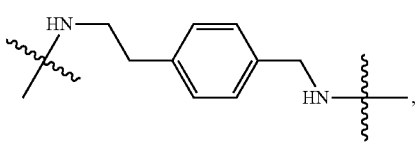

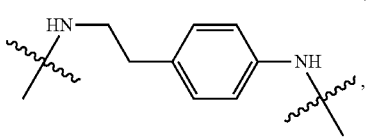

-continued

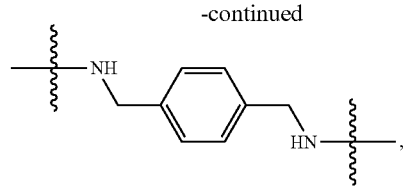

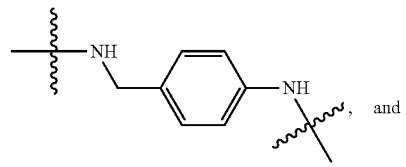

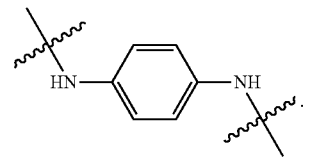

19. The conjugate of any one of the preceding embodiments, wherein the linker increases the selectivity or preference of the conjugate for COX-2 (e.g., increases the selectivity or preference of the conjugate for COX-2 over COX-1).

20. The conjugate of any one of the preceding embodiments, wherein the COX-2-targeting moiety is selected from the group in embodiment 6, the platinum-containing antitumor agent is selected from the group in embodiment 13, and the linker is selected from the group in embodiment 18.

21. The conjugate of embodiment 20, which is selected from the group consisting of:

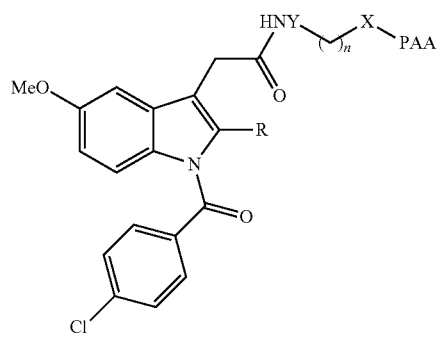

R = CH$_3$ or CF$_3$
X is optionally O or NH
Y is optionally SO$_2$
n is 4 to 10

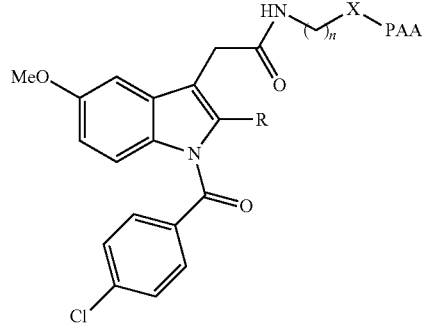

R = CH$_3$ or CF$_3$
X is absent or NH
n is 4 to 10

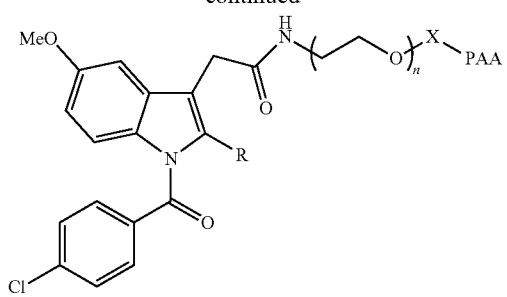

R = CH₃ or CF₃
X is optionally CH₂ or CH₂CH₂
n is 1 to 3

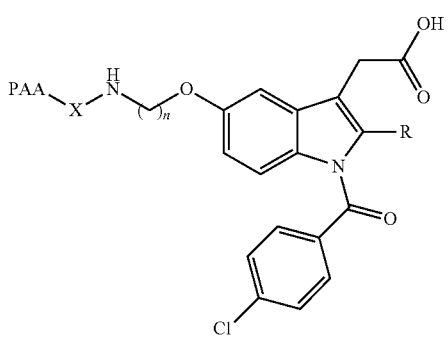

R = CH₃ or CF₃
X is optionally C=O
n is 4 to 10

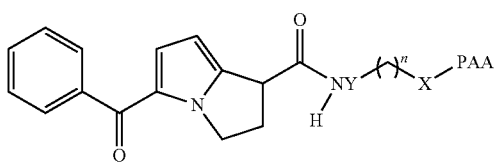

X is optionally O or NH
Y is optionally SO₂
n is 4 to 10

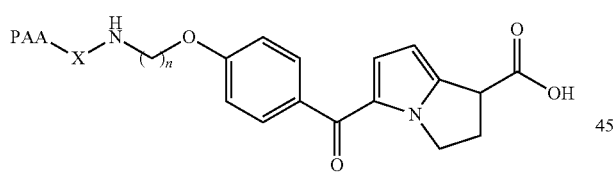

X is optionally C=O
n is 4 to 10

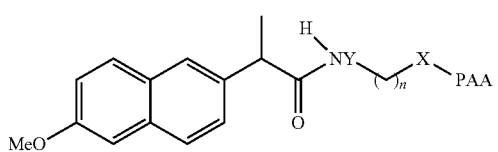

X is optionally O or NH
Y is optionally SO₂
n is 4 to 10

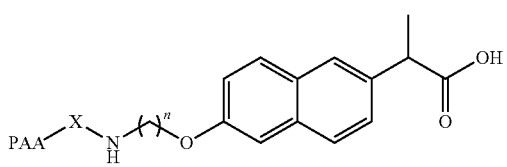

X is optionally C=O
n is 4 to 10

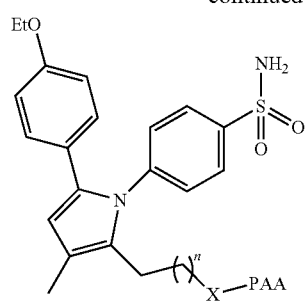

X is optionally O or NH
n is 3 to 10

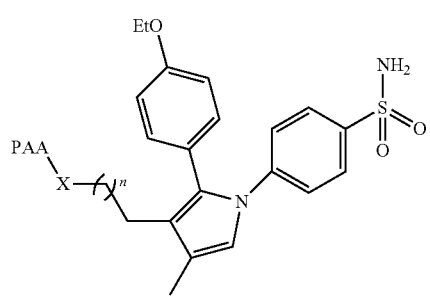

X is optionally O or NH
n is 3 to 10

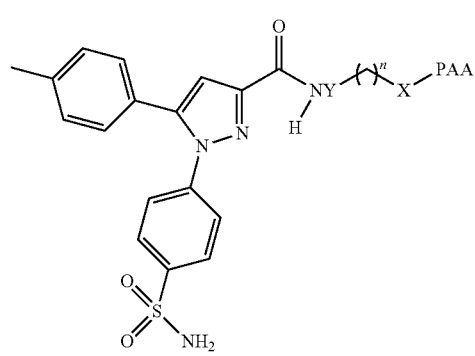

X is optionally O or NH
Y is optionally SO₂
n is 4 to 10

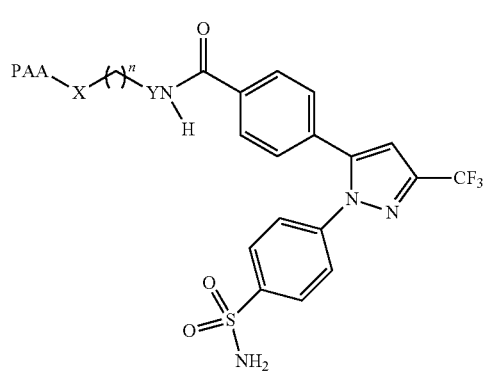

X is optionally O or NH
Y is optionally SO₂
n is 4 to 10

177
-continued
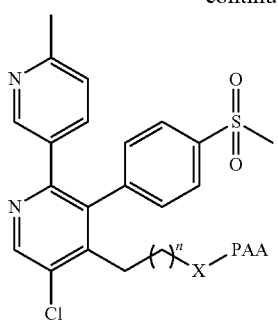
X is optionally O or NH
n is 3 to 10
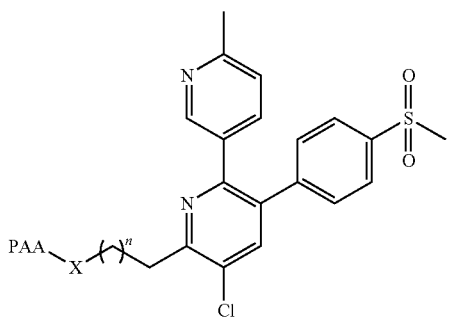
X is optionally O or NH
n is 3 to 10
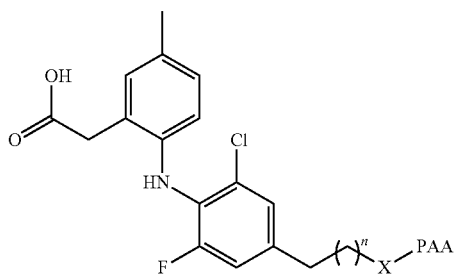
X is optionally O or NH
n is 3 to 10
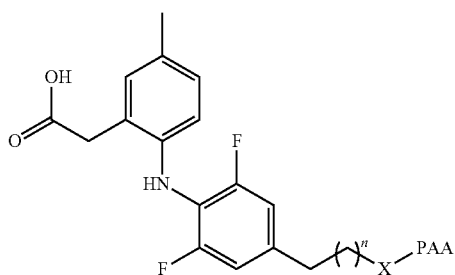
X is optionally O or NH
n is 3 to 10
178
-continued
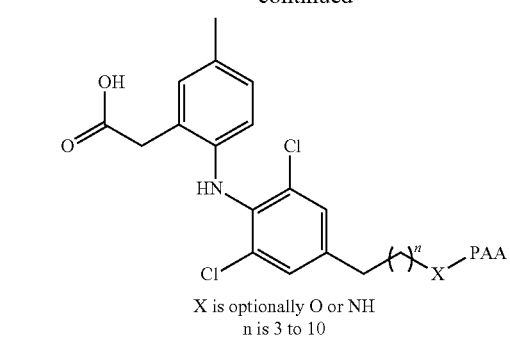
X is optionally O or NH
n is 3 to 10
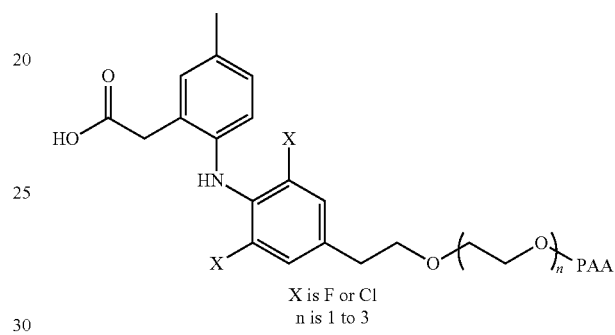
X is F or Cl
n is 1 to 3
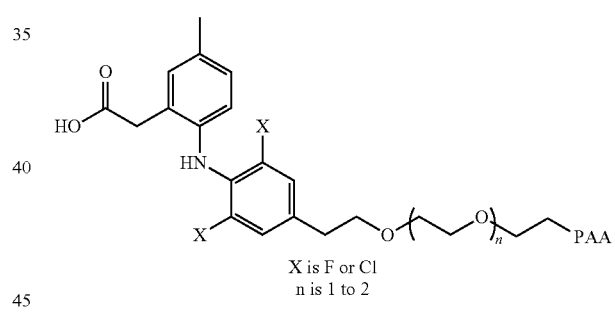
X is F or Cl
n is 1 to 2
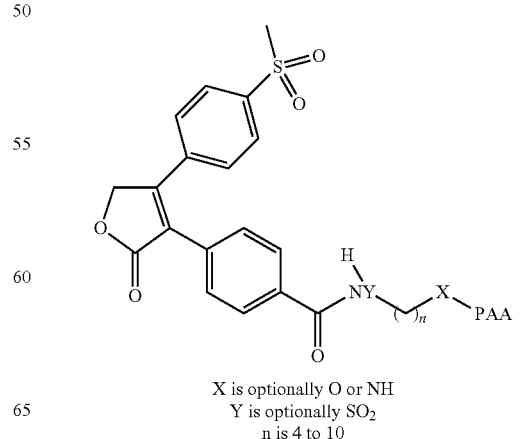
X is optionally O or NH
Y is optionally $SO_2$
n is 4 to 10

-continued

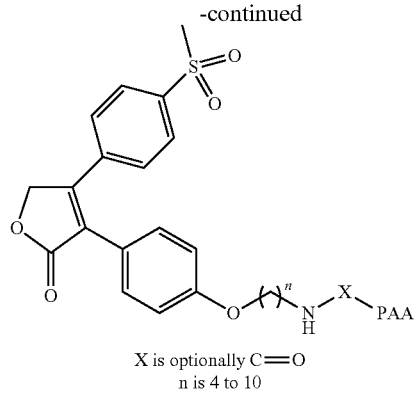

X is optionally C═O
n is 4 to 10

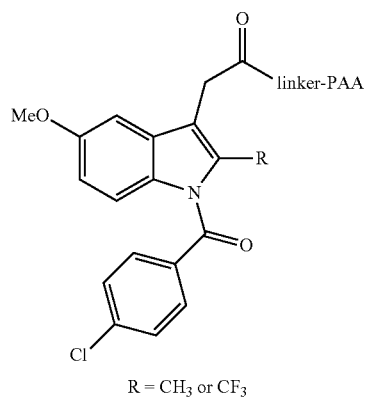

R = CH₃ or CF₃

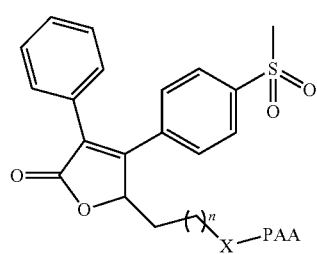

X is optionally O or NH
n is 3 to 10

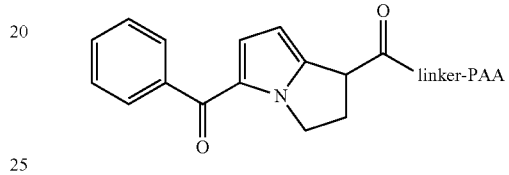

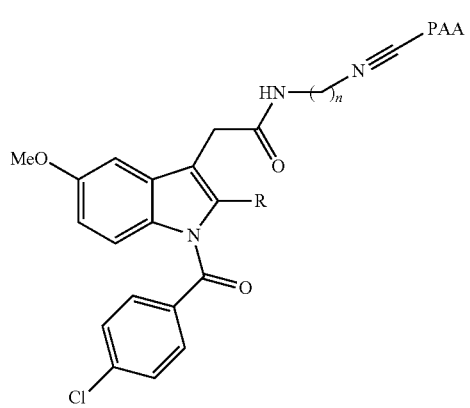

R = CH₃ or CF₃
n is 4 to 10

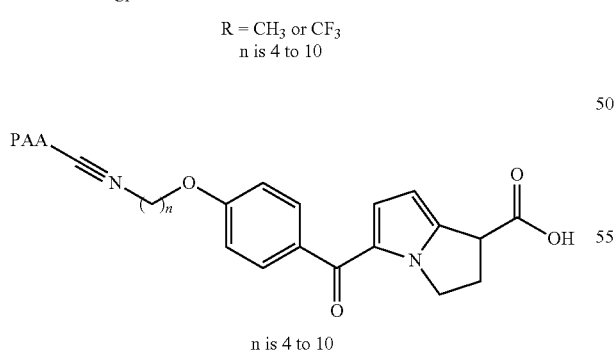

n is 4 to 10

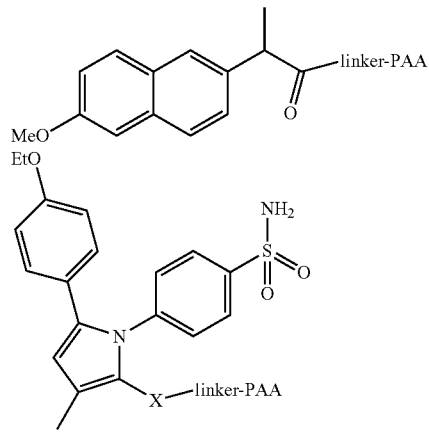

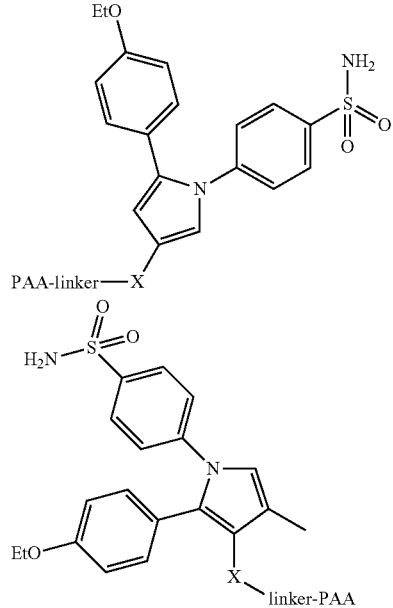

and pharmaceutically acceptable salts thereof, wherein PAA denotes platinum-containing antitumor agent and the COX-2-targeting moiety can be part of an equatorial ligand or an axial ligand on the platinum metal.

22. The conjugate of embodiment 20, which is selected from the group consisting of:

-continued
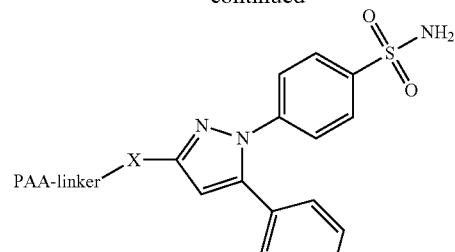
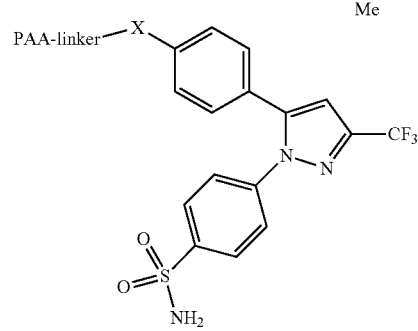
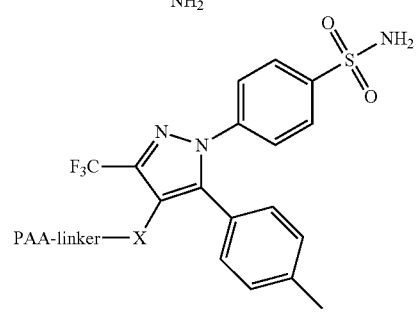
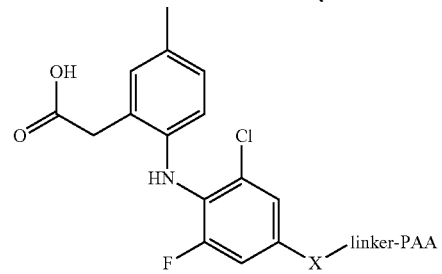
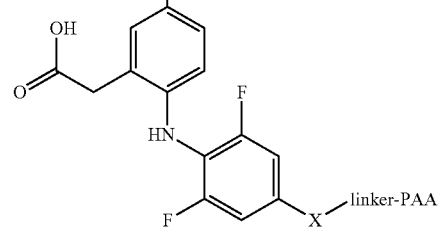
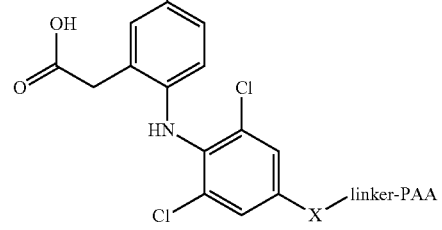
-continued
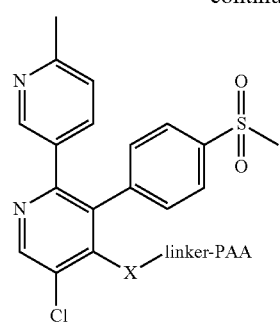
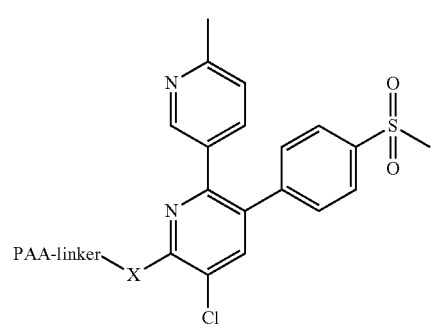
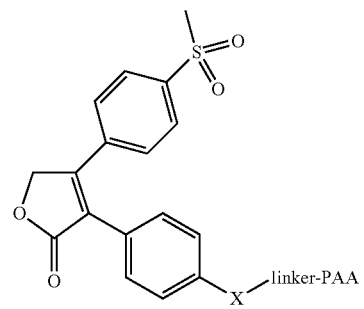
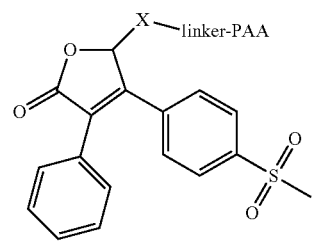
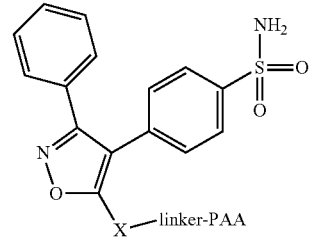

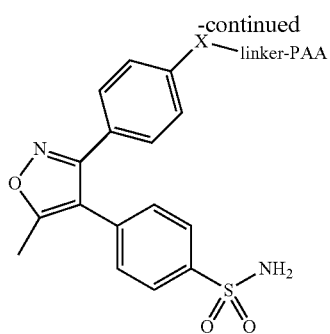

and pharmaceutically acceptable salts thereof, wherein:
PAA denotes platinum-containing antitumor agent;
the COX-2-targeting moiety can be part of an equatorial ligand or an axial ligand on the platinum metal;
X is absent or is —C(=O)—, —OC(=O)— (capable of forming carbamate bonds), or —S(=O)$_2$—; and
the linker, in the direction from the COX-2-targeting moiety to the PAA, is selected from the group consisting of:
1) —NH(CH$_2$)$_n$NH— and —NH(CH$_2$)$_n$NMe-, wherein n is an integer from 2 or 4 to 10;
2) —NHCH$_2$CH$_2$OCH$_2$CH$_2$NH— and —NHCH$_2$CH$_2$O(—CH$_2$CH$_2$O—)$_n$CH$_2$CH$_2$NH—, wherein n is 1 or 2; and
3)

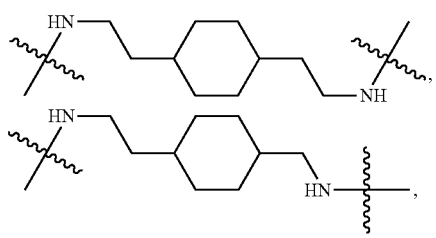
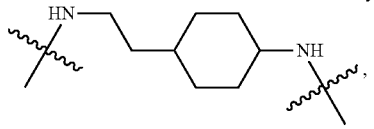
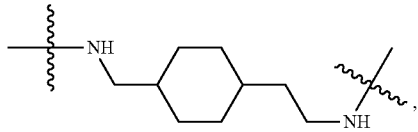
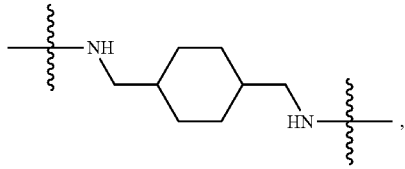
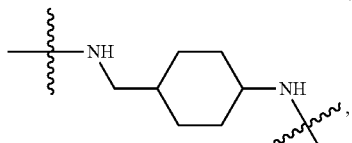
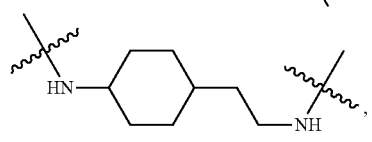
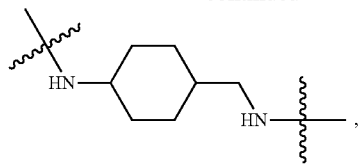
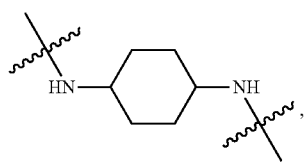
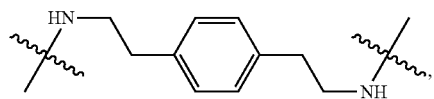
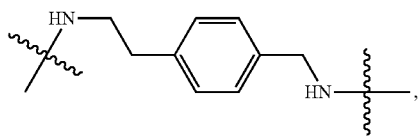
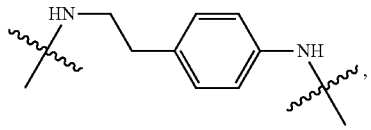
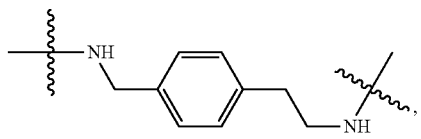
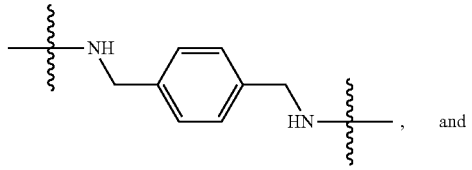, and
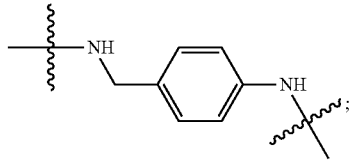;

wherein the nitrogen atom at the right end of the linker can optionally coordinate to the platinum metal of the PAA (e.g. in place of an ammine group on cisplatin, carboplatin, nedaplatin, picoplatin or satraplatin).

23. The conjugate of any one of the preceding embodiments, which is selected from:

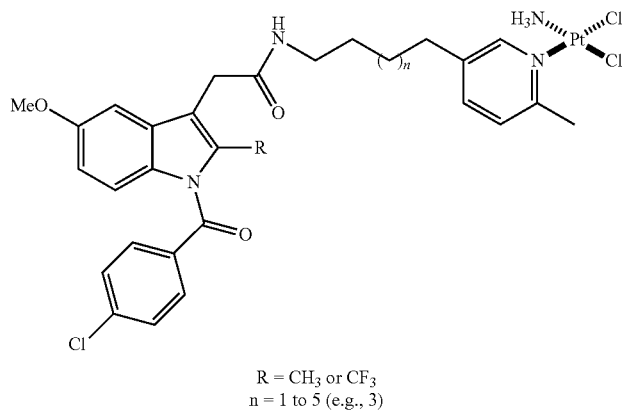
R = CH₃ or CF₃
n = 1 to 5 (e.g., 3)
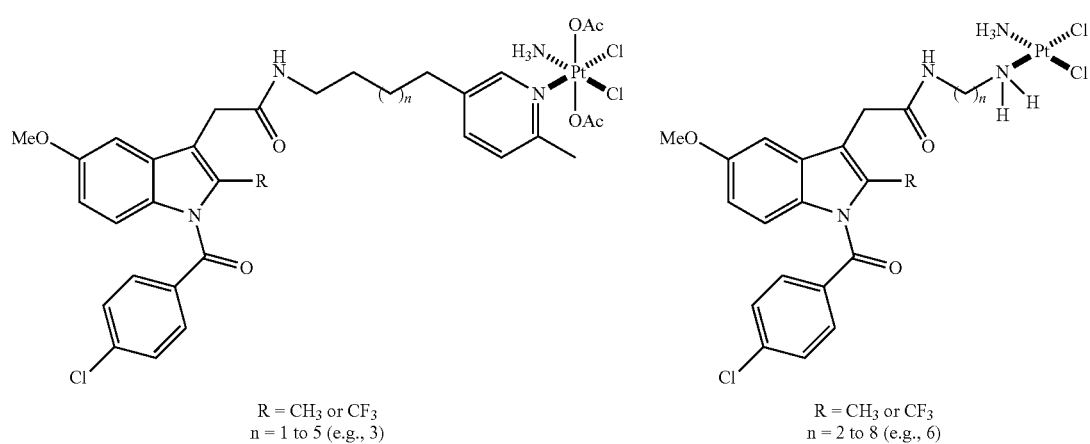
R = CH₃ or CF₃
n = 1 to 5 (e.g., 3)
R = CH₃ or CF₃
n = 2 to 8 (e.g., 6)
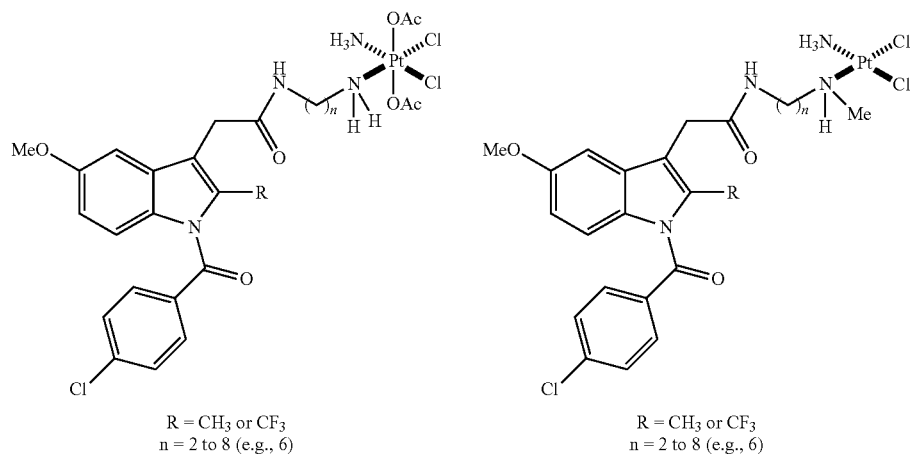
R = CH₃ or CF₃
n = 2 to 8 (e.g., 6)
R = CH₃ or CF₃
n = 2 to 8 (e.g., 6)

-continued
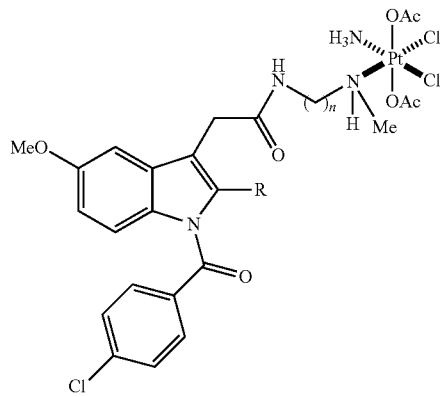
R = CH₃ or CF₃
n = 2 to 8 (e.g., 6)
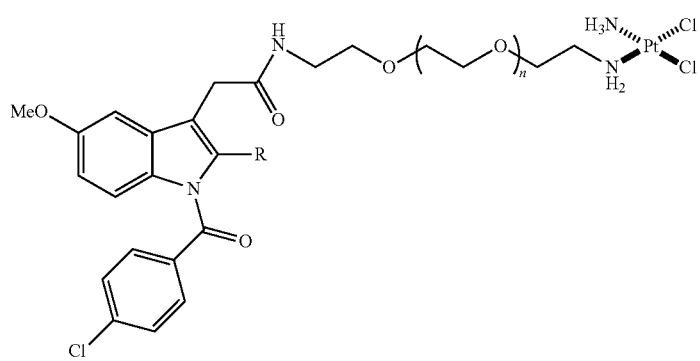
R = CH₃ or CF₃
n = 0, 1 or 2
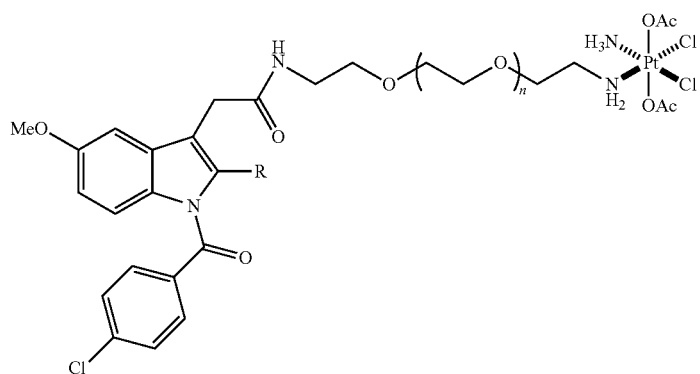
R = CH₃ or CF₃
n = 0, 1 or 2

189
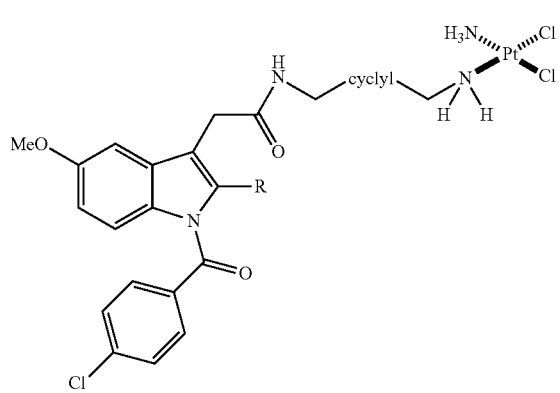
R = CH₃ or CF₃
cyclyl = 1,4-cyclohexyl or 1,4-phenyl
190
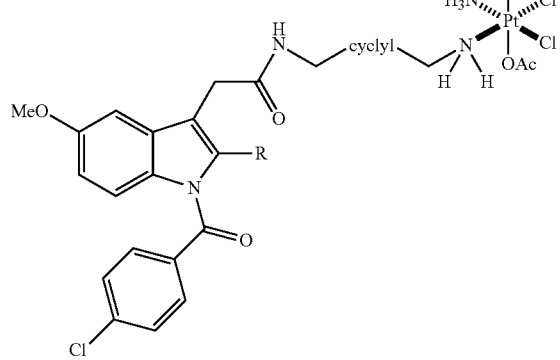
R = CH₃ or CF₃
cyclyl = 1,4-cyclohexyl or 1,4-phenyl
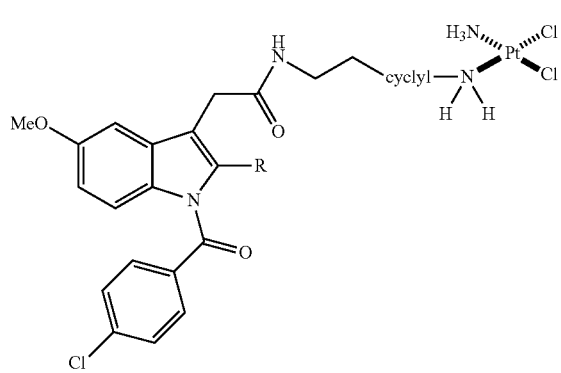
R = CH₃ or CF₃
cyclyl = 1,4-cyclohexyl or 1,4-phenyl
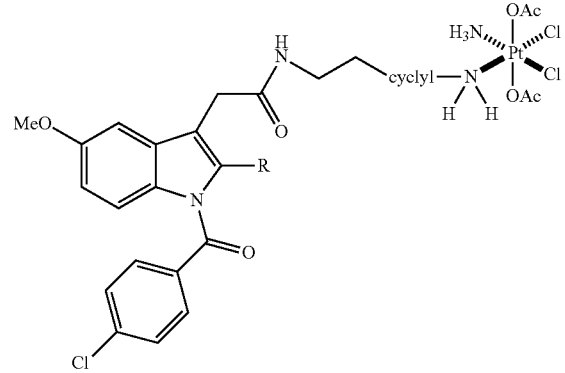
R = CH₃ or CF₃
cyclyl = 1,4-cyclohexyl or 1,4-phenyl
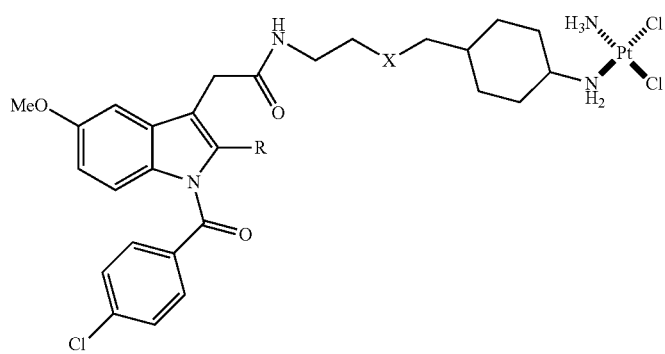
1) R = Me & X = CH₂; or
2) R = Me & X = O; or
3) R = CF₃ & X = CH₂; or
4) R = CF₃ & X = O 191 192
-continued
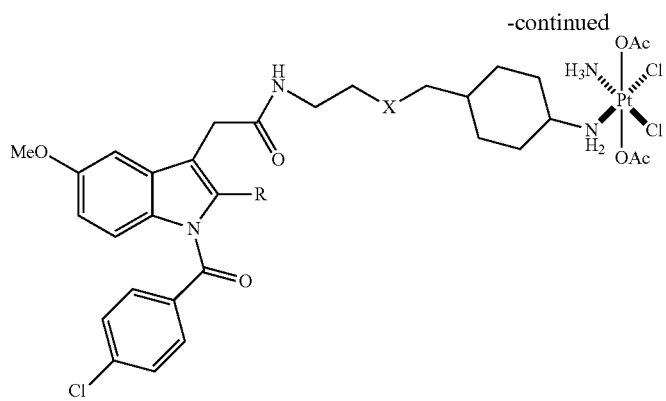
1) R = Me & X = CH₂; or
2) R = Me & X = O; or
3) R = CF₃ & X = CH₂; or
4) R = CF₃ & X = O
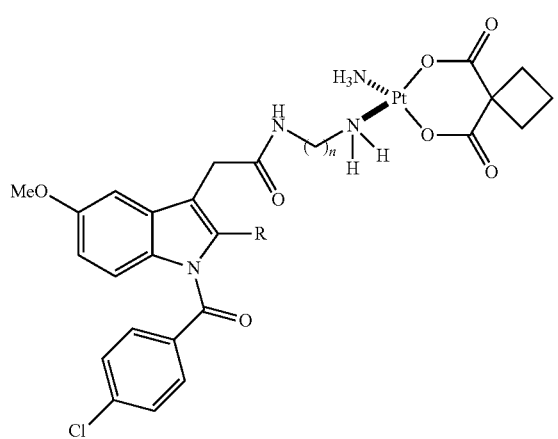
R = CH₃ or CF₃
n = 2 to 8 (e.g., 6)
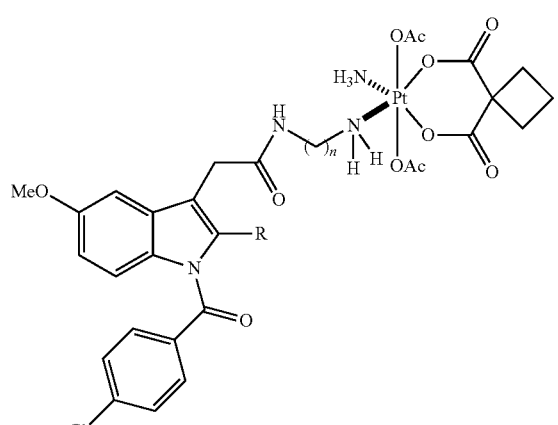
R = CH₃ or CF₃
n = 2 to 8 (e.g., 6)
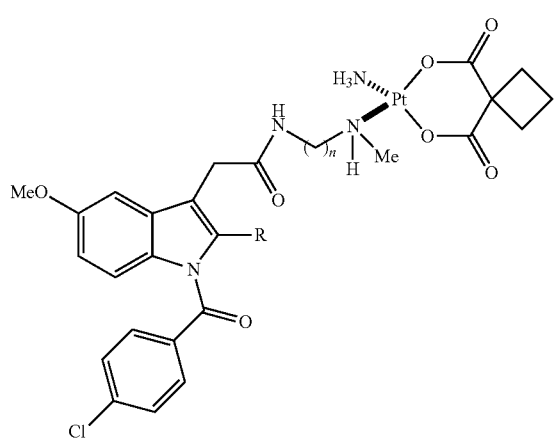
R = CH₃ or CF₃
n = 2 to 8 (e.g., 6)
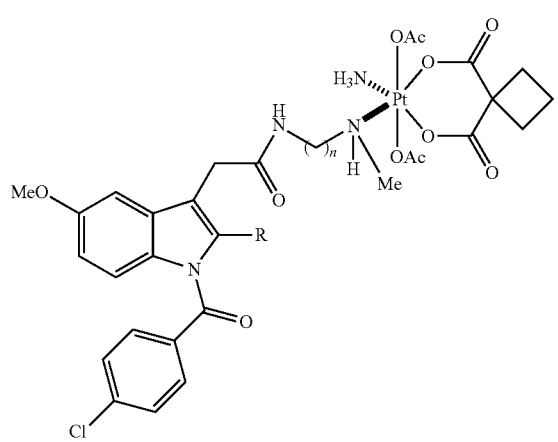
R = CH₃ or CF₃
n = 2 to 8 (e.g., 6)

-continued
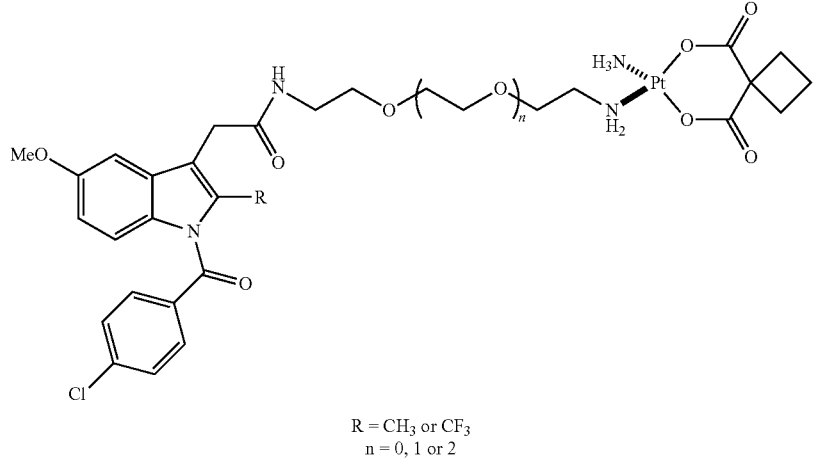
R = CH₃ or CF₃
n = 0, 1 or 2
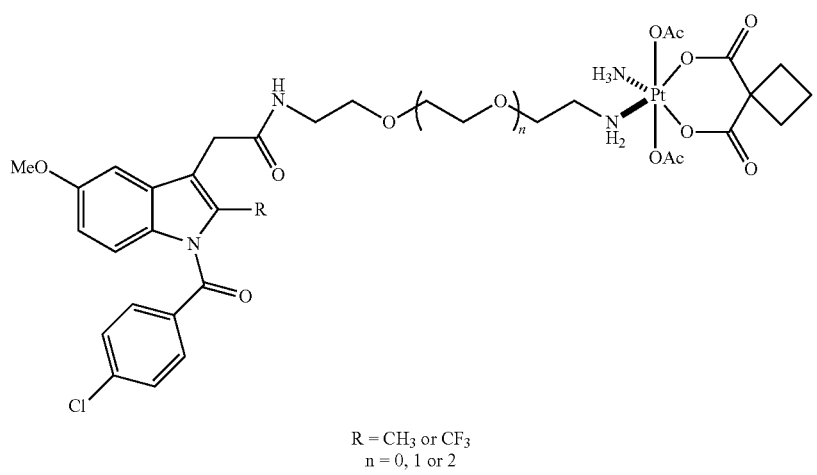
R = CH₃ or CF₃
n = 0, 1 or 2
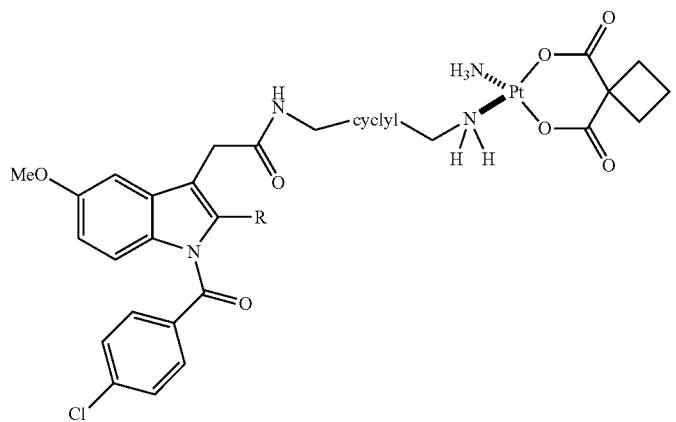
R = CH₃ or CF₃
cyclyl = 1,4-cyclohexyl or 1,4-phenyl -continued
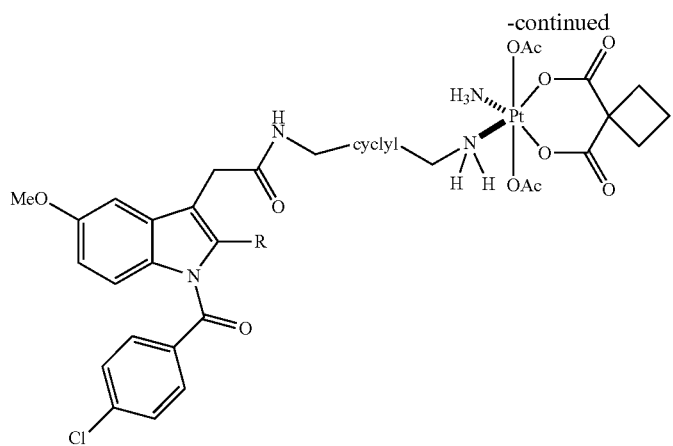
R = CH₃ or CF₃
cyclyl = 1,4-cyclohexyl or 1,4-phenyl
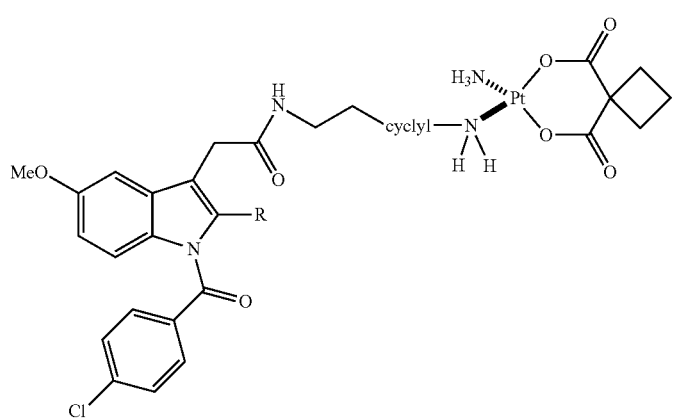
R = CH₃ or CF₃
cyclyl = 1,4-cyclohexyl or 1,4-phenyl
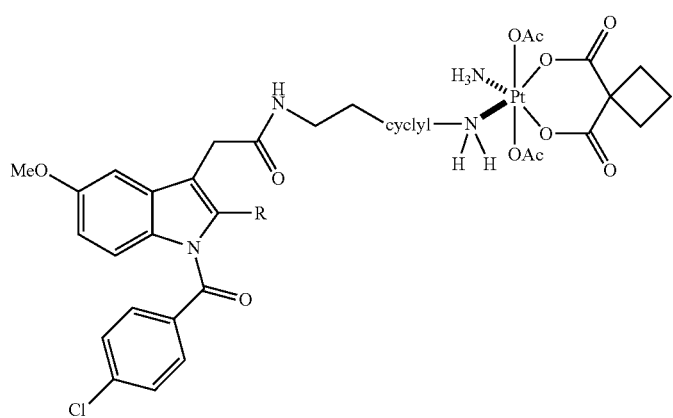
R = CH₃ or CF₃
cyclyl = 1,4-cyclohexyl or 1,4-phenyl -continued
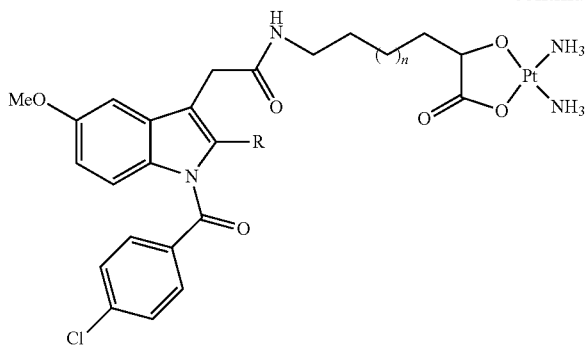
R = CH₃ or CF₃
n = 1 to 5 (e.g., 3)
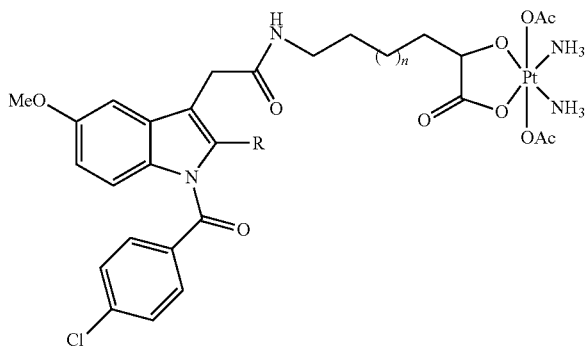
R = CH₃ or CF₃
n = 1 to 5 (e.g., 3)
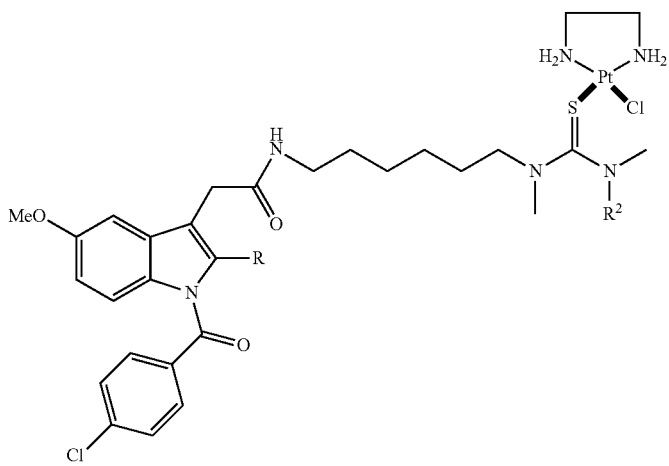
1) R¹ = Me & R² = H; or
2) R¹ = Me & R² = Me; or
3) R¹ = CF₃ & R² = H; or
4) R¹ = CF₃ & R² = Me

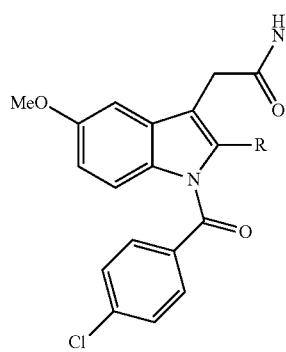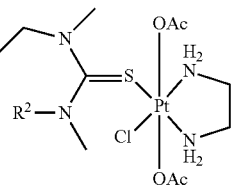
-continued
1) $R^1$ = Me & $R^2$ = H; or
2) $R^1$ = Me & $R^2$ = Me; or
3) $R^1$ = $CF_3$ & $R^2$ = H; or
4) $R^1$ = $CF_3$ & $R^2$ = Me
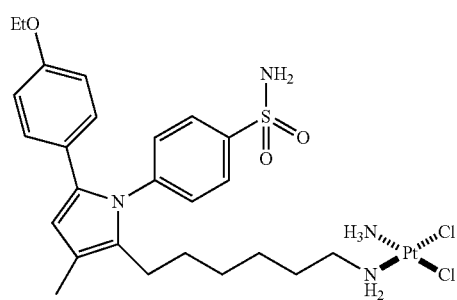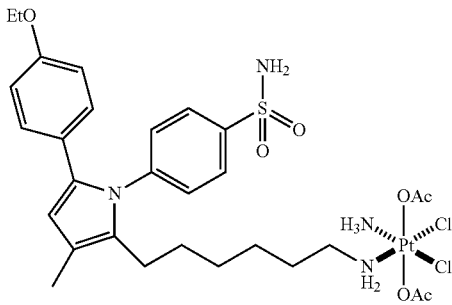
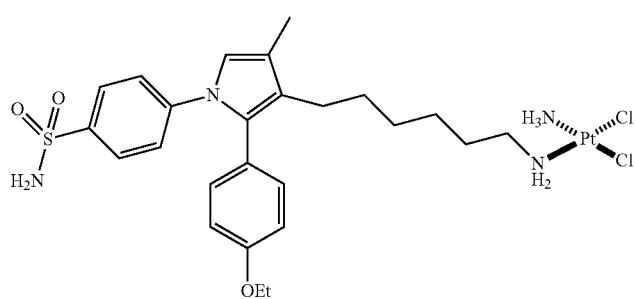
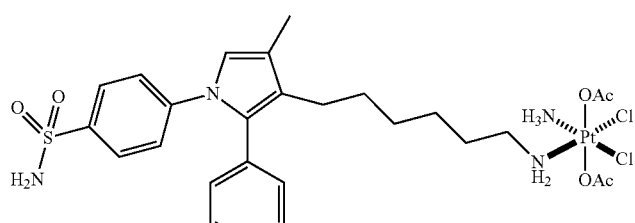
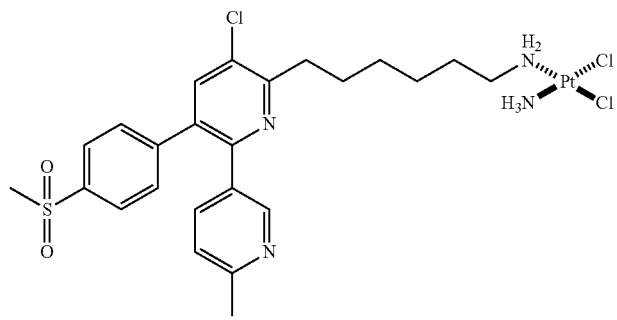

201
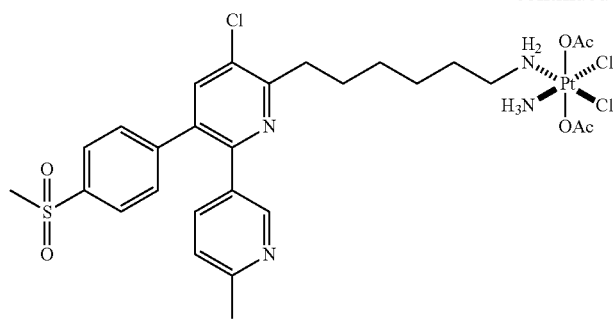
202
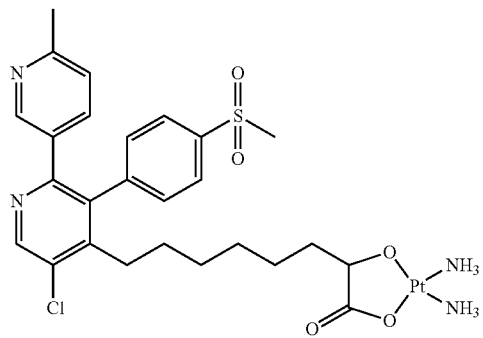
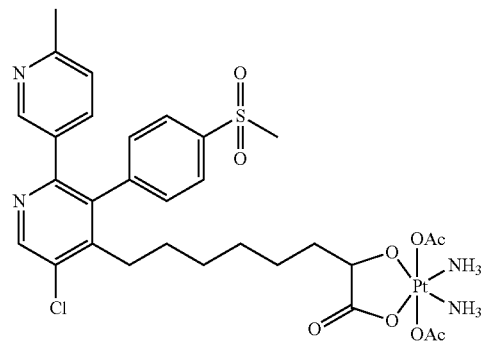
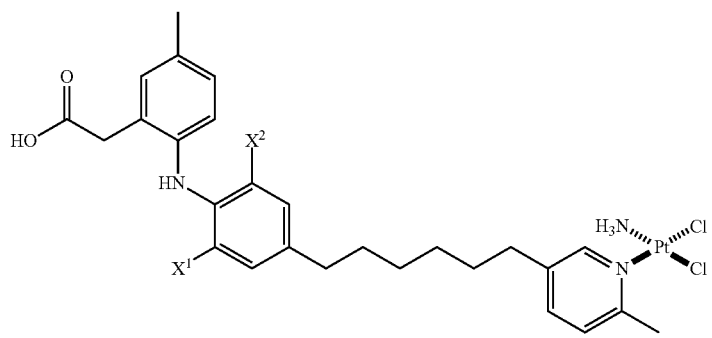
1) X¹ = F & X² = Cl; or
2) X¹ = X² = F; or
3) X¹ = X² = Cl
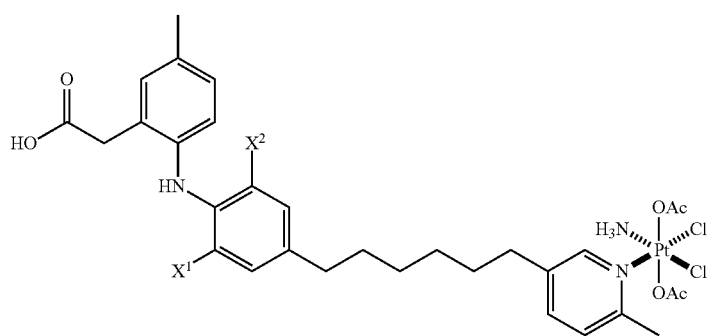
1) X¹ = F & X² = Cl; or
2) X¹ = X² = F; or
3) X¹ = X² = Cl -continued
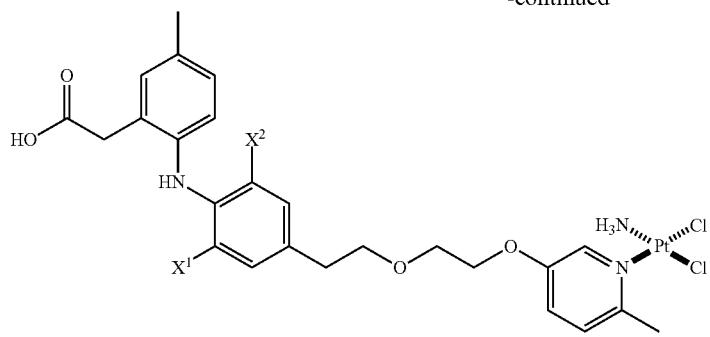
1) X¹ = F & X² = Cl; or
2) X¹ = X² = F; or
3) X¹ = X² = Cl
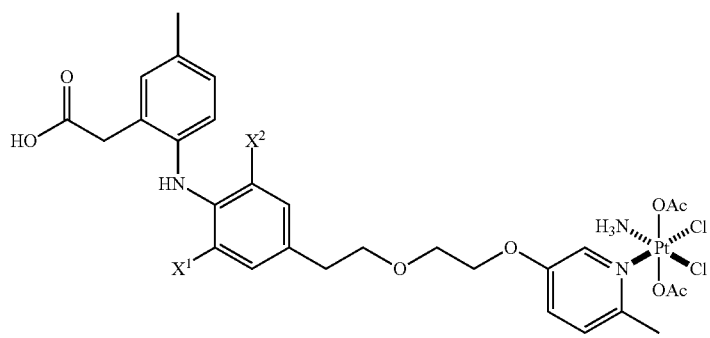
1) X¹ = F & X² = Cl; or
2) X¹ = X² = F; or
3) X¹ = X² = Cl
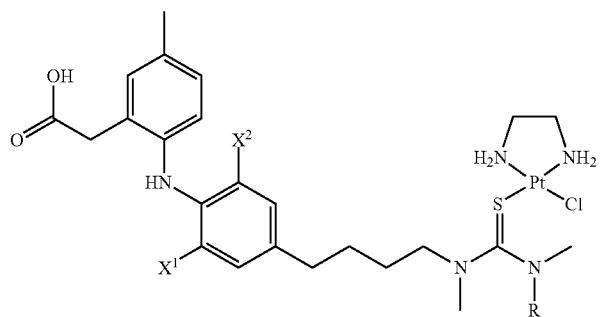
1) X¹ = F, X² = Cl, & R = H; or
2) X¹ = F, X² = Cl, & R = Me; or
3) X¹ = X² = F & R = H; or
4) X¹ = X² = F & R = Me; or
5) X¹ = X² = Cl & R = H; or
6) X¹ = X² = Cl & R = Me

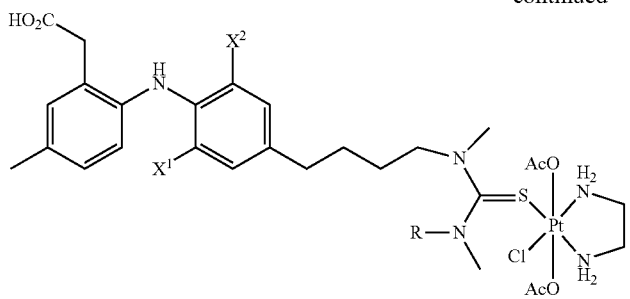
1) $X^1 = F$, $X^2 = Cl$, & $R = H$; or
2) $X^1 = F$, $X^2 = Cl$, & $R = Me$; or
3) $X^1 = X^2 = F$ & $R = H$; or
4) $X^1 = X^2 = F$ & $R = Me$; or
5) $X^1 = X^2 = Cl$ & $R = H$; or
6) $X^1 = X^2 = Cl$ & $R = Me$
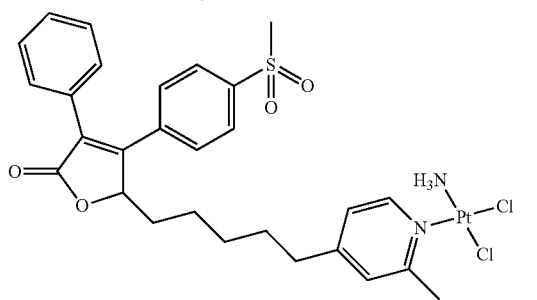
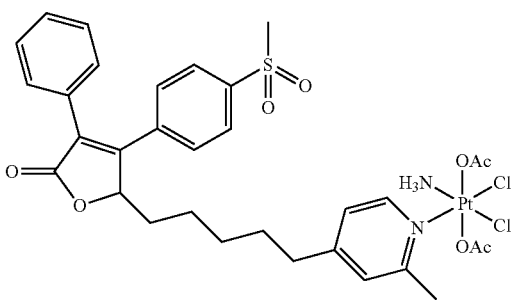
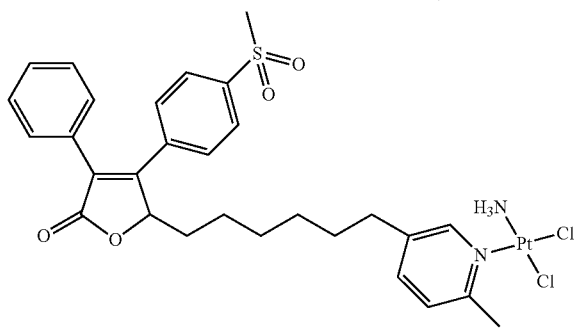
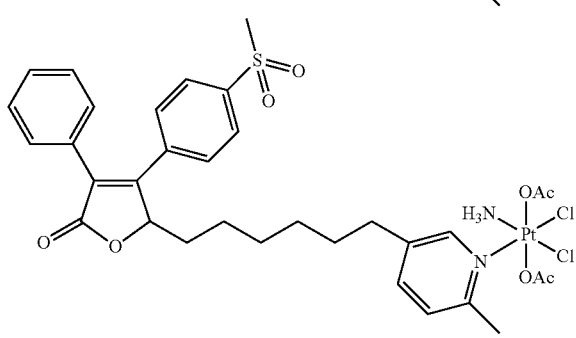
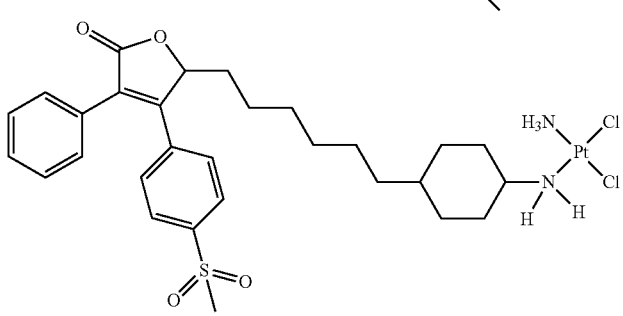

-continued
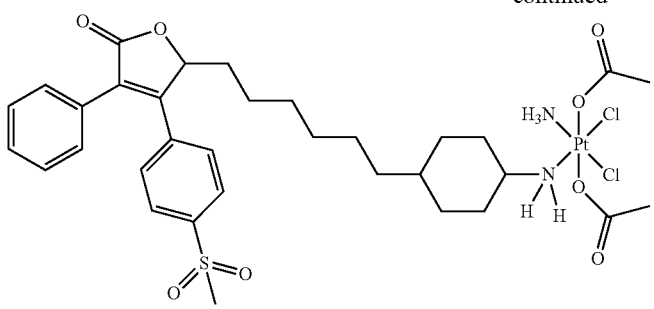
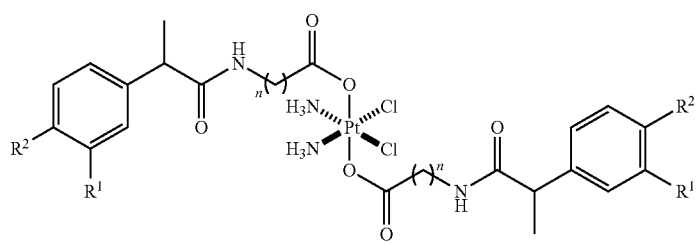
1) $R^1$ = H & $R^2$ = —CH$_2$CHMe$_2$
2) $R^1$ = H & $R^2$ = —CH$_2$-(2-cyclopentanone)
3) $R^1$ = F & $R^2$ = phenyl
n = 4 to 8
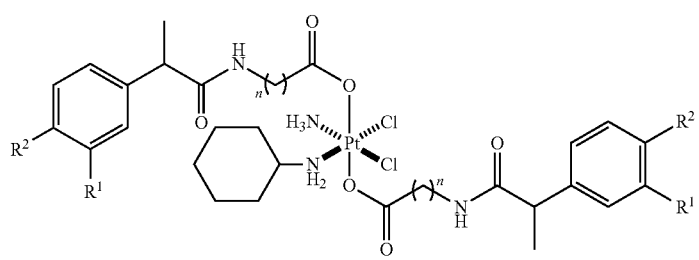
1) $R^1$ = H & $R^2$ = —CH$_2$CHMe$_2$
2) $R^1$ = H & $R^2$ = —CH$_2$-(2-cyclopentanone)
3) $R^1$ = F & $R^2$ = phenyl
n = 4 to 8
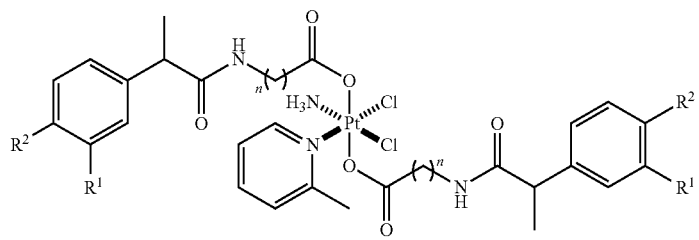
1) $R^1$ = H & $R^2$ = —CH$_2$CHMe$_2$
2) $R^1$ = H & $R^2$ = —CH$_2$-(2-cyclopentanone)
3) $R^1$ = F & $R^2$ = phenyl
n = 4 to 8

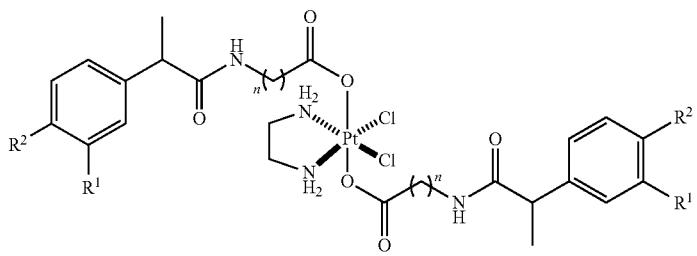
1) $R^1$ = H & $R^2$ = —CH$_2$CHMe$_2$
2) $R^1$ = H & $R^2$ = —CH$_2$-(2-cyclopentanone)
3) $R^1$ = F & $R^2$ = phenyl
n = 4 to 8
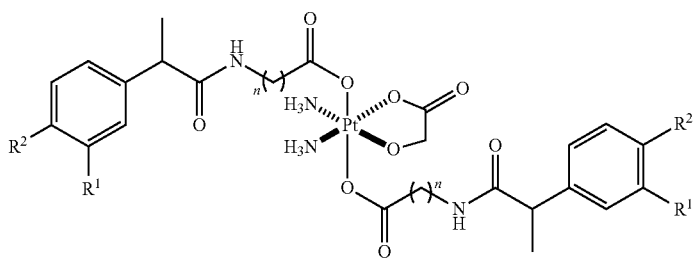
1) $R^1$ = H & $R^2$ = —CH$_2$CHMe$_2$
2) $R^1$ = H & $R^2$ = —CH$_2$-(2-cyclopentanone)
3) $R^1$ = F & $R^2$ = phenyl
n = 4 to 8
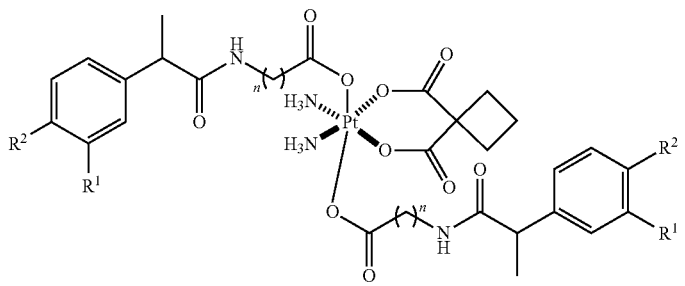
1) $R^1$ = H & $R^2$ = —CH$_2$CHMe$_2$
2) $R^1$ = H & $R^2$ = —CH$_2$-(2-cyclopentanone)
3) $R^1$ = F & $R^2$ = phenyl
n = 4 to 8
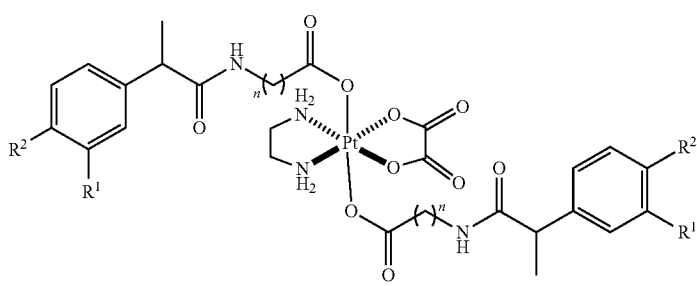
1) $R^1$ = H & $R^2$ = —CH$_2$CHMe$_2$
2) $R^1$ = H & $R^2$ = —CH$_2$-(2-cyclopentanone)
3) $R^1$ = F & $R^2$ = phenyl
n = 4 to 8

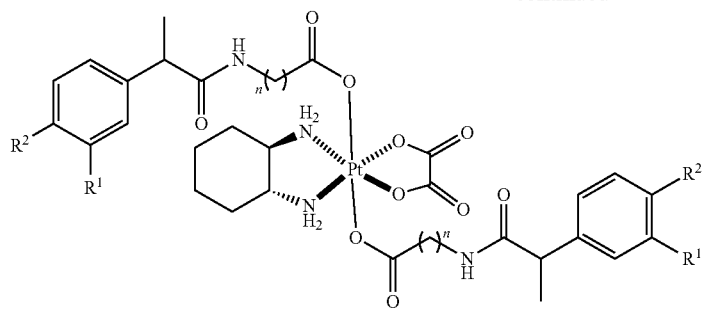
1) R¹ = H & R² = —CH$_2$CHMe$_2$
2) R¹ = H & R² = —CH$_2$-(2-cyclopentanone)
3) R¹ = F & R² = phenyl
n = 4 to 8
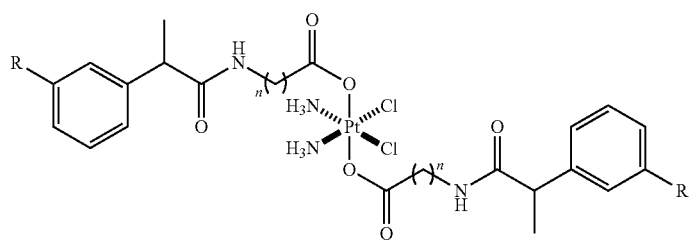
1) R = —O-phenyl
2) R = —C(=O)-phenyl
n = 4 to 8
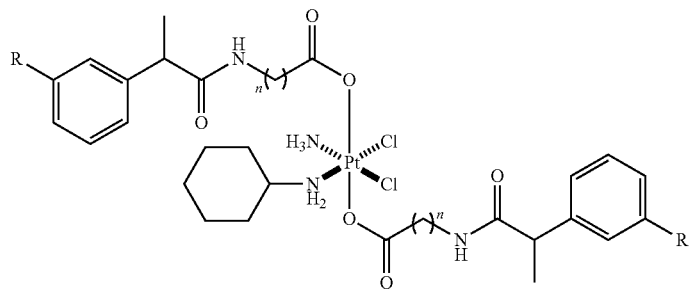
1) R = —O-phenyl
2) R = —C(=O)-phenyl
n = 4 to 8
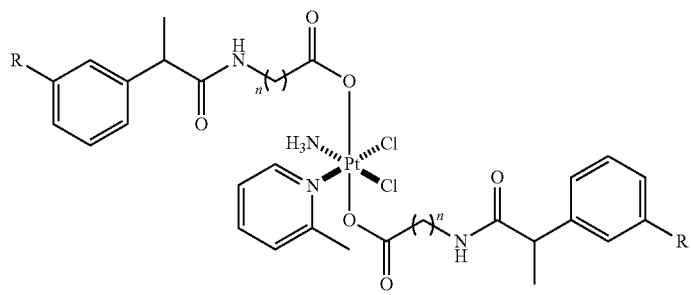
1) R = —O-phenyl
2) R = —C(=O)-phenyl
n = 4 to 8

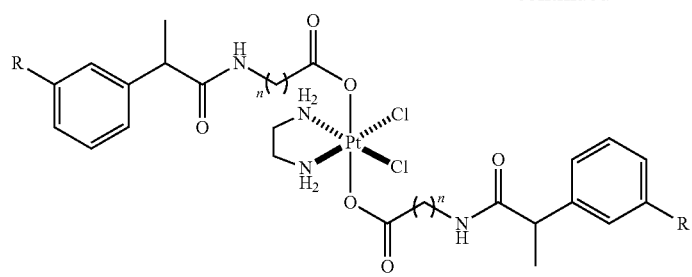
1) R = —O-phenyl
2) R = —C(=O)-phenyl
n = 4 to 8
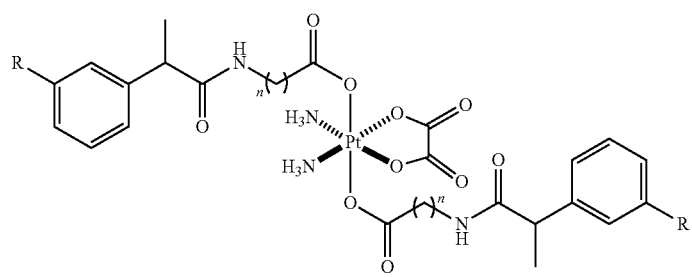
1) R = —O-phenyl
2) R = —C(=O)-phenyl
n = 4 to 8
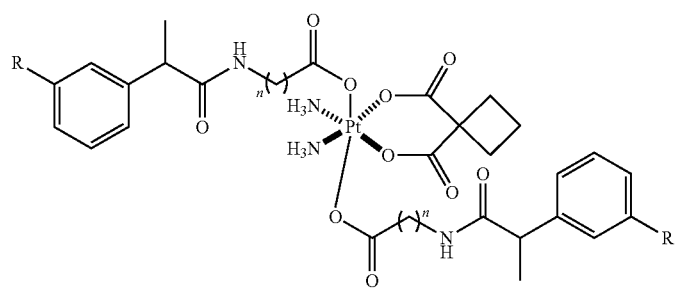
1) R = —O-phenyl
2) R = —C(=O)-phenyl
n = 4 to 8
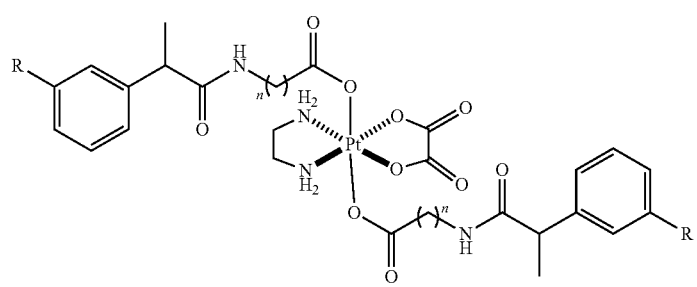
1) R = —O-phenyl
2) R = —C(=O)-phenyl
n = 4 to 8

-continued
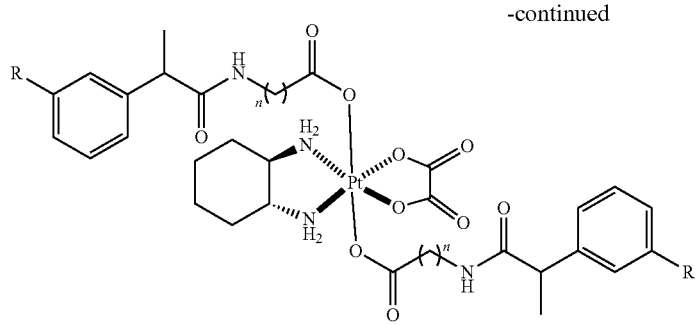
1) R = —O-phenyl
2) R = —C(=O)-phenyl
n = 4 to 8
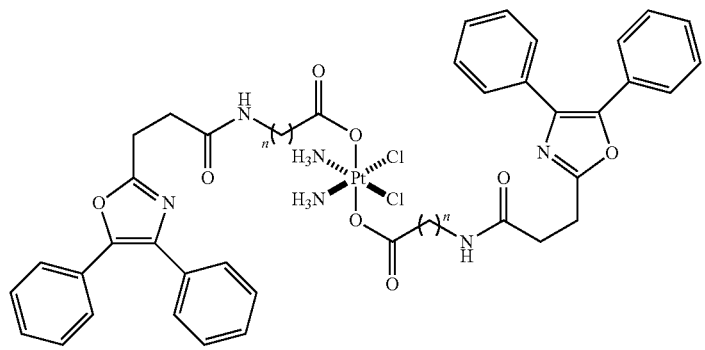
n = 4 to 8
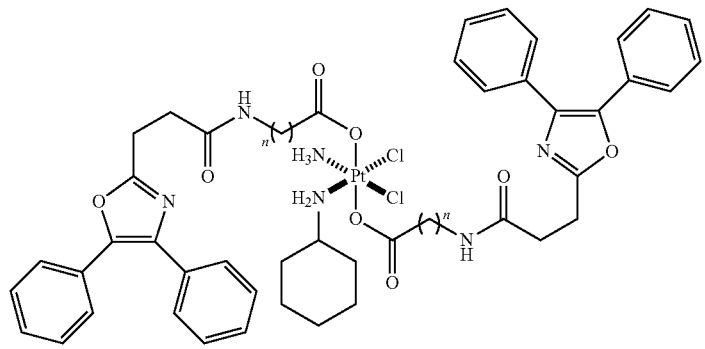
n = 4 to 8
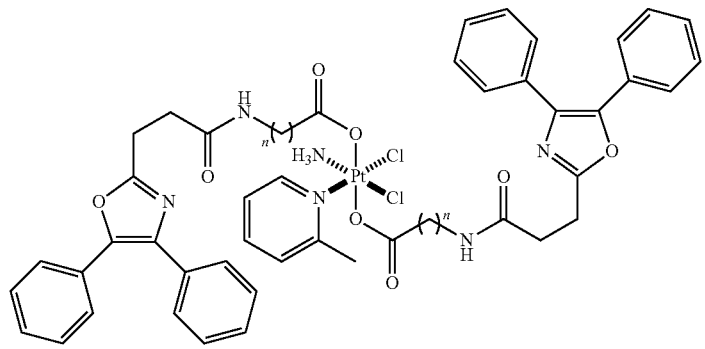
n = 4 to 8

-continued
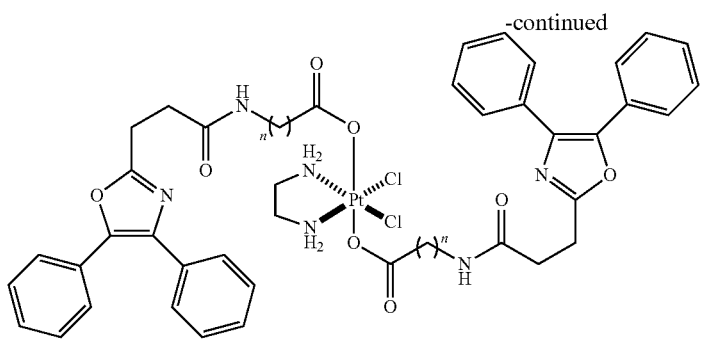
n = 4 to 8
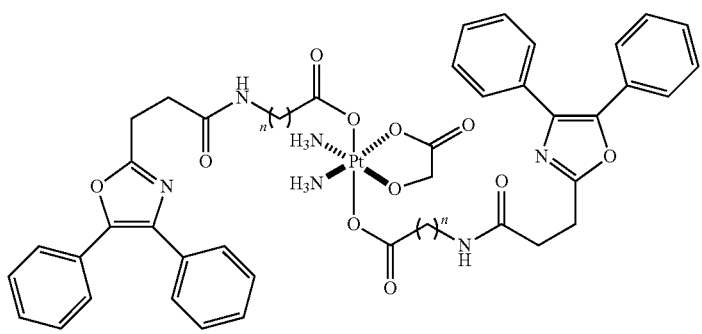
n = 4 to 8
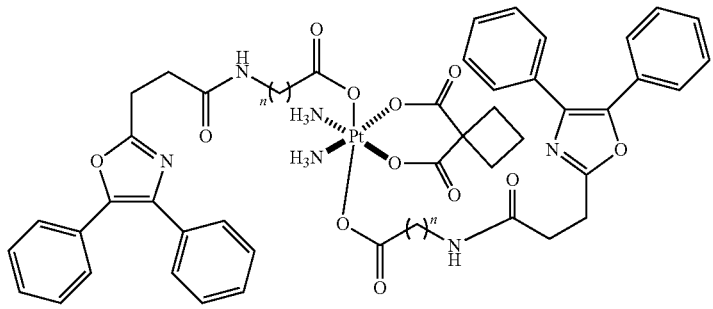
n = 4 to 8
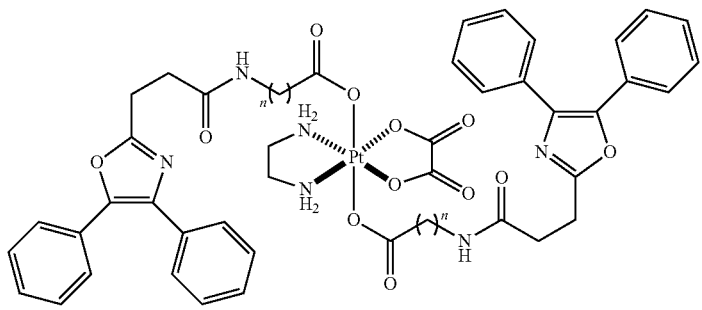
n = 4 to 8

-continued
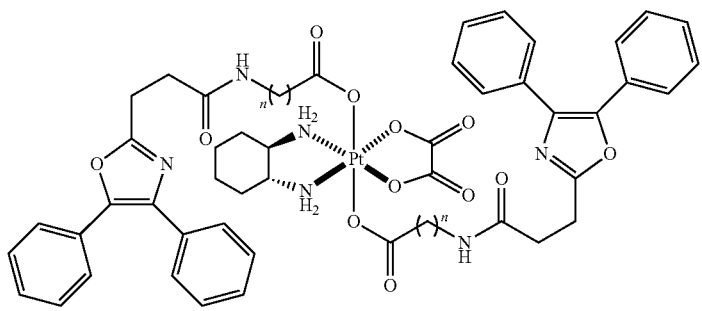
n = 4 to 8
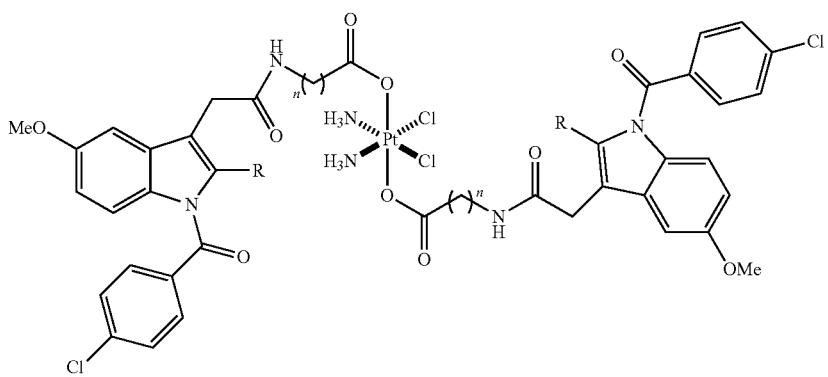
R = CH₃ or CF₃
n = 4 to 8
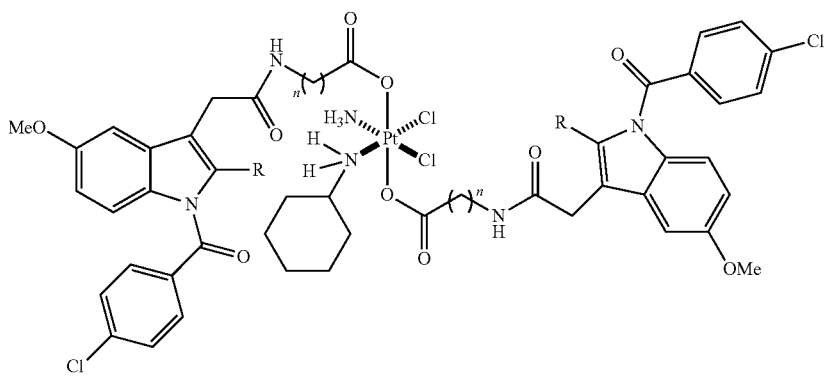
R = CH₃ or CF₃
n = 4 to 8
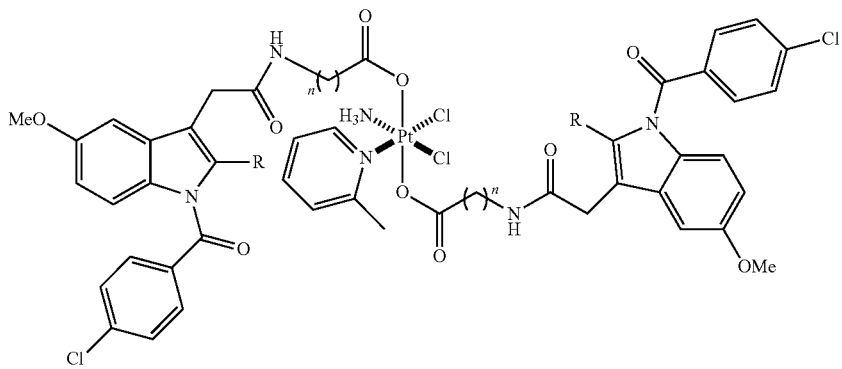
R = CH₃ or CF₃
n = 4 to 8

-continued
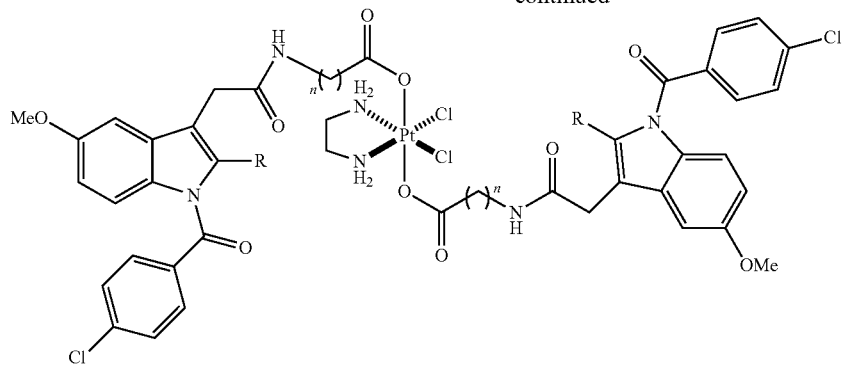
R = CH₃ or CF₃
n = 4 to 8
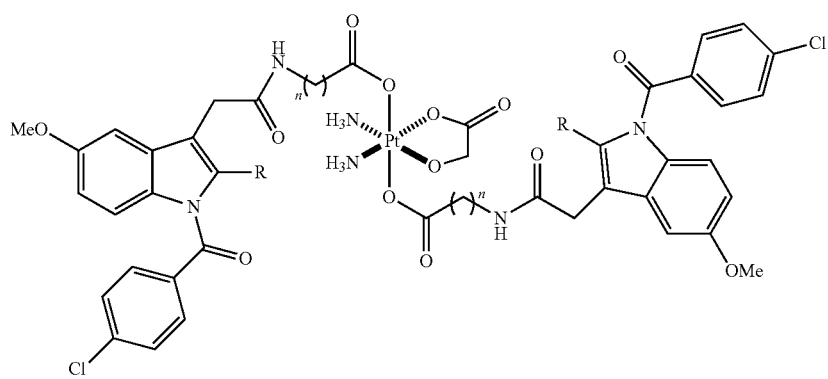
R = CH₃ or CF₃
n = 4 to 8
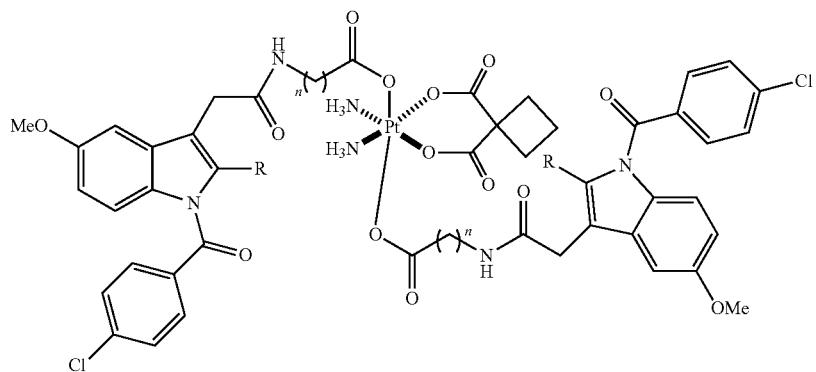
R = CH₃ or CF₃
n = 4 to 8
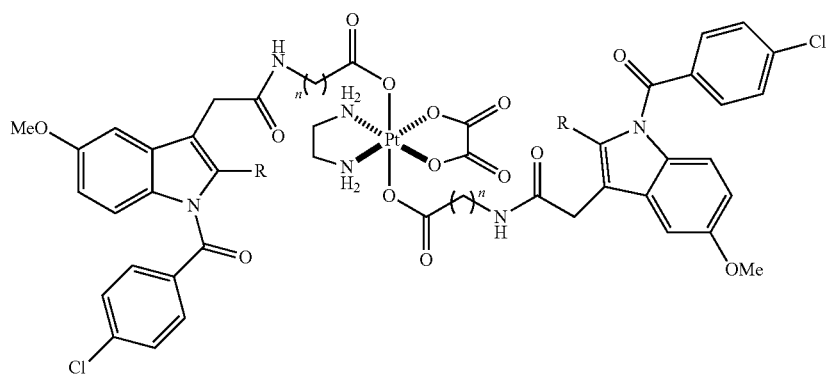
R = CH₃ or CF₃
n = 4 to 8

-continued
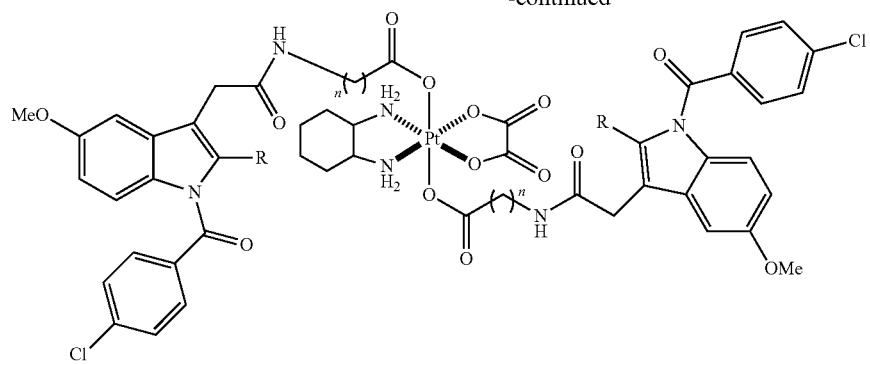
R = CH₃ or CF₃
n = 4 to 8
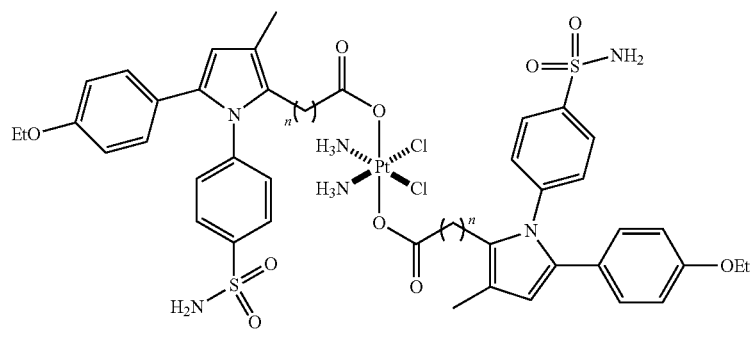
n = 4 to 10
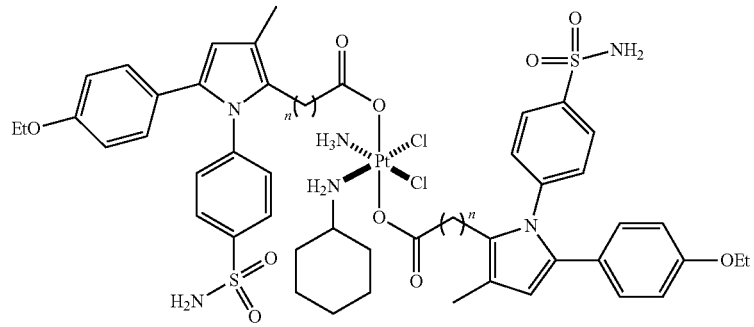
n = 4 to 10
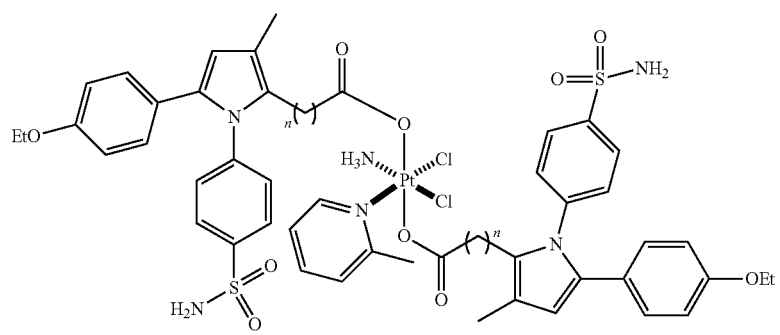
n = 4 to 10

-continued
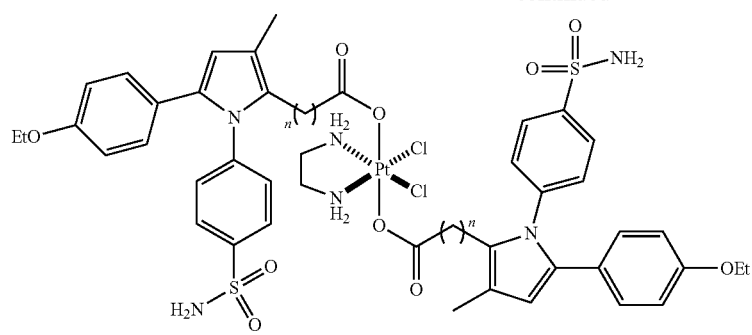
n = 4 to 10
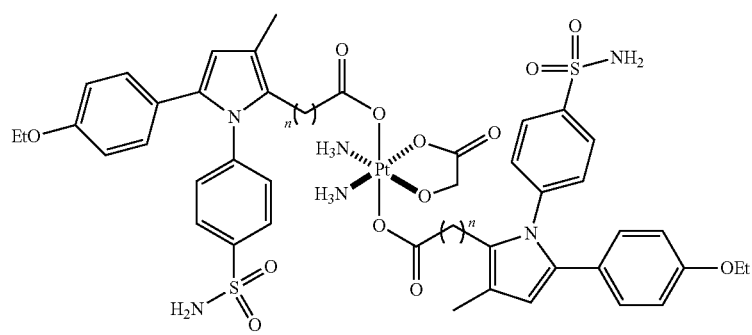
n = 4 to 10
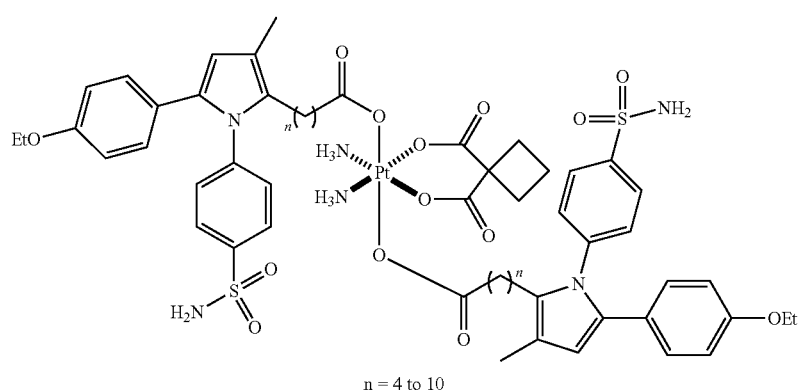
n = 4 to 10
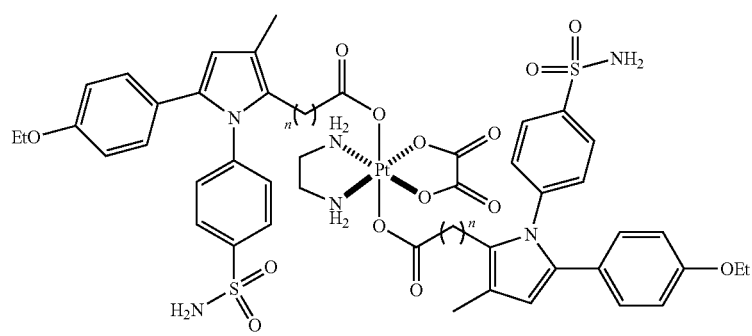
n = 4 to 10

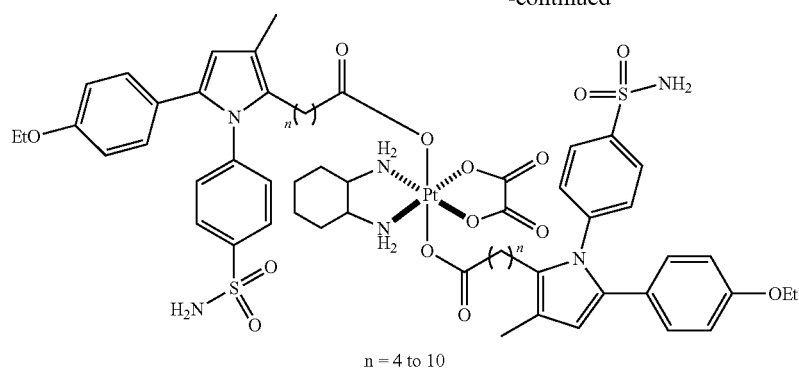
n = 4 to 10
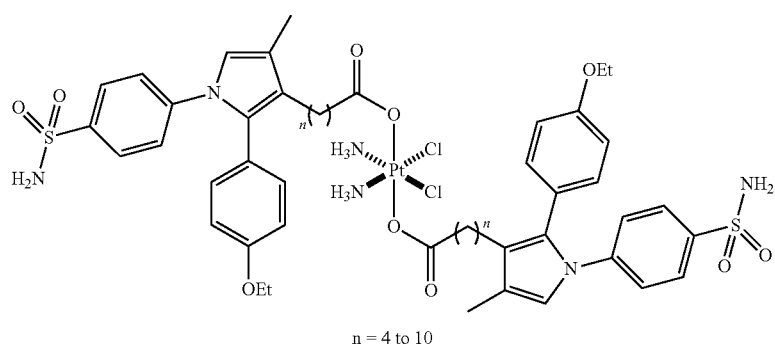
n = 4 to 10
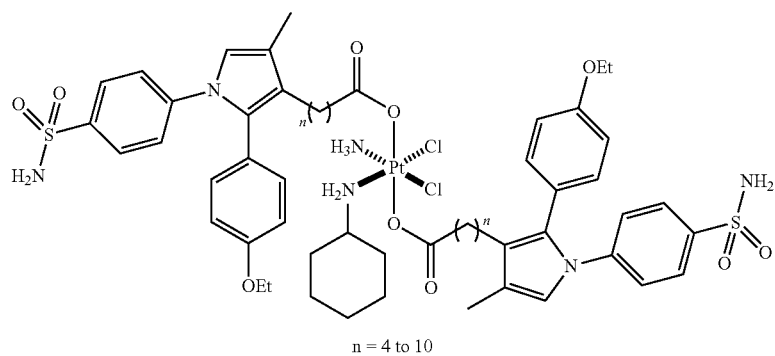
n = 4 to 10
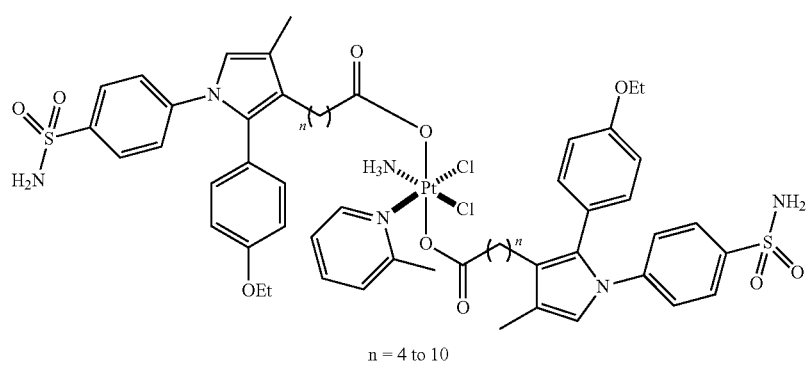
n = 4 to 10

-continued
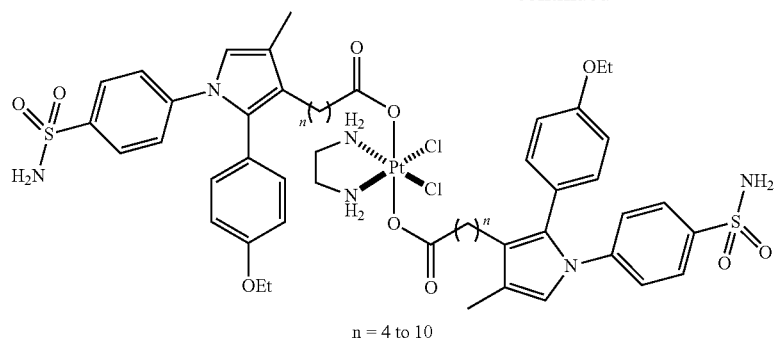
n = 4 to 10
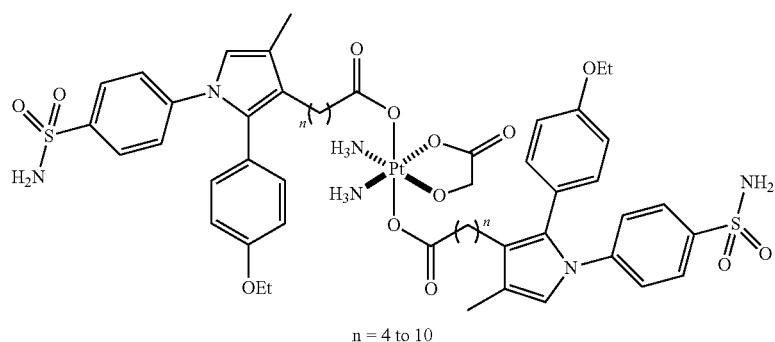
n = 4 to 10
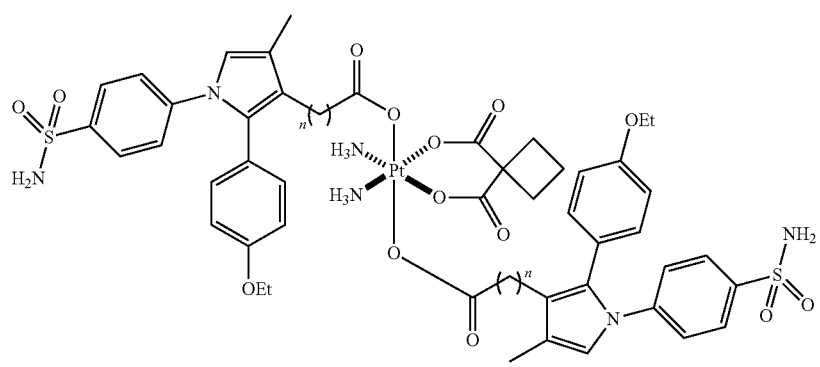
n = 4 to 10
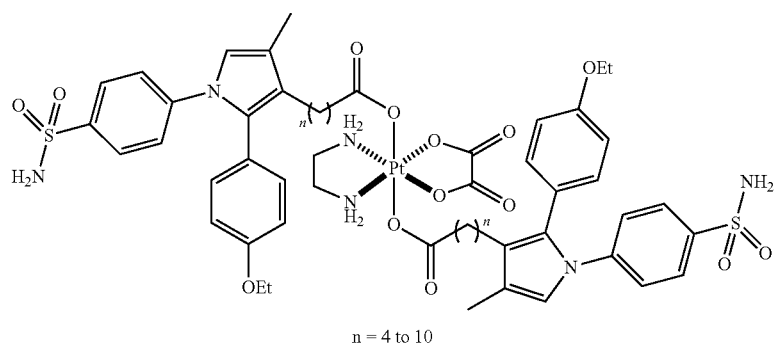
n = 4 to 10

-continued
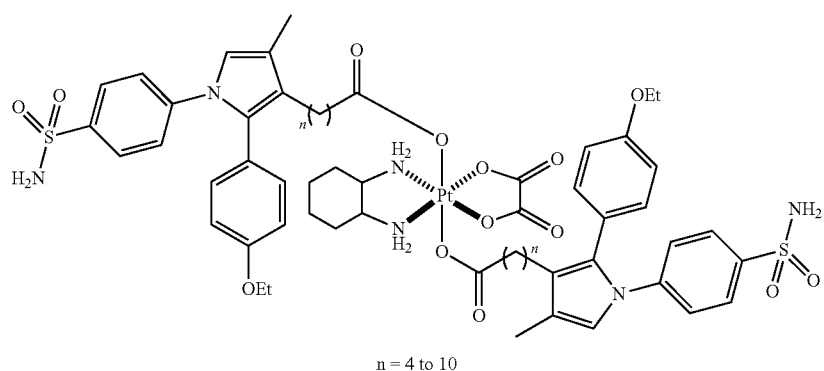
n = 4 to 10
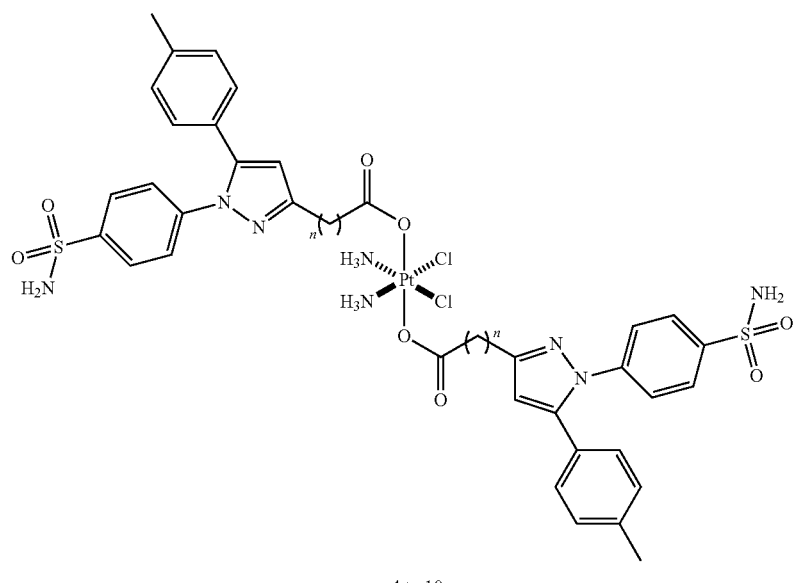
n = 4 to 10
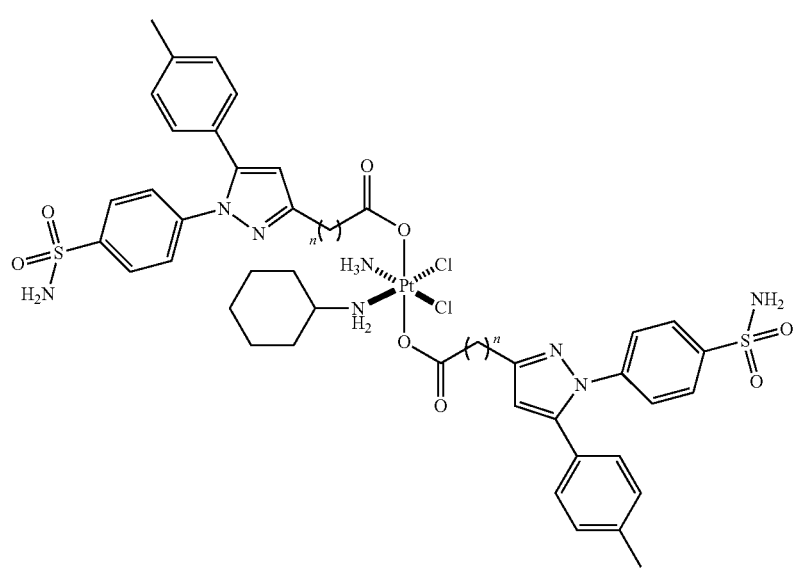
n = 4 to 10

-continued
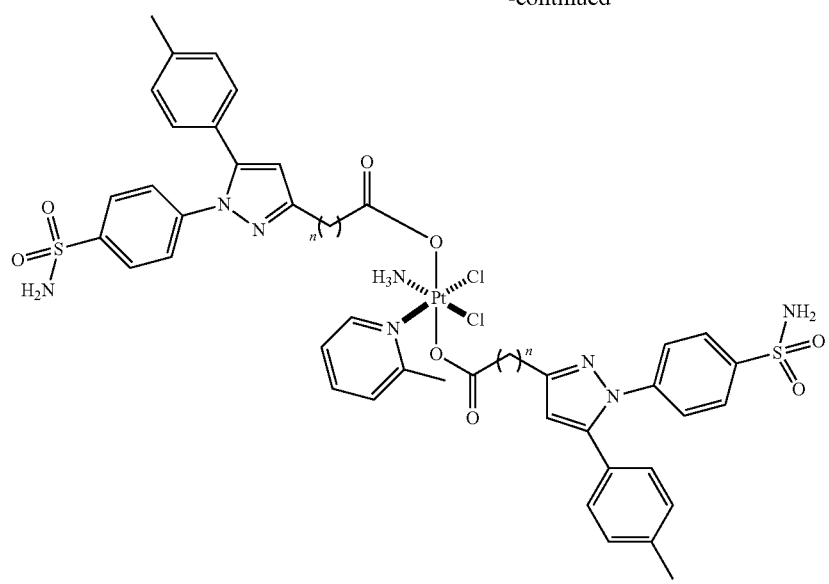
n = 4 to 10
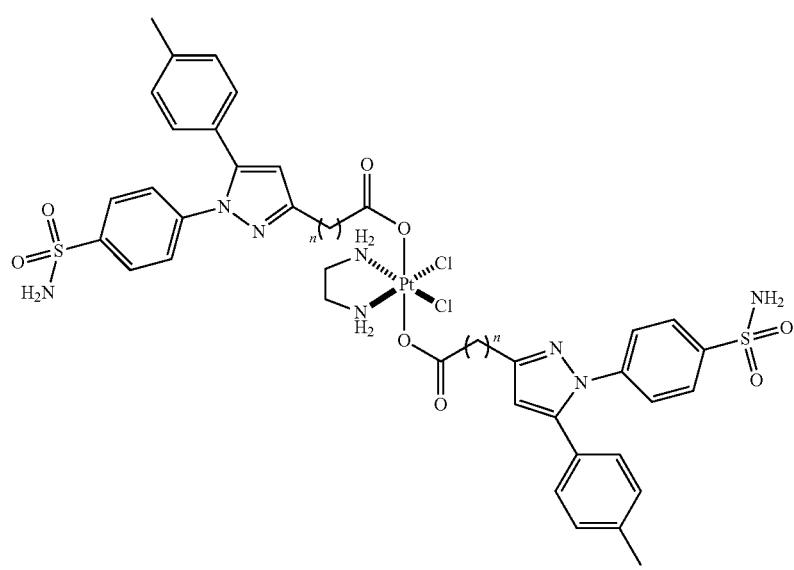
n = 4 to 10

-continued
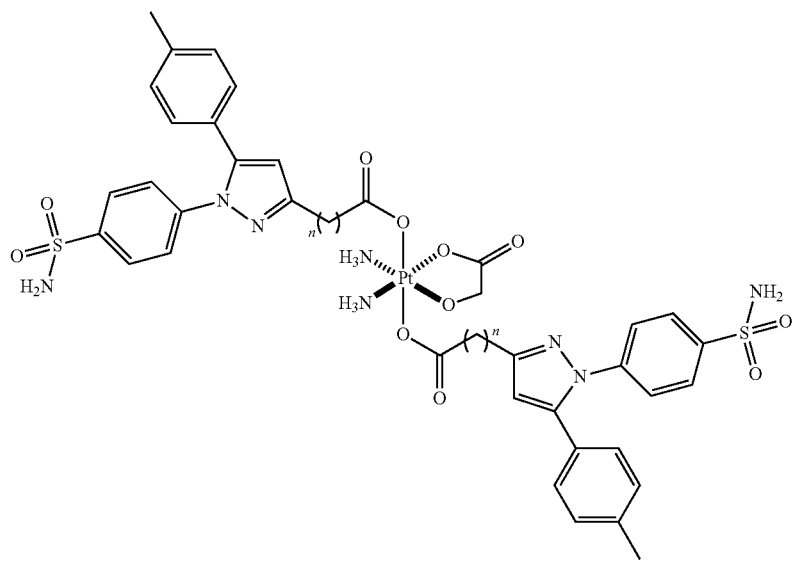
n = 4 to 10
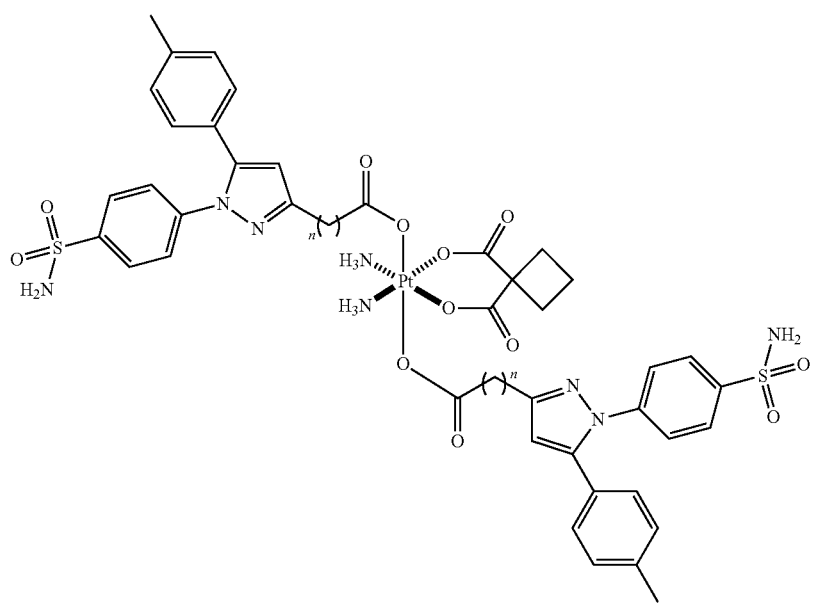
n = 4 to 10

-continued
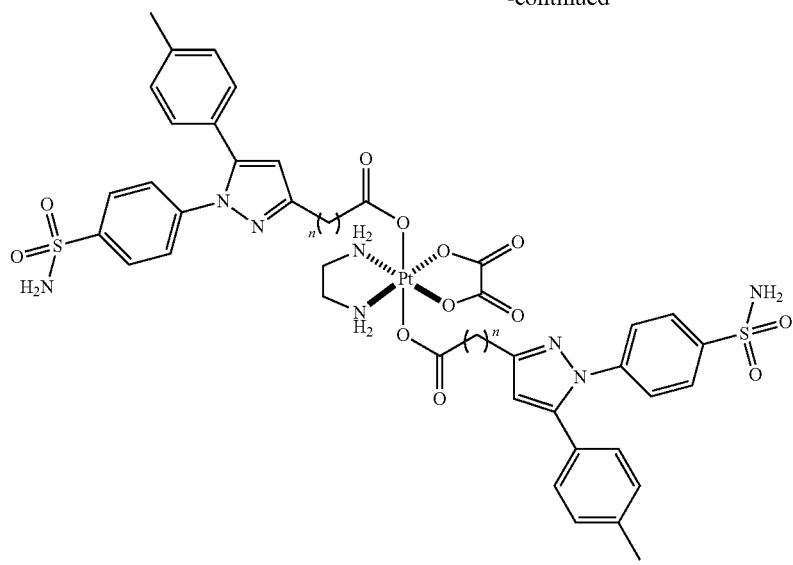
n = 4 to 10
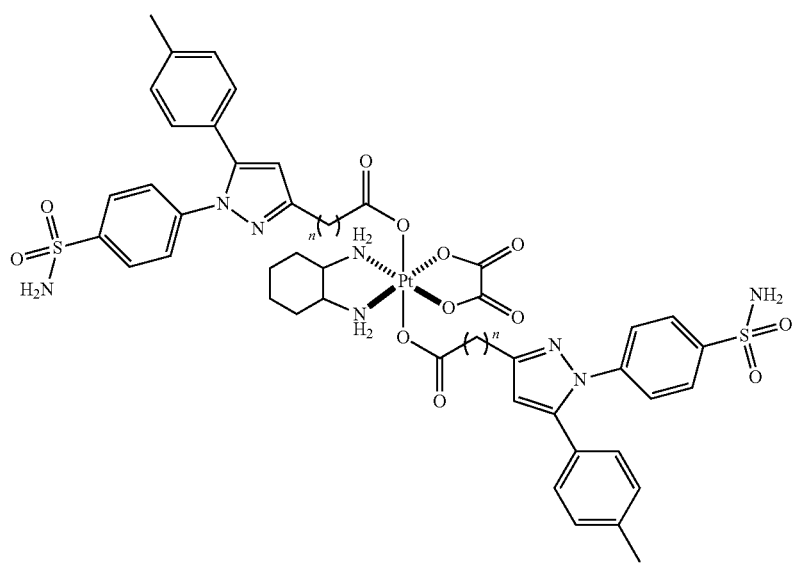
n = 4 to 10
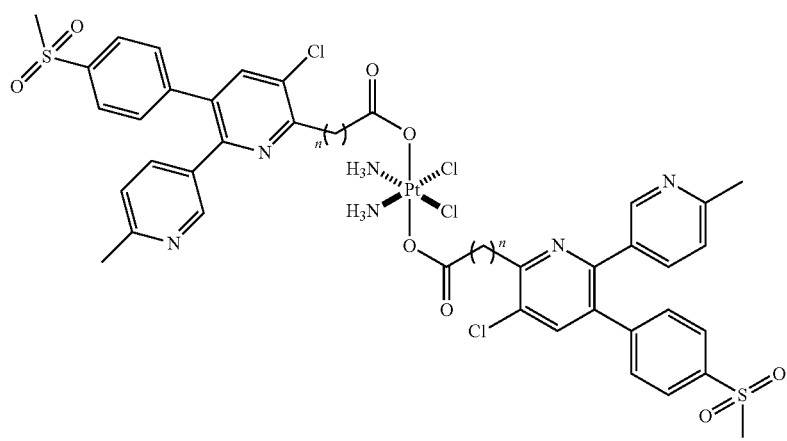
n = 4 to 10

-continued
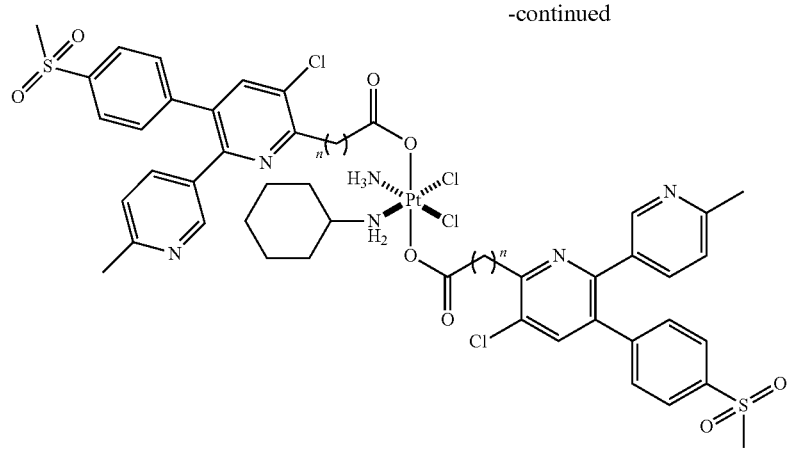
n = 4 to 10
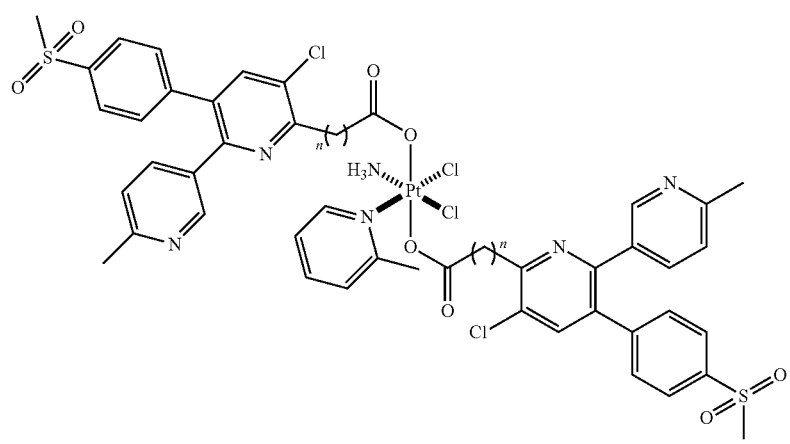
n = 4 to 10
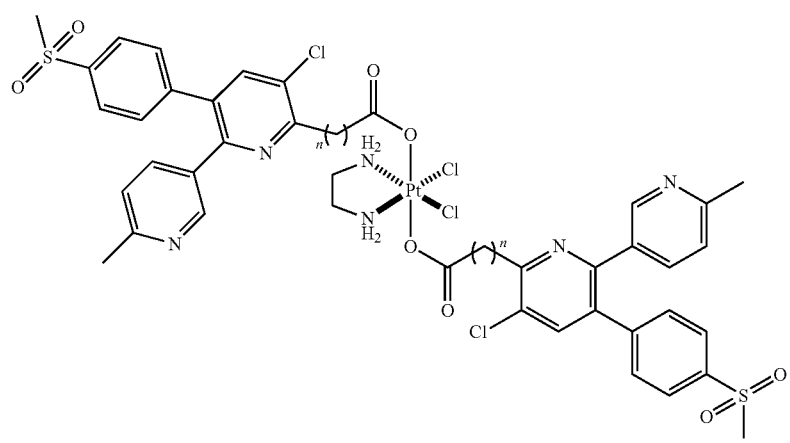
n = 4 to 10

-continued
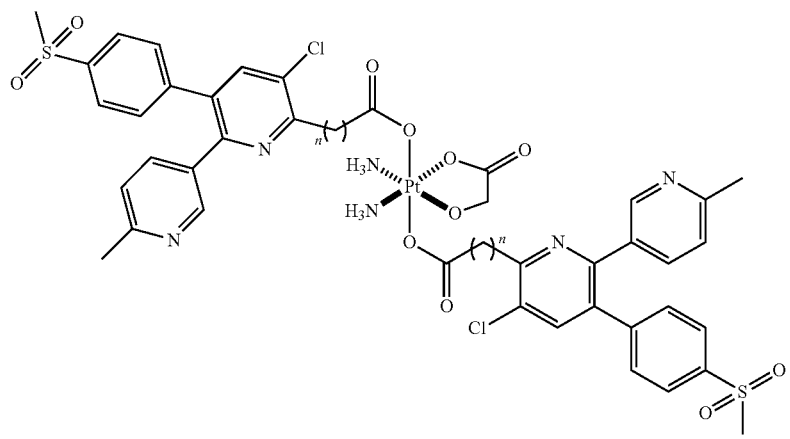
n = 4 to 10
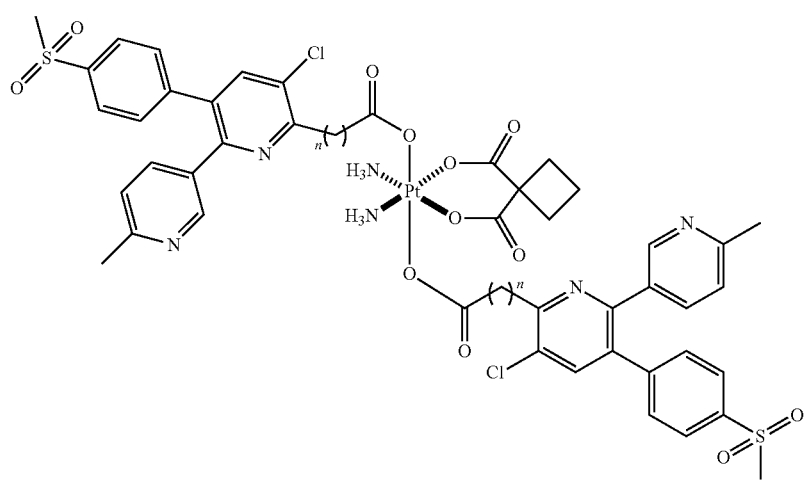
n = 4 to 10
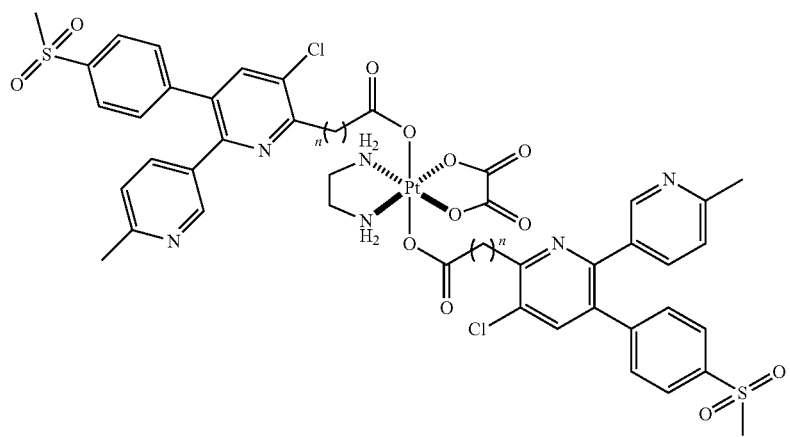
n = 4 to 10

-continued
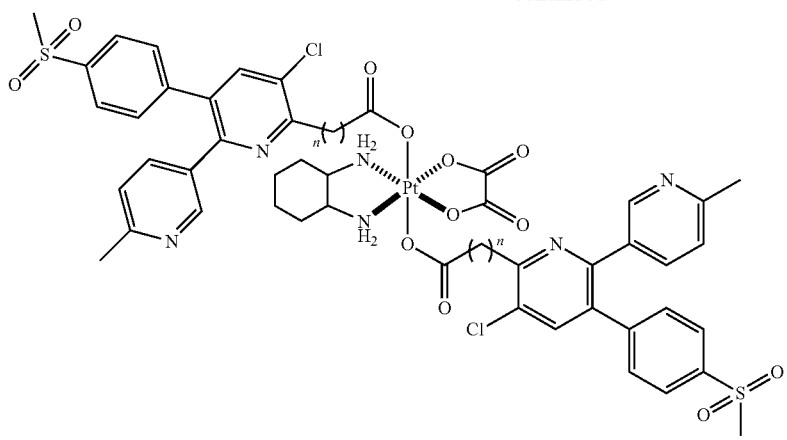
n = 4 to 10
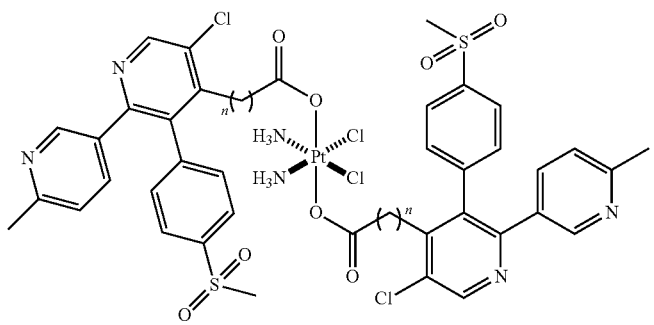
n = 4 to 10
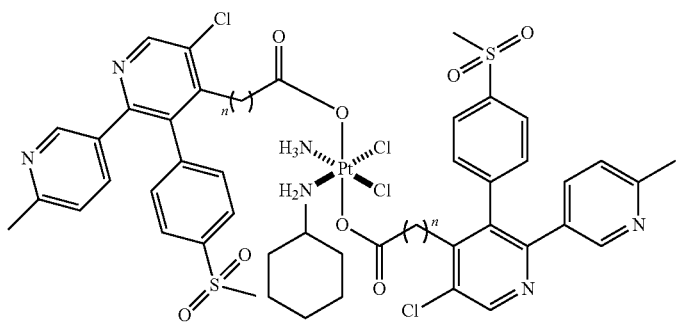
n = 4 to 10
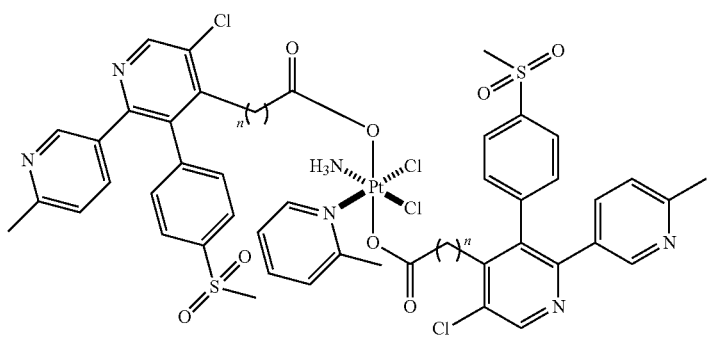
n = 4 to 10

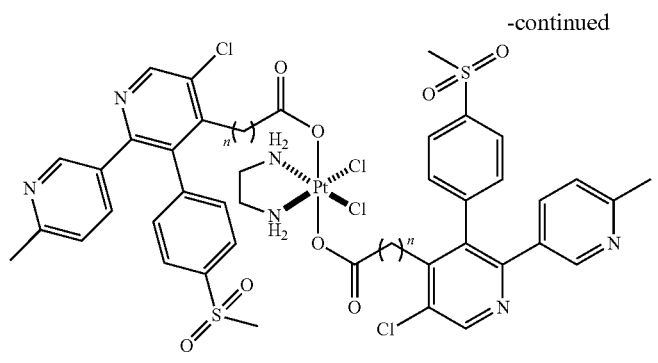
n = 4 to 10
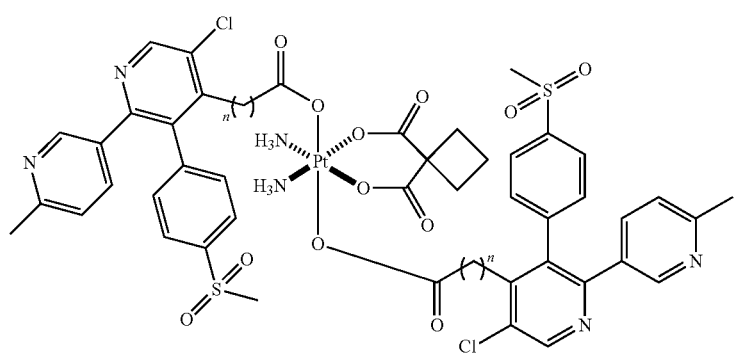
n = 4 to 10
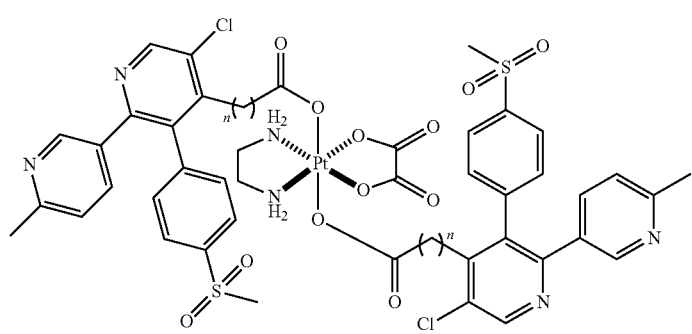
n = 4 to 10
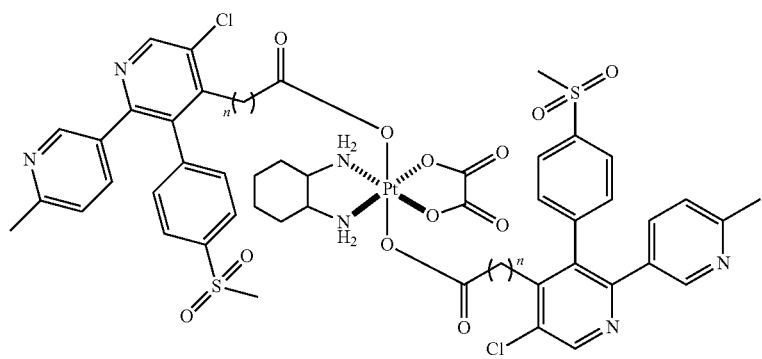
n = 4 to 10

-continued
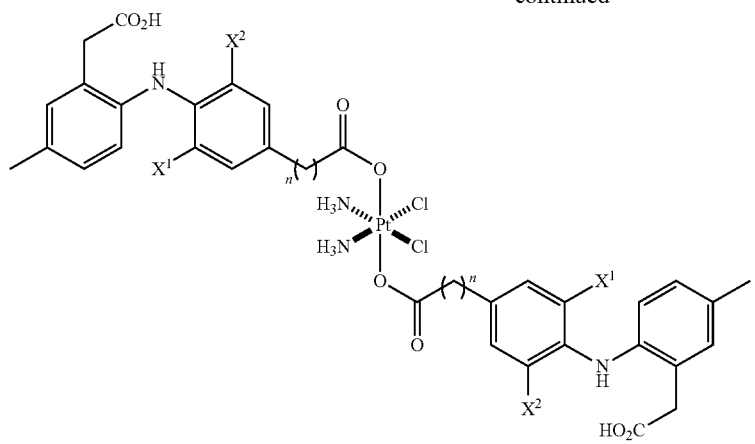
1) $X^1$ = F & $X^2$ = Cl;
2) $X^1$ = $X^2$ = F; or
3) $X^1$ = $X^2$ = Cl
n = 4 to 10
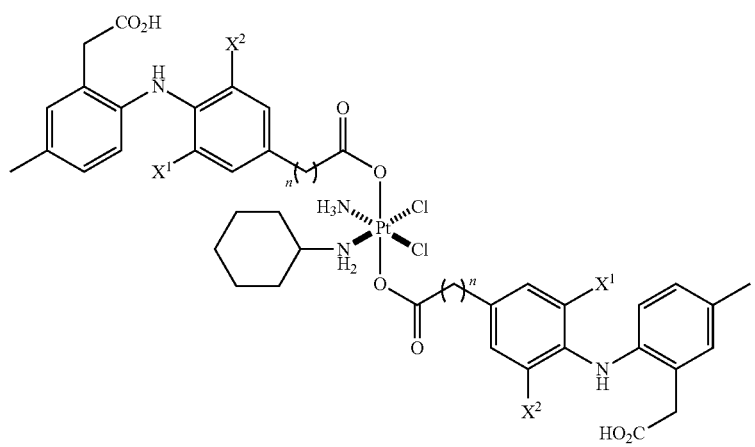
1) $X^1$ = F & $X^2$ = Cl;
2) $X^1$ = $X^2$ = F; or
3) $X^1$ = $X^2$ = Cl
n = 4 to 10
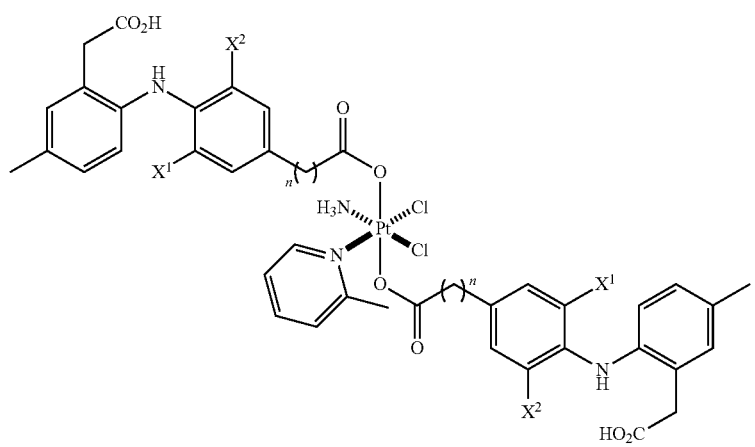
1) $X^1$ = F & $X^2$ = Cl;
2) $X^1$ = $X^2$ = F; or
3) $X^1$ = $X^2$ = Cl
n = 4 to 10

-continued
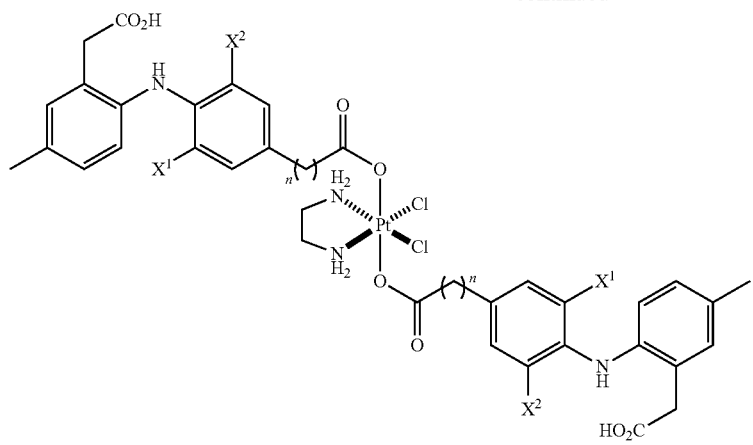
1) $X^1$ = F & $X^2$ = Cl;
2) $X^1$ = $X^2$ = F; or
3) $X^1$ = $X^2$ = Cl
n = 4 to 10
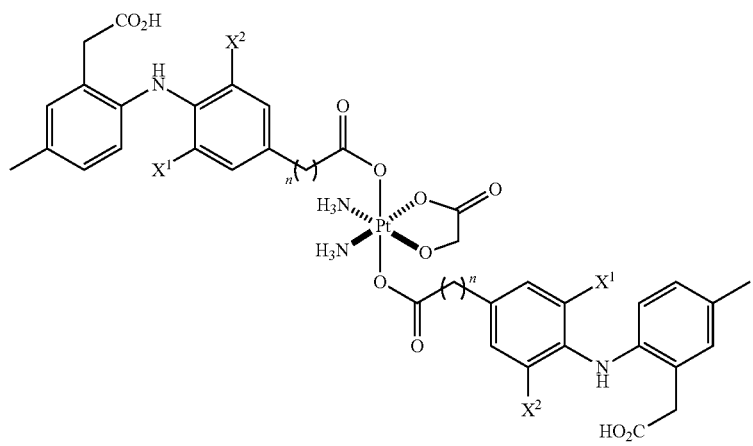
1) $X^1$ = F & $X^2$ = Cl;
2) $X^1$ = $X^2$ = F; or
3) $X^1$ = $X^2$ = Cl
n = 4 to 10
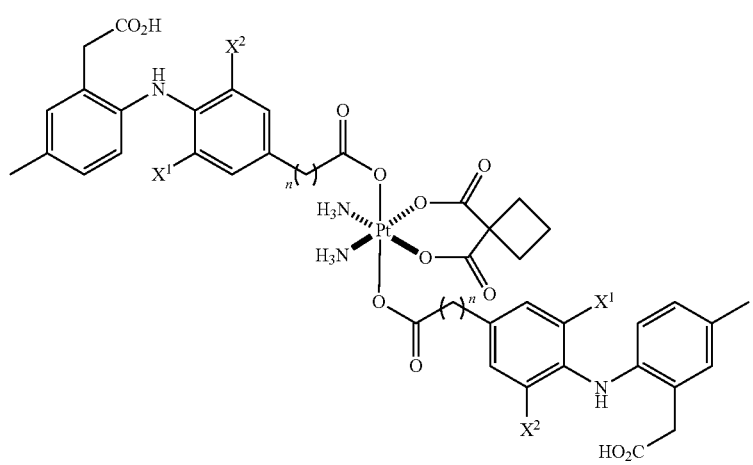
1) $X^1$ = F & $X^2$ = Cl;
2) $X^1$ = $X^2$ = F; or
3) $X^1$ = $X^2$ = Cl
n = 4 to 10

-continued
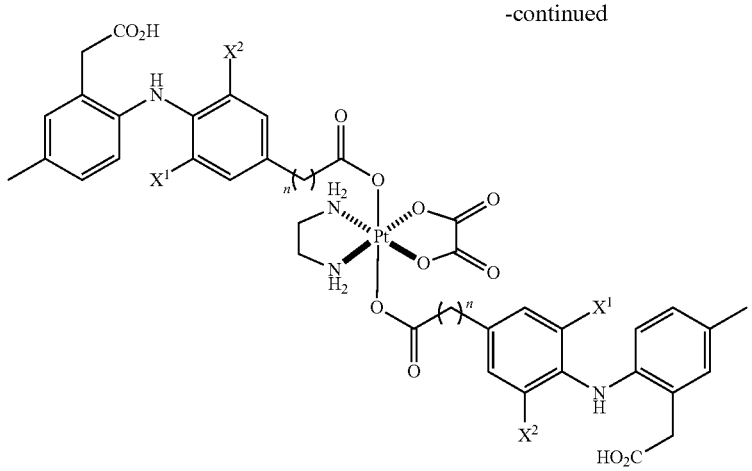
1) $X^1 = F$ & $X^2 = Cl$;
2) $X^1 = X^2 = F$; or
3) $X^1 = X^2 = Cl$
n = 4 to 10
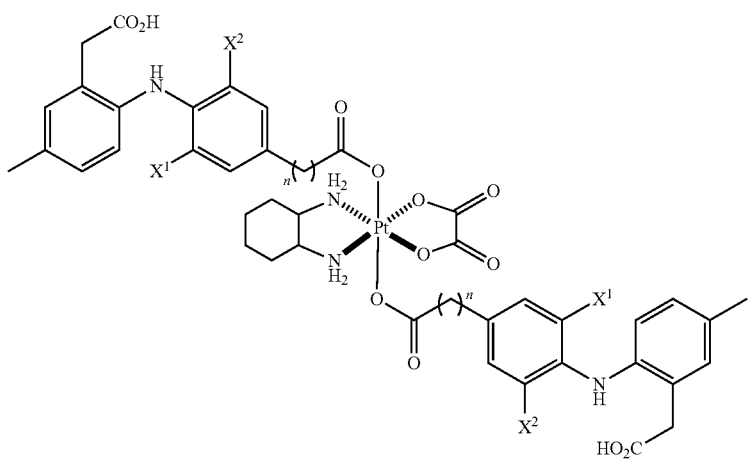
1) $X^1 = F$ & $X^2 = Cl$;
2) $X^1 = X^2 = F$; or
3) $X^1 = X^2 = Cl$
n = 4 to 10
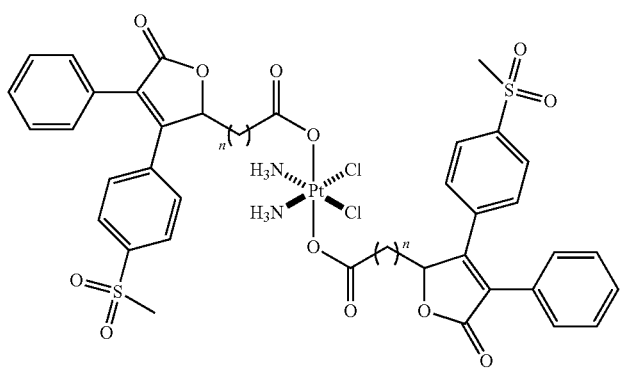
n = 4 to 10

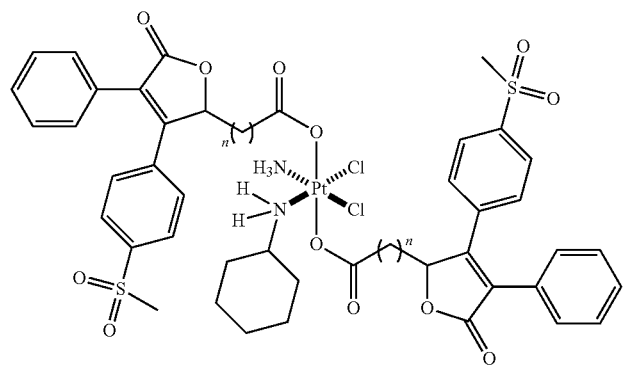
n = 4 to 10
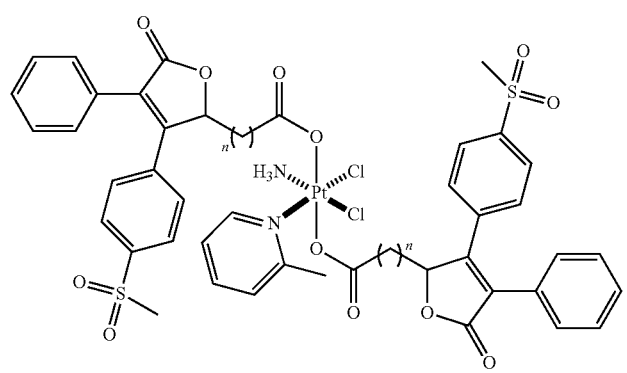
n = 4 to 10
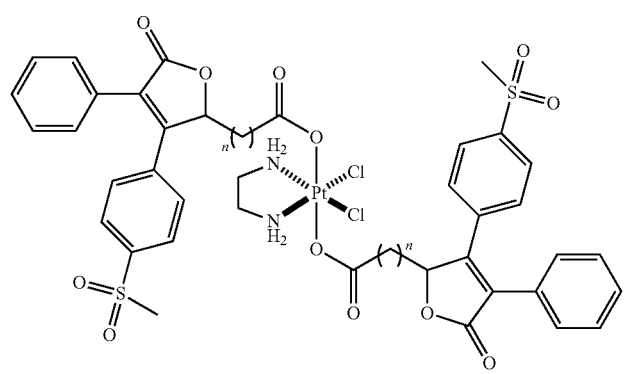
n = 4 to 10
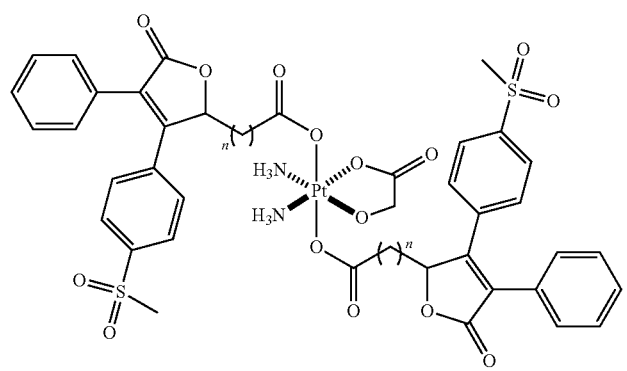
n = 4 to 10

-continued
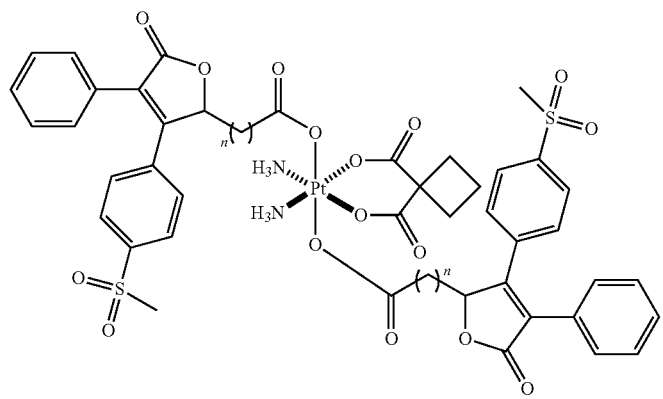
n = 4 to 10
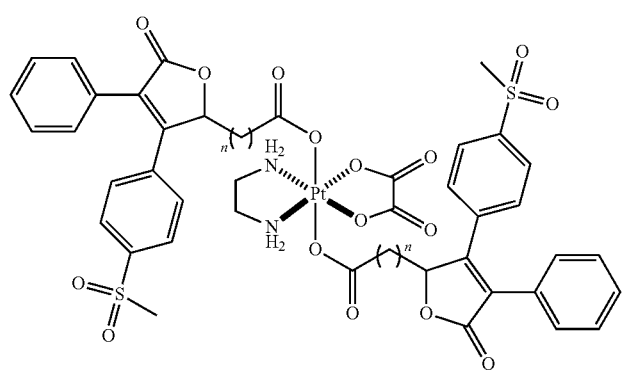
n = 4 to 10
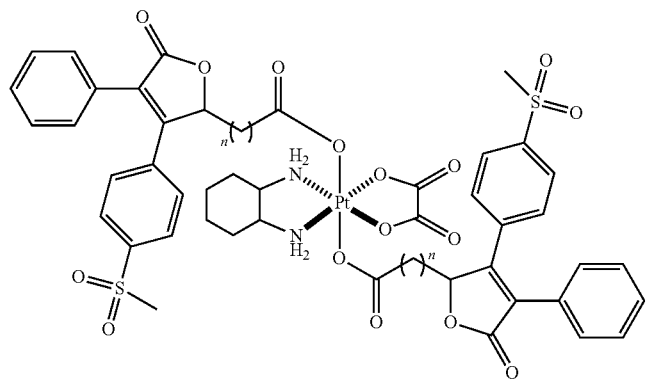
n = 4 to 10
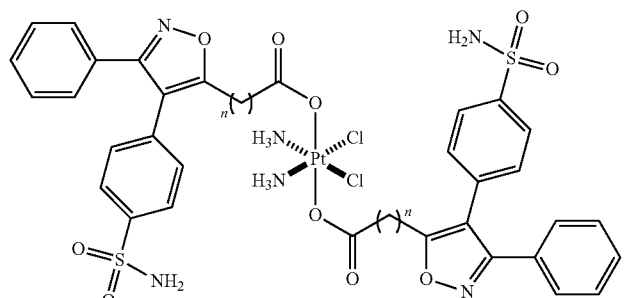
n = 4 to 10

-continued
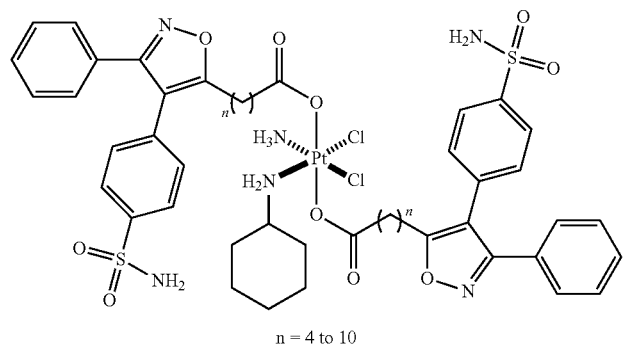
n = 4 to 10
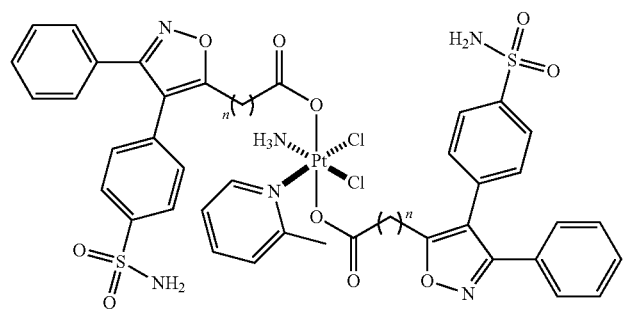
n = 4 to 10
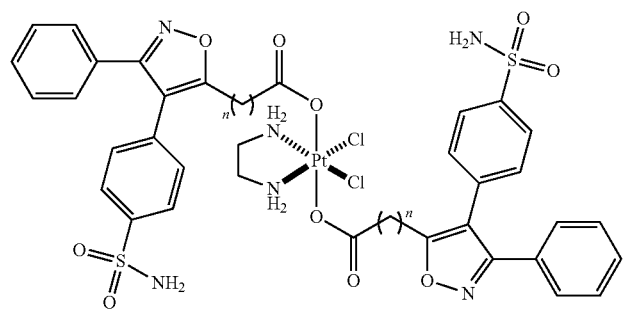
n = 4 to 10
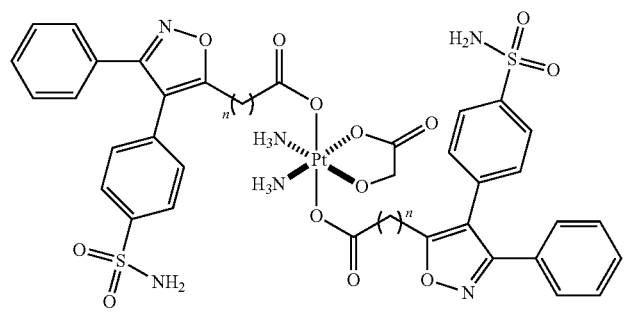
n = 4 to 10

-continued

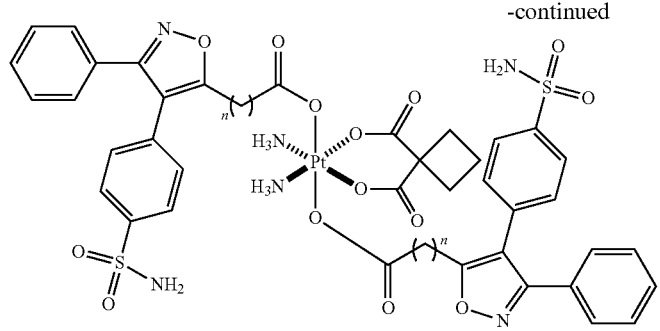

n = 4 to 10

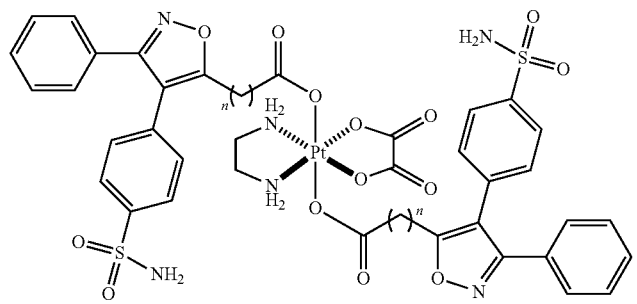

n = 4 to 10

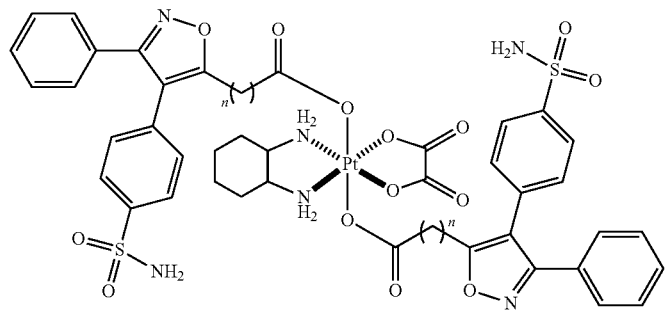

n = 4 to 10 and corresponding conjugates in which the platinum metal is connected to a COX-2-targeting moiety at one axial position and has a —OC(=O)$R^{10}$ or —OC(=O)-(4-phenyl-$R^{11}$) ligand at the other axial position, wherein $R^{10}$ is $C_1$-$C_{10}$ alkyl and $R^{11}$ is —H or $C_1$-$C_6$ alkyl, and pharmaceutically acceptable salts thereof.

24. The conjugate of any one of the preceding embodiments, which has a dissociation constant ($K_d$) with COX-2 of no more than about 100 nM, 50 nM, 10 nM or 1 nM.
25. The conjugate of any one of the preceding embodiments, which has a half maximal inhibitory concentration ($IC_{50}$) of no more than about 1000 nM, 500 nM, 250 nM, 100 nM, 50 nM or 10 nM (e.g., no more than about 250 nM or 100 nM) for inhibition of COX-2 (e.g., in an enzyme assay or a cell-based assay).
26. The conjugate of any one of the preceding embodiments, which targets COX-2 selectively or preferentially (e.g., targets COX-2 selectively or preferentially over COX-1).
27. A pharmaceutical composition comprising the conjugate of any one of the preceding embodiments and a pharmaceutically acceptable carrier or excipient.
28. A method of treating a tumor or cancer, comprising administering to a subject in need of treatment a therapeutically effective amount of the conjugate of any one of embodiments 1 to 26.
29. The method of embodiment 28, wherein the tumor or cancer is characterized by overexpression of COX-2.
30. The method of embodiment 28 or 29, wherein the tumor or cancer is a tumor or cancer of the nervous system (e.g., myelin), central nervous system (e.g., brain and meninges), head or neck (e.g, mouth, tongue, nasal cavity, paranasal sinus, nasopharynx, hypopharynx, throat, parathyroid or thyroid), gastrointestinal tract (e.g., esophagus, stomach, duodenum, small or large intestine, colon or rectum), lung, pancreas, gallbladder, liver, kidney, bladder, breast, uterus (e.g., endometrium), cervix, ovary, prostate, testicle, skin (e.g., melanoma), smooth muscle (e.g., leiomyoma or leiomyosarcoma), epithelial tissue or cells (e.g., adenoma, adenocarcinoma or carcinoma of the head or neck, pituitary gland, gastrointestinal tract, appendix, lung, bronchi, pancreas, gallbladder, liver, kidney, adrenal gland, bladder, urothelium, breast, uterus [e.g., endometrium], cervix, ovary, prostate, skin, or squamous cells), connective tissue (e.g., bone [e.g., adamantinoma, Ewing's sarcoma or osteosarcoma], cartilage [e.g., chondrosarcoma], nerve [e.g., neurofibrosarcoma] or fat [e.g., liposarcoma]), hematopoietic or lymphoid tissue or cells (e.g., leukemia, lymphoma, myeloma or myeloproliferative neoplasm [e.g., polycythemia vera]), germ cells (e.g., of the testicle or ovary), or immature/precursor cells (e.g., glioblastoma, hepatoblastoma, neuroblastoma or retinoblastoma).
31. The method of any one of embodiments 28 to 30, wherein the tumor or cancer is a COX-2-overexpressing tumor or cancer selected from the group consisting of tumors and cancers of the nervous system (e.g., nerve sheath tumors, such as peripheral nerve sheath tumors), central nervous system (e.g., meningioma), brain (e.g., glioblastoma), head and neck (e.g., mouth, tongue, nasal cavity, paranasal sinuses, nasopharynx, hypopharynx, throat, parathyroid and thyroid), gastrointestinal tract (e.g., esophagus, stomach, duodenum, small and large intestine, colon and rectum), lung, pancreas, gallbladder, liver, kidney, bladder, breast, uterus (e.g., endometrium), cervix, ovary, prostate, skin (e.g., melanoma), epithelial tissues and cells (e.g., adenomas, adenocarcinomas and carcinomas of the head and neck [e.g., mouth, nasopharynx, hypopharynx and thyroid], gastrointestinal tract [e.g., esophagus, stomach, duodenum, small and large intestine, colon and rectum], lung, bronchi, pancreas, gallbladder, liver, kidney, bladder, urothelium, breast, uterus [e.g., endometrium], cervix, ovary, prostate, skin, squamous cells, and mesothelial cells [e.g., mesothelioma]), mesenchymal cells (e.g., chondrosarcoma and osteosarcoma), and hematopoietic and lymphoid tissues and cells (e.g., chronic lymphocytic leukemia, chronic myeloid leukemia, Hodgkin's lymphoma, non-Hodgkin's lymphoma and multiple myeloma).
32. The method of any one of embodiments 28 to 31, wherein the tumor or cancer is benign, in situ (potentially malignant), malignant, metastatic, primary or secondary, or any combination thereof.
33. The method of any one of embodiments 28 to 32, wherein the conjugate is administered orally or parenterally (e.g., intramuscularly, subcutaneously, intravascularly, intravenously or intraarterially).
34. The method of any one of embodiments 28 to 33, further comprising administering an additional antitumor agent.
35. The method of embodiment 34, wherein the additional antitumor agent is selected from the group consisting of cytotoxic agents, immune system stimulators, immune checkpoint inhibitors, angiogenesis inhibitors, directed antitumor therapeutics, and other kinds of antitumor agents.
36. A method of inhibiting cell growth or proliferation, comprising contacting a cell with the conjugate of any one of embodiments 1 to 26.
37. The method of embodiment 36, wherein the cell is a tumor or cancer cell that overexpresses COX-2.
38. The method of embodiment 36 or 37, wherein the conjugate has a half maximal effective concentration ($EC_{50}$), or a half maximal inhibitory concentration ($IC_{50}$), of no more than about 500 nM, 250 nM, 100 nM, 50 nM, 10 nM or 1 nM (e.g., no more than about 100 nM).

VII. EXAMPLES

The following examples are intended only to illustrate the disclosure. Other procedures, methodologies, reagents, conditions and tests may alternatively be used and done as appropriate.

Example 1

Inhibition of COX-1 and COX-2 in an Enzyme Assay

The ability of compounds to inhibit ovine COX-1 and human COX-2 is determined using a commercially available enzyme immunoassay (EIA) kit (Catalog No. 701090 [COX-1] and Catalog No. 701080 [COX-2], Cayman Chemical Co., Ann Arbor, Mich., USA) according to the manufacturer's protocol. COX catalyzes the first step in the biosynthesis of arachidonic acid (AA) to prostaglandin H2 (PGH2). PGF2α, produced from PGH2 by reduction with stannous chloride, is measured by EIA (ACE™ competitive EIA, Cayman Chemical Co.). Briefly, to a series of supplied reaction buffer solutions [960 µL 0.1 M Tris-HCl (pH 8.0) containing 5 mM EDTA and 2 mM phenol] with either COX-1 or COX-2 enzyme (10 µL) in the presence of heme (10 µL), 10 µL of various concentrations of test compound solutions is added. The resulting solutions are incubated at 37° C. for 15 min, and then 10 µL AA solution (100 µM) is added. The COX reaction is stopped by the addition of 30 µL stannous chloride after 2 min, which is mixed immediately, and supernatants are diluted 2000 fold. The produced PGF2α is measured by EIA. This assay is based on the competition between PGs and a PG-acetylcholinesterase conjugate (PG tracer) for a limited amount of PG antiserum. The amount of PG tracer that is able to bind to the PG antiserum is inversely proportional to the concentration of PGs in the wells because the concentration of the PG tracer is held constant while the concentration of PGs varies. The specific antiserum-PG complex binds to a mouse anti-rabbit IgG previously attached to the well. The plate is washed to remove any unbound reagents and 200 µL Ellman's reagent [5,5'-dithiobis-(2-nitrobenzoic acid)], which contains the substrate of acetylcholine esterase, is added to the well. The product of this enzymatic reaction generates a distinct yellow color that absorbs at 406 nm. The intensity of this color, determined by spectrophotometry, is proportional to the amount of PG tracer bound to the well, which is inversely proportional to the amount of PGs present in the well during the incubation. Percent inhibition is calculated by comparison of the compounds treated to various control incubations. Dose-response curves are generated using XLFit (IDBS, Surrey, UK) or Prism (GraphPad Software, La Jolla, Calif., USA) to calculate $IC_{50}$ values for each compound tested.

Example 2

Cytotoxicity Assays Using HT29 and S/KS Cells

Two colon carcinoma cell lines, HT29 and S/KS, are used. It has been reported that according to Western immunoblotting analysis of crude cell lysates using a COX-2 antibody, HT29 cells constitutively express the COX-2 protein, whereas S/KS cells do not express levels of COX-2 detectable by this method.

The cytotoxicity of conjugates described herein and a positive control (e.g., cisplatin) is evaluated using two methodologies—SRB and colony-counting assays. The cells are grown in DMEM (GIBCO/BRL) supplemented with about 10% FBS, an antibiotic/antimycotic solution (GIBCO), and about 2 mM L-glutamine HT29 and S/KS cells are grown in RPMI-1640 media (ATCC) containing about 10% FBS and 1× antibiotic/antimycotic solution. All cells are incubated at about 37° C. under about 5% $CO_2$ atmosphere. For the SRB assay, HT29 and S/KS cells are seeded onto 96-well plates at a density of about 1,000 cells per well and allowed to grow for about 24 hours.

Cisplatin and conjugates described herein are diluted to the following concentrations: about 0.001 (or lower), 0.01, 0.1, 1, 2, 5, 10, and 100 (or higher) µM. The cells are treated with cisplatin or the conjugates and incubated for about 4 hours. The cells are then fixed and permeabilized with about 25% acetic acid in methanol for about 10 min at room temperature, washed with PBS, and incubated with an approximately 1:100 dilution of anti-HMGB1 polyclonal antibody at about 37° C. for about 1 hour. The cells are subsequently incubated with an approximately 1:200 dilution of goat anti-rabbit IgG conjugated to FITC at about 37° C. for about 1 hour. The cover slips are then placed on microscope slides, fixed with gelvatol, and incubated at about 4° C. for about 12 hours. HMGB1 levels are then visualized under a fluorescent light microscope equipped with a digital camera.

For the colony-counting assay, HT29 and S/KS cells are seeded onto 6-well plates at a density of about 1,000 cells per well in about 2 mL media and allowed to grow at about 37° C. for about 24 hours. Cells are then treated for about 72 hours with cisplatin or the conjugates at the following concentrations: about 0.001 (or lower), 0.01, 0.1, 1, 2, 5, 10, and 100 (or higher) µM. After about 72 hours, cells are washed with PBS, and fresh medium is added. After about 7 days, the colonies are counted by staining with an about 1% methylene blue/50% ethanol (v/v) solution.

It is understood that, while particular embodiments have been illustrated and described, various modifications may be made thereto and are contemplated herein. It is also understood that the disclosure is not limited by the specific examples provided herein. The description and illustration of embodiments and examples of the disclosure herein are not intended to be construed in a limiting sense. It is further understood that all aspects of the disclosure are not limited to the specific depictions, configurations or relative proportions set forth herein, which may depend upon a variety of conditions and variables. Various modifications and variations in form and detail of the embodiments and examples of the disclosure will be apparent to a person skilled in the art. It is therefore contemplated that the disclosure also covers any and all such modifications, variations and equivalents.

What is claimed is:

1. A conjugate comprising a moiety that targets cyclooxygenase II (COX-2), a platinum-containing antitumor agent, and a linker connecting the COX-2-targeting moiety to the platinum-containing antitumor agent,
wherein the platinum-containing antitumor agent is of Formula I or a pharmaceutically acceptable salt thereof:

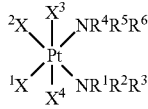

(I)

wherein:
$X^1$ and $X^2$ independently are —Cl, —OH, optionally substituted —O-(alkyl or cyclyl), optionally substituted —O-(alkyl or cyclyl)-C(=O)OR$^7$, optionally substituted —O-(alkyl or cyclyl)-C(=O)NR$^8$R$^9$, optionally substituted —OC(=O)-(alkyl or cyclyl), optionally substituted —OC(=O)-(alkyl or cyclyl)-C(=O)OR$^7$, optionally substituted —OC(=O)-(alkyl or cyclyl)-C(=O)NR$^8$R$^9$, or optionally substituted thiourea, wherein:
cyclyl is an optionally substituted cycloalkyl, heterocyclyl, aryl or heteroaryl group;

$R^7$ is —H, optionally substituted alkyl, optionally substituted cycloalkyl or optionally substituted heterocyclyl; and
$R^8$ and $R^9$ independently are —H, optionally substituted alkyl, optionally substituted cycloalkyl or optionally substituted heterocyclyl; or
$R^8$ and $R^9$, together with the nitrogen atom to which they are attached, form an optionally substituted heterocyclyl group; and
$X^1$ and $X^2$ can be cis or trans relative to each other; or
$X^1$ and $X^2$ together are part of a sulfate (SO$_4^{-2}$) group; or
$X^1$ and $X^2$ together form

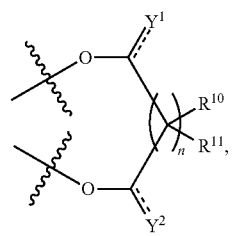

wherein:
$Y^1$ and $Y^2$ independently are —H, —OH, oxo (forming a carbonyl group with the adjacent carbon atom), or optionally substituted alkyl;
$R^{10}$ and $R^{11}$ independently are —H, —OH, —NH$_2$, optionally substituted alkyl, optionally substituted —O-alkyl, optionally substituted —O-alkyl-C(=O)OR$^7$, optionally substituted —O-alkyl-C(=O)NR$^8$R$^9$, optionally substituted —OC(=O)-alkyl, optionally substituted —OC(=O)-alkyl-C(=O)OR$^7$, optionally substituted —OC(=O)-alkyl-C(=O)NR$^8$R$^9$, —NR$^{12}$R$^{13}$, optionally substituted —NH-alkyl-C(=O)OR$^7$, optionally substituted —NH-alkyl-C(=O)NR$^8$R$^9$, optionally substituted —NHC(=O)-alkyl, —NHC(=O)-alkyl-C(=O)OR$^7$, or optionally substituted —NHC(=O)-alkyl-C(=O)NR$^8$R$^9$, wherein:
$R^7$ is —H, optionally substituted alkyl, optionally substituted cycloalkyl or optionally substituted heterocyclyl;
$R^8$ and $R^9$ independently are —H, optionally substituted alkyl, optionally substituted cycloalkyl or optionally substituted heterocyclyl; or
$R^8$ and $R^9$, together with the nitrogen atom to which they are attached, form an optionally substituted heterocyclyl group; and
$R^{12}$ and $R^{13}$ independently are —H, optionally substituted alkyl, optionally substituted cycloalkyl, optionally substituted heterocyclyl, optionally substituted aryl or optionally substituted heteroaryl; or
$R^{12}$ and $R^{13}$, together with the nitrogen atom to which they are attached, form an optionally substituted heterocyclyl or heteroaryl group; or
$R^{10}$ and $R^{11}$, together with the carbon atom to which they are attached, form an optionally substituted cycloalkyl ring; and
n is 0 or 1;
$X^3$ and $X^4$ independently are absent or are —Cl, —OH, optionally substituted —O-(alkyl or cyclyl), optionally substituted —O-(alkyl or cyclyl)-C(=O)OR$^7$, optionally substituted —O-(alkyl or cyclyl)-C(=O)NR$^8$R$^9$, optionally substituted —OC(=O)-(alkyl or cyclyl), optionally substituted —OC(=O)-(alkyl or cyclyl)-C(=O)OR⁷, optionally substituted —OC(=O)-(alkyl or cyclyl)-C(=O)NR⁸R⁹, or optionally substituted thiourea, wherein:

cyclyl is an optionally substituted cycloalkyl, heterocyclyl, aryl or heteroaryl group;

R⁷ is —H, optionally substituted alkyl, optionally substituted cycloalkyl or optionally substituted heterocyclyl; and R⁸ and R⁹ independently are —H, optionally substituted alkyl, optionally substituted cycloalkyl or optionally substituted heterocyclyl; or R⁸ and R⁹, together with the nitrogen atom to which they are attached, form an optionally substituted heterocyclyl group;

R¹, R², R³, R⁴, R⁵ and R⁶ independently are —H, optionally substituted alkyl, optionally substituted cycloalkyl, optionally substituted heterocyclyl, optionally substituted aryl or optionally substituted heteroaryl; or NR¹R²R³ and NR⁴R⁵R⁶ independently are optionally substituted heterocyclyl or optionally substituted heteroaryl; or NR¹R²R³ and NR⁴R⁵R⁶ together are part of an optionally substituted alkyldiamine, cycloalkyldiamine, heterocyclyldiamine, aryldiamine or heteroaryldiamine group, or part of a nitrogen-containing heterocyclyl or heteroaryl group substituted with an aminoalkyl group, or part of a cycloalkyl, heterocyclyl, aryl or heteroaryl group substituted with at least two aminoalkyl groups wherein the platinum-containing antitumor agent is selected from the group consisting of:

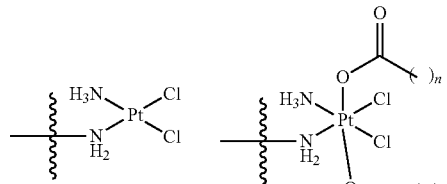

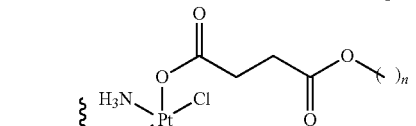

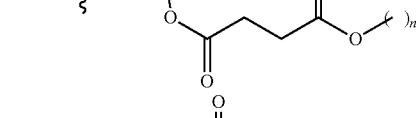

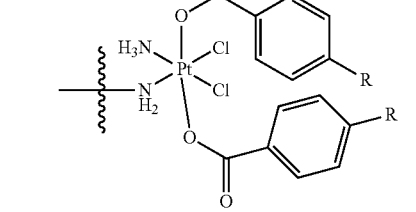

-continued

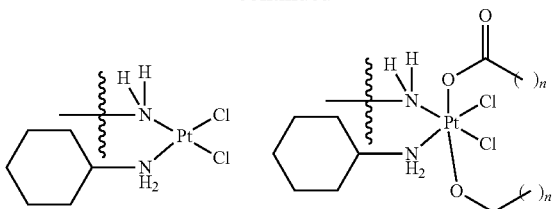

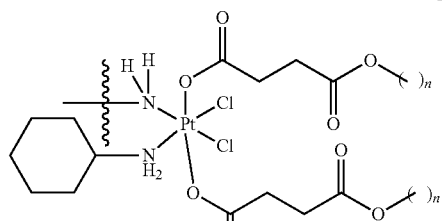

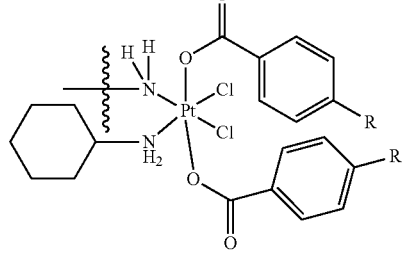

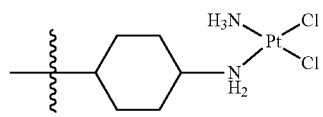

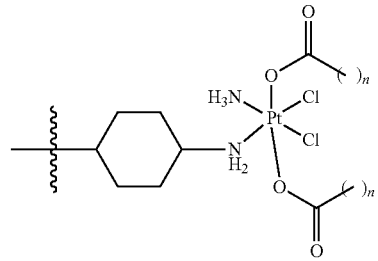

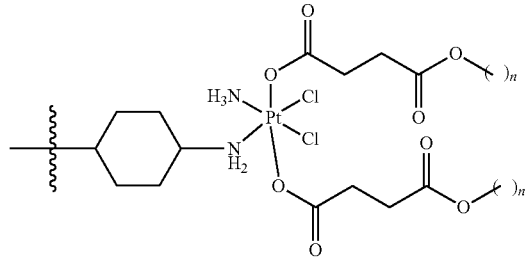

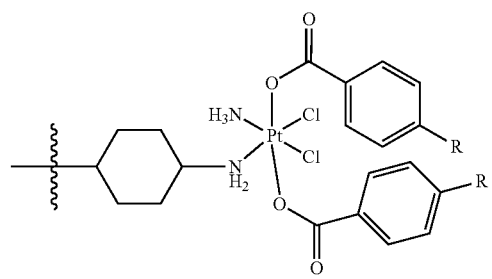

267
-continued
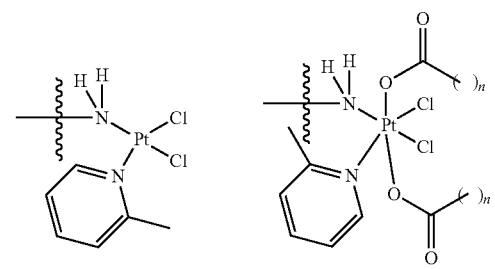
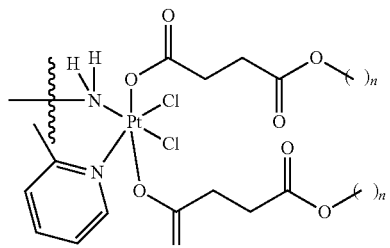
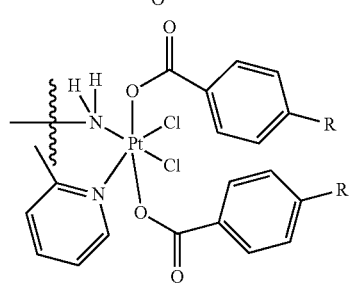
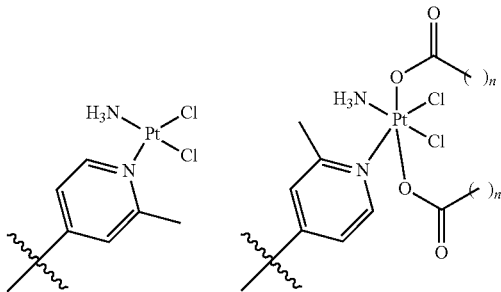
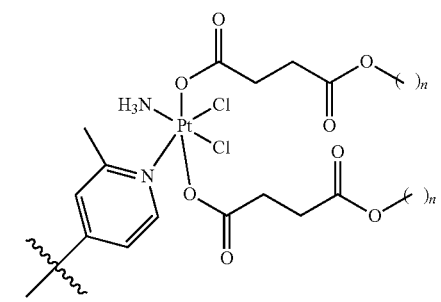
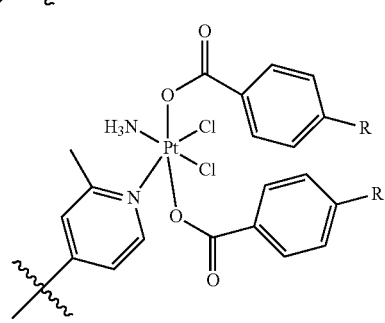
268
-continued
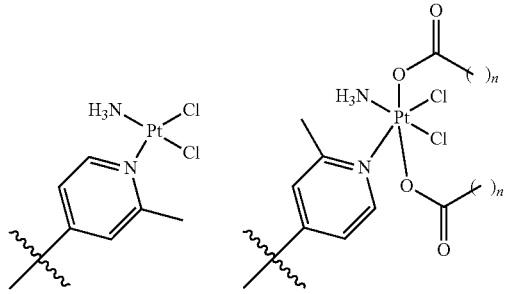
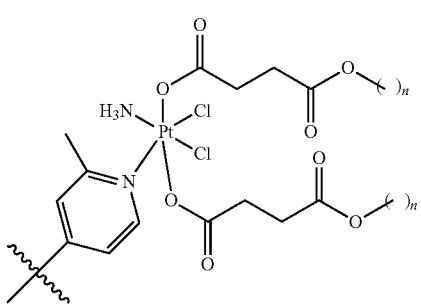
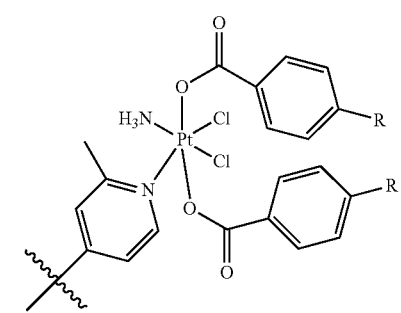
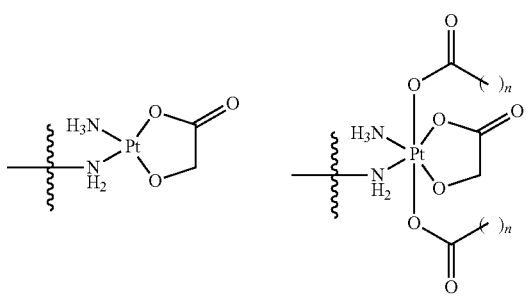
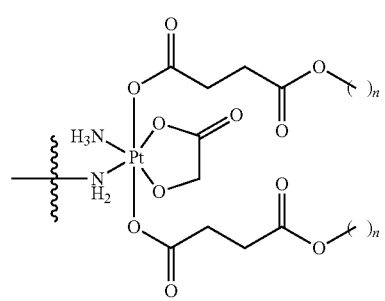

269
-continued
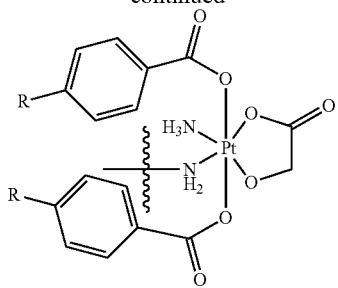
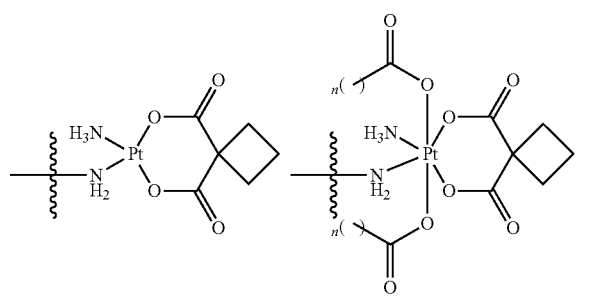
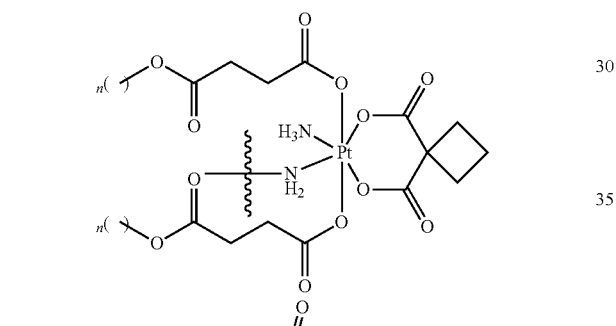
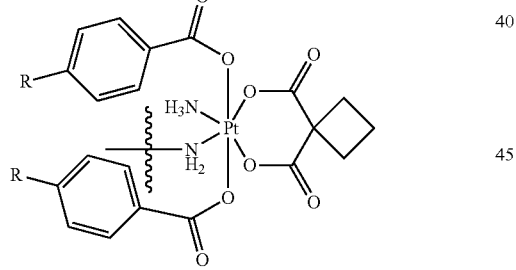
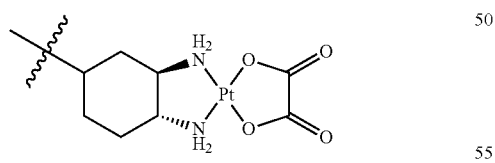
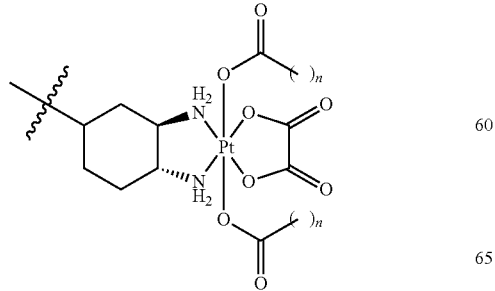
270
-continued
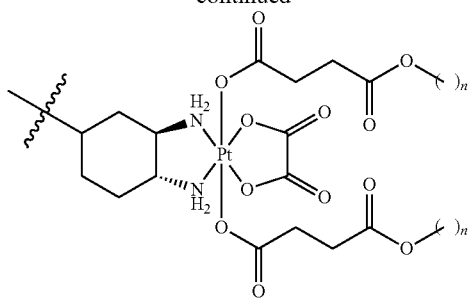
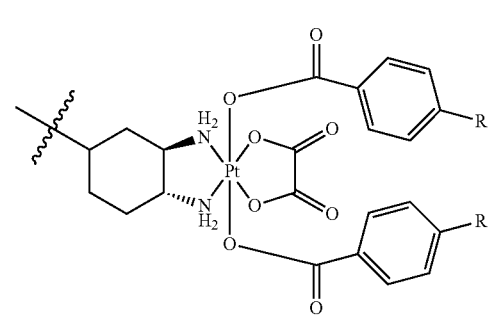
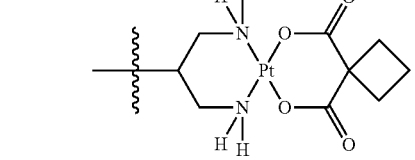
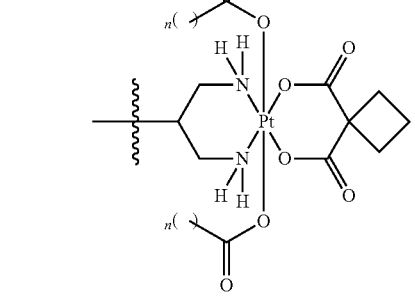
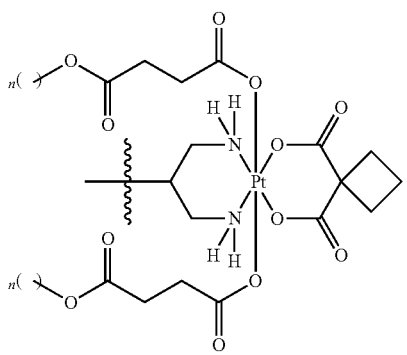

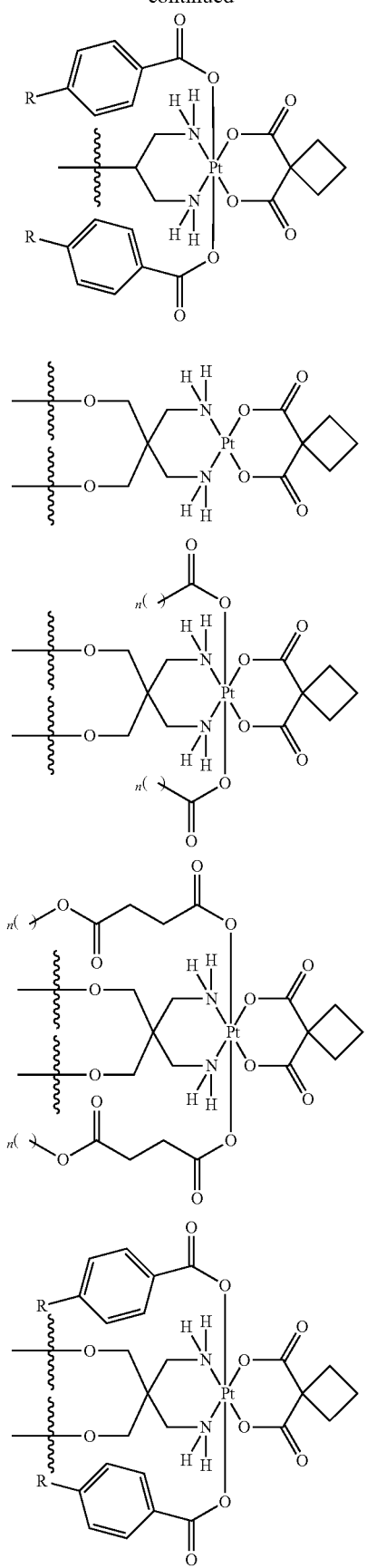
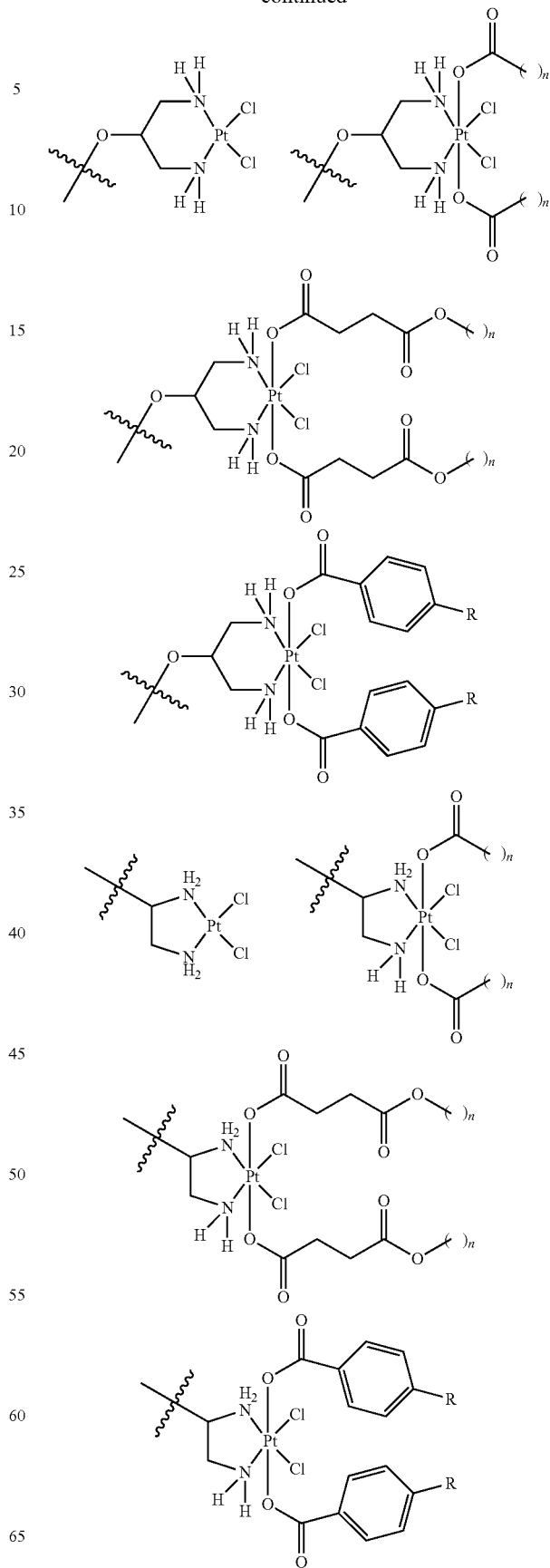

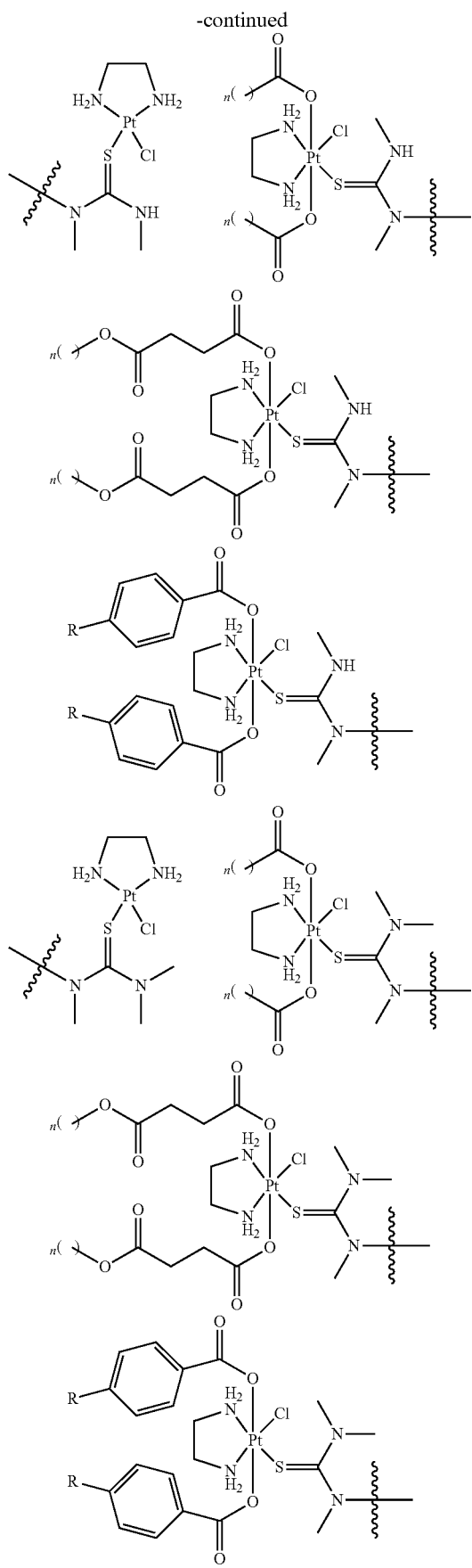
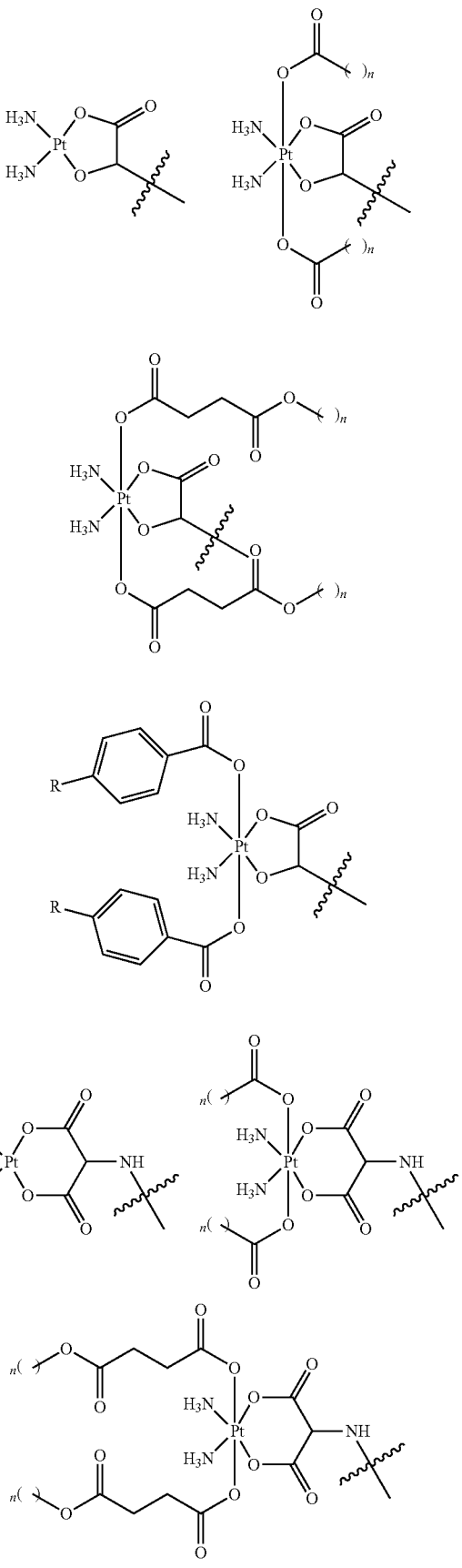

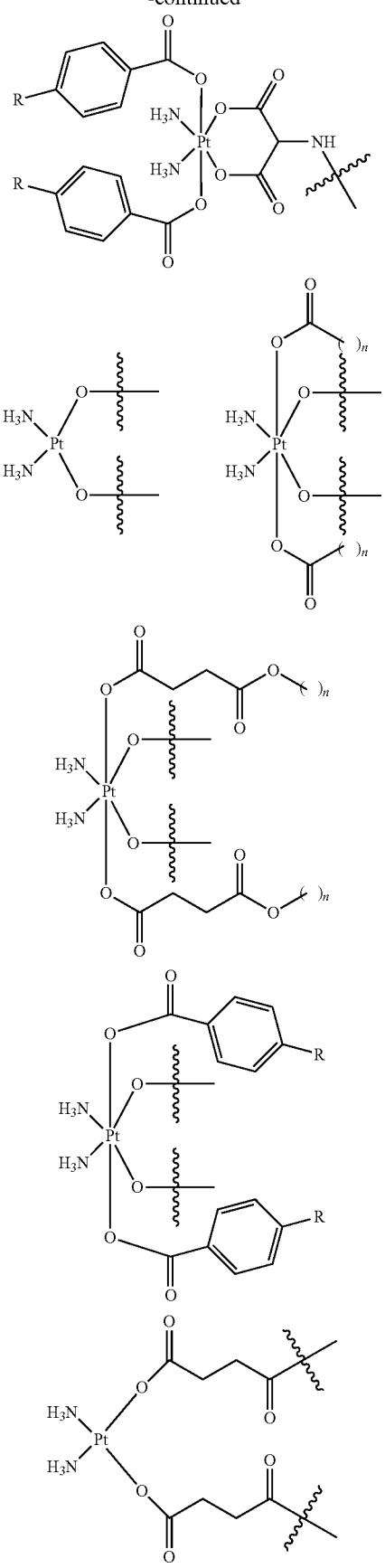
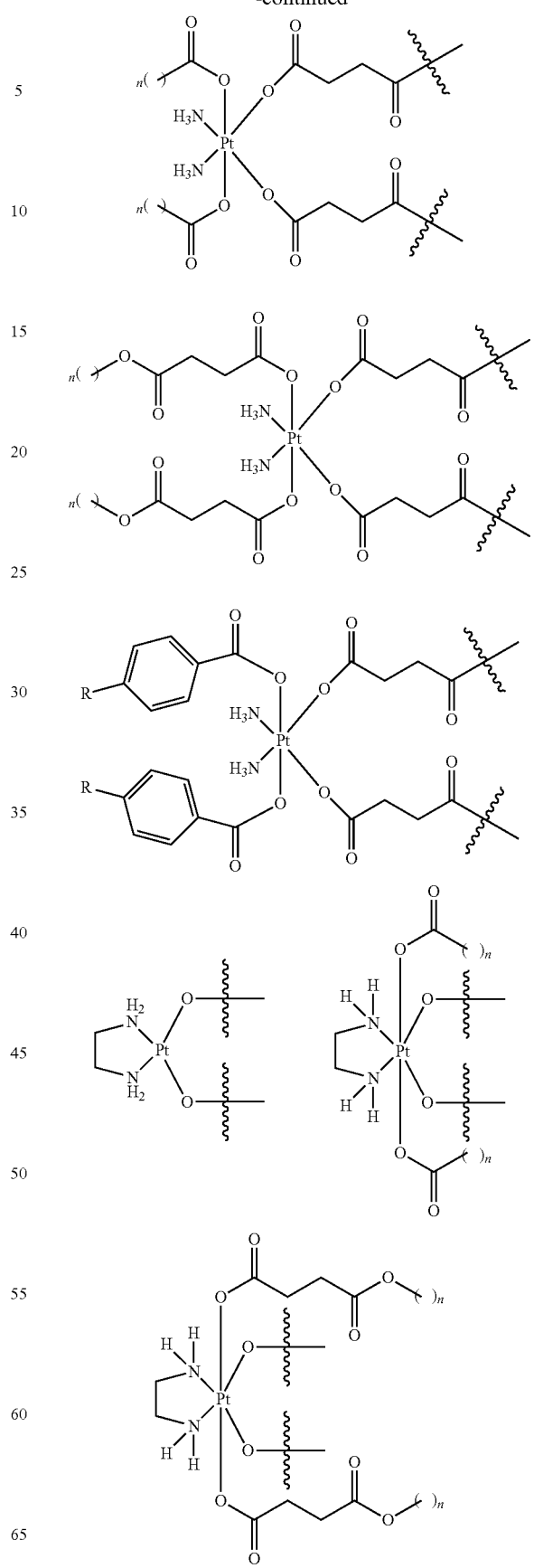

277
-continued
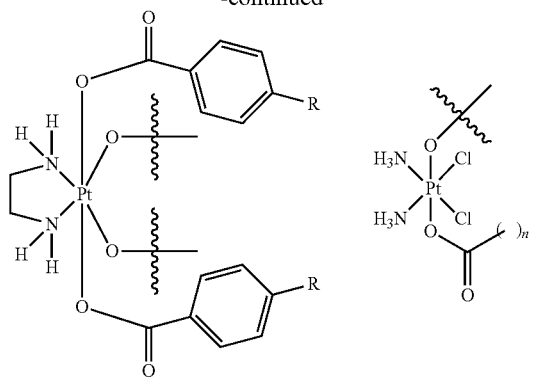
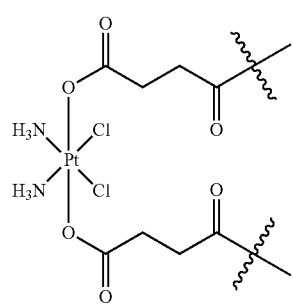
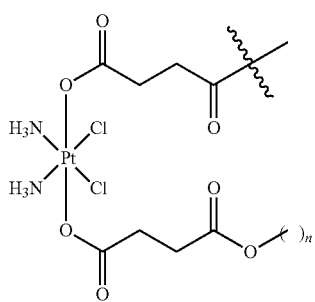
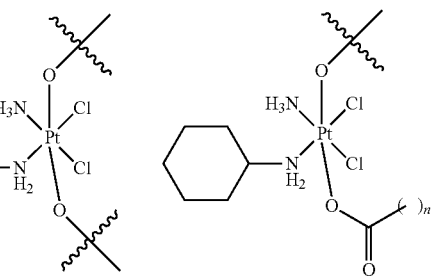
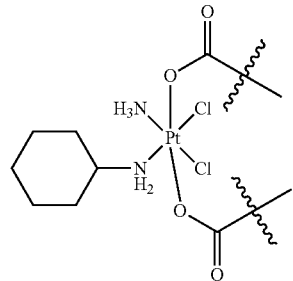
278
-continued
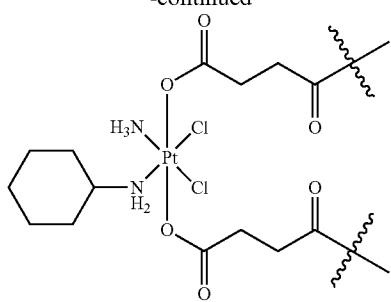
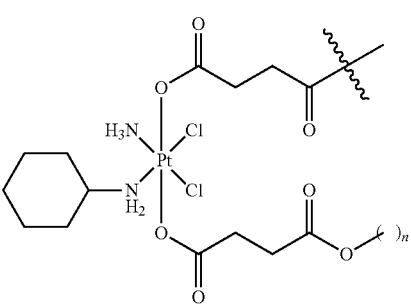
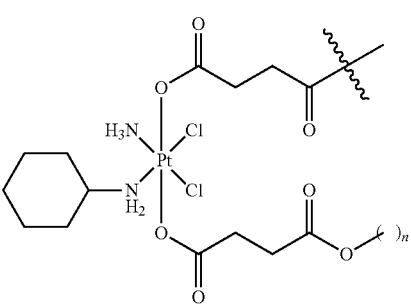
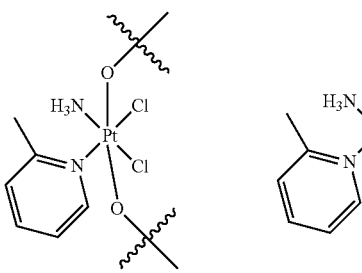
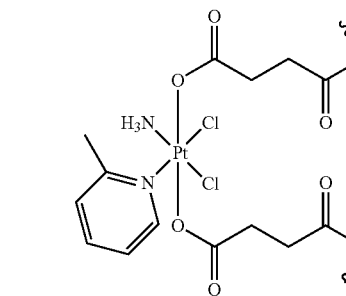

-continued
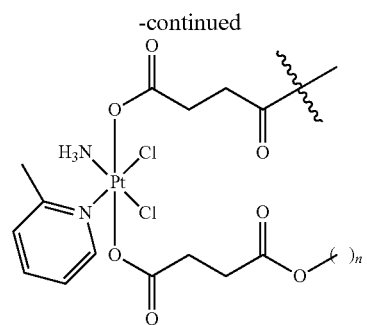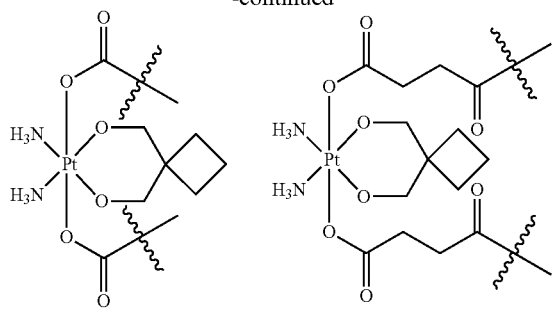
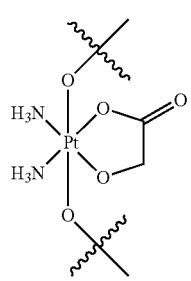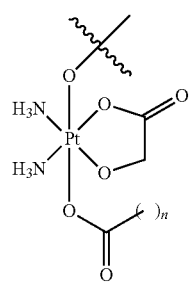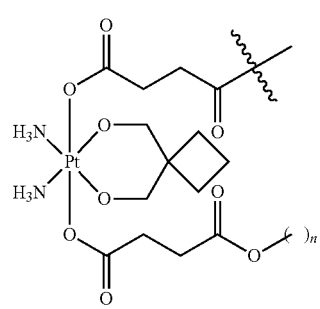
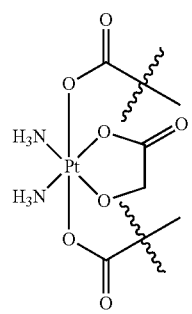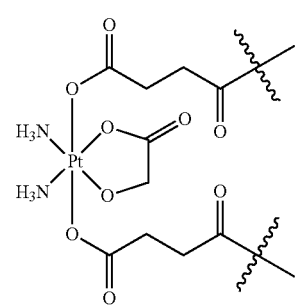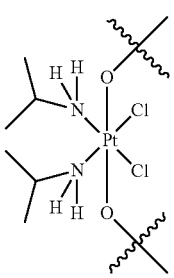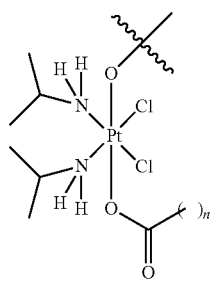
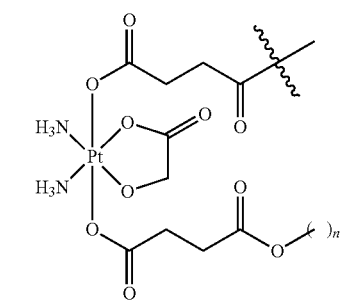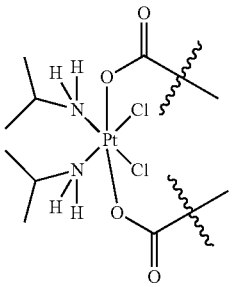
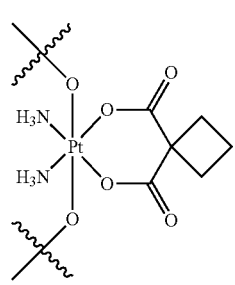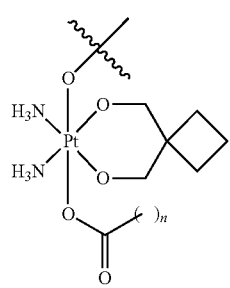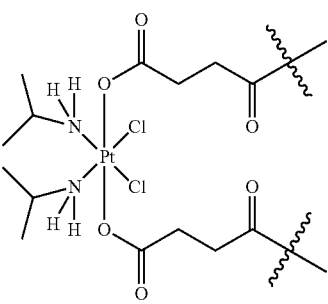

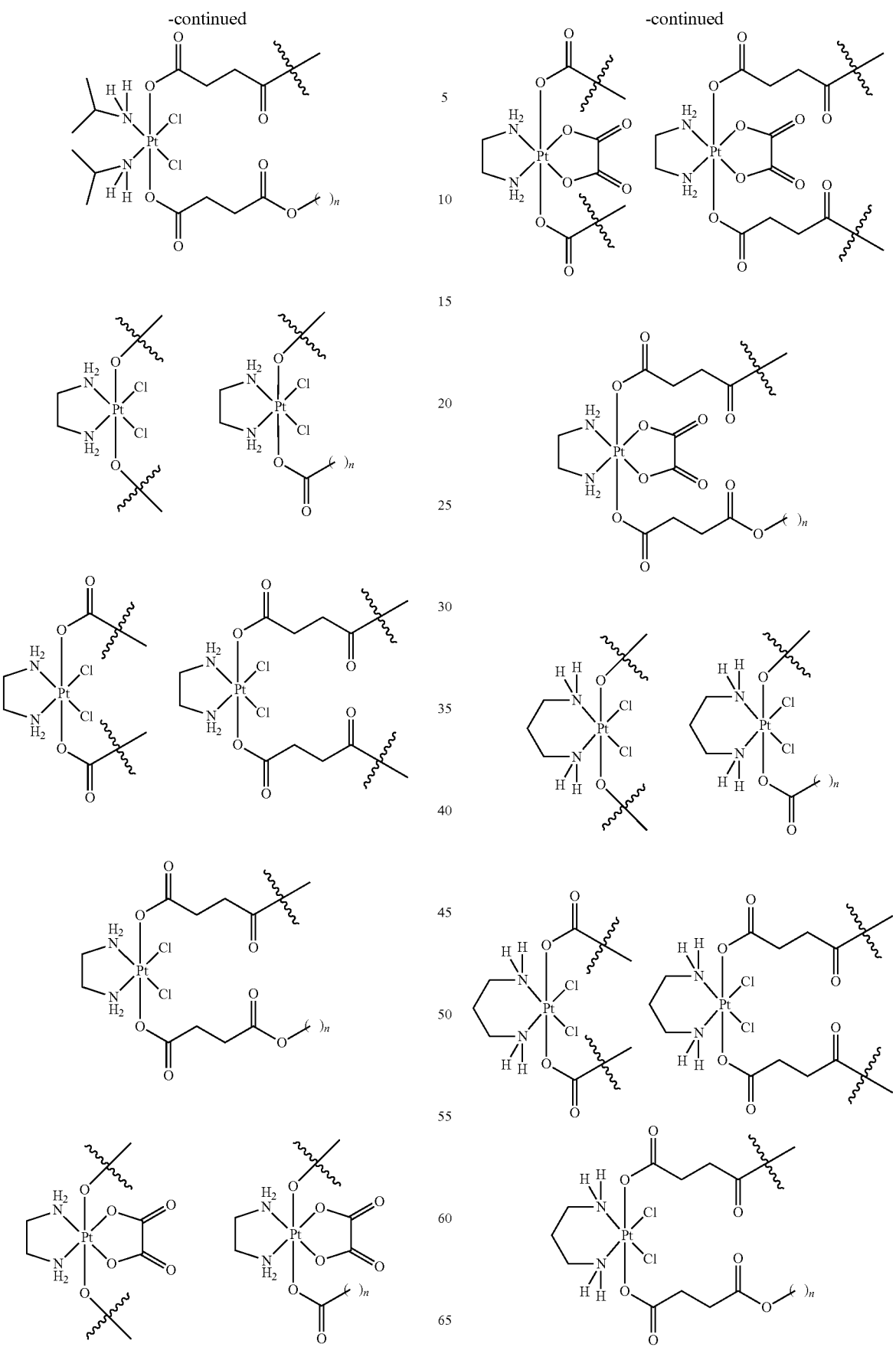

-continued
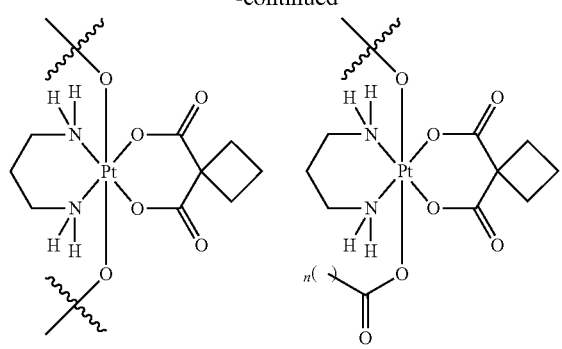
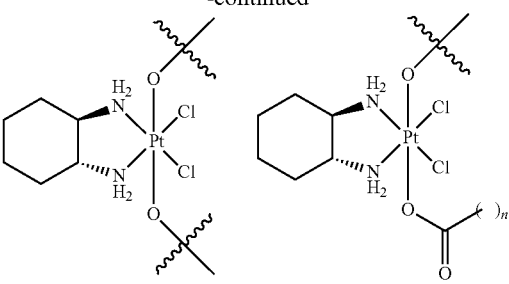
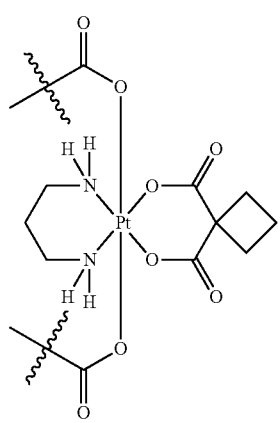
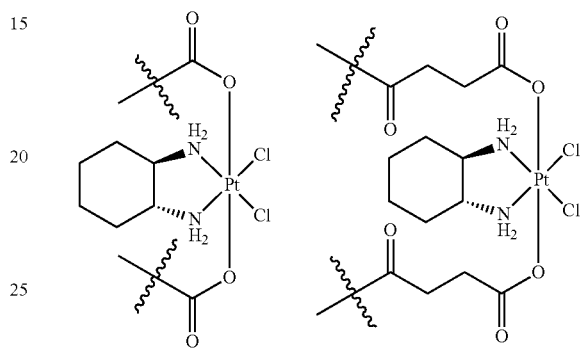
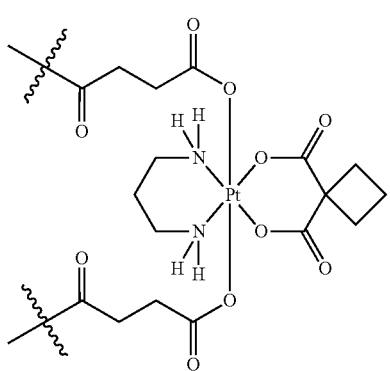
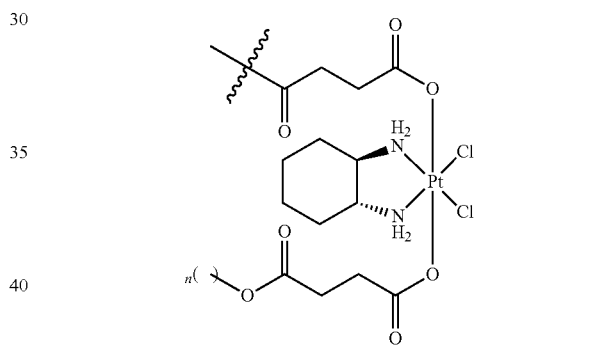
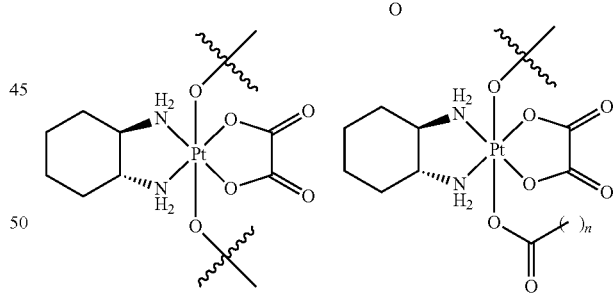
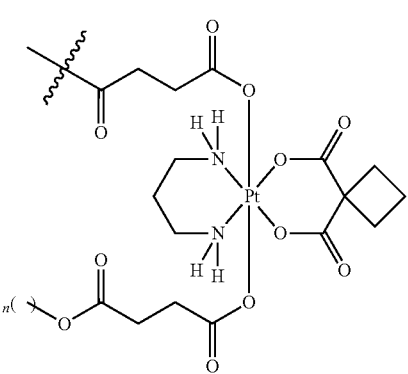
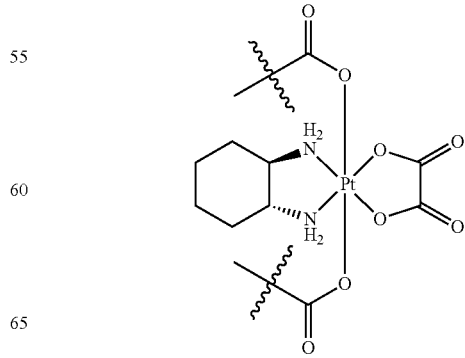

-continued

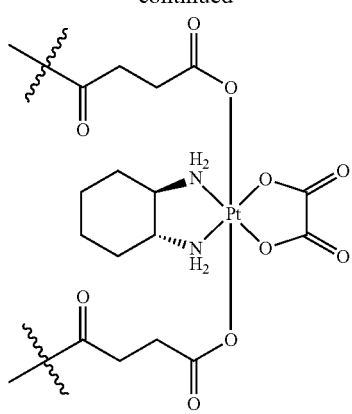

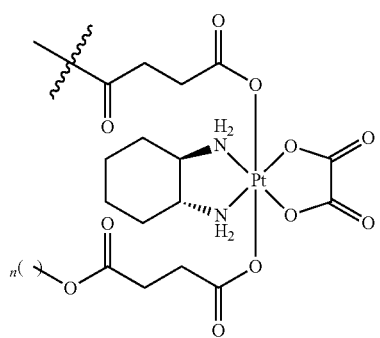

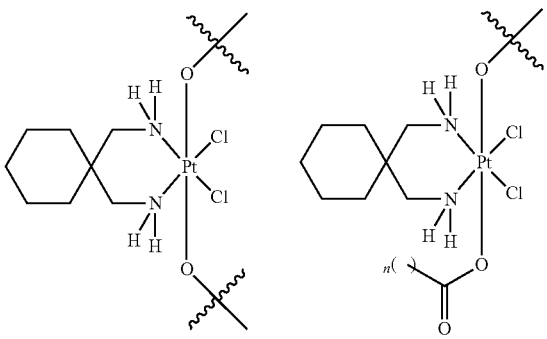

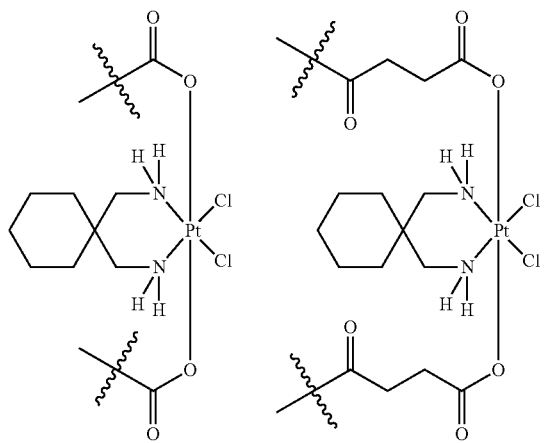

-continued

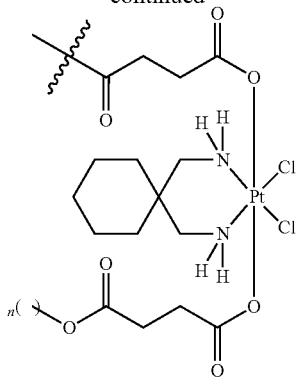

and corresponding platinum complexes that can be connected to a COX-2-targeting moiety at one axial position and have a —OC(=O)-(4-phenyl-R) ligand at the other axial position, and pharmaceutically acceptable salts thereof, wherein:
R is —H or $C_1$-$C_6$ alkyl;
n is an integer from 1 to 15; and
an atom adjacent to a wavy line is a site where the platinum-containing antitumor agent is connected to the remainder of the conjugate.

2. A conjugate comprising a moiety that targets cyclooxygenase II (COX-2), a platinum-containing antitumor agent, and a linker connecting the COX-2-targeting moiety to the platinum-containing antitumor agent, wherein the linker is selected from the group consisting of:

1) —$(CH_2)_n$—, —$O(CH_2)_n$—, —$O(CH_2)_nO$—, —$N(R^1)(CH_2)_n$—, —$N(R^1)(CH_2)_nN(R^2)$—, and —$N(R^1)(CH_2)_nO$—, wherein $R^1$ and $R^2$ independently are —H or $C_1$-$C_6$ alkyl, and n is an integer from 2 to 20;

2) —$(CX^1X^2)_m(CH_2)_n$—, wherein each occurrence of $X^1$ and $X^2$ independently is —H or —F, m is an integer from 1 to 6, and n is an integer from 0 to 20;

3) (—$CH_2CH_2O$—)$_n$ and (—$CH_2CH(CH_3)O$—)$_n$, wherein n is an integer from 1 to 12;

4) —$X^1CH_2CH_2OCH_2CH_2X^2$— and —$X^1CH_2CH_2O(-CH_2CH_2O-)_nCH_2CH_2X^2$—, wherein $X^1$ and $X^2$ independently are absent or are —O— or —N(R)—, each occurrence of R independently is —H or $C_1$-$C_6$ alkyl, and n is an integer from 1 to 12;

5) —$X^1CH_2(-CH_2CH_2O-)_n(CH_2)_3X^2$—, wherein $X^1$ and $X^2$ independently are absent or are —O— or —N(R)—, each occurrence of R independently is —H or $C_1$-$C_6$ alkyl, and n is an integer from 1 to 12;

6) —$C(=O)(CH_2)_nX$—, wherein X is absent or is —O— or —N(R)—, R is —H or $C_1$-$C_6$ alkyl, and n is an integer from 1 to 20;

7) —$C(=O)(CH_2)_nC(=O)$—, wherein n is an integer from 2 to 20;

8) —$C(=O)CH_2CH_2C(=O)N(R)(CH_2)_nC(=O)$—, wherein R is —H or $C_1$-$C_6$ alkyl, and n is an integer from 1 to 20;

9) —$C(=O)CH_2CH_2C(=O)N(R^1)CH_2(-CH_2CH_2O-)_n(CH_2)_3X$—, wherein X is —O—, —$N(R^2)$— or —$C(=O)$—, $R^1$ and $R^2$ independently are —H or $C_1$-$C_6$ alkyl, and n is an integer from 1 to 12;

10) —$C(=O)CH_2(-OCH_2CH_2-)_nO$— and —$C(=O)CH_2(-OCH_2CH_2-)_nOCH_2C(=O)$—, wherein n is an integer from 1 to 12; and 11) —$X^1(CH_2)_m$-cyclyl-$(CH_2)_nX^2$—, wherein $X^1$ and $X^2$ independently are absent or are —O— or —N(R)—, each occurrence of R independently is —H or $C_1$-$C_6$ alkyl, cyclyl is cycloalkyl, aryl, heterocyclyl or heteroaryl, and m and n independently are integers from 0 to 6.

3. A conjugate comprising a moiety that targets cyclooxygenase II (COX-2), a platinum-containing antitumor agent, and a linker connecting the COX-2-targeting moiety to the platinum-containing antitumor agent, wherein the linker is selected from the group consisting of:
1) —$(CH_2)_n$—, —$(CH_2)_nO$— and —$(CH_2)_nN(R)$—, wherein R is —H or $C_1$-$C_6$ alkyl and n is an integer from 4 to 10;
2) —$(CF_2)_m(CH_2)_n$—, wherein m is an integer from 1 to 4, and n is an integer from 1 to 15;
3) —$CH_2CH_2OCH_2CH_2$—, —$CH_2CH_2O$(—$CH_2CH_2O$—$)_n$, —$CH_2CH_2O$(—$CH_2CH_2O$—$)_nCH_2CH_2$—, and —NH(—$CH_2CH_2O$—$)_nX$, wherein X is absent or is —$CH_2$— or —$CH_2CH_2$—, and n is an integer from 1 to 4;
4) —$NHCH_2CH_2OCH_2CH_2NH$— and —$NHCH_2CH_2O$(—$CH_2CH_2O$—$)_nCH_2CH_2NH$—, wherein n is an integer from 1 to 4;
5) —$NH(CH_2)_nNH$—, —$NH(CH_2)_nNMe$—, and —$NMe(CH_2)_nNMe$—, wherein n is an integer from 2 or 4 to 10;
6) —$O(CH_2)_n$—, —$O(CH_2)_n$—, —$NHX(CH_2)_n$—, —$NHX(CH_2)_nNH$—, and —$NHX(CH_2)_nO$—, wherein X is absent or is —$S(=O)_2$—, and n is an integer from 4 to 10;
7) —$C(=O)(CH_2)_n$— and —$C(=O)(CH_2)_nX$—, wherein X is —O— or —N(R)—, R is —H or $C_1$-$C_6$ alkyl, and n is an integer from 4 to 10;
8) —$C(=O)(CH_2)_nC(=O)$—, wherein n is an integer from 2 or 4 to 10;
9) —$C\equiv N(CH_2)_mX$—, wherein X is absent or is —O— or —NH—, and m is an integer from 4 to 10;
10) 1,2-cyclopropyldimethylene, 1,2-cyclobutyldimethylene, 1,3-cyclobutyldimethylene, 1,2-cyclopentyldimethylene, 1,3-cyclopentyldimethylene, 1,2-cyclohexyldimethylene, 1,3-cyclohexyldimethylene, and 1,4-cyclohexyldimethylene; and
11)

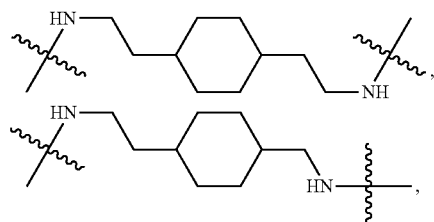

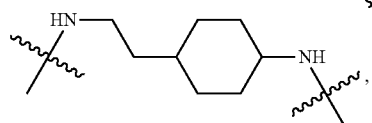

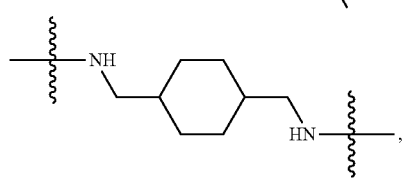

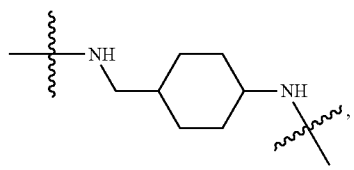

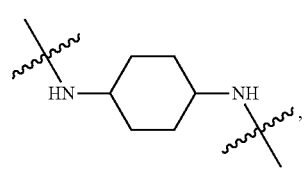

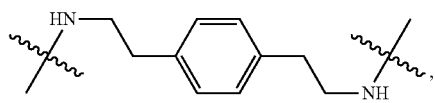

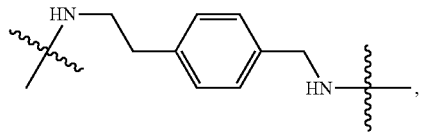

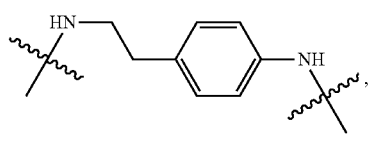

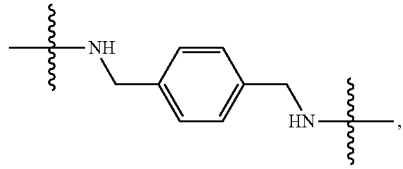

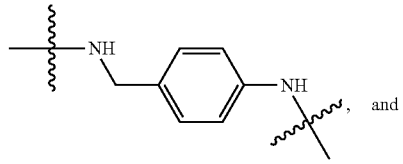

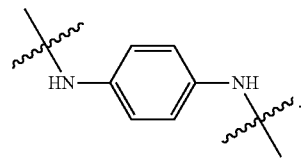

4. A conjugate comprising a moiety that targets cyclooxygenase II (COX-2), a platinum-containing antitumor agent, and a linker connecting the COX-2-targeting moiety to the platinum-containing antitumor agent, which is selected from the group consisting of:

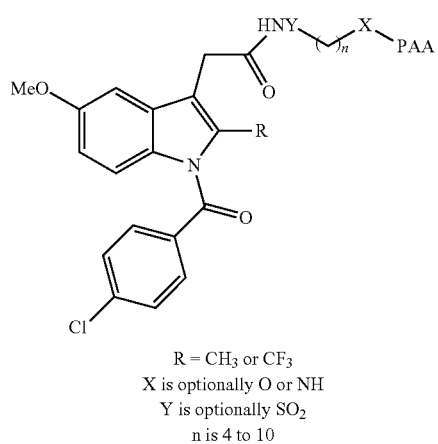

R = CH₃ or CF₃
X is optionally O or NH
Y is optionally SO₂
n is 4 to 10

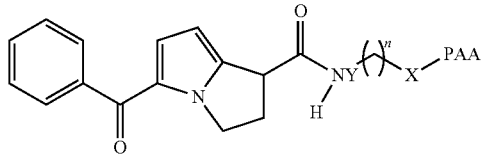

X is optionally O or NH
Y is optionally SO₂
n is 4 to 10

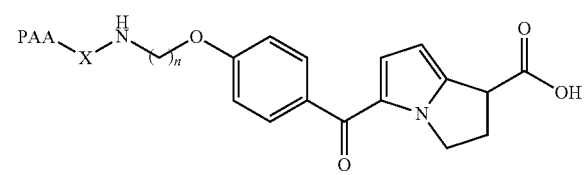

X is optionally C=O
n is 4 to 10

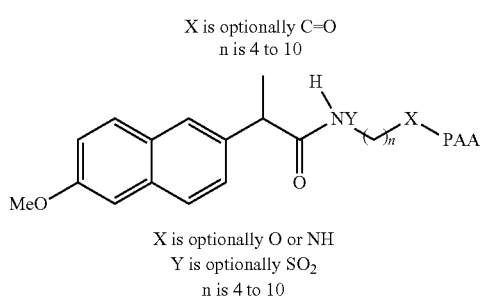

R = CH₃ or CF₃
X is absent or NH
n is 4 to 10

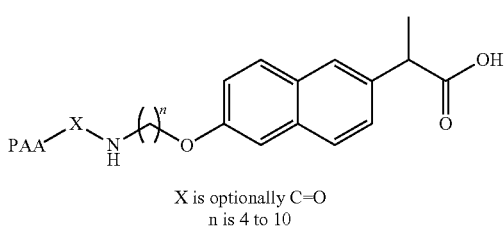

X is optionally O or NH
Y is optionally SO₂
n is 4 to 10

R = CH₃ or CF₃
X is optionally CH₂ or CH₂CH₂
n is 1 to 3

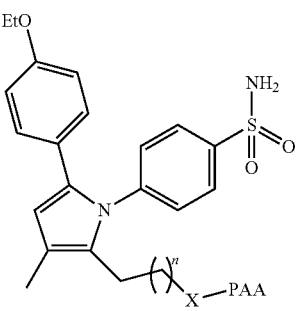

X is optionally C=O
n is 4 to 10

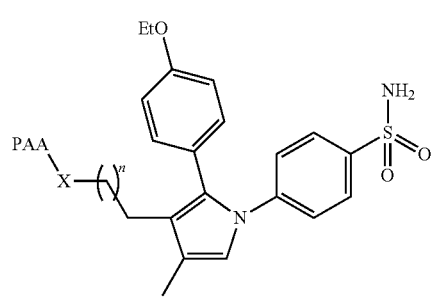

X is optionally O or NH
n is 3 to 10

R = CH₃ or CF₃
X is optionally C=O
n is 4 to 10

X is optionally O or NH
n is 3 to 10

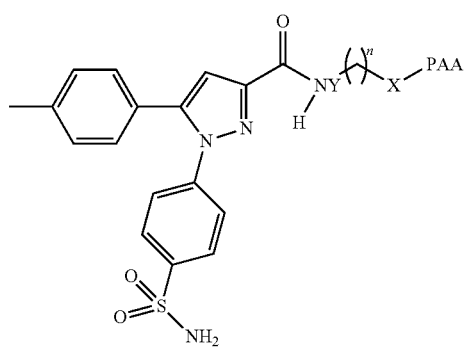
X is optionally O or NH
Y is optionally SO₂
n is 4 to 10
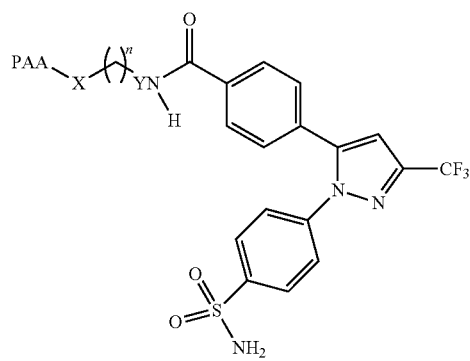
X is optionally O or NH
Y is optionally SO₂
n is 4 to 10
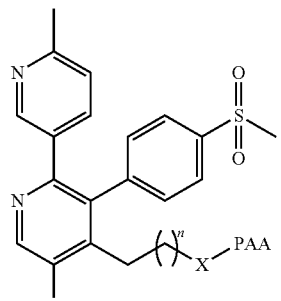
X is optionally O or NH
n is 3 to 10
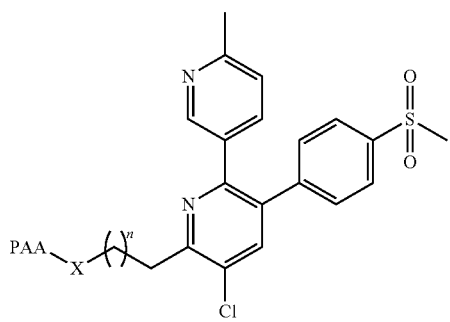
X is optionally O or NH
n is 3 to 10
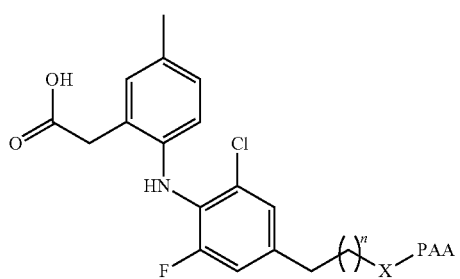
X is optionally O or NH
n is 3 to 10
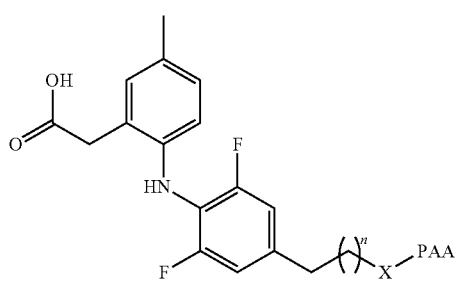
X is optionally O or NH
n is 3 to 10
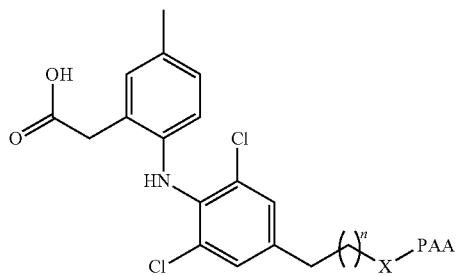
X is optionally O or NH
n is 3 to 10
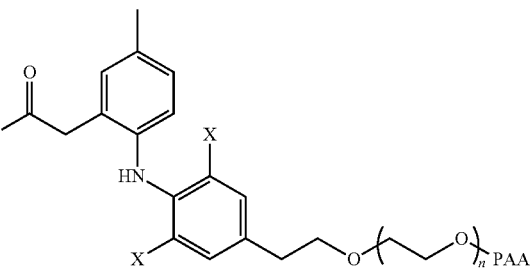
X is F or Cl
n is 1 to 3
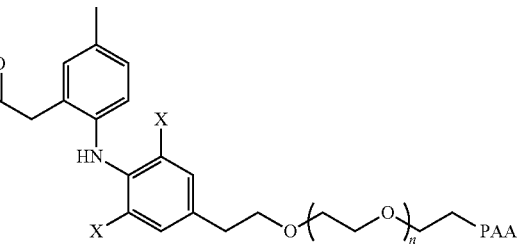
X is F or Cl
n is 1 or 2

-continued

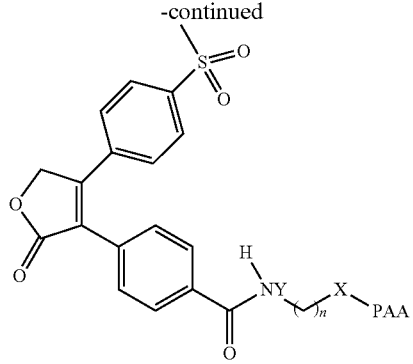

X is optionally O or NH
Y is optionally SO₂
n is 4 to 10

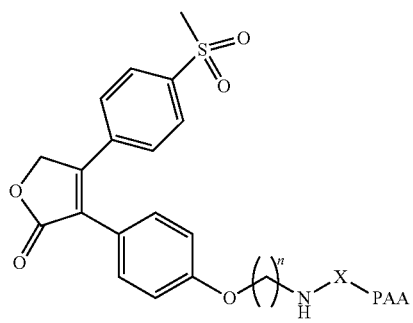

X is optionally C=O
n is 4 to 10

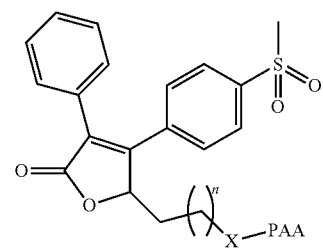

X is optionally O or NH
n is 3 to 10

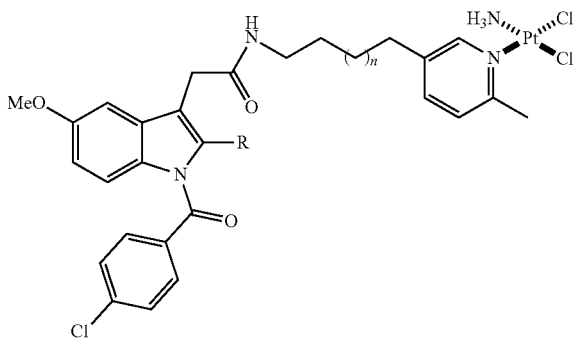

R = CH₃ or CF₃
n = 1 to 5 (e.g., 3)

-continued

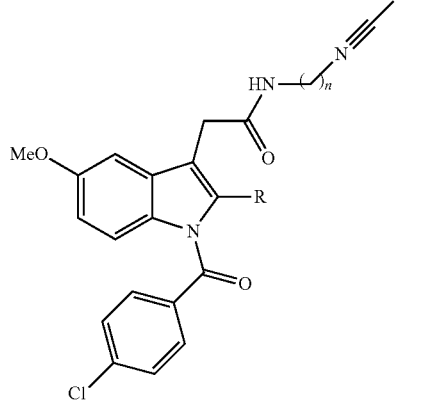

R = CH₃ or CF₃
n is 4 to 10 n is 4 to 10 and pharmaceutically acceptable salts thereof, wherein PAA denotes platinum-containing antitumor agent and the COX-2-targeting moiety can be part of an equatorial ligand or an axial ligand on the platinum metal.

5. A conjugate comprising a moiety that targets cyclooxygenase II (COX-2), a platinum-containing antitumor agent, and a linker connecting the COX-2-targeting moiety to the platinum-containing antitumor agent, which is selected from the group consisting of:

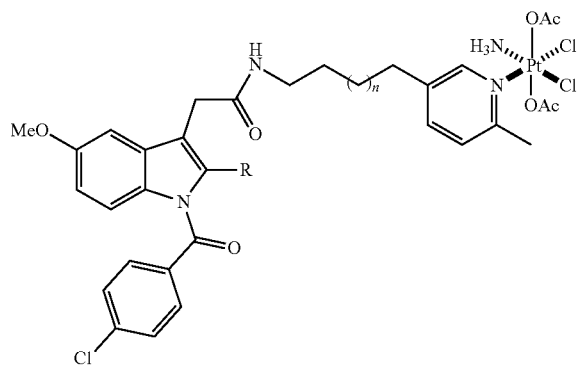

R = CH₃ or CF₃
n = 1 to 5 (e.g., 3)

295
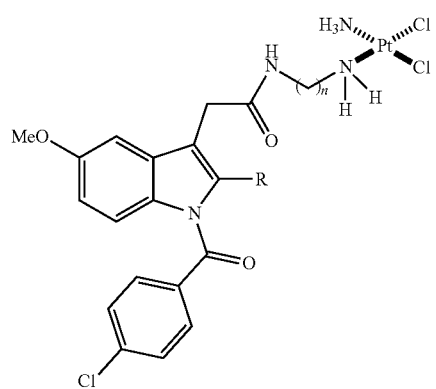
R = CH₃ or CF₃
n = 2 to 8 (e.g., 6)
296
-continued
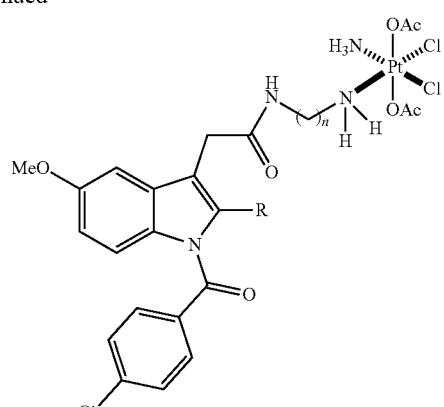
R = CH₃ or CF₃
n = 2 to 8 (e.g., 6)
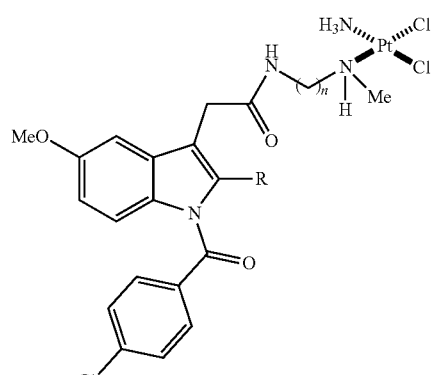
R = CH₃ or CF₃
n = 2 to 8 (e.g., 6)
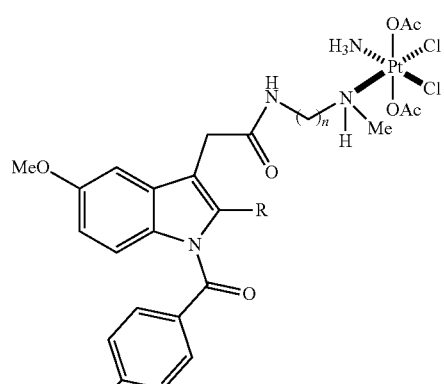
R = CH₃ or CF₃
n = 2 to 8 (e.g., 6)
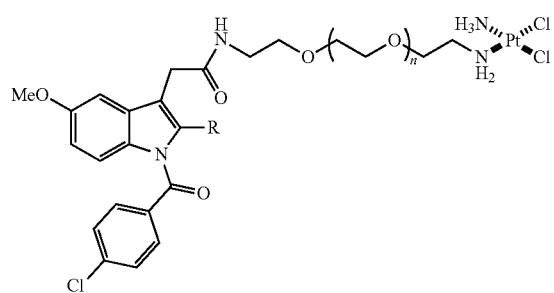
R = CH₃ or CF₃
n = 0.1 or 2
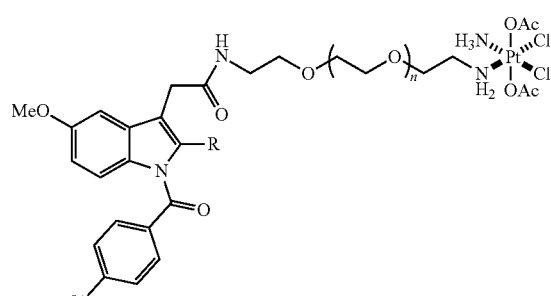
R = CH₃ or CF₃
n = 0.1 or 2

297
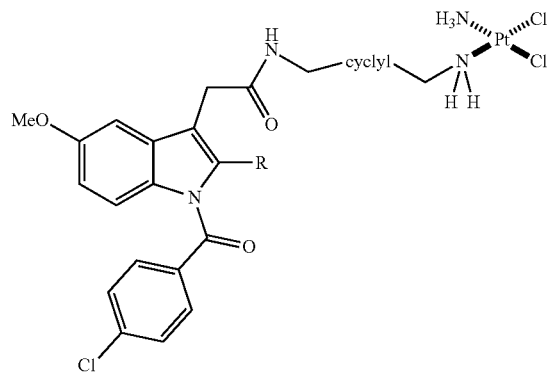
R = CH₃ or CF₃
cyclyl = 1,4-cyclohexyl or 1,4-phenyl
298
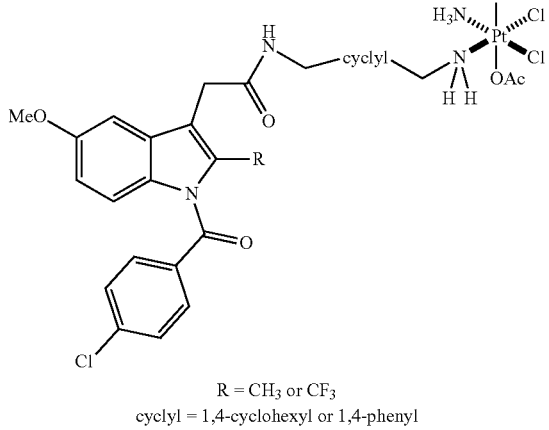
R = CH₃ or CF₃
cyclyl = 1,4-cyclohexyl or 1,4-phenyl
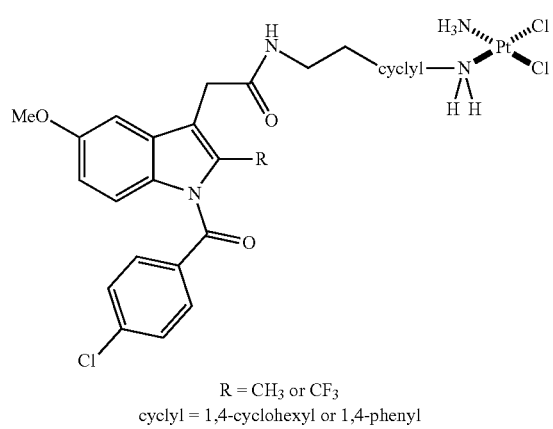
R = CH₃ or CF₃
cyclyl = 1,4-cyclohexyl or 1,4-phenyl
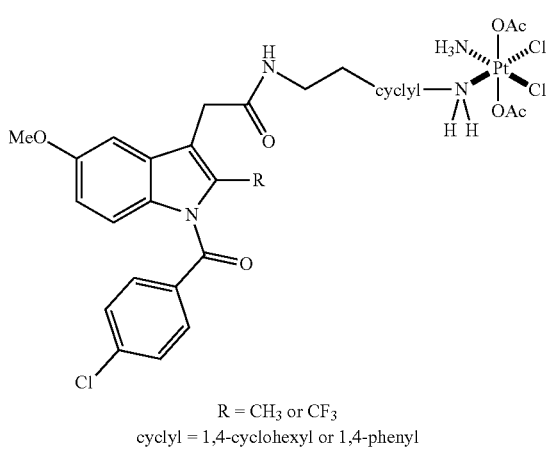
R = CH₃ or CF₃
cyclyl = 1,4-cyclohexyl or 1,4-phenyl
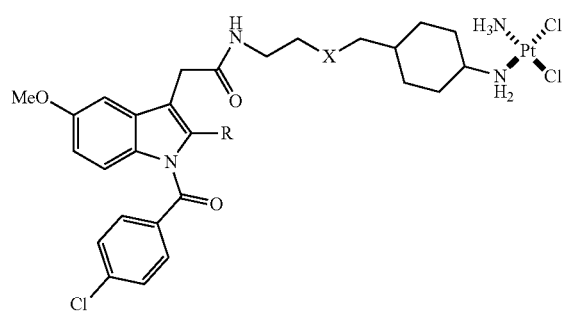
1) R = Me & X = CH₂; or
2) R = Me & X = O; or
3) R = CF₃ & X = CH₂; or
4) R = CF₃ & X = O
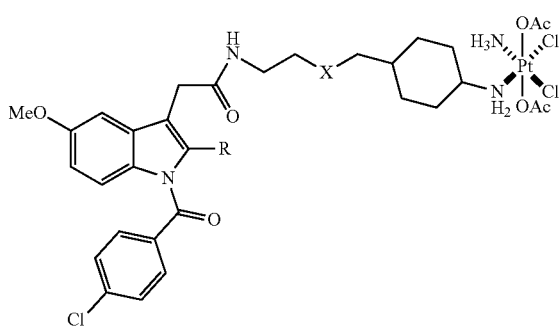
1) R = Me & X = CH₂; or
2) R = Me & X = O; or
3) R = CF₃ & X = CH₂; or
4) R = CF₃ & X = O

299
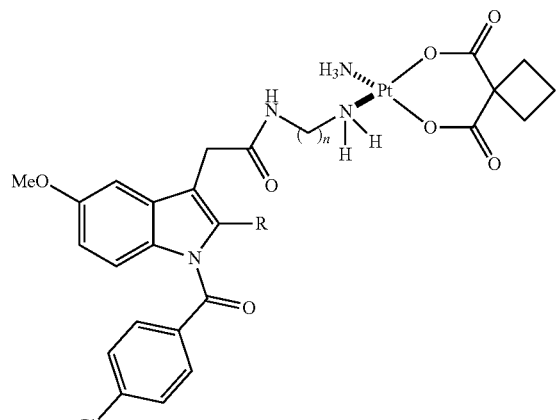
R = CH₃ or CF₃
n = 2 to 8 (e.g., 6)
300
-continued
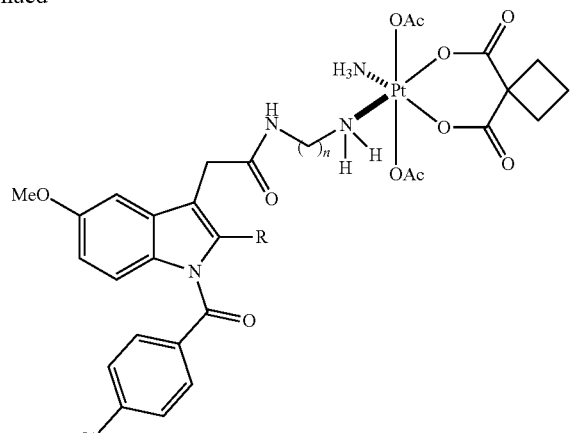
R = CH₃ or CF₃
n = 2 to 8 (e.g., 6)
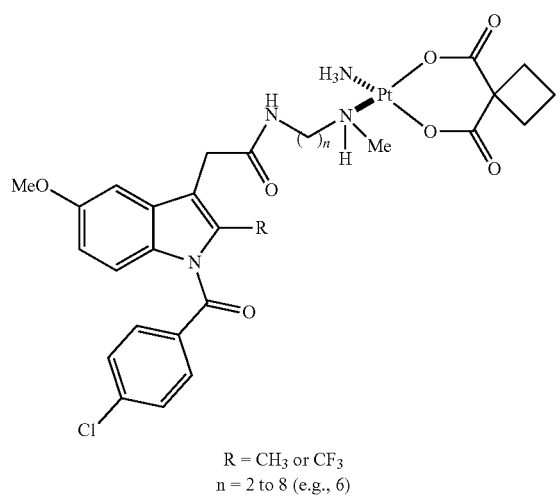
R = CH₃ or CF₃
n = 2 to 8 (e.g., 6)
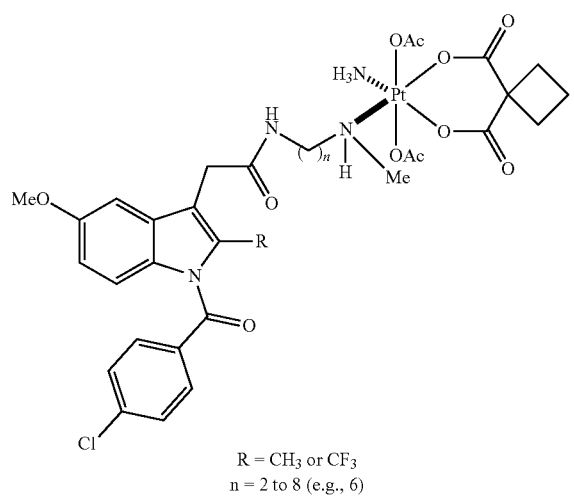
R = CH₃ or CF₃
n = 2 to 8 (e.g., 6)
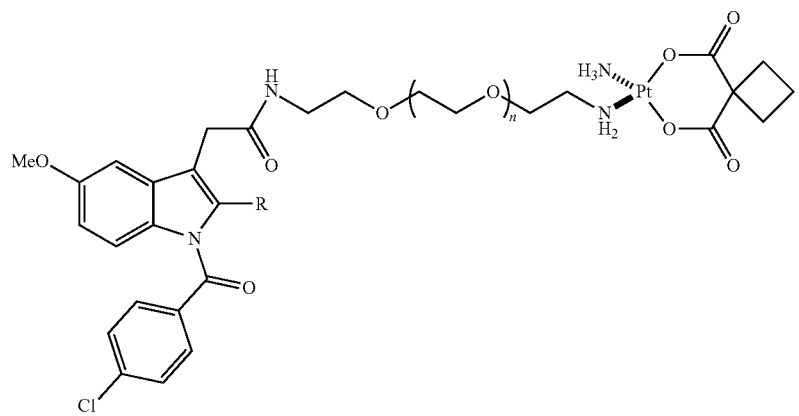
R = CH₃ or CF₃
n = 0, 1, or 2

301
302
-continued
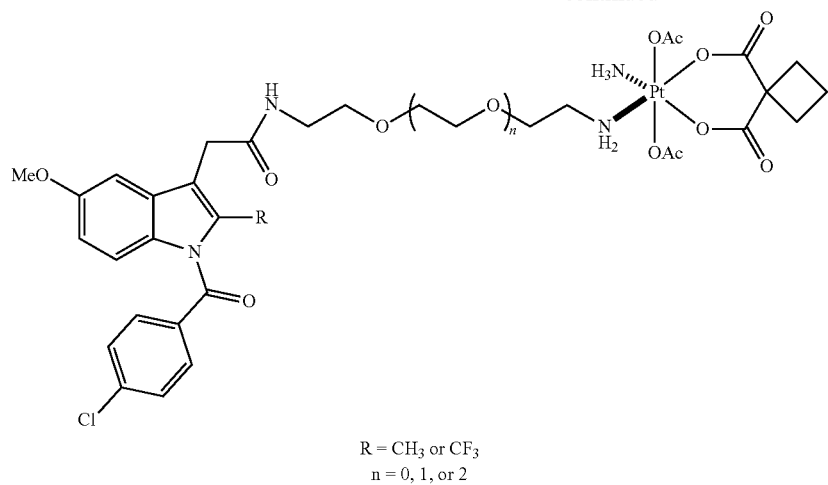
R = CH₃ or CF₃
n = 0, 1, or 2
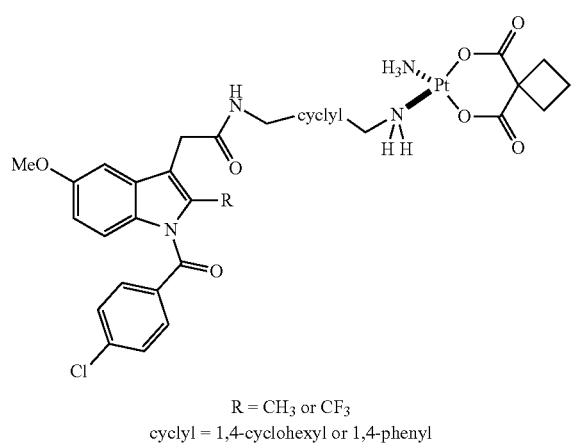
R = CH₃ or CF₃
cyclyl = 1,4-cyclohexyl or 1,4-phenyl
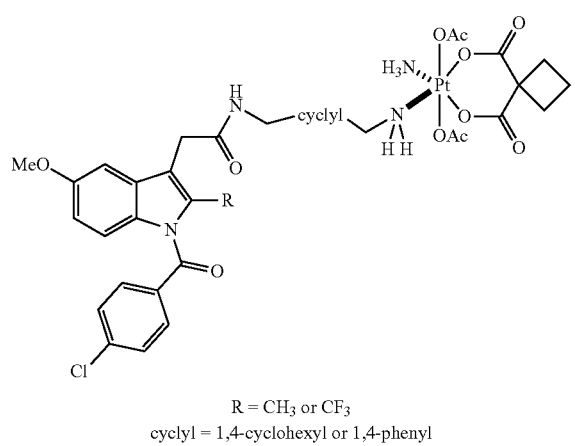
R = CH₃ or CF₃
cyclyl = 1,4-cyclohexyl or 1,4-phenyl
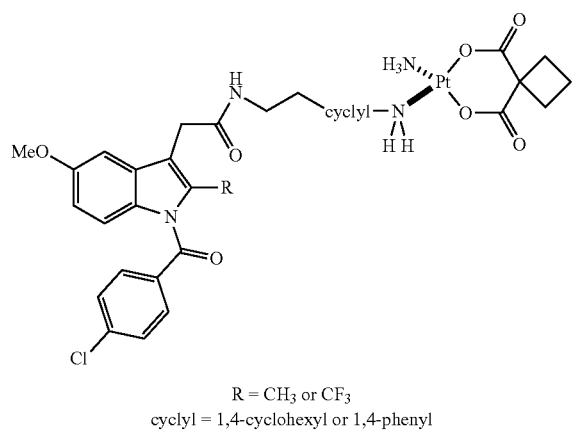
R = CH₃ or CF₃
cyclyl = 1,4-cyclohexyl or 1,4-phenyl
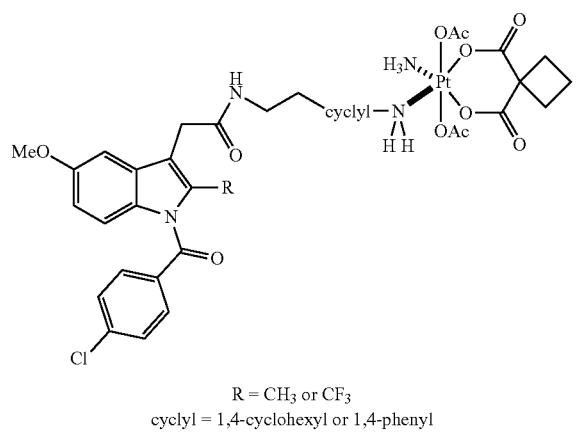
R = CH₃ or CF₃
cyclyl = 1,4-cyclohexyl or 1,4-phenyl

303
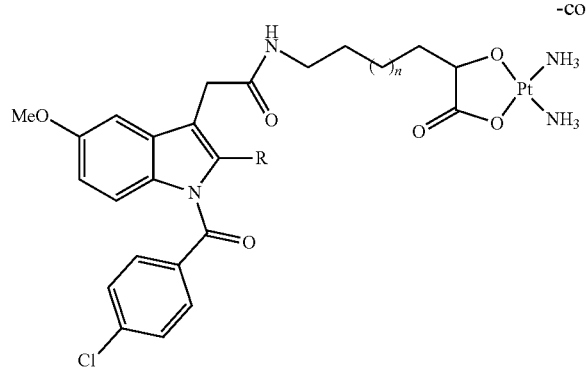
R = CH₃ or CF₃
n = 1 to 5 (e.g., 3)
304
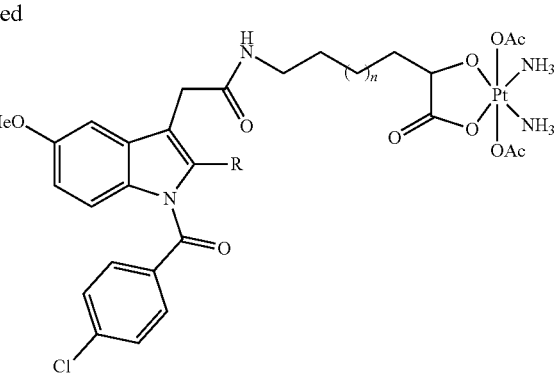
R = CH₃ or CF₃
n = 1 to 5 (e.g., 3)
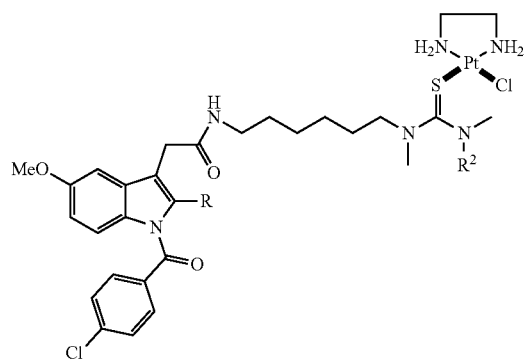
1) R¹ = Me & R₂ = H; or
2) R¹ = Me & R₂ = Me; or
3) R¹ = CF₃ & R₂ = H; or
4) R¹ = CF₃ & R₂ = Me
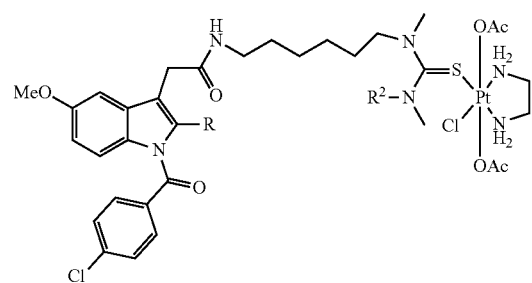
1) R¹ = Me & R₂ = H; or
2) R¹ = Me & R₂ = Me; or
3) R¹ = CF₃ & R₂ = H; or
4) R¹ = CF₃ & R₂ = Me
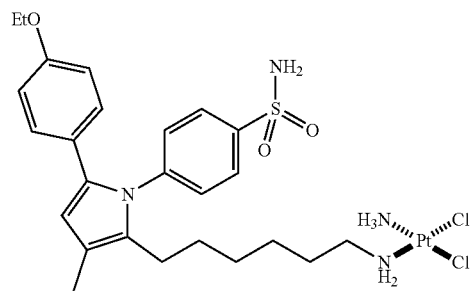
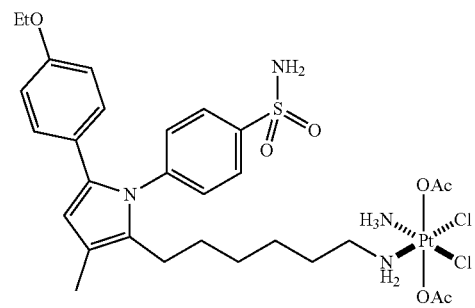
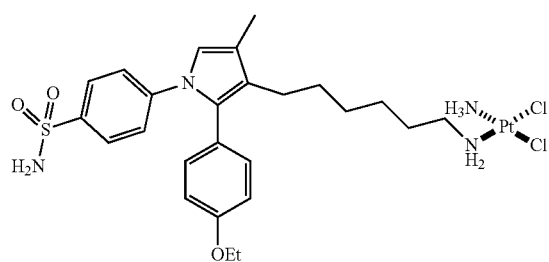
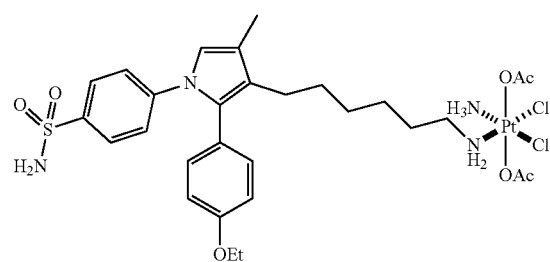

-continued
305
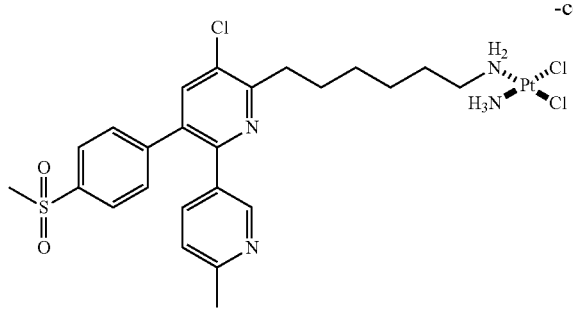
306
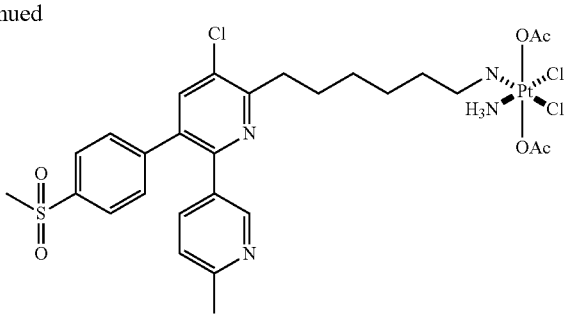
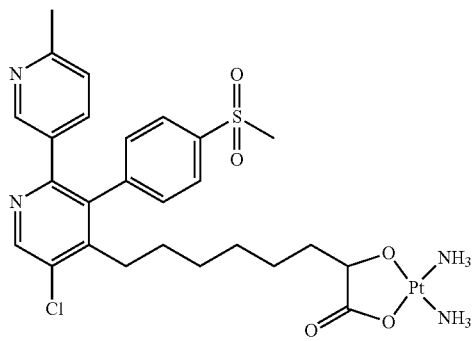
1) $X^1 = F$ & $X^2 = Cl$; or
2) $X^1 = X^2 = F$; or
3) $X^1 = X^2 = Cl$
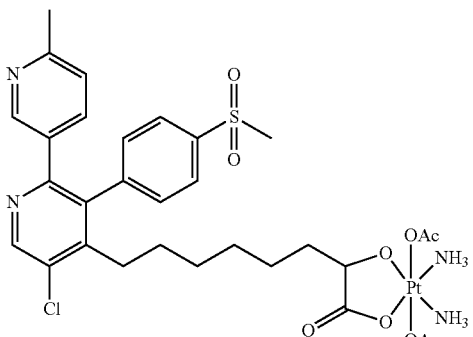
1) $X^1 = F$ & $X^2 = Cl$; or
2) $X^1 = X^2 = F$; or
3) $X^1 = X^2 = Cl$
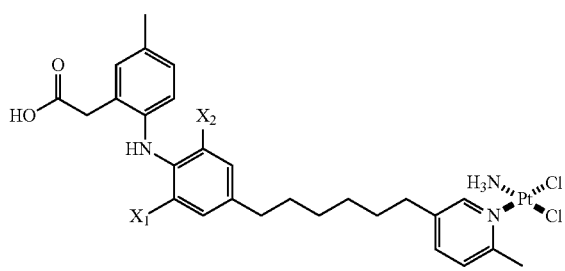
1) $X^1 = F$ & $X^2 = Cl$; or
2) $X^1 = X^2 = F$; or
3) $X^1 = X^2 = Cl$
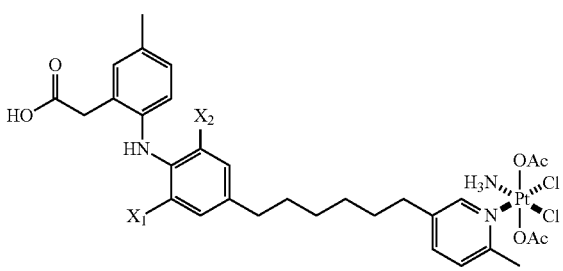
1) $X^1 = F$ & $X^2 = Cl$; or
2) $X^1 = X^2 = F$; or
3) $X^1 = X^2 = Cl$
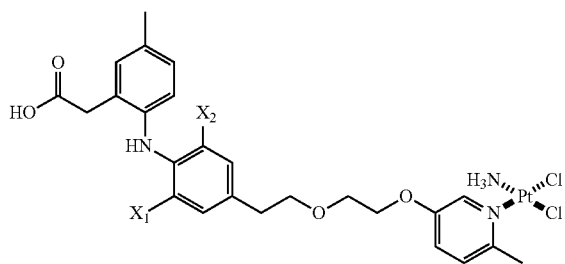
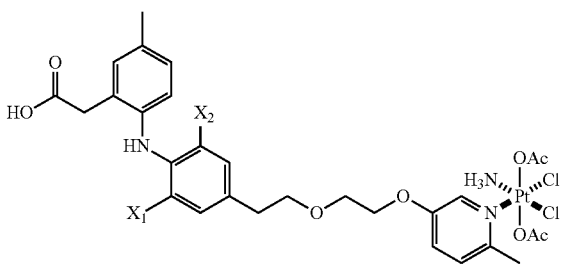

307

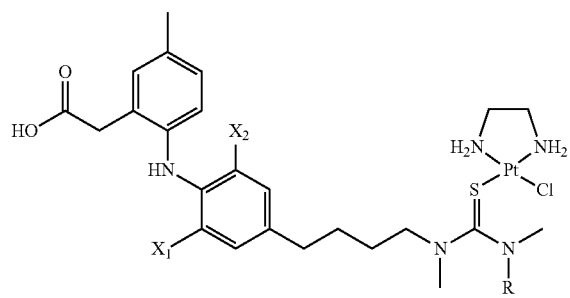

1) $X^1$ = F, $X^2$ = Cl, & R = H; or
1) $X^1$ = F, $X^2$ = Cl, & R = Me; or
1) $X^1$ = $X^2$ = F & R = H; or
1) $X^1$ = $X^2$ = F & R = H; or
1) $X^1$ = $X^2$ = Cl & R = H; or
1) $X^1$ = $X^2$ = Cl & R = Me

308

-continued

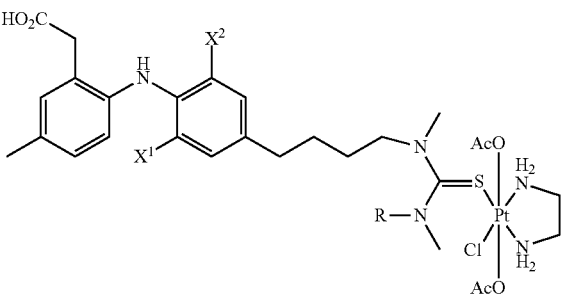

1) $X^1$ = F, $X^2$ = Cl, & R = H; or
1) $X^1$ = F, $X^2$ = Cl, & R = Me; or
1) $X^1$ = $X^2$ = F & R = H; or
1) $X^1$ = $X^2$ = F & R = H; or
1) $X^1$ = $X^2$ = Cl & R = H; or
1) $X^1$ = $X^2$ = Cl & R = Me

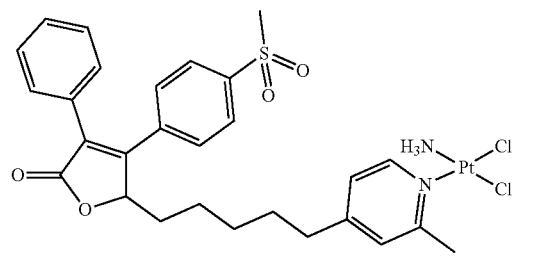

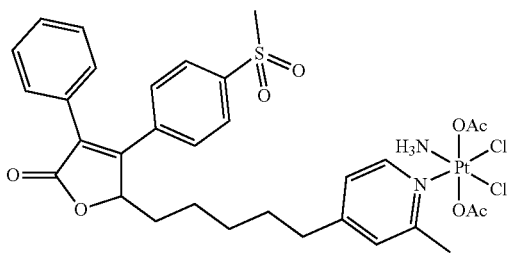

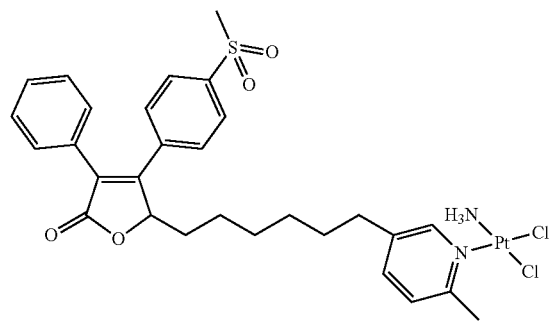

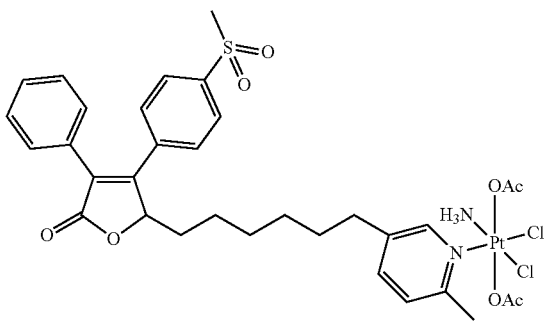

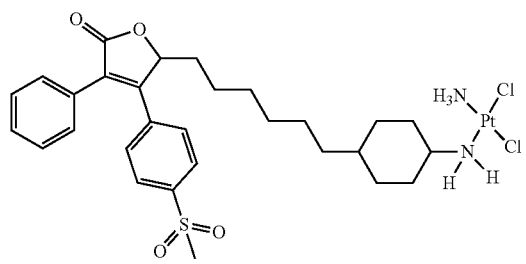

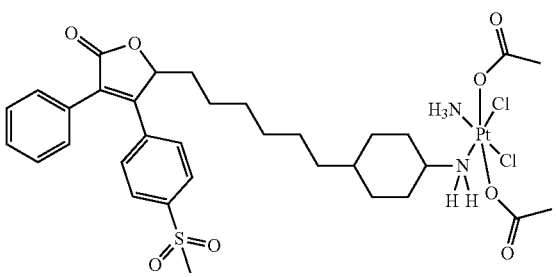

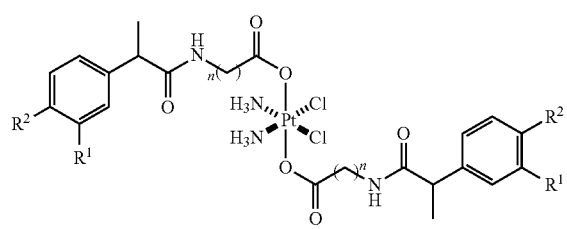

1) $R^1$ = H & $R^2$ = —$CH_2CHMe_2$
2) $R^1$ = H & $R^2$ = —$CH_2$—(2-cyclopentanone)
3) $R^1$ = F & $R^2$ = phenyl n = 4 or 8

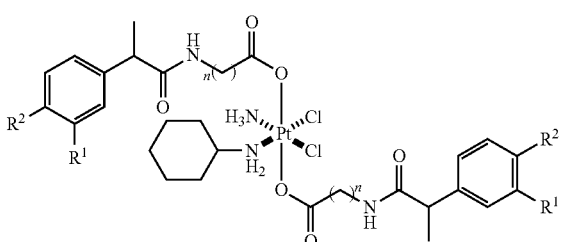

1) $R^1$ = H & $R^2$ = —$CH_2CHMe_2$
2) $R^1$ = H & $R^2$ = —$CH_2$—(2-cyclopentanone)
3) $R^1$ = F & $R^2$ = phenyl n = 4 or 8

-continued

309

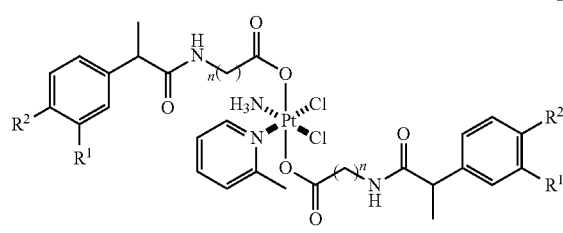

1) R¹ = H & R² = —CH₂CHMe₂
2) R¹ = H & R² = —CH₂—(2-cyclopentanone)
3) R¹ = F & R² = phenyl
n = 4 or 8

310

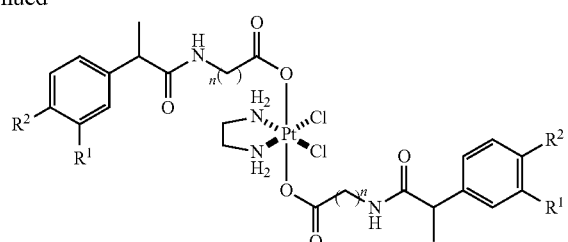

1) R¹ = H & R² = —CH₂CHMe₂
2) R¹ = H & R² = —CH₂—(2-cyclopentanone)
3) R¹ = F & R² = phenyl
n = 4 or 8

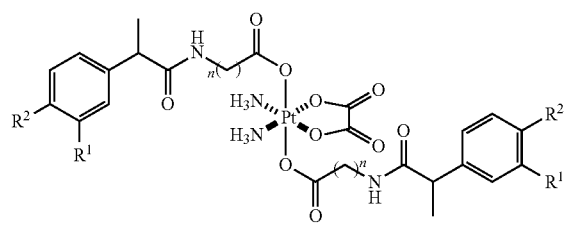

1) R¹ = H & R² = —CH₂CHMe₂
2) R¹ = H & R² = —CH₂—(2-cyclopentanone)
3) R¹ = F & R² = phenyl
n = 4 or 8

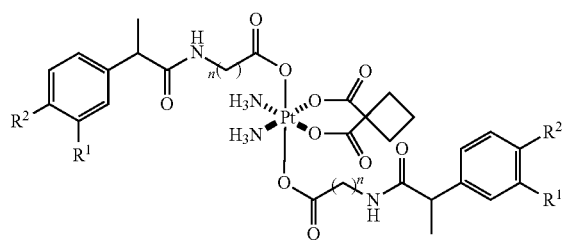

1) R¹ = H & R² = —CH₂CHMe₂
2) R¹ = H & R² = —CH₂—(2-cyclopentanone)
3) R¹ = F & R² = phenyl
n = 4 or 8

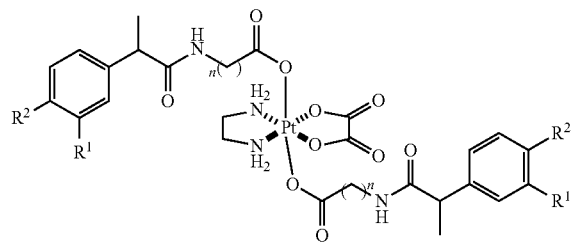

1) R¹ = H & R² = —CH₂CHMe₂
2) R¹ = H & R² = —CH₂—(2-cyclopentanone)
3) R¹ = F & R² = phenyl
n = 4 or 8

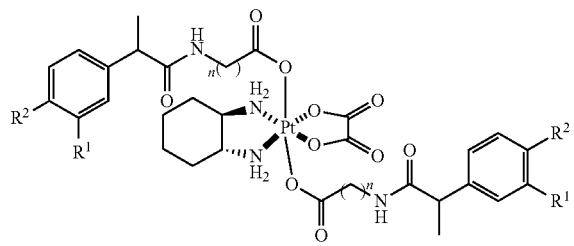

1) R¹ = H & R² = —CH₂CHMe₂
2) R¹ = H & R² = —CH₂—(2-cyclopentanone)
3) R¹ = F & R² = phenyl
n = 4 or 8

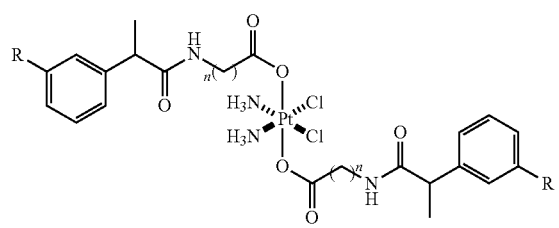

1) R = —O-phenyl
2) R = —C(=O)-phenyl
n = 4 or 8

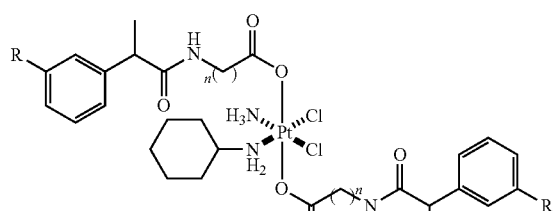

1) R = —O-phenyl
2) R = —C(=O)-phenyl
n = 4 or 8

311
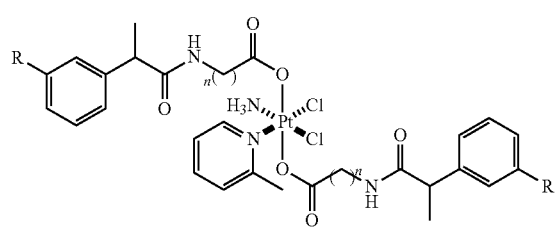
1) R = —O-phenyl
2) R = —C(=O)-phenyl
n = 4 or 8
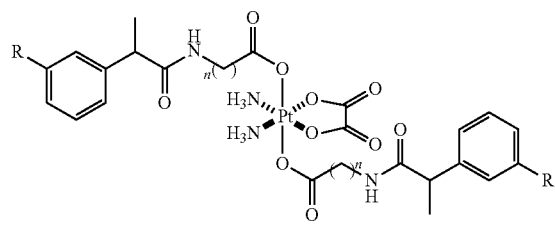
1) R = —O-phenyl
2) R = —C(=O)-phenyl
n = 4 or 8
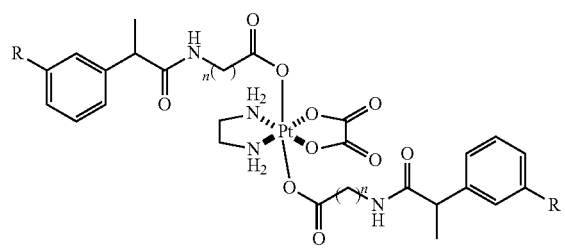
1) R = —O-phenyl
2) R = —C(=O)-phenyl
n = 4 or 8
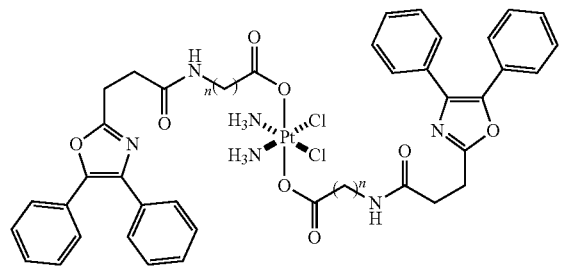
n = 4 or 8
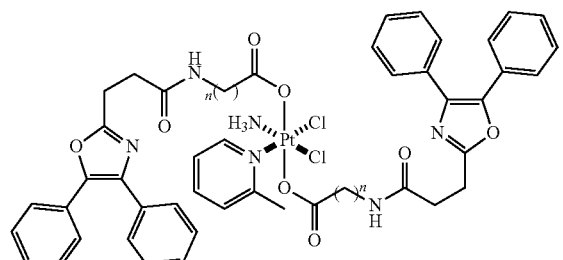
n = 4 or 8
312
-continued
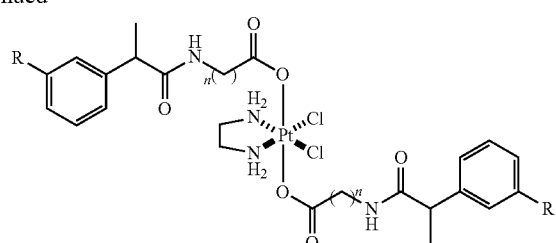
1) R = —O-phenyl
2) R = —C(=O)-phenyl
n = 4 or 8
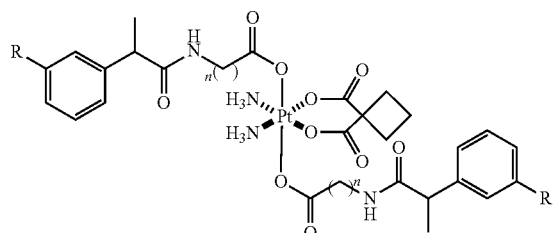
1) R = —O-phenyl
2) R = —C(=O)-phenyl
n = 4 or 8
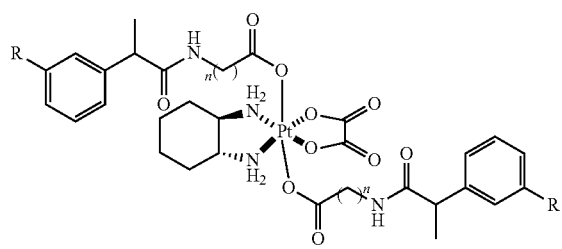
1) R = —O-phenyl
2) R = —C(=O)-phenyl
n = 4 or 8
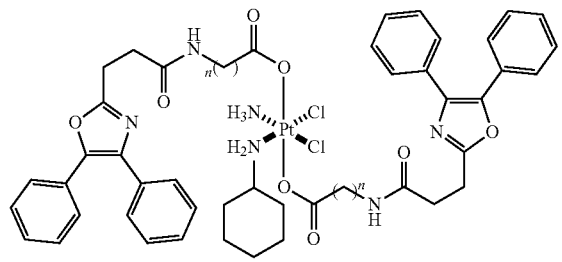
n = 4 or 8
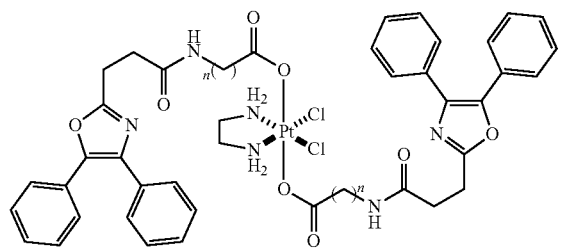
n = 4 or 8

-continued
313
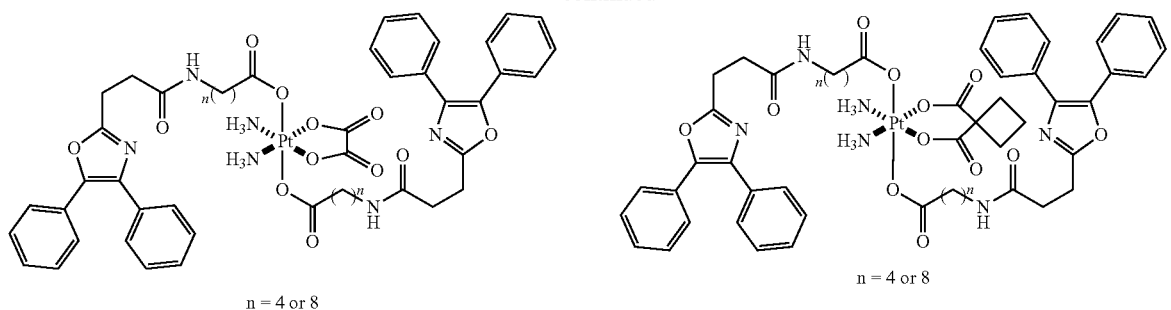
314
n = 4 or 8
n = 4 or 8
n = 4 or 8
n = 4 or 8
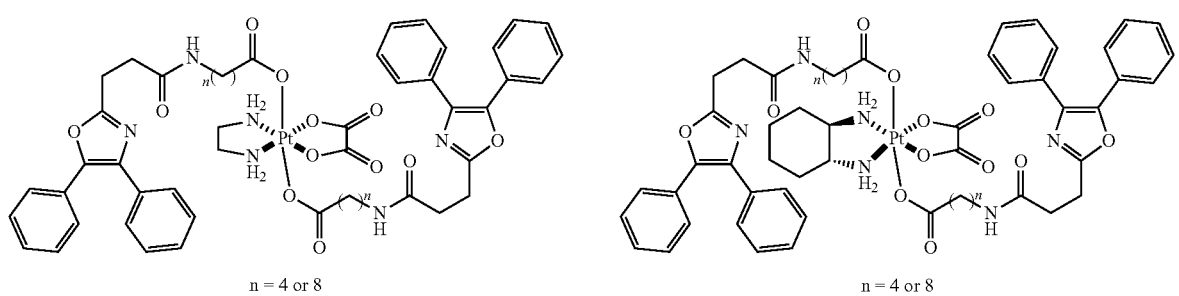
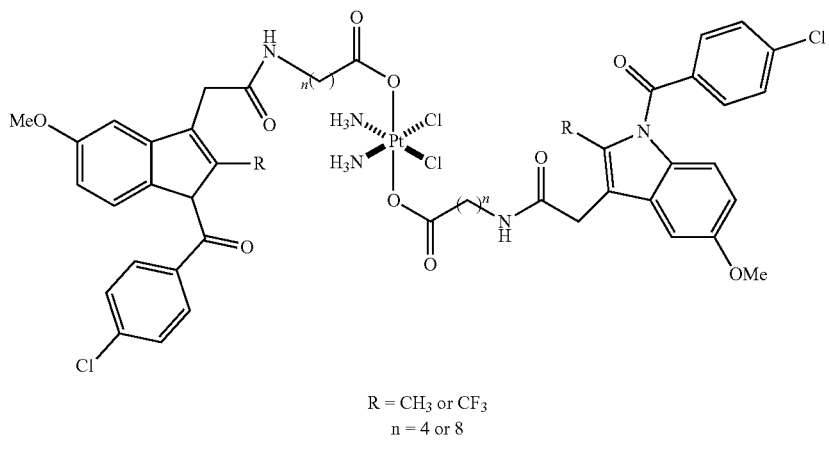
R = CH$_3$ or CF$_3$
n = 4 or 8
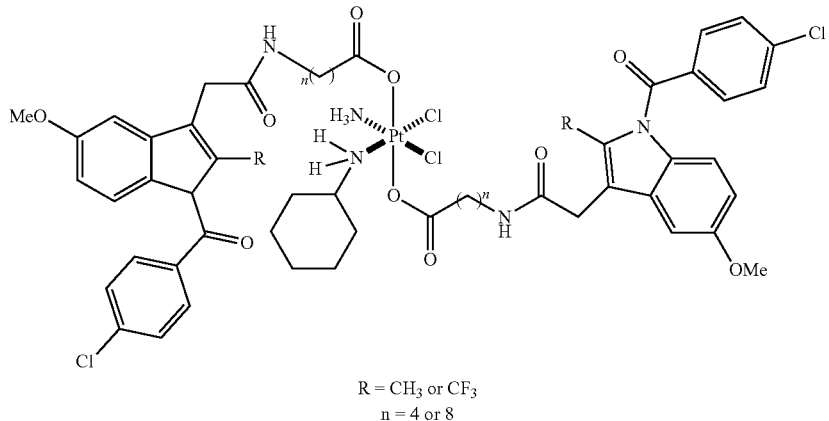
R = CH$_3$ or CF$_3$
n = 4 or 8

-continued
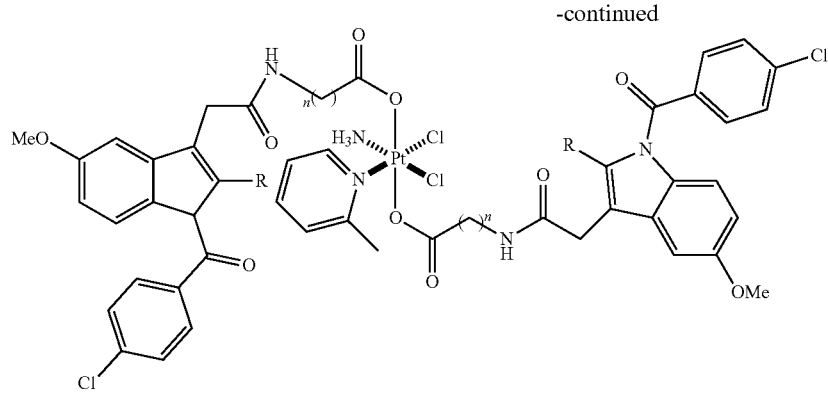
R = CH₃ or CF₃
n = 4 or 8
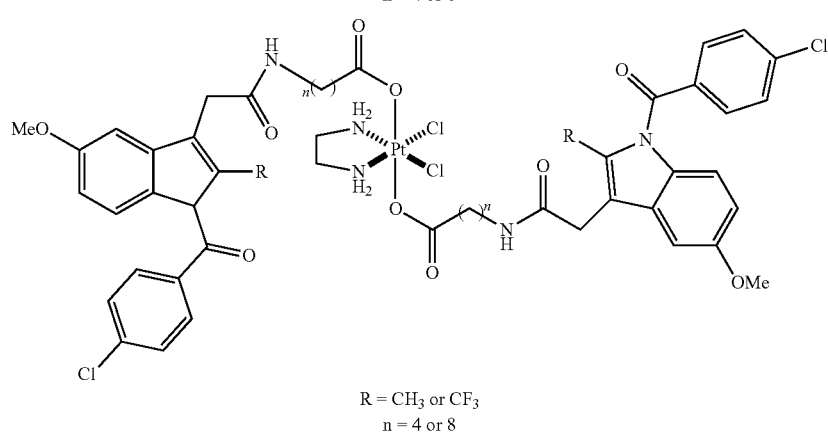
R = CH₃ or CF₃
n = 4 or 8
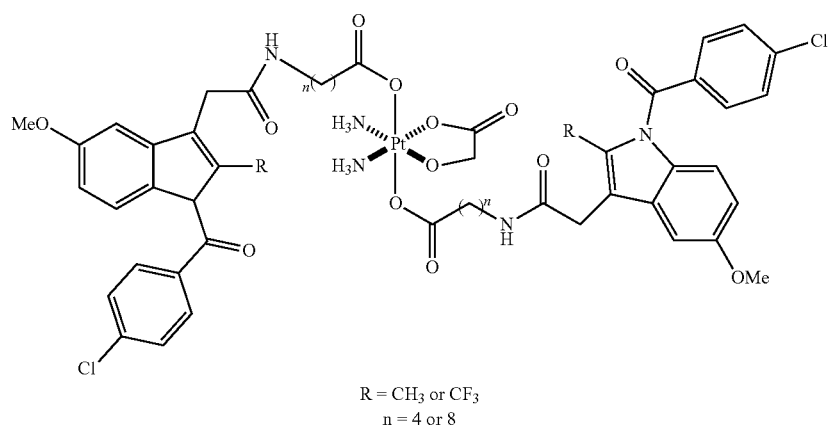
R = CH₃ or CF₃
n = 4 or 8
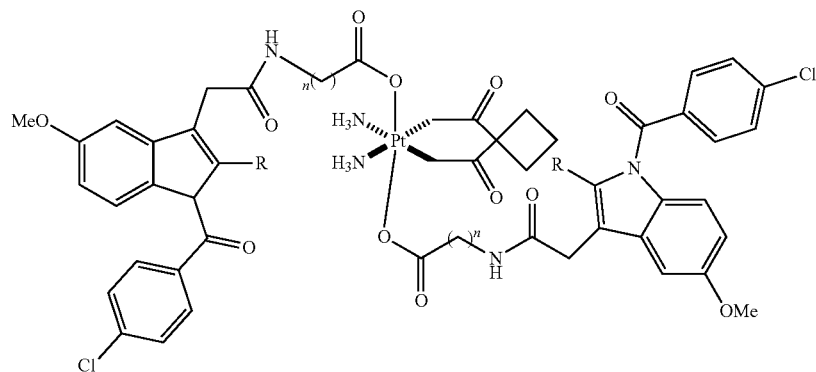
R = CH₃ or CF₃
n = 4 or 8

-continued
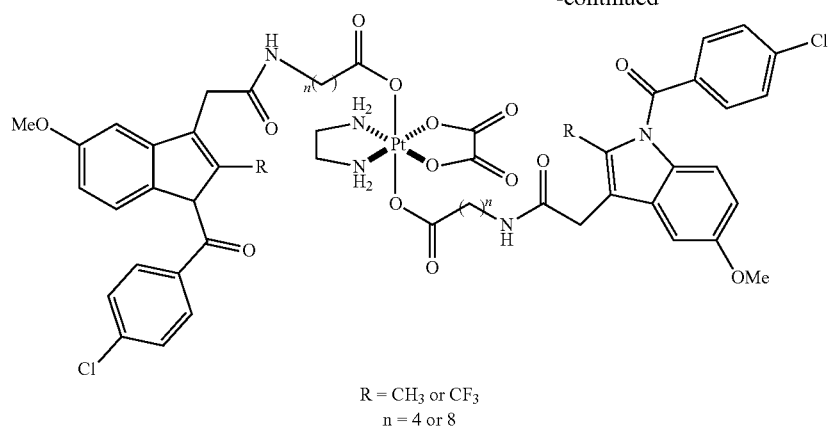
R = CH₃ or CF₃
n = 4 or 8
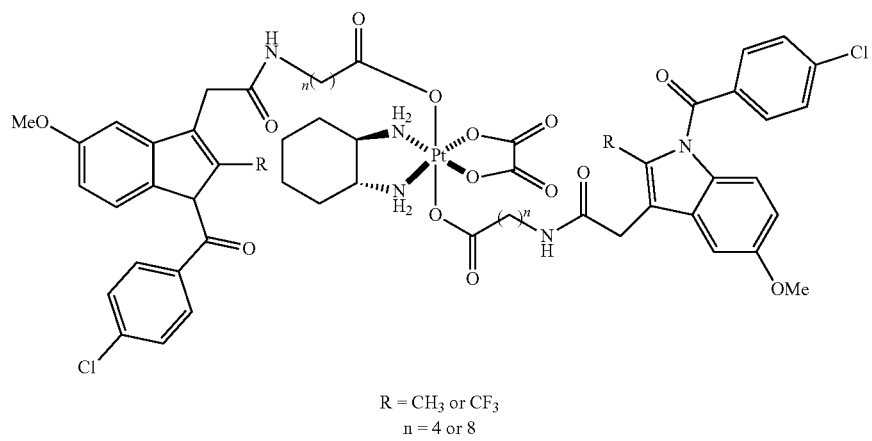
R = CH₃ or CF₃
n = 4 or 8
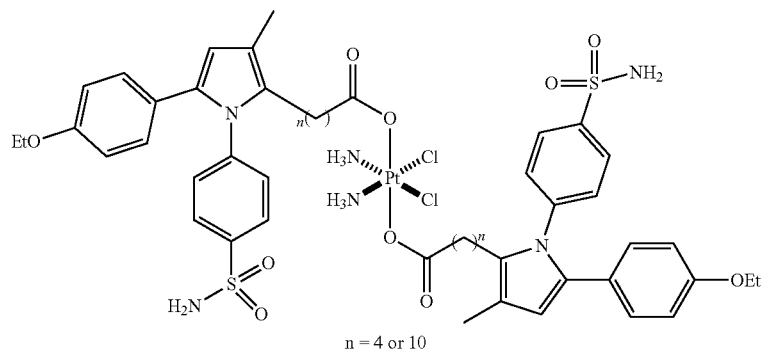
n = 4 or 10
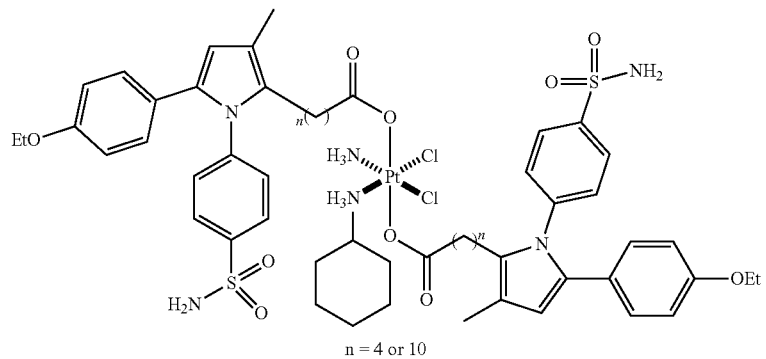
n = 4 or 10

-continued
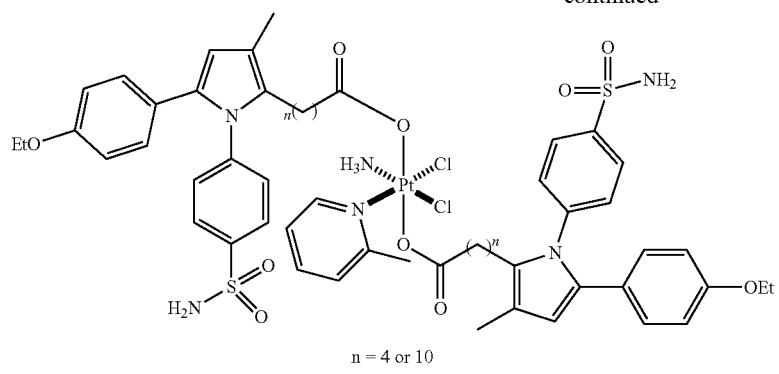
n = 4 or 10
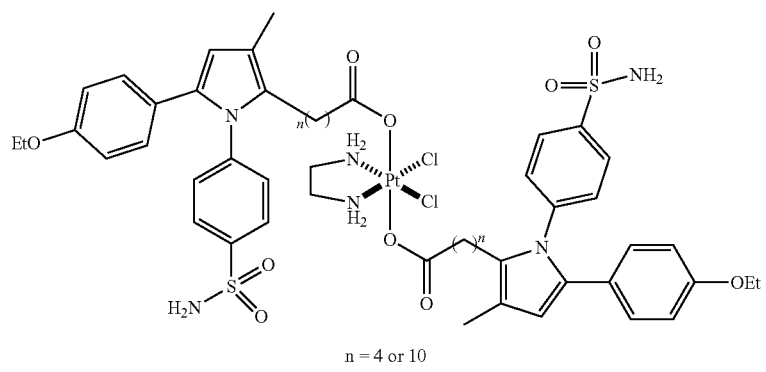
n = 4 or 10
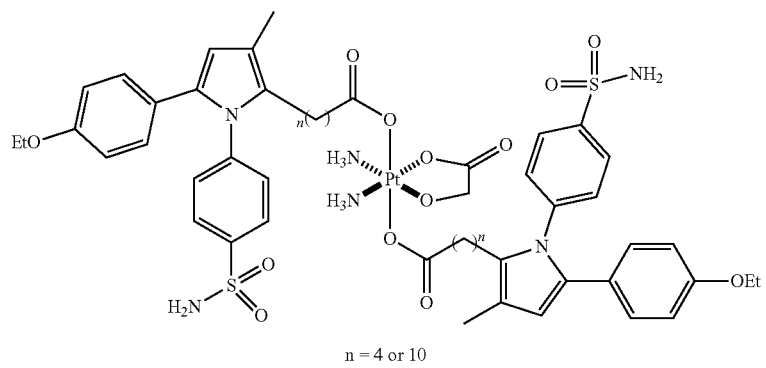
n = 4 or 10
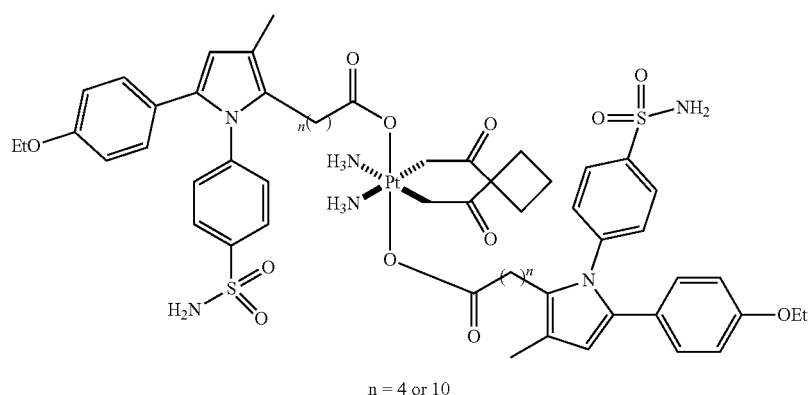
n = 4 or 10

-continued
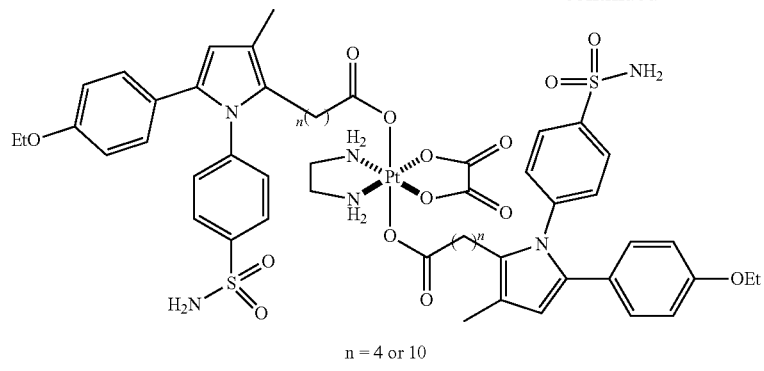
n = 4 or 10
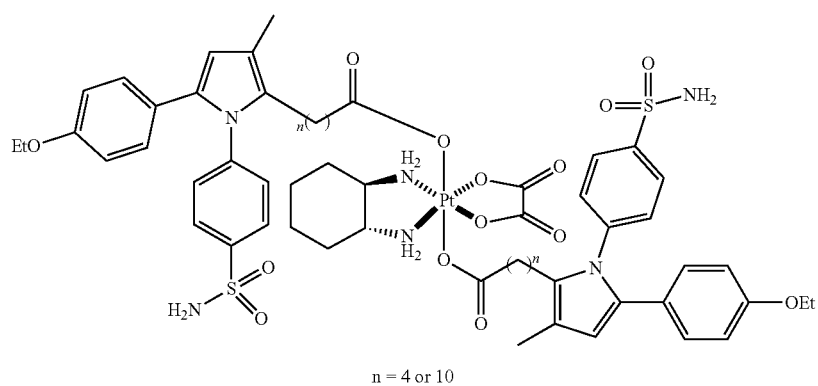
n = 4 or 10
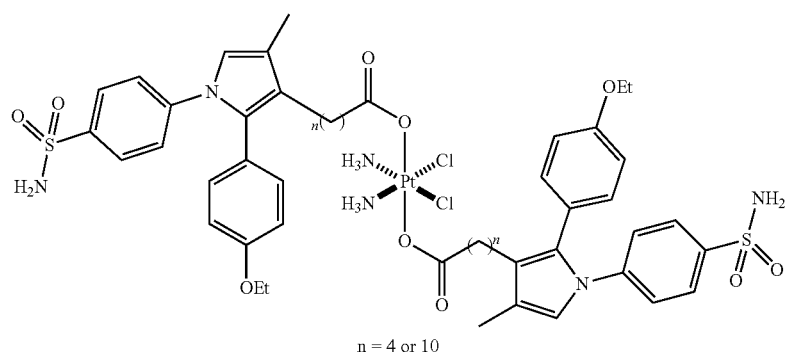
n = 4 or 10
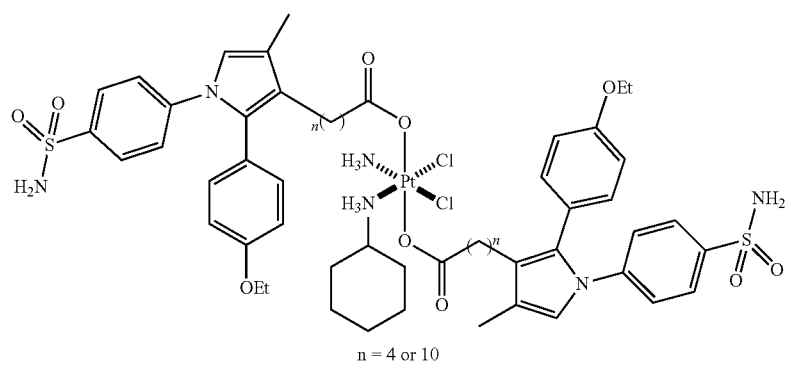
n = 4 or 10

-continued
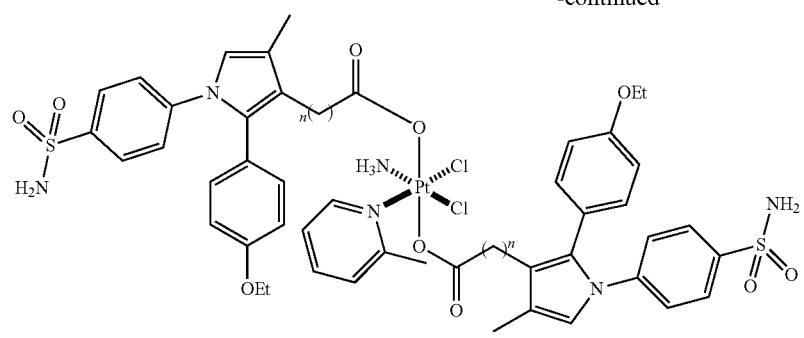
n = 4 or 10
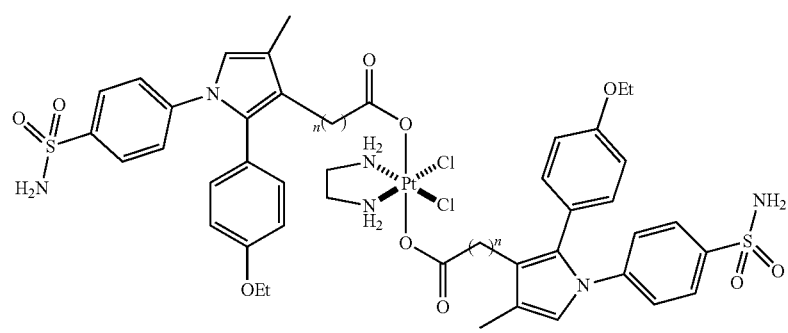
n = 4 or 10
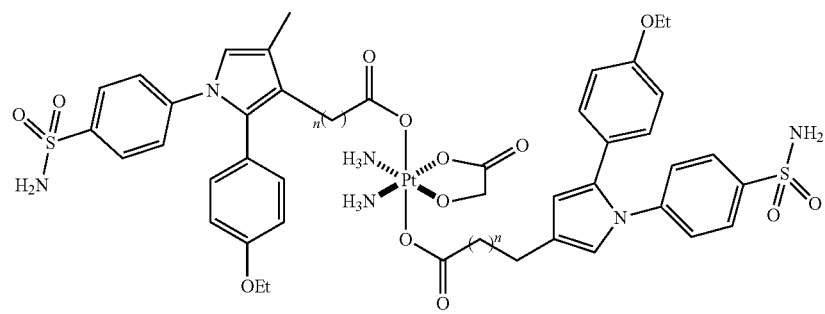
n = 4 or 10
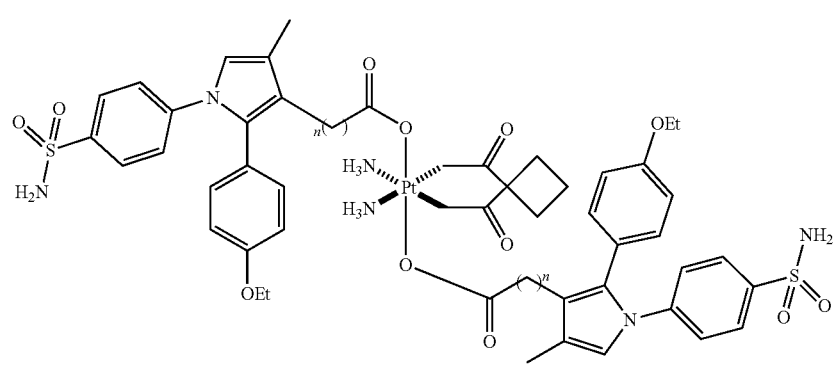
n = 4 or 10

-continued
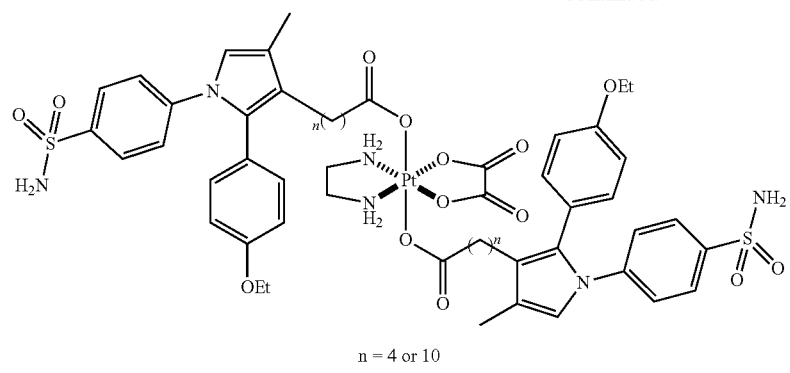
n = 4 or 10
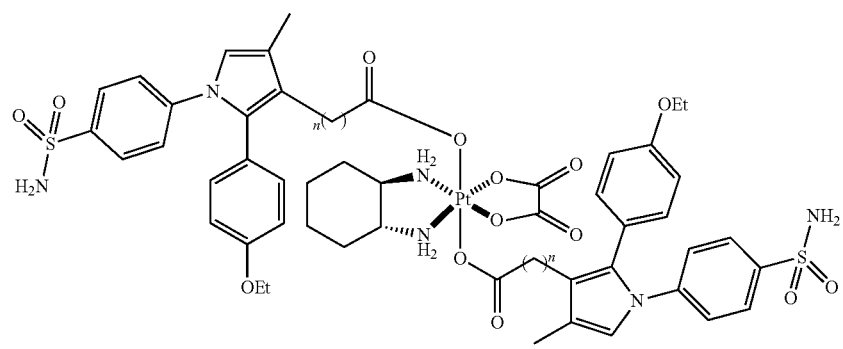
n = 4 or 10
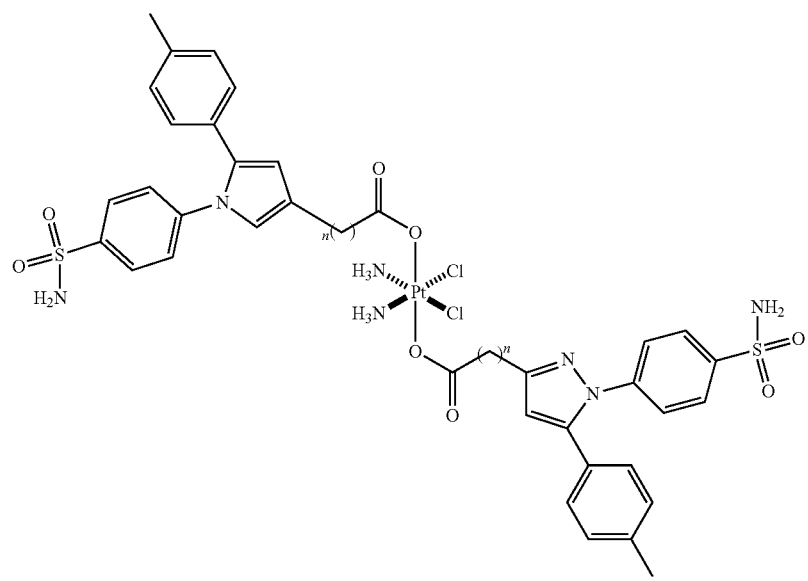
n = 4 or 10

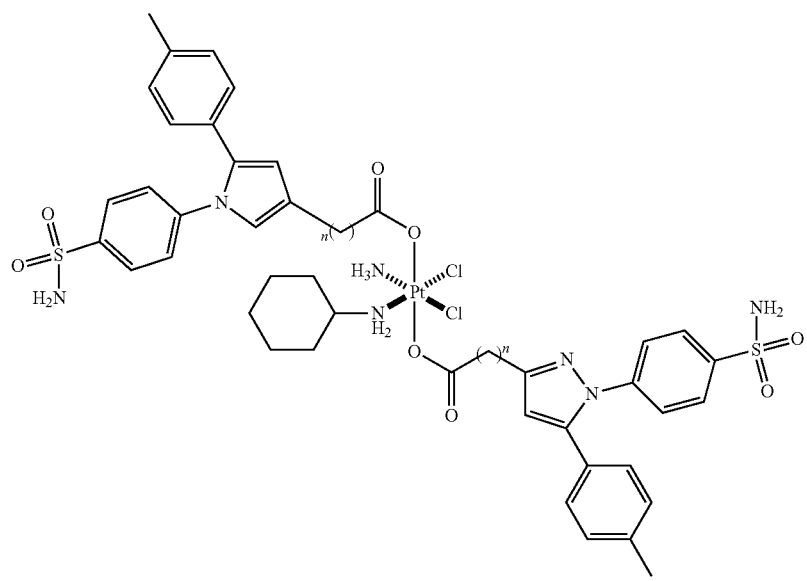
n = 4 or 10
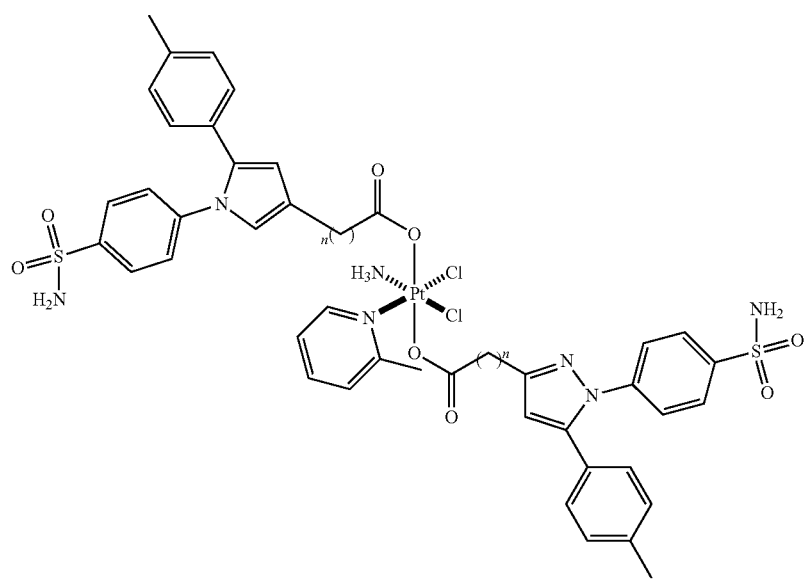
n = 4 or 10

-continued
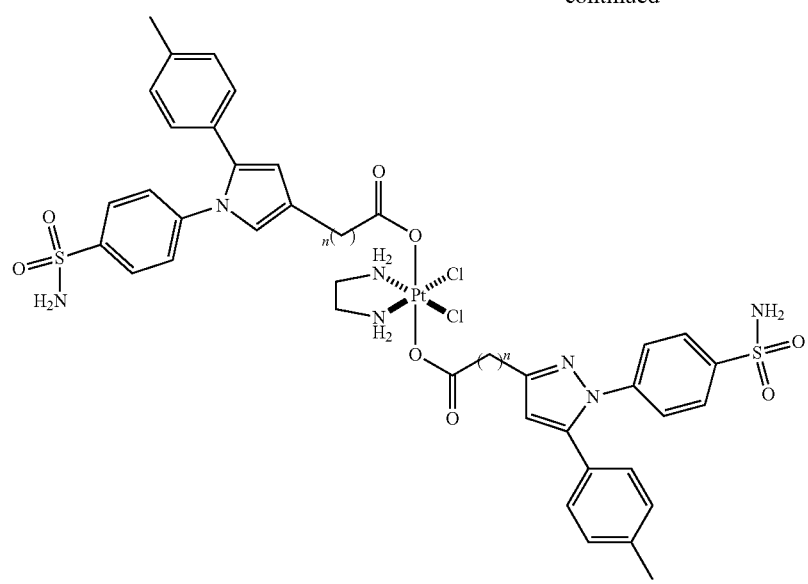
n = 4 or 10
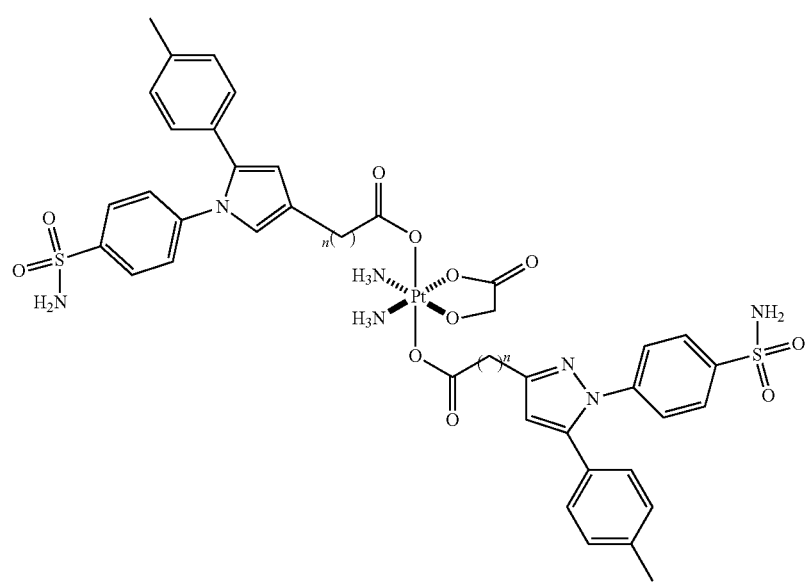
n = 4 or 10

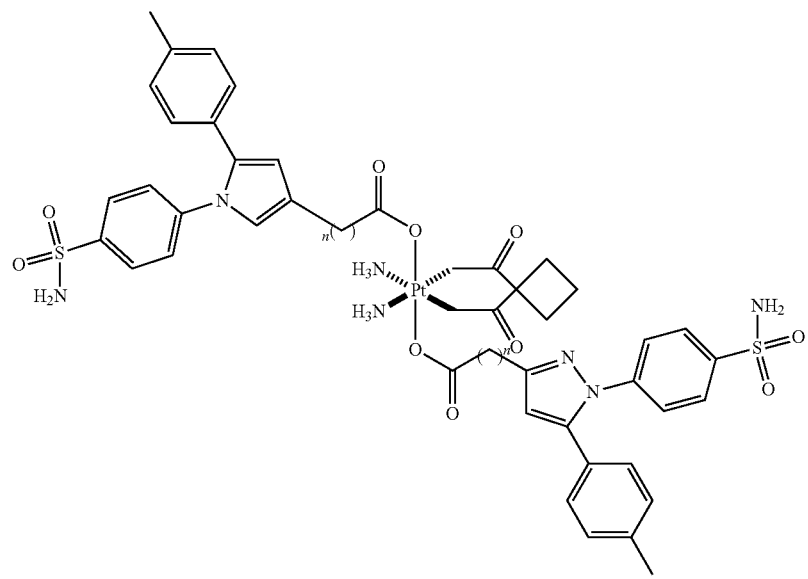
n = 4 or 10
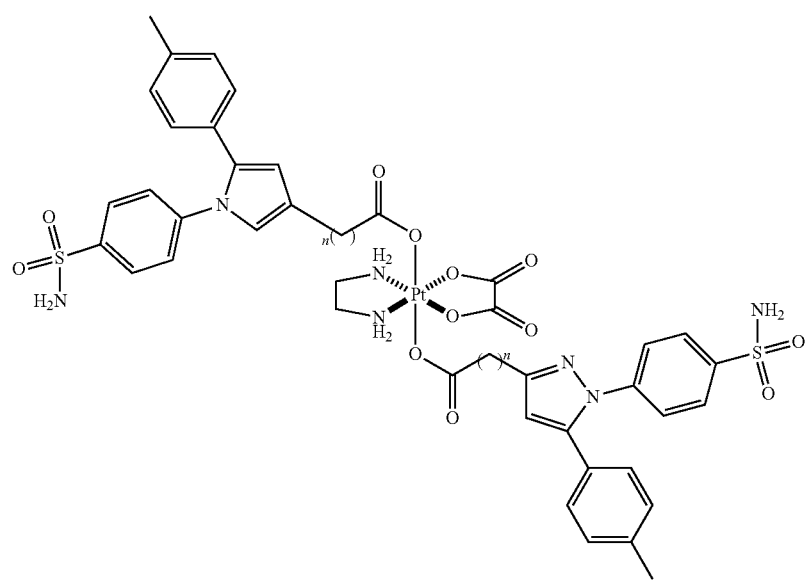
n = 4 or 10

-continued
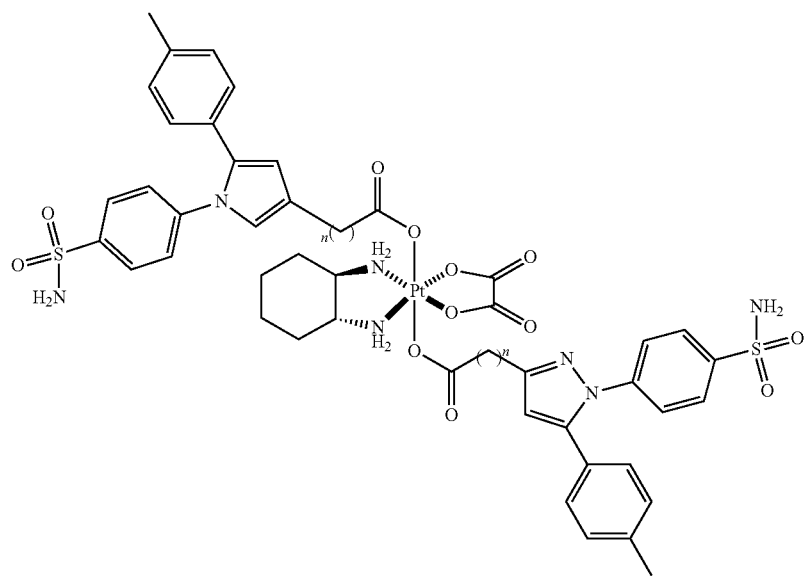
n = 4 or 10
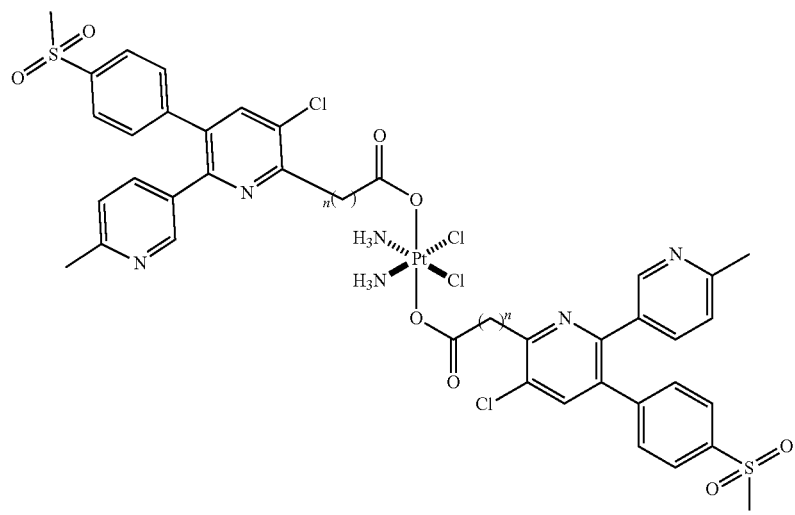
n = 4 or 10
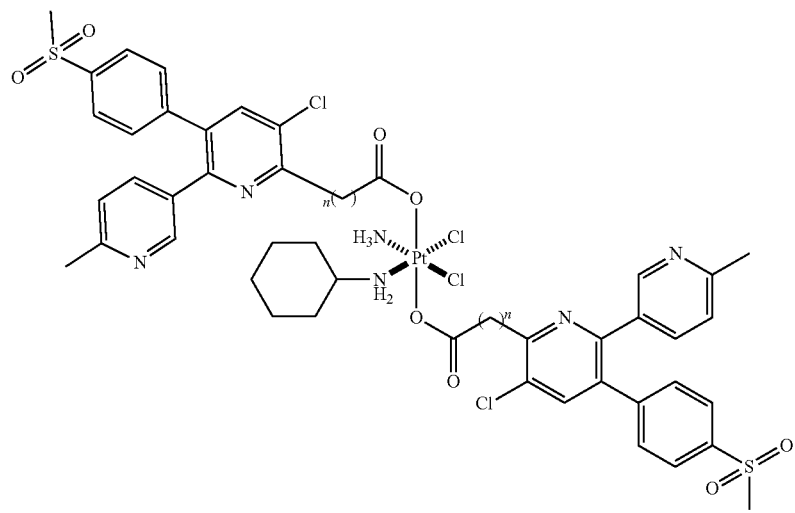
n = 4 or 10

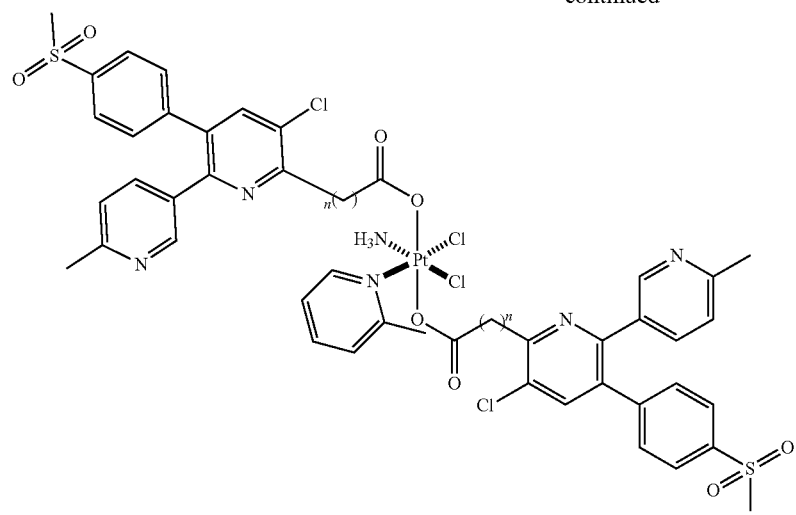
n = 4 or 10
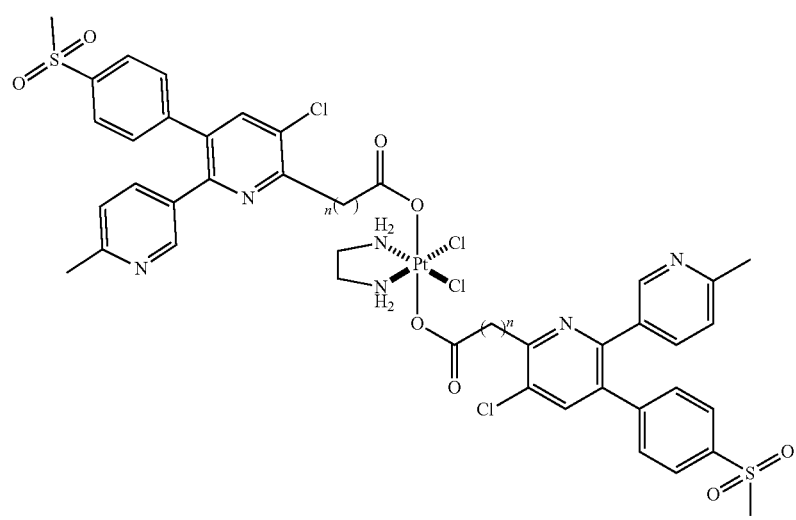
n = 4 or 10
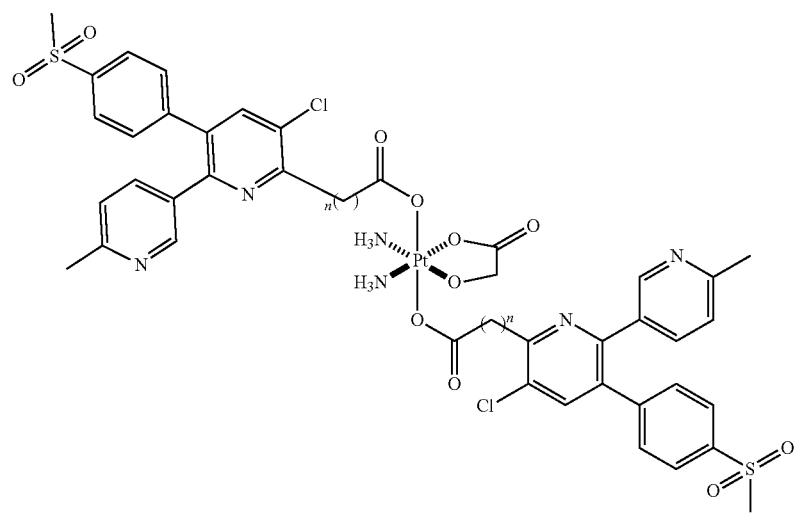
n = 4 or 10

-continued
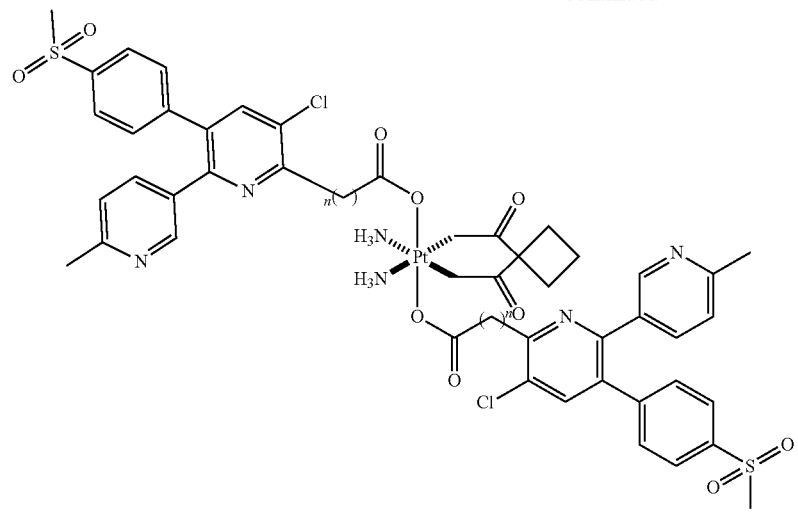
n = 4 or 10
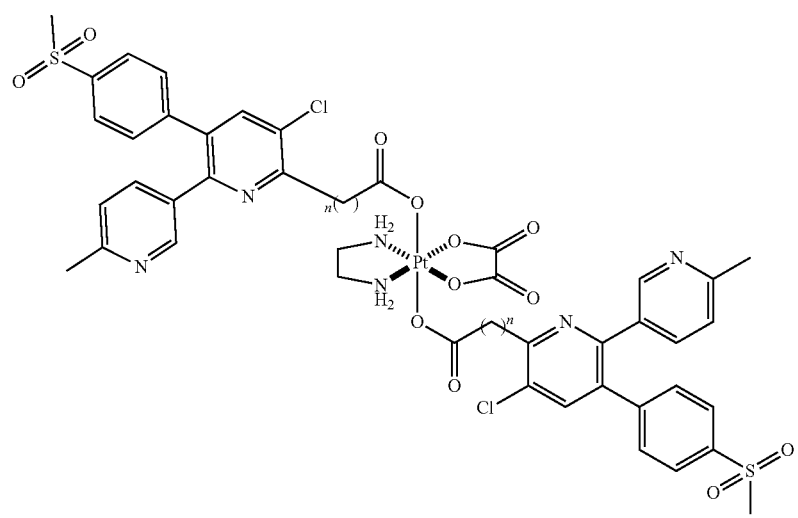
n = 4 or 10
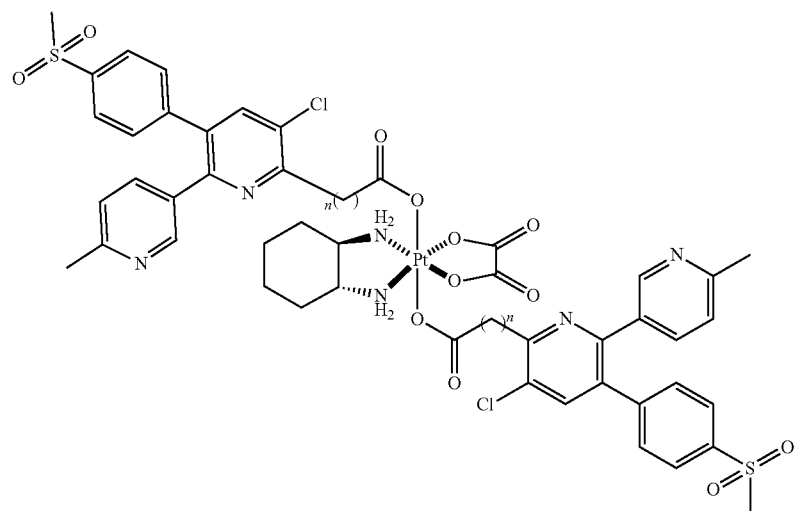
n = 4 or 10

-continued
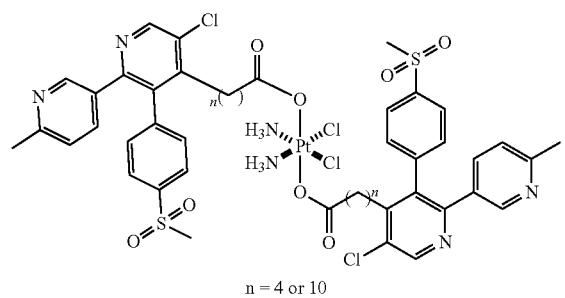
n = 4 or 10
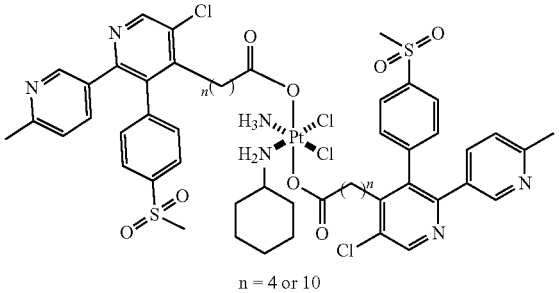
n = 4 or 10
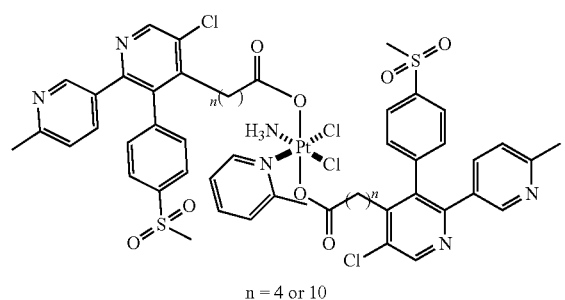
n = 4 or 10
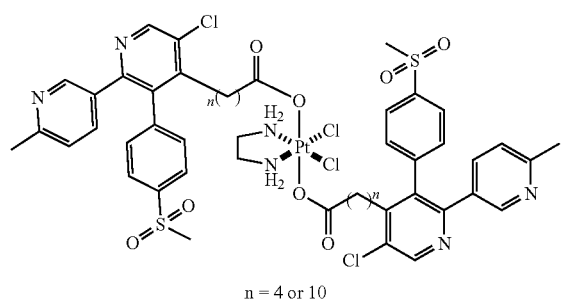
n = 4 or 10
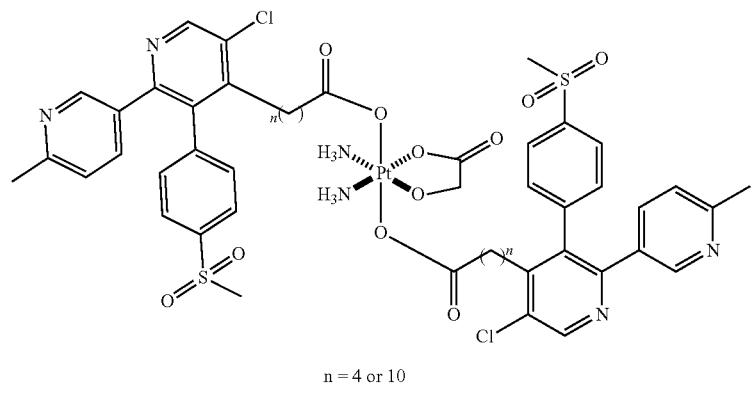
n = 4 or 10
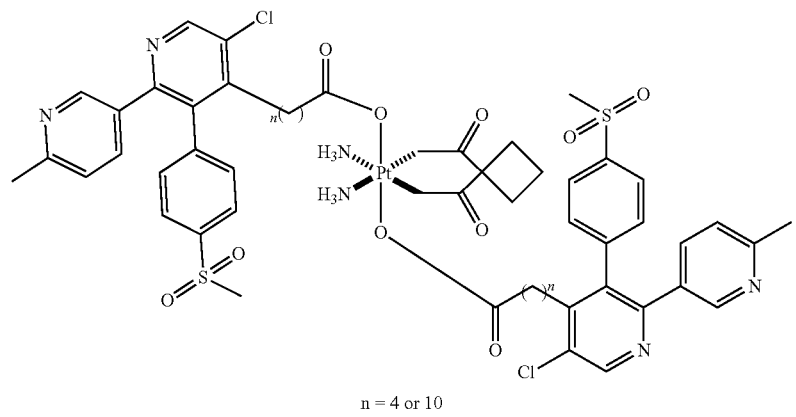
n = 4 or 10

-continued
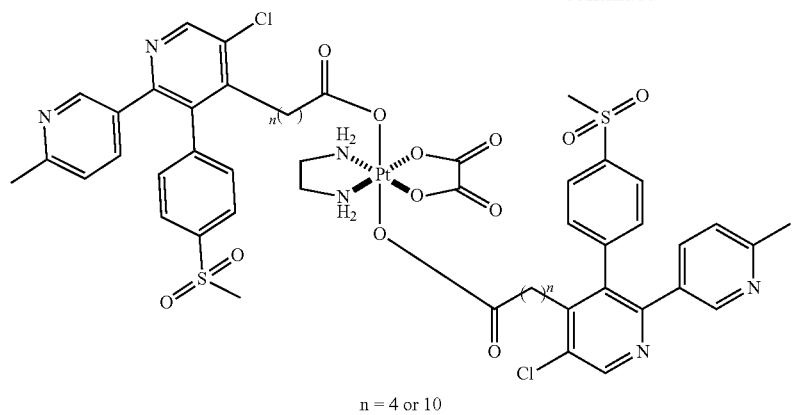
n = 4 or 10
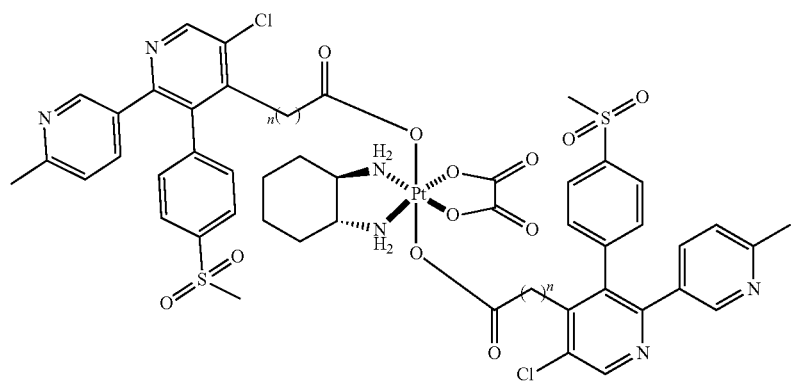
n = 4 or 10
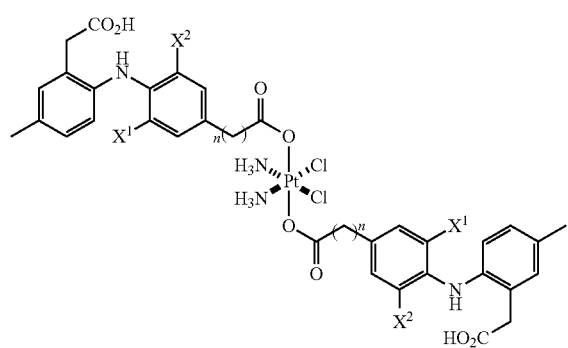
1) $X^1$ = F & $X^2$ = Cl;
2) $X^1$ = $X^2$ =F; or
3) $X^1$ = $X^2$ =Cl
n = 4 to 10
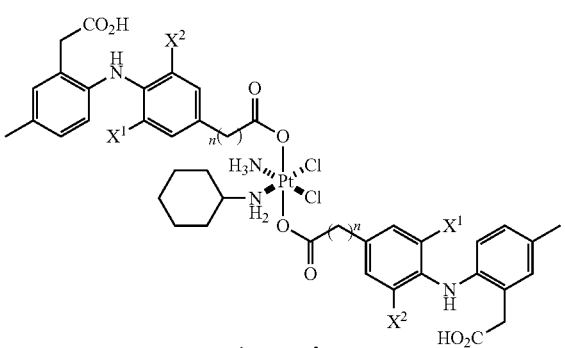
1) $X^1$ = F & $X^2$ = Cl;
2) $X^1$ = $X^2$ =F; or
3) $X^1$ = $X^2$ =Cl
n = 4 to 10
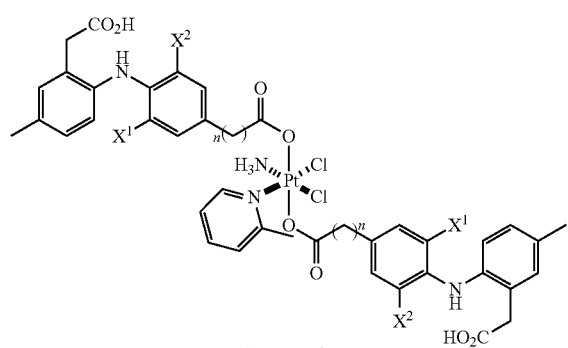
1) $X^1$ = F & $X^2$ = Cl;
2) $X^1$ = $X^2$ =F; or
3) $X^1$ = $X^2$ =Cl
n = 4 to 10
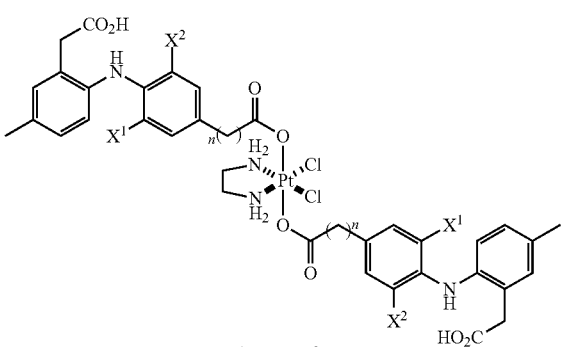
1) $X^1$ = F & $X^2$ = Cl;
2) $X^1$ = $X^2$ =F; or
3) $X^1$ = $X^2$ =Cl
n = 4 to 10

343
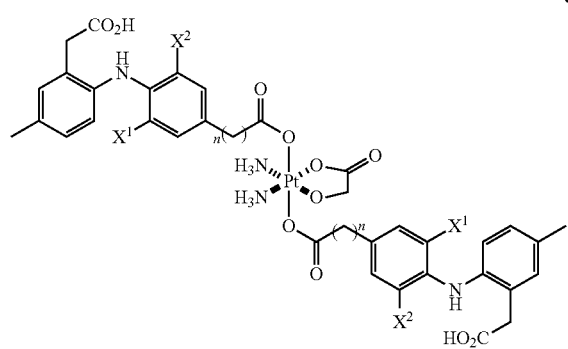
1) $X^1$ = F & $X^2$ = Cl;
2) $X^1$ = $X^2$ = F; or
3) $X^1$ = $X^2$ = Cl
n = 4 to 10
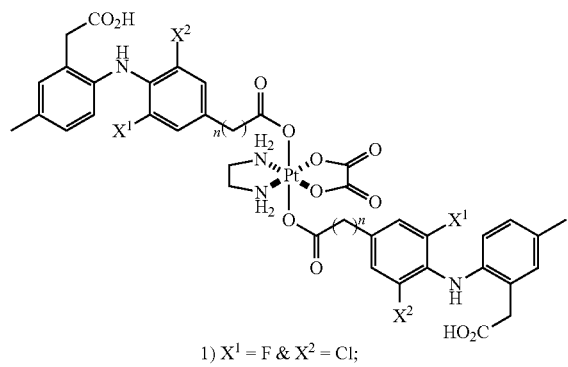
1) $X^1$ = F & $X^2$ = Cl;
2) $X^1$ = $X^2$ = F; or
3) $X^1$ = $X^2$ = Cl
n = 4 to 10
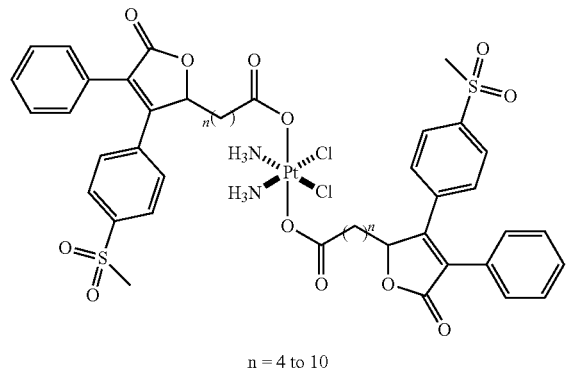
n = 4 to 10
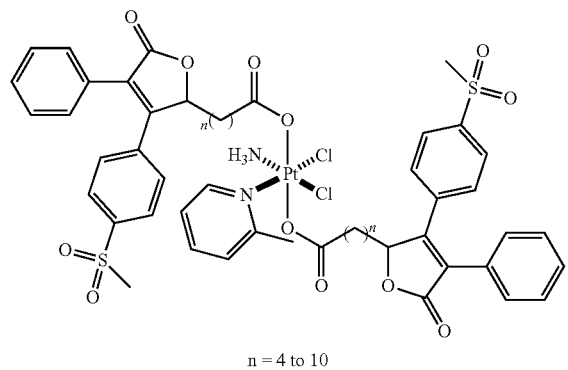
n = 4 to 10
344
-continued
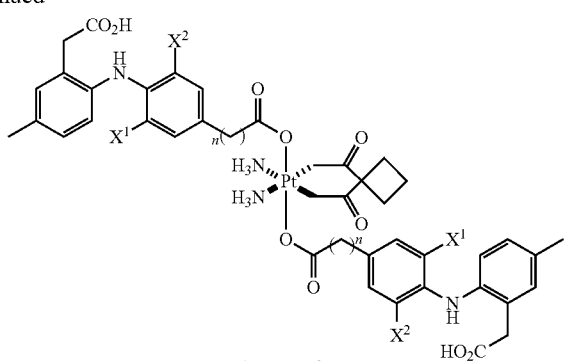
1) $X^1$ = F & $X^2$ = Cl;
2) $X^1$ = $X^2$ = F; or
3) $X^1$ = $X^2$ = Cl
n = 4 to 10
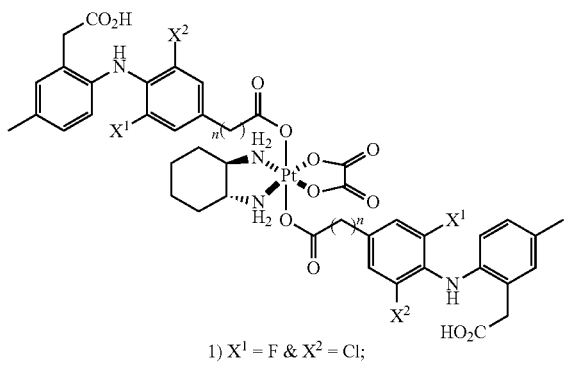
1) $X^1$ = F & $X^2$ = Cl;
2) $X^1$ = $X^2$ = F; or
3) $X^1$ = $X^2$ = Cl
n = 4 to 10
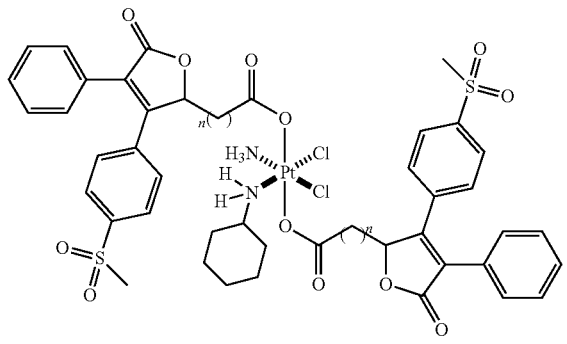
n = 4 to 10
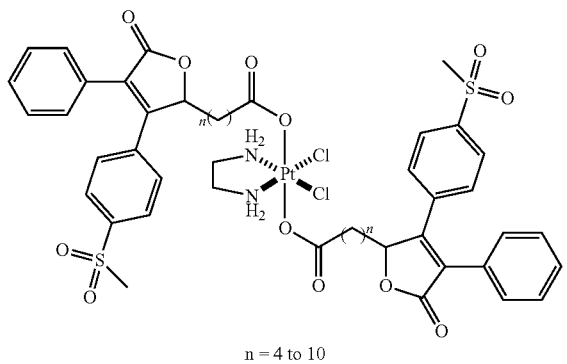
n = 4 to 10

-continued
| 345 | 346 |
|---|---|
| 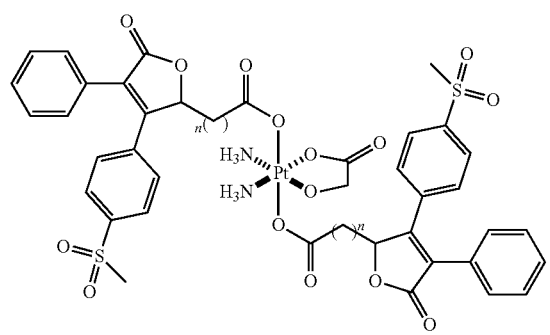<br>n = 4 to 10 | 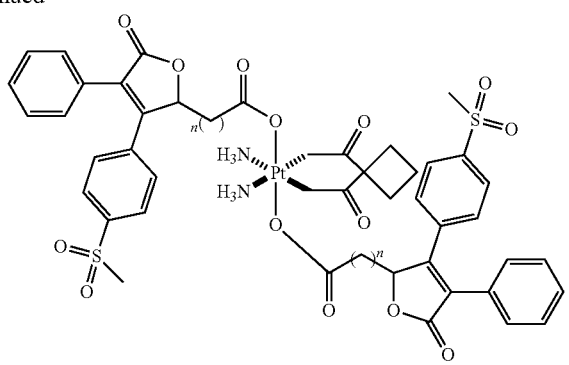<br>n = 4 to 10 |
| 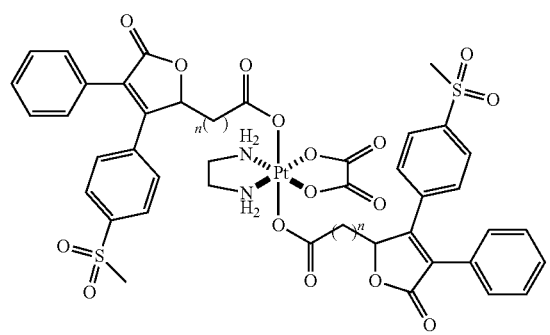<br>n = 4 to 10 | 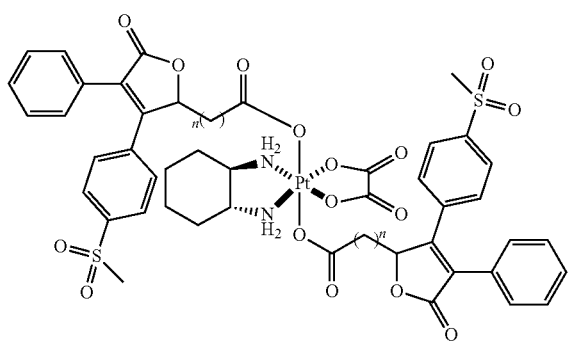<br>n = 4 to 10 |
| 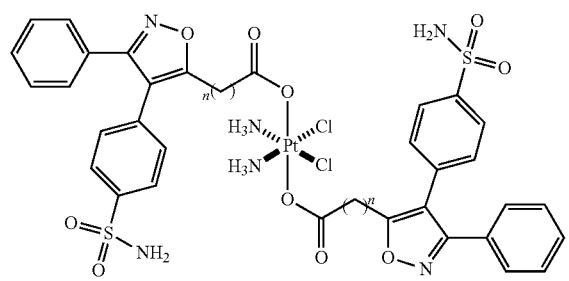<br>n = 4 to 10 | 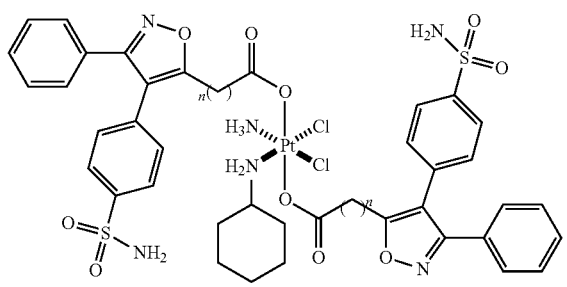<br>n = 4 to 10 |
| 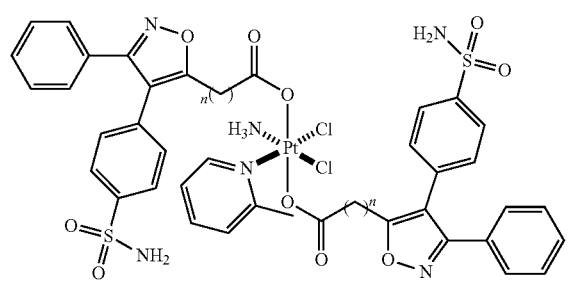<br>n = 4 to 10 | 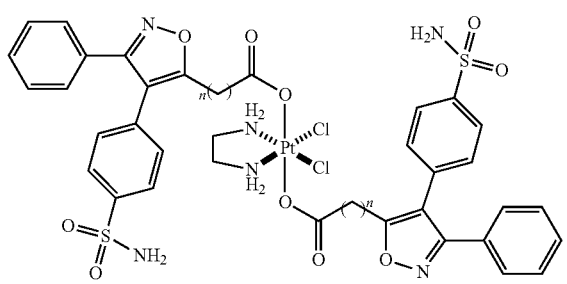<br>n = 4 to 10 |

347
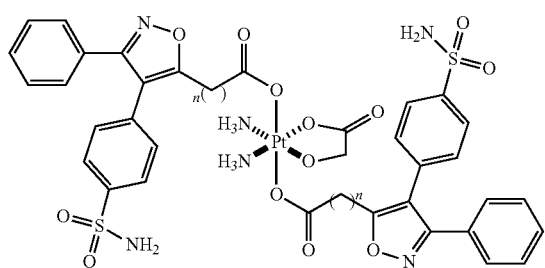
n = 4 to 10
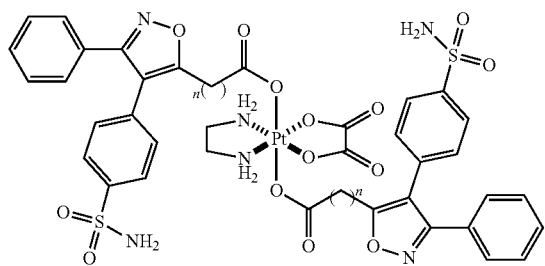
n = 4 to 10
348
-continued
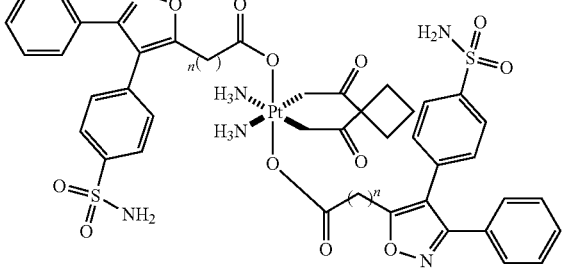
n = 4 to 10
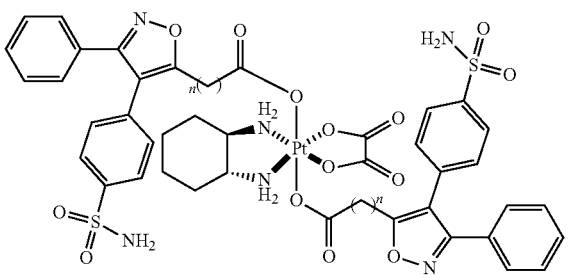
n = 4 to 10
and corresponding conjugates in which the platinum metal is connected to a COX-2-targeting moiety at one axial position and has a —OC(=O)$R^{10}$ or —OC(=O)-(4-phenyl-$R^{11}$) ligand at the other axial position, wherein $R^{10}$ is $C_1$-$C_{10}$ alkyl and $R^{11}$ is —H or $C_1$-$C_6$ alkyl, and pharmaceutically acceptable salts thereof.
* * * * *